US008945577B2

(12) United States Patent
Blais et al.

(10) Patent No.: US 8,945,577 B2
(45) Date of Patent: Feb. 3, 2015

(54) **FUSION PROTEINS AND COMBINATION VACCINES COMPRISING *HAEMOPHILUS INFLUENZAE* PROTEIN E AND PILIN A**

(75) Inventors: Normand Blais, Laval (CA); Steve Labbe, Laval (CA); Jan Poolman, Haarlem (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 0 days.

(21) Appl. No.: 14/110,857

(22) PCT Filed: Apr. 12, 2012

(86) PCT No.: PCT/CA2012/050236
§ 371 (c)(1),
(2), (4) Date: Oct. 9, 2013

(87) PCT Pub. No.: WO2012/139225
PCT Pub. Date: Oct. 18, 2012

(65) Prior Publication Data
US 2014/0056934 A1    Feb. 27, 2014

Related U.S. Application Data

(60) Provisional application No. 61/474,779, filed on Apr. 13, 2011, provisional application No. 61/534,012, filed on Sep. 13, 2011.

(51) Int. Cl.
*A61K 39/00* (2006.01)
*A61K 39/385* (2006.01)
*A61K 39/102* (2006.01)
*C07K 1/00* (2006.01)
*C07K 14/00* (2006.01)
*C07K 17/00* (2006.01)
*C12P 21/08* (2006.01)
*C07K 14/285* (2006.01)

(52) U.S. Cl.
CPC .............. *C07K 14/285* (2013.01); *A61K 39/102* (2013.01); *A61K 2039/543* (2013.01); *A61K 2039/55544* (2013.01); *A61K 2039/55566* (2013.01); *C07K 2319/00* (2013.01); *C07K 2319/02* (2013.01); *C07K 2319/50* (2013.01); *A61K 2039/70* (2013.01)
USPC .................. 424/185.1; 424/192.1; 424/193.1; 424/256.1; 530/350; 530/387.3

(58) Field of Classification Search
CPC ........... C07K 2319/00; C07K 16/1242; C07K 14/195; C07K 14/285; A61K 2039/543; A61K 2039/55544
See application file for complete search history.

(56) References Cited

FOREIGN PATENT DOCUMENTS

| WO | 2007/006665 | 1/2007 |
|---|---|---|
| WO | 2007/008527 | 1/2007 |
| WO | 2007/084053 | 7/2007 |

*Primary Examiner* — Gary Nickol
*Assistant Examiner* — Lakia Tongue
(74) *Attorney, Agent, or Firm* — Alice P. Bradney

(57) ABSTRACT

The present invention relates to compositions comprising *Haemophilus influenzae* Protein E and Pilin A. More particularly, the present application relates to fusion proteins and immunogenic compositions comprising Protein E and PilA, vaccines comprising such immunogenic compositions and therapeutic uses of the same.

6 Claims, 23 Drawing Sheets

Legend:

I = insoluble fraction

S = soluble fraction

M = media

Ind. = induction

Legend:

Ft = Flow through
W = Wash
E = Elution (a)

(b)

(a) Experiment 1

(b) Experiment 2

(c) Experiment 3

| Construct ID | % fusion protein gel #1 | % fusion protein gel #2 | % fusion protein gel #3 | Average % fusion protein | SD deviation |
|---|---|---|---|---|---|
| LVL291 | 9.3 | 8.98 | 9.43 | 9.24 | 0.231588716 |
| LVL702 | 7.2 | 8.85 | 8.37 | 8.14 | 0.848704896 |
| LVL736 | 11.16 | 10.2 | 11.94 | 11.10 | 0.871550343 |
| LVL737 | 8.18 | 8.33 | 9.32 | 8.61 | 0.619435227 |
| LVL738 | 8.56 | 8.55 | 7.97 | 8.36 | 0.337786915 |
| LVL739 | 8.91 | 8.88 | 9.21 | 9.00 | 0.182482876 |
| LVL740 | 7.69 | 7.49 | 8 | 7.73 | 0.256969518 |

FUSION PROTEINS AND COMBINATION VACCINES COMPRISING *HAEMOPHILUS INFLUENZAE* PROTEIN E AND PILIN A

This application is filed pursuant to 35 U.S.C. §371 as a United States National Phase Application of International Patent Application Serial No. PCT/CA2012/050236 filed Apr. 12, 2012, which claims priority to U.S. Provisional Application No. 61/534,012 filed Sep. 13, 2011, and to U.S. Provisional Application No. 61/474,779 filed Apr. 13, 2011, and the entire contents of each of the foregoing applications are hereby incorporated by reference.

FIELD OF THE INVENTION

The present invention relates to compositions comprising *Haemophilus influenzae* (*H. influenzae*) Protein E and Pilin A. More particularly, the present application relates to fusion proteins and immunogenic compositions comprising Protein E and Pilin A, vaccines comprising such immunogenic compositions and therapeutic uses of the same.

BACKGROUND OF THE INVENTION

Protein E (PE) is an outer membrane lipoprotein with adhesive properties. It plays a role in the adhesion/invasion of non-typeable *Haemophilus influenzae* (NTHi) to epithelial cells. (J. Immunology 183: 2593-2601 (2009); The Journal of Infectious Diseases 199:522-531 (2009), Microbes and Infection 10:87-96 (2008)). It is highly conserved in both encapsulated *Haemophilus influenzae* and non-typeable *H. influenzae* and has a conserved epithelial binding domain. (The Journal of Infectious Diseases 201:414-419 (2010)). Thirteen different point mutations have been described in different *Haemophilus* species when compared with *Haemophilus influenzae* Rd as a reference strain. Its expression is observed on both logarithmic growing and stationary phase bacteria. (WO2007/084053).

Protein E is also involved in human complement resistance through binding vitronectin. (Immunology 183: 2593-2601 (2009)). PE, by the binding domain PKRYARSVRQYKILN-CANYH LTQVR (SEQ ID NO. 1, corresponding to amino acids 84-108 of SEQ ID NO. 4), binds vitronectin which is an important inhibitor of the terminal complement pathway. (J. Immunology 183:2593-2601 (2009)).

Pilin A (PilA) is likely the major pilin subunit of *H. influenzae* Type IV Pilus (Tfp) involved in twitching motility (Infection and Immunity, 73: 1635-1643 (2005)). NTHi PilA is a conserved adhesin expressed in vivo. It has been shown to be involved in NTHi adherence, colonization and biofilm formation. (Molecular Microbiology 65: 1288-1299 (2007)).

Non-typeable *Haemophilus influenzae* is an important and common respiratory pathogen that causes otitis media in infants and children. NTHi is, after *Streptococcus pneumoniae*, the most common cause of acute otitis media in children (J. Immunology 183: 2593-2601 (2009), Pediatrics 113: 1451-1465 (2004)). It is an important cause of sinusitis in children and adults. (Current Infectious Disease Reports 11:177-182 (2009)). It has been associated with increased risk of exacerbations in chronic obstructive pulmonary disease (COPD) in adults. (Journal of Chronic Obstructive Pulmonary Disease 3:109-115 (2006)). In addition, non-typeable *H. influenzae* causes community-acquired pneumonia in adults and may cause pneumonia in children in developing countries. (Current Infectious Disease Reports 11:177-182 (2009)).

A need for vaccines for NTHi exists.

BRIEF SUMMARY OF THE INVENTION

As a first aspect, the present invention provides fusion proteins of formula (I).

$$(X)_m\text{—}(R_1)_n\text{-A-}(Y)_o\text{—B—}(Z)_p \qquad \text{(formula I)}$$

wherein:
X is a signal peptide or MHHHHHH (SEQ ID NO. 2);
m is 0 or 1;
$R_1$ is an amino acid;
n is 0, 1, 2, 3, 4, 5 or 6;
A is Protein E from *Haemophilus influenzae* or an immunogenic fragment thereof, or PilA from *Haemophilus influenzae* or an immunogenic fragment thereof;
Y is selected from the group consisting of GG, SG, SS, GGG and $(G)_h$, wherein h is 4, 5, 6, 7, 8, 9, or 10;
o is 0 or 1;
B is PilA from *Haemophilus influenzae* or an immunogenic fragment thereof, or Protein E from *Haemophilus influenzae* or an immunogenic fragment thereof;
Z is GGHHHHHH (SEQ ID NO. 3); and
p is 0 or 1.

As a second aspect, the present invention provides immunogenic compositions comprising fusion proteins of formula (I). The composition may further comprise a pharmaceutically acceptable adjuvant. The composition may comprise an excipient.

In a third aspect, the present invention provides a method for the treatment or prevention of a condition or disease caused wholly or in part by *Haemophilus influenzae*. The method comprises administering to a subject in need thereof a therapeutically effective amount of the fusion protein of formula (I).

In a fourth aspect, the present invention provides a method for the treatment or prevention of otitis media. The method comprises administering to a subject in need thereof a therapeutically effective amount of the fusion protein of formula (I).

In a fifth aspect, the present invention provides a method for the treatment or prevention of exacerbations in chronic obstructive pulmonary disease. The method comprises administering to a subject in need thereof a therapeutically effective amount of the fusion protein of formula (I).

In a sixth aspect, the present invention provides a method for the treatment or prevention of pneumonia. The method comprises administering to a subject in need thereof a therapeutically effective amount of the fusion protein of formula (I).

In a seventh aspect, the present invention provides a pharmaceutical composition comprising a fusion protein of formula (I) for use in the treatment or prevention of a condition or disease caused wholly or in part by *Haemophilus influenzae*. Pharmaceutical compositions may further comprise a pharmaceutically acceptable adjuvant.

In an eighth aspect, the present invention provides nucleic acids encoding the proteins of the invention.

In a ninth aspect, the present invention provides a process of producing nucleic acids of the invention.

Further aspects of the present invention are described in the detailed description of particular embodiments, examples and claims which follow.

DETAILED DESCRIPTION OF THE INVENTION

Figure 1:
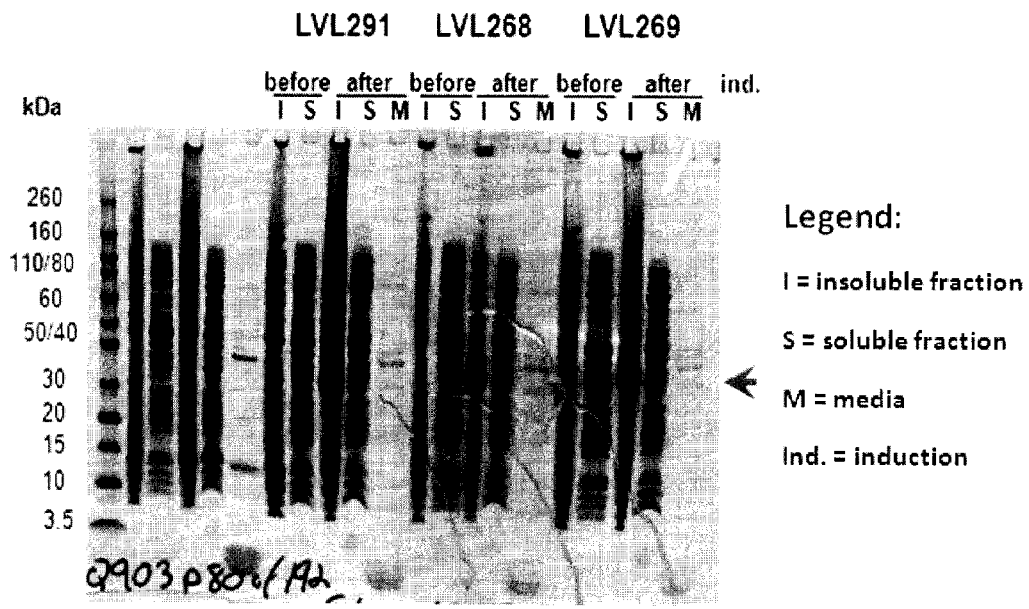
FIG. 1. SDS-PAGE of induced bacterial extracts for fusion protein constructs LVL291, LVL268 and LVL269. Insoluble fraction (I), Soluble fraction (S) and Culture Media fraction (M) were loaded for LVL291, LVL268 and LVL269 before and after induction (ind).

Unless otherwise explained or defined herein, all technical and scientific terms used herein have the same meaning as commonly understood by one of ordinary skill in the art to which this disclosure belongs. For example, definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen may be approximate. Thus, where a concentration is indicated to be (for example) approximately 200 pg, it is intended that the concentration includes values slightly more or slightly less than ("about" or "~") 200 pg.

Although methods and materials similar or equivalent to those described herein can be used in the practice or testing of this disclosure, suitable methods and materials are described below.

The term "comprises" means "includes". Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of terms are provided. Additional terms and explanations are provided in the context of this disclosure.

A "subject" as used herein is a mammal, including humans, non-human primates, and non-primate mammals such as members of the rodent genus (including but not limited to mice and rats) and members of the order Lagomorpha (including but not limited to rabbits).

As used herein "Protein E", "protein E", "Prot E", and "PE" mean Protein E from *H. influenzae*. Protein E may consist of or comprise the amino acid sequence of SEQ ID NO. 4 (MKKIILTLSL GLLTACSAQI QKAEQNDVKL APPTDVRSGY IRLVKNVNYY IDSESIWVDN QEPQIVHFDA VVNLDKGLYV YPEPKRYARS VRQYKILNCA NYHLTQVRTD FYDEFWGQGL RAAPKKQKKH TLSLTPDTTL YNAAQIICAN YGEAFSVDKK) as well as sequences with at least or exactly 75%, 77%, 80%, 85%, 90%, 95%, 97%, 99% or 100% identity, over the entire length, to SEQ ID NO. 4. Comparison of 53 sequences of Protein E from *Haemophilus influenzae* (Table 1, SEQ ID NO. 5-SEQ ID NO. 57) demonstrated approximately 77% to approximately 100% identity to Protein E as set forth in SEQ ID NO. 4. For example, in the amino acid sequence of Protein E, amino acid #20 may be isoleucine (I) or threonine (T); amino acid #23 may be alanine (A) or valine (V); amino acid #24 may be lysine (K) or glutamic acid (E); amino acid #31 may be alanine (A) or threonine (T); amino acid #32 may be proline (P) or alanine (A); amino acid #34 may be threonine (T) or alanine (A); amino acid #37 may be arginine (R) or glutamine (Q); amino acid #47 may be valine (V) or alanine (A); amino acid #57 may be tryptophane O) or may be absent (–); amino acid #70 may be alanine (A) or threonine (T); amino acid #93 may be glutamine (Q) or absent (–); amino acid #109 may be threonine (T) or isoleucine (I); amino acid #119 may be glycine (G) or serine (S); amino acid #153 may be glutamic acid (E) or lysine (K); amino acid #156 may be serine (S) or leucine (L); amino acid #160 may be lysine (K) or asparagine (N); amino acid #161 may be lysine (K), isoleucine (I) or absent (–); amino acids #162-#195 may be absent, or as set forth in SEQ ID NO. 15 (with (–) indicating amino acid #166 is absent) or as set forth in SEQ ID NO. 16; or any combination thereof.

Protein E may consist of or comprise an amino acid sequence that differs from SEQ ID NO. 4 at any one or more amino acid selected from the group consisting of: amino acid #20, amino acid #23, amino acid #24, amino acid #31, amino acid #32, amino acid #34, amino acid #37, amino acid #47, amino acid #57, amino acid #70, amino acid #93, amino acid #109, amino acid #119, amino acid #153, amino acid #156, amino acid #160, amino acid #161 and amino acids #162-#195, wherein amino acid #20 is threonine (T); amino acid #23 is valine (V); amino acid #24 is lysine (K); amino acid #31 is threonine (T); amino acid #32 is alanine (A); amino acid #34 is alanine (A); amino acid #37 is glutamine (Q); amino acid #47 is alanine (A); amino acid #57 is absent (–); amino acid #70 is threonine (T); amino acid #93 is absent (–); amino acid #109 is isoleucine (I); amino acid #119 is serine (S); amino acid #153 is lysine (K); amino acid #156 is leucine (L); amino acid #160 is asparagine (N); amino acid #161 is lysine (K) or isoleucine (I); or amino acids #162-#195 are as set forth in SEQ ID NO. 15 (with (–) indicating amino acid #166 is absent) or as set forth in SEQ ID NO. 16.

TABLE 1

Protein E amino acid sequences from 53 strains of *Haemophilus influenzae* (SEQ ID NO. 5-SEQ ID NO. 57). – indicates amino acid is absent.

| Strain Name | Protein E sequence |
|---|---|
| 3224A | MKKIILTLSLGLLTACSAQIQKAKQNDVKLAPPTDVRSGYIRLVKNVNYYIDSESIWVDNQEPQ IVHFDAVVNLDKGLYVYPEPKRYARSVRQYKILNCANYHLTQVRTDFYDEFWGQGLRAAPKKQK KHTLSLTPDTTLYNAAQIICANYGEAFSVDKK (SEQ ID NO. 5) |
| RdKW20 | MKKIILTLSLGLLTACSAQIQKAEQNDVKLAPPTDVRSGYIRLVKNVNYYIDSESIWVDNQEPQ IVHFDAVVNLDRGLYVYPEPKRYARSVRQYKILNCANYHLTQIRTDFYDEFWGQGLRAAPKKQK KHTLSLTPDTTLYNAAQIICANYGKAFSVDKK (SEQ ID NO. 6) |
| 86-028NP | MKKIILTLSLGLLTACSAQIQKAKQNDVKLAPPTDVRSGYIRLVKNVNYYIDSESIWVDNQEPQ IVHFDAVVNLDKGLYVYPEPKRYARSVRQYKILNCANYHLTQVRTDFYDEFWGQGLRAAPKKQK KHTLSLTPDTTLYNAAQIICANYGEAFSVDKK (SEQ ID NO. 7) |
| R2846 | MKKIILTLSLGLLTACSAQIQKAEQNDVKLAPPTDVRSGYIRLVKNVNYYIDSESIWVDNQEPQ IVHFDAVVNLDKGLYVYPEPKRYARSVRQYKILNCANYHLTQVRTDFYDEFWGQGLRAAPKKQK KHTLSLTPDTTLYNAAQIICANYGKAFSVDKK (SEQ ID NO. 8) |
| R2866 | MKKIILTLSLGLLTACSAQIQKAEQNDVKLAPPTDVRSGYIRLVKNVNYYIDSESIWVDNQEPQ IVHFDAVVNLDKGLYVYPEPKRYARSVRQYKILNCANYHLTQVRTDFYDEFWGQGLRAAPKKQK KHTLSLTPDTTLYNAAQIICANYGKAFSVDKK (SEQ ID NO. 9) |
| 3655 | MKKIILTLSLGLLTACSAQIQKAEQNDMKLAPPTDVRSGYIRLVKNVNYYIDSESIWVDNQEPQ IVHFDAVVNLDKGLYVYPEPKRYARSVRQYKILNCANYHLTQVRTDFYDEFWGQGLRAAPKKQK KHTLSLTPDTTLYNAAQIICANYGKAFSVDKK (SEQ ID NO. 10) |
| PittAA | MKKIILTLSLGLLTACSAQIQKAKQNDVKLAPPTDVRSGYIRLVKNVNYYIDSESIWVDNQEPQ IVHFDAVVNLDKGLYVYPEPKRYARSVRQYKILNCANYHLTQVRTDFYDEFWGQGLRAAPKKQK KHTLSLTPDTTLYNAAQIICANYGEAFSVDKK (SEQ ID NO. 11) |
| PittEE | MKKIILTLSLGLLTACSAQIQKAEQNDMKLAPPTDVRSGYIRLVKNVNYYIDSESI-VDNQEPQ IVHFDAVVNLDKGLYVYPEPKRYARSVRQYKILNCANYHLTQVRTDFYDEFWGQGLRAAPKKQK KHTLSLTPDTTLYNAAQIICANYGKAFSVDKK (SEQ ID NO. 12) |
| PittHH | MKKIILTLSLGLLTACSAQIQKAEQNDVKLAPPTDVRSGYIRLVKNVNYYIDSESIWVDNQEPQ IVHFDTVVNLDKGLYVYPEPKRYARSVRQYKILNCANYHLTQVRTDFYDEFWGQGLRAAPKKQK KHTLSLTPDTTLYNAAQIICANYGKAFSVDKK (SEQ ID NO. 13) |
| PittII | MKKIILTLSLGLLTACSAQIQKAEQNDVKLAPPTDVRSGYIRLVKNVNYYIDSESIWVDNQEPQ IVHFDAVVNLDKGLYVYPEPKRYARSVRQYKILNCANYHLTQVRTDFYDEFWGQGLRAAPKKQK KHTLSLTPDTTLYNAAQIICANYGKAFSVDKK (SEQ ID NO. 14) |

TABLE 1-continued

Protein E amino acid sequences from 53 strains of *Haemophilus influenzae* (SEQ ID NO. 5-SEQ ID NO. 57). - indicates amino acid is absent.

Strain Name  Protein E sequence

R3021        MKKIILTLSLGLLTACSAQTQKAEQNDVKLTPPTDVQSGYVRLVKNVNYYIDSESIWVDNQEPQ
             IVHFDAVVNLDKGLYVYPEPKRYARSVRQYKILNCANYHLTQVRIDFYDEFWGQGLRAAPKKQK
             KHTLSLTPDTTLYNAAQIICANYGKAFSVDKNKKICT-LISLNFIQLLGCREYSIFLQLLLFYC
             WHF (SEQ ID NO. 15)

22.4-21      MKKIILTLSLGLLTACSAQIQKAEQNDVKLAPPTDVRSGYIRLVKNVNYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGKAFSVDKKIKKICTLISLNFIQLLGCREYSIFLQLLLFYC
             WHF (SEQ ID NO. 16)

3219C        MKKIILTLSLGLLTACSAQIQKAEQNDMKLAPPTDVRSGYIRLVKNVNYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGKAFSVDKK (SEQ ID NO. 17)

3185         MKKIILTLSLGLLTACSAQIQKAEQNDVKLAPPTDVRSGYIRLVKNVNYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGKAFSVDKK (SEQ ID NO. 18)

3241A        MKKIILTLSLGLLTACSAQIQKAKQNDVKLAPPTDVRSGYIRLVKNVNYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGEAFSVDKK (SEQ ID NO. 19)

038144S1     MKKIILTLSLGLLTACSAQTQKVEQNDVKLTAPTDVRSGFVRLVKNVNYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGKAFLVDKK (SEQ ID NO. 20)

810956       MKKIILTLSLGLLTACSAQIQKAKQNDVKLAPPTDVRSGYIRLVKNVNYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGEAFSVDKK (SEQ ID NO. 21)

821246       MKKIILTLSLGLLTACSAQIQKAEQNDVKLAPPTDVRSGYIRLVKNVNYYIDSESIWVDNQEPQ
             IVHFDAVVNLDKGLYVYPEPKRYARSVRQYKILNCANYHLTQIRTDFYDEFWGQGLRAAPKKQK
             KHTLSLTPDTTLYNAAQIICANYGKAFSVDKK (SEQ ID NO. 22)

840645       MKKIILTLSLGLLTACSAQIQKAKQNDVKLAPPTDVRSGYIRLVKNVNYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGEAFSVDKK (SEQ ID NO. 23)

902550Z19    MKKIILTLSLGLLTACSAQTQKVEQNDVKLTPPTDVRSGYVRLVKNVNYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGKAFSVDKK (SEQ ID NO. 24)

A840177      MKKIILTLSLGLLTACSAQIQKAKQNDVKLAPPTDVRSGYIRLVKNVNYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGEAFSVDKK (SEQ ID NO. 25)

A860514      MKKIILTLSLGLLTACSAQTQKVEQNDVKLTAPTDVRSGYVRLVKNANYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGKAFSVDKK (SEQ ID NO. 26)

A950014      MKKIILTLSLGLLTACSAQIQKAEQNDVKLAPPTDVRSGYIRLVKNVNYYIDSESIWVDNQEPQ
             IVHFDAVVNLDKGLYVYPEPKRYARSVRQYKILNCANYHLTQVRIDFYDEFWGQGLRAAPKKQK
             KHTLSLTPDTTLYNAAQIICANYGKAFSVDKK (SEQ ID NO. 27)

306543X4     MKKIILTLSLGLLTACSAQIQKAEQNDVKLAPPTDVRSGYIRLVKNVNYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGKAFSVDKK(SEQ ID NO. 28)

A930105      MKKIILTLSLGLLTACSAQIQKAEQNDVKLAPPTDVRSGYIRLVKNVNYYIDSESIWVDNQEPQ
             IVHFDTVVNLDKGLYVYPEPKRYARSVRQYKILNCANYHLTQVRTDFYDEFWGQGLRAAPKKQK
             KHTLSLTPDTTLYNAAQIICANYGKAFSVDKK(SEQ ID NO. 29)

901905U      MKKIILTLSLGLLTACSAQIQKAEQNDVKLAPPTDVRSGYIRLVKNVNYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGKAFSVDKK (SEQ ID NO. 30)

A920030      MKKIILTLSLGLLTACSAQIQKAKQNDVKLAPPTDVRSGYIRLVKNVNYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGEAFSVDKK (SEQ ID NO. 31)

3221B        MKKIILTLSLGLLTACSAQIQKAEQNDVKLAPPTDVRSGYIRLVKNVNYYIDSESIWVDNQEPQ
             IVHFDAVVNLDKGLYVYPEPKRYARSVRQYKILNCANYHLTQVRTDFYDEFWGQGLRAAPKKQK
             KHTLSLTPDTTLYNAAQIICANYGKAFSVDKK (SEQ ID NO. 32)

TABLE 1-continued

Protein E amino acid sequences from 53 strains of Haemophilus influenzae
(SEQ ID NO. 5-SEQ ID NO. 57). - indicates amino acid is absent.

| Strain Name | Protein E sequence |
|---|---|
| 27W116791N | MKKIILTLSLGLLTACSAQTQKVEQNDVKLTPPTDVRSGYVRLVKNVNYYIDSESIWVDNQEPQ<br>IVHFDAVVNLDKGLYVYPEPKRYARSVRQYKILNCANYHLTQVRTDFYDEFWGQGLRAAPKKQK<br>KHTLSLTPDTTLYNAAQIICANYGKAFSVDKK (SEQ ID NO. 33) |
| N218 | MKKIILTLSLGLLTACSAQIQKAEQNDVKLAPPTDVRSGYIRLVKNVNYYIDSESIWVDNQEPQ<br>IVHFDAVVNLDKGLYVYPEPKRYARSVRQYKILNCANYHLTQVRTDFYDEFWGQGLRAAPKKQK<br>KHTLSLTPDTTLYNAAQIICANYGKAFSVDKK (SEQ ID NO. 34) |
| N163 | MKKIILTLSLGLLTACSAQIQKAKQNDVKLAPPTDVRSGYIRLVKNVNYYIDSESIWVDNQEPQ<br>IVHFDAVVNLDKGLYVYPEPKRYARSVRQYKILNCANYHLTQVRTDFYDEFWGQGLRAAPKKQK<br>KHTLSLTPDTTLYNAAQIICANYGEAFSVDKK (SEQ ID NO. 35) |
| N162 | MKKIILTLSLGLLTACSAQIQKAKQNDVKLAPPTDVRSGYIRLVKNVNYYIDSESIWVDNQEPQ<br>IVHFDAVVNLDKGLYVYPEPKRYARSVRQYKILNCANYHLTQVRTDFYDEFWGQGLRAAPKKQK<br>KHTLSLTPDTTLYNAAQIICANYGEAFSVDKK (SEQ ID NO. 36) |
| N107 | MKKIILTLSLGLLTACSAQTQKAEQNDVKLAPPTDVRSGYIRLVKNVNYYIDSESIWVDNQEPQ<br>IVHFDAVVNLDKGLYVYPEPKRYARSVRQYKILNCANYHLTQIRTDFYDEFWGQGLRAAPKKQK<br>KHTLSLTPDTTLYNAAQIICANYGKAFSVDKK (SEQ ID NO. 37) |
| N91 | MKKIILTLSLGLLTACSAQTQKVEQNDVKLTAPADVRSGYVRLVKNVNYYIDSESIWVDNQEPQ<br>IVHFDAVVNLDKGLYVYPEPKRYARSVRQYKILNCANYHLTQVRTDFYDEFWGQGLRAAPKKQK<br>KHTLSLTPDTTLYNAAQIICANYGKAFSVDKK (SEQ ID NO. 38) |
| D211PG | MKKIILTLSLGLLTACSAQIQKAKQNDVKLAPPTDVRSGYIRLVKNVNYYIDSESIWVDNQEPQ<br>IVHFDAVVNLDKGLYVYPEPKRYARSVR-YKILNCANYHLTQVRTDFYDEFWGQGLRAAPKKQK<br>KHTLSLTPDTTLYNAAQIICANYGEAFSVDKK (SEQ ID NO. 39) |
| D211PD | MKKIILTLSLGLLTACSAQIQKAKQNDVKLAPPTDVRSGYIRLVKNVNYYIDSESIWVDNQEPQ<br>IVHFDAVVNLDKGLYVYPEPKRYARSVR-YKILNCANYHLTQVRTDFYDEFWGQGLRAAPKKQK<br>KHTLSLTPDTTLYNAAQIICANYGEAFSVDKK (SEQ ID NO. 40) |
| D201PG | MKKIILTLSLGLLTACSAQIQKAEQNDVKLAPPTDVRSGYIRLVKNVNYYIDSESIWVDNQEPQ<br>IVHFDAVVNLDKGLYVYPEPKRYARSVRQYKILNCANYHLTQVRTDFYDEFWGQGLRAAPKKQK<br>KHTLSLTPDTTLYNAAQIICANYGKAFSVDKK (SEQ ID NO. 41) |
| D201PD | MKKIILTLSLGLLTACSAQIQKAEQNDVKLAPPTDVRSGYIRLVKNVNYYIDSESIWVDNQEPQ<br>IVHFDAVVNLDKGLYVYPEPKRYARSVRQYKILNCANYHLTQVRTDFYDEFWGQGLRAAPKKQK<br>KHTLSLTPDTTLYNAAQIICANYGKAFSVDKK (SEQ ID NO. 42) |
| D198PG | MKKIILTLSLGLLTACSAQIQKAEQNDVKLAPPTDVRSGYIRLVKNVNYYIDSESIWVDNQEPQ<br>IVHFDAVVNLDKGLYVYPEPKRYARSVRQYKILNCANYHLTQVRTDFYDEFWGQGLRAAPKKQK<br>KHTLSLTPDTTLYNAAQIICANYGKAFSVDKK (SEQ ID NO. 43) |
| D198PD | MKKIILTLSLGLLTACSAQIQKAEQNDVKLAPPTDVRSGYIRLVKNVNYYIDSESIWVDNQEPQ<br>IVHFDAVVNLDKGLYVYPEPKRYARSVRQYKILNCANYHLTQVRTDFYDEFWGQGLRAAPKKQK<br>KHTLSLTPDTTLYNAAQIICANYGKAFSVDKK (SEQ ID NO. 44) |
| D195PD | MKKIILTLSLGLLTACSAQIQKAEQNDVKLAPPTDVRSGYIRLVKNVNYYIDSESIWVDNQEPQ<br>IVHFDTVVNLDKGLYVYPEPKRYARSVRQYKILNCANYHLTQVRTDFYDEFWGQSLRAAPKKQK<br>KHTLSLTPDTTLYNAAQIICANYGKAFSVDKK (SEQ ID NO. 45) |
| D189PG | MKKIILTLSLGLLTACSAQTQKVEQNDVKLTPPTDVRSGYVRLVKNVNYYIDSESIWVDNQEPQ<br>IVHFDAVVNLDKGLYVYPEPKRYARSVRQYKILNCANYHLTQVRTDFYDEFWGQGLRAAPKKQK<br>KHTLSLTPDTTVYNAAQIICANYGKAFSVDKK (SEQ ID NO. 46) |
| D189PD | MKKIILTLSLGLLTACSAQTQKVEQNDVKLTPPTDVRSGYVRLVKNVNYYIDSESIWVDNQEPQ<br>IVHFDAVVNLDKGLYVYPEPKRYARSVRQYKILNCANYHLTQVRTDFYDEFWGQGLRAAPKKQK<br>KHTLSLTPDTTVYNAAQIICANYGKAFSVDKK (SEQ ID NO. 47) |
| D129CG | MKKIILTLSLGLLTACSAQIQKAKQNDVKLAPPTDVRSGYIRLVKNVNYYIDSESIWVDNQEPQ<br>IVHFDAVVNLDKGLYVYPEPKRYARSVRQYKILNCANYHLTQVRTDFYDEFWGQGLRAAPKKQK<br>KHTLSLTPDTTLYNAAQIICANYGEAFSVDKK (SEQ ID NO. 48) |
| D124PG | MKKIILTLSLGLLTACSAQIQKAEQNDVKLAPPTDVRSGYIRLVKNVNYYIDSESIWVDNQEPQ<br>IVHFDTVVNLDKGLYVYPEPKRYARSVRQYKILNCANYHLTQVRTDFYDEFWGQGLRAAPKKQK<br>KHTLSLTPDTTLYNAAQIICANYGKAFSVDKK (SEQ ID NO. 49) |
| D124PD | MKKIILTLSLGLLTACSAQIQKAEQNDVKLAPPTDVRSGYIRLVKNVNYYIDSESIWVDNQEPQ<br>IVHFDTVVNLDKGLYVYPEPKRYARSVRQYKILNCANYHLTQVRTDFYDEFWGQGLRAAPKKQK<br>KHTLSLTPDTTLYNAAQIICANYGKAFSVDKK(SEQ ID NO. 50) |
| D58PG | MKKIILTLSLGLLTACSAQTQKAEQNDVKLTPPTDVRSGYIRLVKNVNYYIDSESIWVDNQEPQ<br>IVHFDAVVNLDKGLYVYPEPKRYARSVRQYKILNCANYHLTQVRTDFYDEFWGQGLRAAPKKQK<br>KHTLSLTPDTTLYNAAQIICANYGKAFSVDKK (SEQ ID NO. 51) |

TABLE 1-continued

Protein E amino acid sequences from 53 strains of *Haemophilus influenzae* (SEQ ID NO. 5-SEQ ID NO. 57). - indicates amino acid is absent.

| Strain Name | Protein E sequence |
|---|---|
| D330D | MKKIILTLSLGLLTACSAQIQKAKQNDVKLAPPTDVRSGYIRLVKNVNYYIDSESIWVDNQEPQ IVHFDAVVNLDKGLYVYPEPKRYARSVRQYKILNCANYHLTQVRTDFYDEFWGQGLRAAPKKQK KHTLSLTPDTTLYNAAQIICANYGKAFSVDKK (SEQ ID NO. 52) |
| BS433 | MKKIILTLSLGLLTACSAQIQKAEQNDVKLAPPTDVRSGYIRLVKNVNYYIDSESIWVDNQEPQ IVHFDTVVNLDKGLYVYPEPKRYARSVRQYKILNCANYHLTQVRTDFYDEFWGQGLRAAPKKQK KHTLSLTPDTTLYNAAQIICANYGKAFSVDKK (SEQ ID NO. 53) |
| BS432 | MKKIILTLSLGLLTACSAQTQKAEQNDVKLAPPTDVRSGYIRLVKNVNYYIDSESIWVDNQEPQ IVHFDAVVNLDKGLYVYPEPKRYARSVRQYKILNCANYHLTQIRTDFYDEFWGQGLRAAPKKQK KHTLSLTPDTTLYNAAQIICANYGKAFSVDKK (SEQ ID NO. 54) |
| 1714 | MKKIILTLSLGLLTACSAQIQKAKQNDVKLAPPTDVRSGYIRLVKNVNYYIDSESIWVDNQEPQ IVHFDAVVNLDKGLYVYPEPKRYARSVRQYKILNCANYHLTQVRTDFYDEFWGQGLRAAPKKQK KHTLSLTPDTTLYNAAQIICANYGEAFSVDKK (SEQ ID NO. 55) |
| 1128 | MKKIILTLSLGLLTACSAQIQKAEQNDVKLAPPTDVRSGYIRLVKNVNYYIDSESIWVDNQEPQ IVHFDAVVNLDKGLYVYPEPKRYARSVRQYKILNCANYHLTQVRTDFYDEFWGQGLRAAPKKQK KHTLSLTPDTTLYNAAQIICANYGKAFSVDKK (SEQ ID NO. 56) |
| BS430 | MKKIILTLSLGLLTACSAQIQKAEQNDMKLAPPTDVRSGYIRLVKNVNYYIDSESI-VDNQEPQ IVHFDAVVNLDKGLYVYPEPKRYARSVRQYKILNCANYHLTQVRTDFYDEFWGQGLRAAPKKQK KHTLSLTPDTTLYNAAQIICANYGKAFSVDKK (SEQ ID NO. 57) |

Protein E may be Protein E from *H. influenzae* strain 3224A, RdKW20, 86-028NP, R2846, R2866, 3655, PittAA, PittEE, PittHH, PittII, R3021, 22.4-21, 3219C, 3185, 3241A, 038144S1, 810956, 821246, 840645, 902550Z19, A840177, A860514, A950014, 306543X4, A930105, 901905U, A920030, 3221B, 27W116791N, N218, N163, N162, N107, N91, D211PG, D211PD, D201PG, D201PD, D198PG, D198PD, D195PD, D189PG, D189PD, D129CG, D124PG, D124PD, D58PG, D330D, BS433, BS432, 1714, 1128 or BS430. Protein E may be Protein E as set forth in any of SEQ ID NO. 5-SEQ ID NO. 57.

Protein E may be a sequence with at least 95% identity, over the entire length, to any of SEQ ID NO. 4-SEQ ID NO. 57. Protein E may be a sequence with at least 95% identity, over the entire length, to any of the sequences set forth in Table 1, SEQ ID NO. 5-SEQ ID NO. 57.

Immunogenic fragments of Protein E comprise immunogenic fragments of at least 7, 10, 15, 20, 25, 30 or 50 contiguous amino acids of SEQ ID NO. 4. The immunogenic fragments may elicit antibodies which can bind SEQ ID NO. 4.

Immunogenic fragments of Protein E may comprise immunogenic fragments of at least 7, 10, 15, 20, 25, 30 or 50 contiguous amino acids of any of SEQ ID NO. 4-SEQ ID NO. 57. The immunogenic fragments may elicit antibodies which can bind the full length sequence from which the fragment is derived.

Immunogenic fragments of Protein E comprise immunogenic fragments of at least 7, 10, 15, 20, 25, 30 or 50 contiguous amino acids of SEQ ID NO. 5-SEQ ID NO. 57. The immunogenic fragments may elicit antibodies which can bind the full length sequence from which the fragment is derived.

As used herein "PilA" means Pilin A from *H. influenzae*. PilA may consist of or comprise the protein sequence of SEQ ID NO. 58 (MKLTTQQTLK KGFTLIELMI VIAIIAILAT IAIPSYQNYT KKAAVSELLQ ASAPYKADVE LCVYST- NETT NCTGGKNGIA ADITTAKGYV KSVTTSNGAI TVKGDGTLAN MEYILQATGN AATGVTWTTT CKGT- DASLFP ANFCGSVTQ) as well as sequences with 80% to 100% identity to SEQ ID NO. 58. For example, PilA may be at least 80%, 85%, 90%, 95%, 97% or 100% identical to SEQ ID NO. 58. Full length comparison of 64 sequences of PilA from *Haemophilus influenzae* (Table 2, SEQ ID NO. 58-SEQ ID NO. 121) demonstrated approximately 80% to 100% identity to PilA as set forth in SEQ ID NO. 58. For example, in the amino acid sequence of PilA, amino acid #6 may be glutamine (Q) or leucine (L); amino acid #7 may be glutamine (Q) or threonine (T); amino acid #37 may be glutamine (Q) or lysine (K); amino acid #44 may be alanine (A) or serine (S); amino acid #57 may be alanine (A) or serine (S); amino acid #67 may be asparagine (N) or glycine (G); amino acid #68 may be glutamic acid (E) or lysine (K); amino acid #69 may be threonine (T) or proline (P); amino acid #71 may be lysine (K), asparagine (N), serine (S) or threonine (T); amino acid #73 may be threonine (T), serine (S) or methionine (M); amino acid #76 may be lysine (K), serine (S) or asparagine (N); amino acid #84 may be threonine (T) or lysine (K); amino acid #86 may be alanine (A) or valine (V); amino acid #91 may be lysine (K) or alanine (A); amino acid #94 may be threonine (T), isoleucine (I) or lysine (K); amino acid #96 may be serine (S) or glutamine (Q); amino acid #97 may be asparagine (N) or serine (S); amino acid #99 may be alanine (A) or glycine (G); amino acid #103 may be alanine (A) or lysine (K); amino acid #109 may be aspartic acid (D), alanine (A) or threonine (T); amino acid #110 may be glycine (G), asparagine (N), or arginine (R); amino acid #112 may be serine (S) or glutamic acid (E); amino acid #114 may be threonine (T) or isoleucine (I); amino acid #116 may be threonine (T) or glutamine (Q); amino acid #118 may be glutamic acid (E), threonine (T), alanine (A), lysine (K) or serine (S); amino acid #121 may be serine (S) or alanine (A); amino acid #122 may be alanine (A) or threonine (T); amino acid #123 may be lysine (K), threonine (T) or alanine (A); amino acid #128 may be lysine (K) or threonine (T); amino acid #135 may be aspartic acid (D) or glutamic acid (E); amino acid #136 may be alanine (A) or threonine (T); amino acid #145 may be glycine (G) or arginine (R); amino acid #149 may be glutamine (Q) or lysine (K); or any combination thereof.

Pil A may consist of or comprise an amino acid sequence that differs from SEQ ID NO. 58 at any or more amino acid selected from the group consisting of amino acid #6, amino acid #7, amino acid #37, amino acid #44, amino acid #57, amino acid #67, amino acid #68, amino acid #69, amino acid #71, amino acid #73, amino acid #76, amino acid #84, amino acid #86, amino acid #91, amino acid #94, amino acid #96, amino acid #97, amino acid #99, amino acid #103, amino acid #109, amino acid #110, amino acid #112, amino acid #114, amino acid #116, amino acid #118 amino acid, #121, amino acid #122, amino acid #123, amino acid #128, amino acid #135, amino acid #136, amino acid #145 and amino acid #149, wherein amino acid #6 is leucine (L); amino acid #7 is threonine (T); amino acid #37 is lysine (K); amino acid #44 is serine (S); amino acid #57 is serine (S); amino acid #67 is glycine (G); amino acid #68 is lysine (K); amino acid #69 is proline (P); amino acid #71 is lysine (K), serine (S) or threonine (T); amino acid #73 is serine (S) or methionine (M); amino acid #76 is serine (S) or asparagine (N); amino acid #84 is lysine (K); amino acid #86 is valine (V); amino acid #91 is alanine (A); amino acid #94 is isoleucine (I) or lysine (K); amino acid #96 is glutamine (O); amino acid #97 is serine (S); amino acid #99 is glycine (G); amino acid #103 is alanine (A); amino acid #109 is aspartic acid (D) or threonine (T); amino acid #110 is glycine (G) or arginine (R); amino acid #112 is serine (S); amino acid #114 is threonine (T); amino acid #116 is threonine (T); amino acid #118 is glutamic acid (E), alanine (A), lysine (K) or serine (S); amino acid #121 is serine (S); amino acid #122 is threonine (T); amino acid #123 is lysine (K) or alanine (A); amino acid #128 is lysine (K); amino acid #135 is glutamic acid (E); amino acid #136 is threonine (T); amino acid #145 is arginine (R); amino acid #149 is lysine (K).

TABLE 2

Pilin A amino acid sequences from 64 strains of *Haemophilus influenzae* (SEQ ID NO. 58 - SEQ ID NO. 121).

| Strain Name | PilA sequence |
|---|---|
| 86-028NP | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 58) |
| NTHi3219C | MKLTTQQTLKKGFTLIELMIVIAIIAILATIAIPSYQNYTKKAAVSELLQASAPYKADVELCVY STNETTKCTGGKNGIAADITTAKGYVKSVTTSNGAITVAGNGTLDGMSYTLTAEGDSAKGVTWK TTCKGTDASLFPANFCGSVTQ (SEQ ID NO. 59) |
| NTHi3224A | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 60) |
| NTHi12 | MKLTTQQTLKKGFTLIELMIVIAIIAILATIAIPSYKNYTKKAAVSELLQASAPYKADVELCVY STGKPSSCSGGSNGIAADITTAKGYVASVITQSGGITVKGDGTLANMEYILQAAGNAAAGVTWT TTCKGTDASLFPANFCGSVTQ (SEQ ID NO. 61) |
| NTHi44 | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 62) |
| NTHi67 | MKLTTQQTLKKGFTLIELMIVIAIIAILATIAIPSYQNYTKKAAVSELLQASAPYKSDVELCVY STGKPSTCSGGSNGIAADITTVKGYVKSVTTSNGAITVAGNGTLDGMSYTLTAEGDSAKGVTWT TTCKGTDASLFPANFCGSVTQ (SEQ ID NO. 63) |
| 1054MEE | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 64) |
| 1729MEE | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 65) |
| 1728MEE | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 66) |
| 1885MEE | MKLTTQQTLKKGFTLIELMIVIAIIAILATIAIPSYKNYTKKAAVSELLQASAPYKADVELCVY STNEITNCMGGKNGIAADITTAKGYVASVKTQSGGITVKGDGTLANMEYILQATGNAAAGVTWT TTCKGTDASLFPANFCGSITQ (SEQ ID NO. 67) |
| 1060MEE | MKLTTQQTLKKGFTLIELMIVIAIIAILATIAIPSYQNYTKKASVSELLQASAPYKADVELCVY STNETTNCTGGKNGIAADITTAKGYVASVKTQSGGITVKGNGTLANMEYILQAKGNATAGVTWT TTCKGTDASLFPANFCRSVTK (SEQ ID NO. 68) |
| RdKW20 | MKLTTLQTLKKGFTLIELMIVIAIIAILATIAIPSYQNYTKKAAVSELLQASAPYKADVELCVY STNETTSCTGGKNGIAADIKTAKGYVASVITQSGGITVKGNGTLANMEYILQAKGNAAAGVTWT TTCKGTDASLFPANFCGSVTK (SEQ ID NO. 69) |
| 214NP | MKLTTQQTLKKGFTLIELMIVIAIIAILATIAIPSYQNYTKKAAVSELLQASAPYKADVELCVY STGKPSSCSGGSNGIAADITTAKGYVKSVTTSNGAITVKGDGTLANMEYILQASGNAATGVTWT TTCKGTDASLFPANFCGSVTQ (SEQ ID NO. 70) |

TABLE 2-continued

Pilin A amino acid sequences from 64 strains of Haemophilus influenzae
(SEQ ID NO. 58 - SEQ ID NO. 121).

| Strain Name | PilA sequence |
|---|---|
| 1236MEE | MKLTTLQTLKKGFTLIELMIVIAIIAILATIAIPSYQNYTKKAAVSELLQASAPYKADVELCVY STNETTSCTGGKNGIAADIKTAKGYVASVITQSGGITVKGNGTLANMEYILQAKGNAAAGVTWT TTCKGTDASLFPANFCGSVTK (SEQ ID NO. 71) |
| 1714MEE | MKLTTLQTLKKGFTLIELMIVIAIIAILATIAIPSYQNYTKKAAVSELLQASAPYKADVELCVY STGKPSTCSGGSNGIAADITTAKGYVASVKTQSGGITVKGNGTLANMEYILQATGNAATGVTWT TTCKGTDASLFPANFCGSVTQ (SEQ ID NO. 72) |
| 1128MEE | MKLTTQQTLKKGFTLIELMIVIAIIAILATIAIPSYQNYTKKASVSELLQASAPYKSDVELCVY STGKPSTCSGGSNGIAADITTAKGYVASVKTQSGGITVKGNGTLANMEYILQAKGNATAGVTWT TTCKGTDASLFPANFCRSVTK (SEQ ID NO. 73) |
| R2846 | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 74) |
| R2866 | MKLTTQQTLKKGFTLIELMIVIAIIAILATIAIPSYQNYTKKAAVSELLQASAPYKADVELCVY STNETTNCTGGKNGIAADITTAKGYVASVKTQSGGITVKGDGTLANMEYILQATGNAATGVTWT TTCKGTEASLFPANFCGSVTQ (SEQ ID NO. 75) |
| 3655 | MKLTTQQTLKKGFTLIELMIVIAIIAILATIAIPSYQNYTKKASVSELLQASAPYKADVELCVY STNETTNCTGGKNGIAADITTAKGYVASVKTQSGGITVKGNGTLANMEYILQAKGNATAGVTWT TTCKGTDASLFPANFCRSVTK (SEQ ID NO. 76) |
| PittAA | MKLTTLQTLKKGFTLIELMIVIAIIAILATIAIPSYQNYTKKAAVSELLQASAPYKADVELCVY STGKPSTCSGGSNGIAADITTAKGYVASVKTQSGGITVKGNGTLANMEYILQATGNAATGVTWT TTCKGTDASLFPANFCGSVTQ (SEQ ID NO. 77) |
| PittGG | MKLTTQQTLKKGFTLIELMIVIAIIAILATIAIPSYQNYTKKAAVSELLQASAPYKADVELCVY STGKPSTCSGGSNGIAADITTAKGYVASVKTQSGGITVKGNGTLANMEYILQAKGNATAGVTWT TTCKGTDASLFPANFCRSVTK (SEQ ID NO. 78) |
| PittII | MKLTTQQTLKKGFTLIELMIVIAIIAILATIAIPSYQNYTKKAAVSELLQASAPYKADVELCVY STNETTNCTGGKNGIAADITTAKGYVASVKTQSGGITVKGDGTLANMEYILQATGNAATGVTWT TTCKGTEASLFPANFCGSVTQ (SEQ ID NO. 79) |
| 3021 | MKLTTQQTLKKGFTLIELMIVIAIIAILATIAIPSYQNYTKKAAVSELLQASAPYKADVELCVY STNETTNCTGGKNGIAADITTAKGYVASVKTQSGGITVKGDGTLANMEYILQATGNAATGVTWT TTCKGTEASLFPANFCGSVTQ (SEQ ID NO. 80) |
| 22.4-21 | MKLTTQQTLKKGFTLIELMIVIAIIAILATIAIPSYQNYTKKAAVSELLQASAPYKSDVELCVY STGKPSTCSGGSNGIAADITTAKGYVKSVTTSNGAITVAGNGTLDGMSYTLTAEGDSAKGVTWK TTCKGTDASLFPANFCGSVTK (SEQ ID NO. 81) |
| 3185A | MKLTTQQTLKKGFTLIELMIVIAIIAILATIAIPSYQNYTKKAAVSELLQASAPYKADVELCVY STNEATKCTGGKNGIAADITTAKGYVKSVTTSNGAITVKGDGTLANMEYILQASGNAATGVTWT TTCKGTDASLFPANFCGSVTQ (SEQ ID NO. 82) |
| 3221B | MKLTTQQTLKKGFTLIELMIVIAIIAILATIAIPSYQNYTKKAAVSELLQASAPYKADVELCVY STNEATKCTGGKNGIAADITTAKGYVKSVTTSNGAITVKGDGTLANMEYILQASGNAATGVTWT TTCKGTDASLFPANFCGSVTQ (SEQ ID NO. 83) |
| 3241A | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 84) |
| 038144S1 | MKLTTQQTLKKGFTLIELMIVIAIIAILATIAIPSYQNYTKKAAISELLQASAPYKSDVELCVY STGKPSTCSGGSNGIAADITTAKGYVASVKTQSGGITVKGNGTLANMEYILQAKGNATAGVTWT TTCKGTDASLFPANFCRSVTK (SEQ ID NO. 85) |
| 821246 | MKLTTQQTLKKGFTLIELMIVIAIIAILATIAIPSYQNYTKKAAVSELLQASAPYKADVELCVY STNETTNCTGGKNGIAADITTAKGYVASVKTQSGGITVKGNGTLANMEYILQATGNAATGVTWT TTCKGTEASLFPANFCGSVTQ (SEQ ID NO. 86) |
| 840645 | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 87) |
| 902550Z19 | MKLTTQQTLKKGFTLIELMIVIAIIAILATIAIPSYQNYTKKAAVSELLQASAPYKSDVELCVY STGKPSTCSGGSNGIAADITTVKGYVKSVTTSNGAITVAGNGTLDGMSYTLTAEGDSAKGVTWT TTCKGTDASLFPANFCGSVTQ (SEQ ID NO. 88) |
| A840177 | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 89) |

TABLE 2-continued

Pilin A amino acid sequences from 64 strains of *Haemophilus influenzae* (SEQ ID NO. 58 - SEQ ID NO. 121).

| Strain Name | PilA sequence |
|---|---|
| A920030 | MKLTTQQTLKKGFTLIELMIVIAIIAILATIAIPSYQNYTKKAAVSELLQASAPYKADVELCVY STNETTNCTGGKNGIAADITTAKGYVASVKTQSGGITVKGNGTLANMEYILQATGNAATGVTWT TTCKGTDASLFPANFCGSVTQ (SEQ ID NO. 90) |
| A950014 | MKLTTQQTLKKGFTLIELMIVIAIIAILATIAIPSYQNYTKKAAVSELLQASAPYKADVELCVY STGKPSTCSGGSNGIAADITTAKGYVKSVTTSNGAITVAGNGTLDRMSYTLTAEGDSAKGVTWT TTCKGTDASLFPANFCGSVTQ (SEQ ID NO. 91) |
| 901905U | MKLTTQQTLKKGFTLIELMIVIAIIAILATIAIPSYQNYTKKAAVSELLQASAPYKADVELCVY STGKPSSCSGGSNGIAADITTAKGYVKSVTTSNGAITVKGDGTLANMEYILQASGNAATGVTWT TTCKGTDASLFPANFCGSVTQ (SEQ ID NO. 92) |
| A920029 | MKLTTQTTLKKGFTLIELMIVIAIIAILATIAIPSYQNYTKKAAVSELLQASAPYKSDVELCVY STNETTNCTGGKNGIAADITTAKGYVASVITQSGGITVKGNGTLTNMEYILQATGNAATGVTWT TTCKGTDASLFPANFCGSITQ (SEQ ID NO. 93) |
| A930105 | MKLTTLQTLKKGFTLIELMIVIAIIAILATIAIPSYQNYTKKAAVSELLQASAPYKADVELCVY STGKPSTCSGGNNGIAADIKTAKGYVASVKTQSGGITVKGDGTLANMEYILQATGNAATGVTWT TTCKGTDASLFPANFCGSVTQ (SEQ ID NO. 94) |
| 306543X4 | MKLTTQQTLKKGFTLIELMIVIAIIAILATIAIPSYQNYTKKAAVSELLQASAPYKADVELCVY STGKPSSCSGGSNGIAADITTAKGYVKSVTTSNGAITVKGDGTLANMEYILQASGNAATGVTWT TTCKGTDASLFPANFCGSVTQ (SEQ ID NO. 95) |
| N218 | MKLTTQQTLKKGFTLIELMIVIAIIAILATIAIPSYQNYTKKAAVSELLQASAPYKADVELCVY STNEATKCTGGKNGIAADITTAKGYVKSVTTSNGAITVKGDGTLANMEYILQASGNAATGVTWT TTCKGTDTSLFPANFCGSVTQ (SEQ ID NO. 96) |
| N163 | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQASGNAATGVTWT TTCKGTDASLFPANFCGSVTQ (SEQ ID NO. 97) |
| N162 | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGNGTLANMEYILQATGNAATGVTWT TTCKGTDASLFPANFCGSVTQ (SEQ ID NO. 98) |
| N120 | MKLTTQQTLKKGFTLIELMIVIAIIAILATIAIPSYQNYTKKAAVSELLQASAPYKADVELCVY STGKPSTCSGGSNGIAADITTAKGYVASVKTQSGGITVKGNGTLANMEYILQAKGNATAGVTWT TTCKGTDASLFPANFCRSVTK (SEQ ID NO. 99) |
| N107 | MKLTTQQTLKKGFTLIELMIVIAIIAILATIAIPSYQNYTKKAAVSELLQASAPYKADVELCVY STGKPSTCSGGSNGIAADITTAKGYVASVKTQSGGITVKGNGTLANMEYILQAKGNATAGVTWT TTCKGTDASLFPANFCRSVTK (SEQ ID NO. 100) |
| N92 | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 101) |
| N91 | MKLTTQQTLKKGFTLIELMIVIAIIAILATIAIPSYQNYTKKAAVSELLQASAPYKADVELCVY STGKPSTCSGGSNGIAADITTAKGYVASVKTQSGGITVKGNGTLANMEYILQAKGNATAGVTWT TTCKGTDASLFPANFCRSVTK (SEQ ID NO. 102) |
| D219PG | MKLTTQQTLKKGFTLIELMIVIAIIAILATIAIPSYQNYTKKAAVSELLQASAPYKADVELCVY STNEATKCTGGKNGIAADITTAKGYVKSVTTSNGAITVKGDGTLANMEYILQASGNAATGVTWT TTCKGTDASLFPANFCGSVTQ (SEQ ID NO. 103) |
| D211PG | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 104) |
| D211PD | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 105) |
| D204CD | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILXATGNAATGVTWT TTCKGTDASLFPANFCGSVTQ (SEQ ID NO. 106) |
| D198PG | MKLTTQQTLKKGFTLIELMIVIAIIAILATIAIPSYQNYTKKAAVSELLQASAPYKADVELCVY STNETTNCTGGKNGIAADITTAKGYVKSVTTSNGAITVKGDGTLANMEYILQATGNAATGVTWT TTCKGTDASLFPANFCGSVTQ (SEQ ID NO. 107) |

TABLE 2-continued

Pilin A amino acid sequences from 64 strains of Haemophilus influenzae
(SEQ ID NO. 58 - SEQ ID NO. 121).

| Strain Name | PilA sequence |
|---|---|
| D198PD | MKLTTQQTLKKGFTLIELMIVIAIIAILATIAIPSYQNYTKKAAVSELLQASAPYKADVELCVY<br>STNETTNCTGGKNGIAADITTAKGYVKSVTTSNGAITVKGDGTLANMEYILQATGNAATGVTWT<br>TTCKGTDASLFPANFCGSVTQ (SEQ ID NO. 108) |
| D195PD | MKLTTLQTLKKGFTLIELMIVIAIIAILATIAIPSYQNYTKKAAVSELLQASAPYKADVELCVY<br>STGKPSTCSGGNNGIAADIKTAKGYVASVKTQSGGITVKGDGTLANMEYILQATGNAATGVTWT<br>TTCKGTDASLFPANFCGSVTQ (SEQ ID NO. 109) |
| D195CD | MKLTTLQTLKKGFTLIELMIVIAIIAILATIAIPSYQNYTKKAAVSELLQASAPYKADVELCVY<br>STGKPSTCSGGNNGIAADIKTAKGYVASVKTQSGGITVKGDGTLANMEYILQATGNAATGVTWT<br>TTCKGTDASLFPANFCGSVTQ (SEQ ID NO. 110) |
| D189PG | MKLTTQQTLKKGFTLIELMIVIAIIAILATIAIPSYQNYTKKAAVSELLQASAPYKADVELCVY<br>STNETTSCTGGKNGIAADITTAKGYVKSVTTSNGAITVAGNGTLDGMSYTLTAEGDSAKGVTWK<br>TTCKGTDASLFPANFCGSVTQ (SEQ ID NO. 111) |
| D189PD | MKLTTQQTLKKGFTLIELMIVIAIIAILATIAIPSYQNYTKKAAVSELLQASAPYKADVELCVY<br>STNETTSCTGGKNGIAADITTAKGYVKSVTTSNGAITVAGNGTLDGMSYTLTAEGDSAKGVTWK<br>TTCKGTDASLFPANFCGSVTQ (SEQ ID NO. 112) |
| D124PG | MKLTTLQTLKKGFTLIELMIVIAIIAILATIAIPSYQNYTKKAAVSELLQASAPYKADVELCVY<br>STGKPSTCSGGNNGIAADIKTAKGYVASVKTQSGGITVKGDGTLANMEYILQATGNAATGVTWT<br>TTCKGTDASLFPANFCGSVTQ (SEQ ID NO. 113) |
| D124PD | MKLTTLQTLKKGFTLIELMIVIAIIAILATIAIPSYQNYTKKAAVSELLQASAPYKADVELCVY<br>STGKPSTCSGGNNGIAADIKTAKGYVASVKTQSGGITVKGDGTLANMEYILQATGNAATGVTWT<br>TTCKGTDASLFPANFCGSVTQ (SEQ ID NO. 114) |
| D124CG | MKLTTLQTLKKGFTLIELMIVIAIIAILATIAIPSYQNYTKKAAVSELLQASAPYKADVELCVY<br>STGKPSTCSGGNNGIAADIKTAKGYVASVKTQSGGITVKGDGTLANMEYILQATGNAATGVTWT<br>TTCKGTDASLFPANFCGSVTQ (SEQ ID NO. 115) |
| D58PG | MKLTTQQTLKKGFTLIELMIVIAIIAILATIAIPSYQNYTKKAAVSELLQASAPYKADVELCVY<br>STNETTNCTGGKNGIAADITTAKGYVASVKTQSGGITVKGDGTLANMEYILQATGNAATGVTWT<br>TTCKGTEASLFPANFCGSVTQ (SEQ ID NO. 116) |
| BS433 | MKLTTLQTLKKGFTLIELMIVIAIIAILATIAIPSYQNYTKKAAVSELLQASAPYKADVELCVY<br>STGKPSTCSGGNNGIAADIKTAKGYVASVKTQSGGITVKGDGTLANMEYILQATGNAATGVTWT<br>TTCKGTDASLFPANFCGSVTQ (SEQ ID NO. 117) |
| BS432 | MKLTTQQTLKKGFTLIELMIVIAIIAILATIAIPSYQNYTKKAAVSELLQASAPYKADVELCVY<br>STGKPSTCSGGSNGIAADITTAKGYVASVKTQSGGITVKGNGTLANMEYILQAKGNATAGVTWT<br>TTCKGTDASLFPANFCRSVTK (SEQ ID NO. 118) |
| BS430 | MKLTTQQTLKKGFTLIELMIVIAIIAILATIAIPSYQNYTKKAAVSELLQASAPYKADVELCVY<br>STNEATKCTGGKNGIAADITTAKGYVKSVTTSNGAITVKGDGTLANMEYILQASGNAATGVTWT<br>TTCKGTDASLFPANFCGSVTQ (SEQ ID NO. 119) |
| 1714 | MKLTTLQTLKKGFTLIELMIVIAIIAILATIAIPSYQNYTKKAAVSELLQASAPYKADVELCVY<br>STGKPSTCSGGSNGIAADITTAKGYVASVKTQSGGITVKGNGTLANMEYILQATGNAATGVTWT<br>TTCKGTDASLFPANFCGSVTQ (SEQ ID NO. 120) |
| 1128 | MKLTTQQTLKKGFTLIELMIVIAIIAILATIAIPSYQNYTKKASVSELLQASAPYKSDVELCVY<br>STGKPSTCSGGSNGIAADITTAKGYVASVKTQSGGITVKGNGTLANMEYILQAKGNATAGVTWT<br>TTCKGTDASLFPANFCRSVTK (SEQ ID NO. 121) |

PilA may be PilA from *H. influenzae* strain NTHi3219C, NTHi3224A, NTHi12, NTHi44, NTHi67, 1054MEE, 1729MEE, 1728MEE, 1885MEE, 1060MEE, RdKW20, 214NP, 1236MEE, 1714MEE, 1128MEE, 86-028NP, R2846, R2866, 3655, PittAA, PittGG, PittII, R3021, 22.4-21, 3185A, 3221B, 3241A, 038144S1, 821246, 840645, 902550Z19, A840177, A920030, A950014, 901905U, A920029, A930105, 306543X4, N218, N163, N162, N120, N107, N92, N91, D219PG, D211PG, D211PD, D204CD, D198PG, D198PD, D195PD, D195CD, D189PG, D189PD, D124PG, D124PD, D124CG, D58PG, BS433, BS432, BS430, 1714 or 1128. An amino acid sequence for PilA from *H. influenzae* strain D204CD is set forth in SEQ ID NO. 106, wherein X at position #116 is either glutamine (Q) or leucine (L); ambiguity as to the amino acid at position #116 could be cleared up by technical resolution of the second nucleotide encoding amino acid #116, clarifying the PilA sequence for strain D204CD. PilA may be PilA as set forth in any of SEQ ID NO. 58-SEQ ID NO. 121.

PilA may be a sequence with at least 95% identity, over the entire length, to any of SEQ ID NO. 58-SEQ ID NO. 121 (as set out in Table 2).

Immunogenic fragments of PilA comprise immunogenic fragments of at least 7, 10, 15, 20, 25, 30 or 50 contiguous amino acids of SEQ ID NO. 58-SEQ ID NO. 121. The immunogenic fragments may elicit antibodies which can bind the full length sequence from which the fragment is derived.

For example, immunogenic fragments of PilA comprise immunogenic fragments of at least 7, 10, 15, 20, 25, 30 or 50 contiguous amino acids of SEQ ID NO. 58. The immunogenic fragments may elicit antibodies which can bind SEQ ID NO. 58.

Identity between polypeptides may be calculated by various algorithms. For example, the Needle program, from the EMBOSS package (Free software; EMBOSS: The European Molecular Biology Open Software Suite (2000). Trends in Genetics 16(6): 276-277) and the Gap program from the GCG® package (Accelrys Inc.) may be used. This Gap program is an implementation of the Needleman-Wunsch algorithm described in: Needleman, S. B. and Wunsch, C. D. (1970) J. Mol. Biol. 48, 443-453. The BLOSUM62 scoring matrix has been used, and the gap open and extension penalties were respectively 8 and 2.

Looking at the computed alignment, identical residues between two compared sequences can be observed. A percentage of identity can be computed by (1) calculating the number of identities divided by the length of the alignment, multiplied by 100 (for example, for the Needle program analysis), (2) calculating the number of identities divided by the length of the longest sequence, multiplied by 100, (3) calculating the number of identities divided by the length of the shortest sequence, multiplied by 100, or (4) calculating the number of identities divided by the number of aligned residues, multiplied by 100 (a residue is aligned if it is in front of another) (for example, for the Gap program analysis).

As used herein, "adjuvant" means a compound or substance that, when administered to a subject in conjunction with a vaccine, immunotherapeutic, or other antigen- or immunogen-containing composition, increases or enhances the subject's immune response to the administered antigen or immunogen (as compared to the immune response that would be obtained in the absence of adjuvant). This is to be distinguished from "adjuvant therapy", defined by the National Cancer Institute of the United States Institutes of Health in the context of cancer treatment as additional treatment given after the primary treatment, to lower the risk that the cancer will recur.

Conservative substitutions are well known and are generally set up as the default scoring matrices in sequence alignment computer programs. These programs include PAM250 (Dayhoft M. O. et al., (1978), "A model of evolutionary changes in proteins", In "Atlas of Protein sequence and structure" 5(3) M. O. Dayhoft (ed.), 345-352), National Biomedical Research Foundation, Washington, and Blosum 62 (Steven Henikoft and Jorja G. Henikoft (1992), "Amino acid substitution matrices from protein blocks"), *Proc. Natl. Acad. Sci. USA* 89 (Biochemistry): 10915-10919. The invention further provides fusion proteins of formula (I) containing conservative amino acid substitutions. For example, the fusion proteins of formula (I) may contain a conservative substitution of any amino acid from PE or PilA of *H. influenzae* as described in any of the sequences set forth herein (for example, any PE sequence set forth in SEQ ID NO. 4-SEQ ID NO. 57 and/or any PilA sequence set forth in SEQ ID NO. 58-SEQ ID NO. 121)

As used herein "signal peptide" refers to a short (less than 60 amino acids, for example, 3 to 60 amino acids) polypeptide present on precursor proteins (typically at the N terminus), and which is typically absent from the mature protein. The signal peptide (sp) is typically rich in hydrophobic amino acids. The signal peptide directs the transport and/or secretion of the translated protein through the membrane. Signal peptides may also be called targeting signals, transit peptides, localization signals, or signal sequences. For example, the signal sequence may be a co-translational or post-translational signal peptide.

A heterologous signal peptide may be cleaved from a fusion protein construct by signal peptide peptidases during or after protein transportation or secretion. For example, the signal peptide peptidase is signal peptide peptidase I. A "heterologous" signal peptide is one which is not associated with the protein as it exists in nature.

As used herein "treatment" means the prevention of occurrence of symptoms of the condition or disease in a subject, the prevention of recurrence of symptoms of the condition or disease in a subject, the delay of recurrence of symptoms of the condition or disease in a subject, the decrease in severity or frequency of symptoms of the condition or disease in a subject, slowing or eliminating the progression of the condition and the partial or total elimination of symptoms of the disease or condition in a subject.

As used herein, "optionally" means that the subsequently described event(s) may or may not occur, and includes both event(s) that occur and events that do not occur.

The pathogenesis of disease caused by NTHi begins with nasopharyngeal colonization. Mechanisms to adhere to and maintain long-term residence within the nasopharyngeal micro-environment are considered 'virulence determinants' for NTHi. (Vaccine 28: 279-289 (2010)).

The importance of NTHi being able to adhere to the mucosal epithelial surfaces of a human host is reflected in the multiplicity of adhesins expressed by NTHi. For example, some NTHi express pili. Other adhesive structures belong to the autotransporter family of proteins; these include Hap, HMW1/HMW2 and Hia/Hsf proteins. Further outer membrane proteins, such as the P2 protein, P5 protein and OapA have been described as adhesions for *Haemophilus influenzae*. (Cellular Microbiology 4:191-200 (2002), Microbes and Infection 10: 87-96 (2008), Vaccine 28: 279-289 (2010)).

Otitis media is a major cause of morbidity in 80% of all children less than 3 years of age. (Expert Rev. Vaccines 5:517-534 (2006)). More than 90% of children develop otitis media before age 7 (Current Opinion in Investigational Drugs 4:953-958 (2003)). In 2000, there were 16 million visits made to office-based physicians for otitis media in the United States and approximately 13 million antibacterial prescriptions dispensed. (Pediatrics 113:1451-1465 (2004)). In European countries, the reported acute otitis media rates range between 0.125 to 1.24 per child-year. (Expert Review of Vaccines 8:1479-1500 (2009)). Otitis media is a costly infection and the most common reason children receive antibiotics. (Current Infectious Disease Reports 11:177-182 (2009)). Bacteria are responsible for approximately 70% of cases of acute otitis media, with *Streptococcus pneumoniae*, non-typeable *Haemophilus influenzae*, and *Moraxella catarrhalis* predominating as the causative agents (Expert Review of Vaccines 5:517-534 (2006)). A subset of children experience recurrent and chronic otitis media and these otitis prone children have protracted middle-ear effusions that are associated with hearing loss and delays in speech and language development. (Current Infectious Disease Reports 11:177-182 (2009)).

Following the introduction of the heptavalent pneumococcal vaccine in many countries, some studies have demonstrated a significant increase in the proportion of acute otitis media caused by *H. influenzae*, with *H. influenzae* becoming the predominant pathogen. (Pediatric Infectious Disease Journal 23:824-828; Pediatric Infectious Disease Journal 23:829-833 (2004)).

Since otitis media is a multifactorial disease, the feasibility of preventing otitis media using a vaccination strategy has been questioned. (Current Infectious Disease Reports 11:177-182 (2009)). However, the results from one study suggest that it is possible for an antigen to induce at least partial protection against non-typeable *H. influenzae*. (Lancet 367:740-748 (2006)). One approach to developing vaccine antigens is to use antigenically conserved regions of genetically heterogeneous but abundantly expressed surface molecules. Another approach is to identify surface proteins that demonstrate sequence or functional epitope conservation. A third consideration for a vaccine antigen could be to select an antigen that is expressed during infection and colonization in a human host. Murphy (Curr. Infect. Disease Reports 11:177-182 (2009) states that, despite the existence of several potential non-typeable *H. influenzae* candidate antigens, one cannot predict with certainty whether the candidate antigen will be effective. (Current Infectious Disease Reports 11:177-182 (2009)). Some of the proteins described as potential vaccine antigens are: *Haemophilus* adhesin protein (Hap), High molecular-weight (HMVV) proteins 1 and 2, *H. influnzae* adhesin (Hia), D15 protein, HtrA heat shock protein, P2 surface protein, lipoprotein D, P5 fimbrin derived peptides, outer membrane protein P4, outer membrane protein (OMP) 26 (OMP26), P6 protein, Protein E, Type IV pilus, lipooligosaccharide and phosphoryl choline. (Current Infectious Disease Reports 11:177-182 (2009); Expert Review of Vaccines 5:517-534 (2006)).

The chinchilla model is a robust and validated animal model of otitis media and its prevention (Expert Review of Vaccines 8:1063-1082 (2009)). While the chinchilla model may mimic the natural course of human infection, others have suggested that results in the chinchilla model may vary from one laboratory to the next. (Current Opinion in Investigational Drugs 4:953-958 (2003)).

Various other rodents have also been used for the induction of otitis media and are summarized in Vaccine 26:1501-1524 (2008). The murine animal model is often studied in otitis media research.

The presence of bactericidal antibody is associated with protection from otitis media due to non-typeable *H. influenzae*. (Current Opinion in Infectious Disease 16:129-134 (2003)). However, an immune response need not be bactericidal to be effective against NTHi. Antibodies that merely react with NTHi surface adhesins can reduce or eliminate otitis media in the chinchilla. (Current Opinion in Investigational Drugs 4:953-958 (2003)).

Chronic obstructive pulmonary disease is a chronic inflammatory disease of the lungs and a major cause of morbidity and mortality worldwide. Approximately one in 20 deaths in 2005 in the U.S. had COPD as the underlying cause. (Drugs and Aging 26:985-999 (2009)). It is projected that in 2020 COPD will rise to the fifth leading cause of disability adjusted life years, chronic invalidating diseases, and to the third most important cause of mortality (Lancet 349:1498-1504 (1997)).

The course of COPD is characterized by progressive worsening of airflow limitation and a decline in pulmonary function. COPD may be complicated by frequent and recurrent acute exacerbations (AE), which are associated with enormous health care expenditure and high morbidity. (Proceedings of the American Thoracic Society 4:554-564 (2007)). One study suggests that approximately 50% of acute exacerbations of symptoms in COPD are caused by non-typeable *Haemophilus influenzae, Moraxella catarrhalis, Streptococcus pneumoniae*, and *Pseudomonas aeruginosa*. (Drugs and Aging 26:985-999 (2009)). *H. influenzae* is found in 20-30% of exacerbations of COPD; *Streptococcus pneumoniae*, in 10-15% of exacerbations of COPD; and *Moraxella catarrhalis*, in 10-15% of exacerbations of COPD. (New England Journal of Medicine 359:2355-2365 (2008)). *Haemophilus influenzae, Streptococcus pneumoniae*, and *Moraxella catarrhalis* have been shown to be the primary pathogens in acute exacerbations of bronchitis in Hong Kong, South Korea, and the Phillipines, while *Klebsiella* spp., *Pseudomonas aeruginosa* and *Acinetobacter* spp. constitute a large proportion of pathogens in other Asian countries/regions including Indonesia, Thailand, Malaysia and Taiwan (Respirology, (2011) 16, 532-539; doi:10.1111/j.1440.1843.2011.01943.x). In Bangladesh, 20% of patients with COPD showed positive sputum culture for *Pseudomonas, Klebsiella, Streptococcus pneumoniae* and *Haemophilus influenzae*, while 65% of patients with AECOPD showed positive cultures for *Pseudomonas, Klebsiella, Acinetobacter, Enterobacter, Moraxella catarrhalis* and combinations thereof. (Mymensingh Medical Journal 19:576-585 (2010)). However, it has been suggested that the two most important measures to prevent COPD exacerbation are active immunizations and chronic maintenance of pharmacotherapy. (Proceedings of the American Thoracic Society 4:554-564 (2007)).

There is a need for effective vaccines against NTHi. Using antigens that may act at different steps in pathogenesis may improve the efficacy of a vaccine. The inventors have found that PilA and PE may be beneficially present in the immunogenic compositions of the invention as fusion proteins.

The present invention relates to fusion proteins of formula (I).

(formula I)

wherein:

X is a signal peptide or MHHHHHH (SEQ ID NO. 2);

m is 0 or 1;

$R_1$ is an amino acid;

n is 0, 1, 2, 3, 4, 5 or 6;

A is Protein E from *Haemophilus influenzae* or an immunogenic fragment thereof, or PilA from *Haemophilus influenzae* or an immunogenic fragment thereof;

Y is selected from the group consisting of GG, SG, SS and $(G)_h$ wherein h is 4, 5, 6, 7, 8, 9, or 10;

o is 0 or 1;

B is PilA from *Haemophilus influenzae* or an immunogenic fragment thereof, or Protein E from *Haemophilus influenzae* or an immunogenic fragment thereof;

Z is GGHHHHHH (SEQ ID NO: 3); and p is 0 or 1.

In one embodiment, the fusion proteins of formula (I) are defined wherein X is selected from the group consisting of the signal sequence from CcmH (cytochrome c membrane protein H), DsbA (periplasmic protein disulfide isomerise I), DsbB (disulfide bond membrane protein B), FlgI (flagellar peptidoglycan ring protein), FocC (F1c Chaperone protein), MalE (maltose transporter subunit E), NadA (quinolinate synthase subunit A), NikA (nickel ABC transporter component A), NspA (Neisserial surface protein A), Omp26 (outer membrane protein 26), OmpA (outer membrane protein A), OspA (outer surface protein A), pelB (pectate lyase B), PhoA (bacterial alkaline phosphatase), PhtD (pneumococcal histidine triad protein D), PhtE (pneumococcal histidine triad protein E), SfmC (periiplasmic pilin chaperone), Sip1 (surface immunogenic protein), TolB (Tol-Pal Cell Envelope Complex Component B), TorA (trimethylamine N-oxide reductase system subunit A), TorT (trimethylamine N-oxide reductase system periplasmic protein T) and YraI (putative periplasmic pilin chaperone); or any subgroup thereof. In one embodiment, X is a co-translational signal peptide or a post-translational signal peptide. In one embodiment X is the signal sequence from FlgI (flgI sp). In another particular embodiment, X is the signal sequence from pelB (pelB sp). In another embodiment, X is a post-translational signal peptide.

In another embodiment, X is selected from the group consisting of the signal sequence from FlgI, NadA and pelB.

In one embodiment, the fusion proteins of formula (I) are defined wherein m is 1. In another embodiment, m is 0.

In one particular embodiment, $R_1$ and n are defined wherein $(R_1)_n$ is 1 to 6 amino acids enriched in small, usually hydrophilic, amino acids. Hydrophilic amino acids include glutamic acid (E), aspartic acid (D) and asparagine (N).

In one embodiment, the fusion proteins of formula (I) are defined wherein n is selected from the group consisting of 0, 1, 2 and 6. In one particular embodiment, $R_1$ and n are defined wherein $(R_1)_n$ is selected from the group consisting of D, E, ATNDDD (SEQ ID NO. 178) and MD, or any subset thereof.

In one particular embodiment, n is selected from the group consisting of 1, 2 and 6. In one particular embodiment, n is 0.

In one embodiment, the fusion proteins of formula (I) are defined wherein A is Protein E from *H. influenzae*. In another embodiment, the fusion proteins of formula (I) are defined wherein A is Protein E as encoded by an amino acid sequence selected from the group consisting of SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, SEQ ID NO. 40, SEQ ID NO. 41, SEQ ID NO. 42, SEQ ID NO. 43 SEQ ID NO. 44, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55, SEQ ID NO. 56 and SEQ ID NO. 57; or any subset of SEQ ID NO. 5 through SEQ ID NO. 57. In another embodiment, the fusion proteins of formula (I) are defined wherein A is Protein E, wherein Protein E is approximately 75% to 100% identical to the Protein E amino acid sequence set forth in SEQ ID NO: 4. In another embodiment, A is Protein E wherein Protein E is approximately 90% to 100% identical to the Protein E amino acid sequence set forth in SEQ ID NO: 4. In another embodiment, A is Protein E wherein Protein E is at least 95% identical to the Protein E amino acid sequence set forth in SEQ ID NO: 4. In additional embodiment, A is Protein E wherein Protein E is at least 95% identical to Protein E as set for in any of SEQ ID NO. 4-SEQ ID NO. 57. In a particular embodiment, A is Protein E having the amino acid sequence set forth in SEQ ID NO. 4.

In another embodiment, the fusion proteins of formula (I) are defined wherein A is an immunogenic fragment of Protein E from *H. influenzae*. In another embodiment, A is an immunogenic fragment of Protein E wherein Protein E has an amino acid sequence selected from the group consisting of SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, SEQ ID NO. 40, SEQ ID NO. 41, SEQ ID NO. 42, SEQ ID NO. 43 SEQ ID NO. 44, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55, SEQ ID NO. 56 and SEQ ID NO. 57; or any subset of SEQ ID NO. 4 through SEQ ID NO. 57. In another embodiment, A is an immunogenic fragment of Protein E, wherein Protein E is approximately 75% to 100% identical to the amino acid sequence set forth in SEQ ID NO: 4. In another embodiment, A is an immunogenic fragment of Protein E, wherein Protein E is approximately 90% to 100% identical to SEQ ID NO. 4. In an additional embodiment, A is an immunogenic fragment of Protein E, wherein Protein E is at least 95% identical to any of SEQ ID NO. 4-SEQ ID NO. 57. More specifically, in one embodiment, A is an immunogenic fragment of Protein E, wherein Protein E is 93% to 100% identical to SEQ ID NO. 124. In a particular embodiment, A is an immunogenic fragment of Protein E wherein Protein E is SEQ ID NO. 4.

In another embodiment, A is an immunogenic fragment of Protein E from *H. influenzae* selected from the group consisting of amino acids 17-160 of SEQ ID NO. 4 (SEQ ID NO. 122), amino acids 18-160 of SEQ ID NO. 4 (SEQ ID NO. 123), amino acids 19-160 of SEQ ID NO. 4 (SEQ ID NO. 124), amino acids 20-160 of SEQ ID NO. 4 (SEQ ID NO. 125) and amino acids 22-160 of SEQ ID NO. 4 (SEQ ID NO. 126). In another embodiment, A is an immunogenic fragment of Protein E from *H. influenzae* selected from the group consisting of amino acids 17-160 of SEQ ID NO. 4 (SEQ ID NO. 122), amino acids 18-160 of SEQ ID NO. 4 (SEQ ID NO. 123), amino acids 19-160 of SEQ ID NO. 4 (SEQ ID NO. 124), amino acids 20-160 of SEQ ID NO. 4 (SEQ ID NO. 125), amino acids 22-160 of SEQ ID NO. 4 (SEQ ID NO. 126), amino acids 23-160 of SEQ ID NO. 4 (SEQ ID NO. 179) and amino acids 24-160 of SEQ ID NO. 4 (SEQ ID NO. 180). In a further embodiment, A is an immunogenic fragment of Protein E from *H. influenzae* selected from the group consisting of amino acids 17-160 of SEQ ID NO. 4 (SEQ ID NO. 122), amino acids 18-160 of SEQ ID NO. 4 (SEQ ID NO. 123), amino acids 20-160 of SEQ ID NO. 4 (SEQ ID NO. 125), amino acids 22-160 of SEQ ID NO. 4 (SEQ ID NO. 126), amino acids 23-160 of SEQ ID NO. 4 (SEQ ID NO. 179) and amino acids 24-160 of SEQ ID NO. 4 (SEQ ID NO. 180). More specifically, in one embodiment, A is SEQ ID NO. 124, amino acids 19-160 of SEQ ID NO. 4. In an additional embodiment, A is SEQ ID NO. 125, amino acids 20-160 of SEQ ID NO. 5. In another embodiment, A is immunogenic fragment of Protein E from *H. influenzae* selected from the group consisting of amino acids 23-160 of SEQ ID NO. 4 (SEQ ID NO. 179) and amino acids 24-160 of SEQ ID NO. 4 (SEQ ID NO. 180).

```
Protein E
                                        SEQ ID NO. 4
MKKIILTLSL GLLTACSAQI QKAEQNDVKL APPTDVRSGY

IRLVKNVNYY IDSESIWVDN QEPQIVHFDA VVNLDKGLYV

YPEPKRYARS VRQYKILNCA NYHLTQVRTD FYDEFWGQGL

RAAPKKQKKH TLSLTPDTTL YNAAQIICAN YGEAFSVDKK

Amino acids 17-160 of Protein E from SEQ ID NO. 4
                                      SEQ ID NO. 122
              SAQI QKAEQNDVKL APPTDVRSGY

IRLVKNVNYY IDSESIWVDN QEPQIVHFDA VVNLDKGLYV

YPEPKRYARS VRQYKILNCA NYHLTQVRTD FYDEFWGQGL

RAAPKKQKKH TLSLTPDTTL YNAAQIICAN YGEAFSVDKK
```

```
Amino acids 18-160 of Protein E from SEQ ID NO. 4
                                      SEQ ID NO. 123
           AQI QKAEQNDVKL APPTDVRSGY

IRLVKNVNYY IDSESIWVDN QEPQIVHFDA VVNLDKGLYV

YPEPKRYARS VRQYKILNCA NYHLTQVRTD FYDEFWGQGL

RAAPKKQKKH TLSLTPDTTL YNAAQIICAN YGEAFSVDKK

Amino acids 19-160 of Protein E from SEQ ID NO. 4
                                      SEQ ID NO. 124
            QI QKAEQNDVKL APPTDVRSGY

IRLVKNVNYY IDSESIWVDN QEPQIVHFDA VVNLDKGLYV

YPEPKRYARS VRQYKILNCA NYHLTQVRTD FYDEFWGQGL

RAAPKKQKKH TLSLTPDTTL YNAAQIICAN YGEAFSVDKK

Amino acids 20-160 of Protein E from SEQ ID NO. 4
                                      SEQ ID NO. 125
             I QKAEQNDVKL APPTDVRSGY

IRLVKNVNYY IDSESIWVDN QEPQIVHFDA VVNLDKGLYV

YPEPKRYARS VRQYKILNCA NYHLTQVRTD FYDEFWGQGL

RAAPKKQKKH TLSLTPDTTL YNAAQIICAN YGEAFSVDKK

Amino acids 22-160 of Protein E from SEQ ID NO. 4
                                      SEQ ID NO. 126
               KAEQNDVKL APPTDVRSGY

IRLVKNVNYY IDSESIWVDN QEPQIVHFDA VVNLDKGLYV

YPEPKRYARS VRQYKILNCA NYHLTQVRTD FYDEFWGQGL

RAAPKKQKKH TLSLTPDTTL YNAAQIICAN YGEAFSVDKK

Amino acids 23-160 of Protein E from SEQ ID NO. 4
                                      SEQ ID NO. 179
                AEQNDVKL APPTDVRSGY

IRLVKNVNYY IDSESIWVDN QEPQIVHFDA VVNLDKGLYV

YPEPKRYARS VRQYKILNCA NYHLTQVRTD FYDEFWGQGL

RAAPKKQKKH TLSLTPDTTL YNAAQIICAN YGEAFSVDKK

Amino acids 24-160 Protein E from SEQ ID NO. 4
                                      SEQ ID NO. 180
                 EQNDVKL APPTDVRSGY

IRLVKNVNYY IDSESIWVDN QEPQIVHFDA VVNLDKGLYV

YPEPKRYARS VRQYKILNCA NYHLTQVRTD FYDEFWGQGL

RAAPKKQKKH TLSLTPDTTL YNAAQIICAN YGEAFSVDKK
```

In another embodiment, the fusion proteins of formula (I) are defined wherein A is PilA from *H. influenzae*. In another embodiment, the fusion proteins of formula (I) are defined wherein A is PilA from *H. influenzae* having an amino acid sequence selected from the group consisting of SEQ ID NO. 58, SEQ ID NO. 59, SEQ ID NO. 60, SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, SEQ ID NO. 93, SEQ ID NO. 94, SEQ ID NO. 95, SEQ ID NO. 96, SEQ ID NO. 97, SEQ ID NO. 98, SEQ ID NO. 99, SEQ ID NO. 100, SEQ ID NO. 101, SEQ ID NO. 102, SEQ ID NO. 103, SEQ ID NO. 104, SEQ ID NO. 105, SEQ ID NO. 106, SEQ ID NO. 107, SEQ ID NO. 108, SEQ ID NO. 109, SEQ ID NO. 110, SEQ ID NO. 111, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120 and SEQ ID NO. 121; or any subset of SEQ ID NO. 58 through SEQ ID NO. 121. In another embodiment, A is PilA wherein PilA is approximately 80% to 100% identical to SEQ ID NO. 58. In another embodiment, A is PilA wherein PilA is at least 95% identical to any of SEQ ID NO. 58-SEQ ID NO. 121. In a particular embodiment, A is PilA of SEQ ID NO. 58.

In another embodiment, the fusion proteins of formula (I) are defined wherein A an immunogenic fragment of PilA from *H. influenzae*. In another embodiment, A is an immunogenic fragment of PilA wherein PilA is approximately 80% to 100% identical to SEQ ID NO. 58. For example, A is an immunogenic fragment of PilA wherein PilA has an amino acid sequence selected from the group consisting of SEQ ID NO. 58, SEQ ID NO. 59, SEQ ID NO. 60, SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, SEQ ID NO. 93, SEQ ID NO. 94, SEQ ID NO. 95, SEQ ID NO. 96, SEQ ID NO. 97, SEQ ID NO. 98, SEQ ID NO. 99, SEQ ID NO. 100, SEQ ID NO. 101, SEQ ID NO. 102, SEQ ID NO. 103, SEQ ID NO. 104, SEQ ID NO. 105, SEQ ID NO. 106, SEQ ID NO. 107, SEQ ID NO. 108, SEQ ID NO. 109, SEQ ID NO. 110, SEQ ID NO. 111, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120 and SEQ ID NO. 121; or any subset SEQ ID NO. 58 through SEQ ID NO. 121. In an additional embodiment, A is an immunogenic fragment of PilA wherein PilA is at least 95% identical to any of SEQ ID NO. 58-SEQ ID NO. 121. In a particular embodiment, A is an immunogenic fragment of PilA from *H. influenzae* strain 86-028NP wherein PilA is SEQ ID NO. 58.

```
PilA from H. influenzae strain 86-028NP
                                      SEQ ID NO. 58
MKLTTQQTLK KGFTLIELMI VIAIIAILAT IAIPSYQNYT

KKAAVSELLQ ASAPYKADVE LCVYSTNETT NCTGGKNGIA

ADITTAKGYV KSVTTSNGAI TVKGDGTLAN MEYILQATGN

AATGVTWTTT CKGTDASLFP ANFCGSVTQ
```

In another embodiment, A is an immunogenic fragment of PilA approximately 75% to 100% identical to SEQ ID NO. 127. More specifically, in one embodiment A is SEQ ID NO. 127, a fragment consisting of amino acids 40-149 of SEQ ID NO. 58.

```
Amino acids 40-149 of PilA from H. influenzae
strain 86-028NP
                                     SEQ ID NO. 127.
                                                    T
KKAAVSELLQ ASAPYKADVE LCVYSTNETT NCTGGKNGIA

ADITTAKGYV KSVTTSNGAI TVKGDGTLAN MEYILQATGN

AATGVTWTTT CKGTDASLFP ANFCGSVTQ
```

In another embodiment, A is an immunogenic fragment of PilA consisting of amino acids 40-149 from any of SEQ ID NO. 58-SEQ ID NO. 121. In an additional embodiment, A is an immunogenic fragment at least 95% identical to amino acids 40-149 from any of SEQ ID NO. 58-SEQ ID NO. 121.

In one embodiment, the fusion proteins of formula (I) are defined wherein Y is selected from the group consisting of GG, SG and SS. In another embodiment, the fusion proteins of formula (I) are defined wherein Y is GG or SG. In one particular embodiment, Y is GG.

In one embodiment, the fusion proteins of formula (I) are defined wherein o is 1. In another embodiment, o is 0.

In one embodiment, the fusion proteins of formula (I) are defined wherein B is PilA from *H. influenzae* or an immunogenic fragment of PilA from *H. influenzae* when A is Protein E from *H. influenzae* or an immunogenic fragment of Protein E from *H. influenzae*. For example, B is PilA from *H. influenzae* strain 86-028NP. In another embodiment, B is PilA from *H. influenzae* having an amino acid sequence selected from the group consisting of SEQ ID NO. 58, SEQ ID NO. 59, SEQ ID NO. 60, SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, SEQ ID NO. 93, SEQ ID NO. 94, SEQ ID NO. 95, SEQ ID NO. 96, SEQ ID NO. 97, SEQ ID NO. 98, SEQ ID NO. 99, SEQ ID NO. 100, SEQ ID NO. 101, SEQ ID NO. 102, SEQ ID NO. 103, SEQ ID NO. 104, SEQ ID NO. 105, SEQ ID NO. 106, SEQ ID NO. 107, SEQ ID NO. 108, SEQ ID NO. 109, SEQ ID NO. 110, SEQ ID NO. 111, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120 and SEQ ID NO. 121; or any subset of SEQ ID NO. 58 through SEQ ID NO. 121. In another embodiment, B is PilA wherein PilA is approximately 80% to 100% identical to SEQ ID NO. 58. In another embodiment, B is PilA wherein PilA is at least 95% identical to any of SEQ ID NO. 58-SEQ ID NO. 121. In a particular embodiment, B is PilA of SEQ ID NO. 58.

In another embodiment, B is PilA wherein PilA is at least 95% identical to any of SEQ ID NO. 58-SEQ ID NO. 121 and A is PE wherein PE is at least 95% identical to any of SEQ ID NO. 4-SEQ ID NO. 57.

In another embodiment, the fusion proteins of formula (I) are defined wherein B is an immunogenic fragment of PilA from *H. influenzae* when A is an immunogenic fragment of Protein E from *H. influenzae*. For example, B is an immunogenic fragment of the PilA from *H. influenzae* strain 86-028NP. In another embodiment, B is an immunogenic fragment of PilA wherein PilA is approximately 80% to 100% identical to SEQ ID NO: 58. In another embodiment, B is an immunogenic fragment of PilA wherein PilA has an amino acid selected from the group consisting of SEQ ID NO. 58, SEQ ID NO. 59, SEQ ID NO. 60, SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, SEQ ID NO. 93, SEQ ID NO. 94, SEQ ID NO. 95, SEQ ID NO. 96, SEQ ID NO. 97, SEQ ID NO. 98, SEQ ID NO. 99, SEQ ID NO. 100, SEQ ID NO. 101, SEQ ID NO. 102, SEQ ID NO. 103, SEQ ID NO. 104, SEQ ID NO. 105, SEQ ID NO. 106, SEQ ID NO. 107, SEQ ID NO. 108, SEQ ID NO. 109, SEQ ID NO. 110, SEQ ID NO. 111, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120 and SEQ ID NO. 121; or any subset of SEQ ID NO. 58 through SEQ ID NO. 121. In another embodiment, B is an immunogenic fragment of PilA wherein PilA is at least 95% identical to any of SEQ ID NO. 58-SEQ ID NO. 121. In a particular embodiment, B is an immunogenic fragment of PilA from *H. influenzae* wherein PilA has the amino acid sequence set forth in SEQ ID NO. 58. In another embodiment, B is an immunogenic fragment of PilA consisting of amino acids 40-149 from any of SEQ ID NO. 58-SEQ ID NO. 121. More specifically, in one embodiment B is the fragment of PilA as set forth in SEQ ID NO. 127. In an additional embodiment, B is an immunogenic fragment at least 95% identical to amino acids 40-149 of any of SEQ ID NO. 58-SEQ ID NO. 121.

In one particular embodiment, B is the fragment of PilA as set forth in SEQ ID NO. 127 and A is an immunogenic fragment of Protein E selected from the group consisting of SEQ ID NO. 122, SEQ ID NO. 124, SEQ ID NO. 125 and SEQ ID NO. 126. More particularly, B is the fragment of PilA as set forth in SEQ ID NO. 127 and A is the fragment of Protein E as set forth in SEQ ID NO. 124, amino acids 19-160 of Protein E from SEQ ID NO. 4. In another embodiment, B is the fragment of PilA as set forth in SEQ ID NO. 127 and A is the fragment of Protein E as set forth in SEQ ID NO. 125.

In another embodiment, B is an immunogenic fragment of PilA wherein PilA is at least 95% identical to any of SEQ ID NO. 58-SEQ ID NO. 121 and A is an immunogenic fragment of PE wherein PE is at least 95% identical to any of SEQ ID NO. 4-SEQ ID NO. 57.

In another embodiment, the fusion proteins of formula (I) are defined wherein B is Protein E from *H. influenzae* when A is PilA from *H. influenzae*. For example, B is Protein E having an amino acid sequence selected from the group consisting of SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, SEQ ID NO. 40, SEQ ID NO. 41, SEQ ID NO. 42, SEQ ID NO. 43 SEQ ID NO. 44, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55, SEQ ID NO. 56 and SEQ ID NO. 57; or any subset of SEQ ID NO. 4 through SEQ ID NO. 57. In another embodiment, the fusion proteins of formula (I) are defined wherein B is Protein E wherein Protein E is approximately 75% to 100% identical to the Protein E amino acid sequence set forth in SEQ ID NO: 4. In another embodiment, B is Protein E wherein Protein E is approximately 90% to 100% identical to the Protein E amino acid sequence set forth in SEQ ID NO: 4. For example, B is Protein E wherein Protein E is at least 95% identical to Protein E as set forth in SEQ ID NO. 4. In another embodiment, B is Protein E wherein Protein E is at least 95% identical to any of SEQ ID NO. 4-SEQ ID NO. 57. In a particular embodiment, B is Protein E having the amino acid sequence set forth in SEQ ID NO. 4.

In another embodiment, the fusion proteins of formula (I) are defined wherein B is an immunogenic fragment of Protein E from *H. influenzae* when A is an immunogenic fragment of PilA from *H. influenzae*. For example, B is an immunogenic fragment of Protein E wherein Protein E has an amino acid sequence selected from the group consisting of SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, SEQ ID NO. 40, SEQ ID NO. 41, SEQ ID NO. 42, SEQ ID NO. 43, SEQ ID NO. 44, SEQ ID NO. 45, SEQ ID NO. 46, SEQ ID NO. 47, SEQ ID NO. 48, SEQ ID NO. 49, SEQ ID NO. 50, SEQ ID NO. 51, SEQ ID NO. 52, SEQ ID NO. 53, SEQ ID NO. 54, SEQ ID NO. 55, SEQ ID NO. 56 and SEQ ID NO. 57; or any subset of SEQ ID NO. 4 through SEQ ID NO. 57. In another embodiment, the fusion proteins of formula (I) are defined wherein B is an immunogenic fragment of Protein E wherein Protein E is approximately 75% to 100% identical to the Protein E amino acid sequence set forth in SEQ ID NO. 4. In another embodiment, B is an immunogenic fragment of Protein E wherein Protein E is approximately 90% to 100% identical to the Protein E amino acid sequence set forth in SEQ ID NO: 4. In a particular embodiment, B is an immunogenic fragment of Protein E having the amino acid sequence set forth in SEQ ID NO. 4. In an additional embodiment, B is an immunogenic fragment of Protein E, wherein Protein E is at least 95% identical to any of SEQ ID NO. 4-SEQ ID NO. 57.

In another embodiment, B is a fragment of Protein E from *H. influenzae* selected from the group consisting of amino acids 17-160 of SEQ ID NO. 4 (SEQ ID NO. 122), amino acids 18-160 of SEQ ID NO. 4 (SEQ ID NO. 123), amino acids 19-160 of SEQ ID NO. 4 (SEQ ID NO. 124), amino acids 20-160 of SEQ ID NO. 4 (SEQ ID NO. 125) and amino acids 22-160 of SEQ ID NO. 4 (SEQ ID NO. 126). In another embodiment, B is an immunogenic fragment of Protein E from *H. influenzae* selected from the group consisting of amino acids 17-160 of SEQ ID NO. 4 (SEQ ID NO. 122), amino acids 18-160 of SEQ ID NO. 4 (SEQ ID NO. 123), amino acids 19-160 of SEQ ID NO. 4 (SEQ ID NO. 124), amino acids 20-160 of SEQ ID NO. 4 (SEQ ID NO. 125), amino acids 22-160 of SEQ ID NO. 4 (SEQ ID NO. 126), amino acids 23-160 of SEQ ID NO. 4 (SEQ ID NO. 179) and amino acids 24-160 of SEQ ID NO. 4 (SEQ ID NO. 180). More specifically, in one embodiment, B is the fragment of Protein E as set forth in SEQ ID NO. 123, amino acids 18-160 of SEQ ID NO. 4.

In one particular embodiment B is an immunogenic fragment of Protein E as set forth in SEQ ID NO. 123, amino acids 18-160 of SEQ ID NO. 4 when A is an immunogenic fragment of PilA as set forth in SEQ ID NO. 127.

In one embodiment, the fusion proteins of formula (I) are defined wherein p is 0. In another embodiment, the fusion proteins of formula (I) are defined wherein p is 1.

In one embodiment, the fusion protein of formula (I) is selected from the group consisting of SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202 and SEQ ID NO. 204; or any subset thereof. In another embodiment, the fusion protein of formula (I) is approximately 95% identical to any of SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202 or SEQ ID NO. 204.

Fusion proteins of formula (I) are useful as immunogens in subjects such as mammals, particularly humans. In particular, the fusion proteins of formula (I) are useful in inducing an immune response against *H. influenzae* in subjects, particularly humans. More specifically, the fusion proteins of formula (I) are useful in the treatment or prevention of otitis media and/or AECOPD and/or pneumonia.

The present invention relates to immunogenic compositions comprising Protein E from *H. influenzae* (or an immunogenic fragment thereof) and PilA from *H. influenzae* (or an immunogenic fragment thereof), and immunogenic compositions comprising fusion proteins of Protein E from *H. influenzae* (or an immunogenic fragment thereof) and PilA from *H. influenzae* (or an immunogenic fragment thereof). The present invention also relates to vaccines comprising such immunogenic compositions and therapeutic uses of the same.

In one embodiment, the immunogenic compositions comprise Protein E from *H. influenzae* (or an immunogenic fragment thereof) and PilA from *H. influenzae* (or an immunogenic fragment thereof). Protein E may be SEQ ID NO. 4 or a Protein E sequence at least 75%, 80%, 85%, 90%, 95%, 96%, 97%, 98% or 99% identical to SEQ ID NO. 4.

The immunogenic fragment of Protein E may be SEQ ID NO. 122, SEQ ID NO. 123, SEQ ID NO. 124, SEQ ID NO. 125 or SEQ ID NO. 126, or a sequence having at least 90%, 95%, 96%, 97%, 98%, 99% sequence identity to any one of SEQ ID NO. 122, SEQ ID NO. 123, SEQ ID NO. 124, SEQ ID NO. 125 or SEQ ID NO. 126. The immunogenic fragment of Protein E may be SEQ ID NO. 122, SEQ ID NO. 123, SEQ ID NO. 124, SEQ ID NO. 125, SEQ ID NO. 126, SEQ ID NO. 179 or SEQ ID NO. 180 or a sequence having at least 90%, 95%, 96%, 97%, 98%, 99% sequence identity to any one of SEQ ID NO. 122, SEQ ID NO. 123, SEQ ID NO. 124, SEQ ID NO. 125, SEQ ID NO. 126, SEQ ID NO. 179 or SEQ ID NO. 180. Amino acid differences have been described in Protein E from various *Haemophilus* species when compared to Protein E from *Haemophilus influenzae* Rd as a reference strain. Microbes & Infection (Corrigendum to "Identification of a novel *Haemophilus influenzae* protein important for adhesion to epithelia cells" [Microbes Infect. 10 (2008) 87-97], available online Jul. 6, 2010, "Article in Press") provides a sequence for Protein E from *H. influenzae* strain 772. WO2002/28889 provides a sequence for Protein E from *H. influenzae* strain 12085.

Protein E contains an epithelial cell binding region (PKRYARSVRQ YKILNCANYH LTQVR, SEQ ID NO. 128) that has been reported to be conserved among more than 100 clinical NTHi isolates, encapsulated *H. influenzae*, and culture collection strains analyzed (Singh et al, J. Infect. Dis. 201(3):414-9 (2010)). Singh et al. reported that Protein E was highly conserved in both NTHi and encapsulated *H. influenzae* (96.9%-100% identity without the signal peptide). In one embodiment, the fragment of Protein E comprises the binding region of SEQ ID NO. 128 (PKRYARSVRQ YKILNCANYH LTQVR).

PilA is a conserved adhesin expressed in vivo. Full length comparison of 64 sequences of PilA from *Haemophilus influenzae* demonstrated approximately 80% to 100% identity.

In another embodiment, the immunogenic composition comprises a fusion protein as defined by formula (I).

In one embodiment, the present immunogenic compositions may be administered with other antigens from *H. influenzae*. For example, the PE and PilA or the fusion protein of formula (I) may be administered with Protein D from *H. influenzae*. Protein D may be as described in WO91/18926. In another embodiment, the immunogenic composition may include the fusion protein of formula (I) and Protein D from *H. influenzae*.

In another embodiment, the immunogenic compositions of the invention may be administered with additional antigens from other bacterial species also known to cause otitis media, AECOPD or pneumonia.

The amount of the immunogenic composition which is required to achieve the desired therapeutic or biological effect will depend on a number of factors such as the use for which it is intended, the means of administration, the recipient and the type and severity of the condition being treated, and will be ultimately at the discretion of the attendant physician or veterinarian. In general, a typical dose for the treatment of a condition caused in whole or in part by *H. influenzae* in a human, for instance, may be expected to lie in the range of from about 0.003 mg to about 0.090 mg. More specifically, a typical dose for the treatment of a condition caused wholly or in part by *H. influenzae* in a human may lie in the range of from about 0.01 mg to about 0.03 mg of fusion protein. The immunogenic composition may contain additional antigens; a typical dose for the treatment of a condition caused wholly or in part by *H. influenzae* in a human may lie in the range of from about 0.01 mg to about 0.03 mg for each additional antigen. This dose may be administered as a single unit dose. Several separate unit doses may also be administered. For example, separate unit doses may be administered as separate priming doses within the first year of life or as separate booster doses given at regular intervals (for example, every 1, 5 or 10 years).

Formulations comprising the immunogenic compositions of the invention may be adapted for administration by an appropriate route, for example, by the intramuscular, sublingual, transcutaneous, intradermal or intranasal route. Such formulations may be prepared by any method known in the art.

The immunogenic compositions of the present invention may additionally comprise an adjuvant. When the term "adjuvant" is used in this specification, it refers to a substance that is administered in conjunction with the immunogenic composition to boost the patient's immune response to the immunogenic component of the composition.

Suitable adjuvants include an aluminum salt such as aluminum hydroxide gel or aluminum phosphate or alum, but may also be a salt of calcium, magnesium, iron or zinc, or may be an insoluble suspension of acylated tyrosine, or acylated sugars, cationically or anionically derivatized saccharides, or polyphosphazenes. In one embodiment, the fusion protein, PE or PilA may be adsorbed onto aluminium phosphate. In another embodiment, the fusion protein, PE or PilA may be adsorbed onto aluminium hydroxide. In a third embodiment, alum may be used as an adjuvant.

Suitable adjuvant systems which promote a predominantly Th1 response include: non-toxic derivatives of lipid A, Monophosphoryl lipid A (MPL) or a derivative thereof, particularly 3-de-O-acylated monophosphoryl lipid A (3D-MPL) (for its preparation see GB 2220211 A); and a combination of monophosphoryl lipid A, preferably 3-de-O-acylated monophosphoryl lipid A, together with either an aluminum salt (for instance aluminum phosphate or aluminum hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen (Thoelen et al. Vaccine (1998) 16:708-14; EP 689454-B1).

AS01 is an Adjuvant System containing MPL (3-O-desacyl-4'-monophosphoryl lipid A), QS21 (*Quillaja saponaria* Molina, fraction 21) Antigenics, New York, N.Y., USA) and liposomes. AS01B is an Adjuvant System containing MPL, QS21 and liposomes (50 μg MPL and 50 μg QS21). AS01E is an Adjuvant System containing MPL, QS21 and liposomes (25 μg MPL and 25 μg QS21). In one embodiment, the immunogenic composition or vaccine comprises AS01. In another embodiment, the immunogenic composition or vaccine comprises AS01B or AS01E. In a particular embodiment, the immunogenic composition or vaccine comprises AS01E.

AS03 is an Adjuvant System containing α-Tocopherol and squalene in an oil/water (o/w) emulsion. $AS03_A$ is an Adjuvant System containing α-Tocopherol and squalene in an o/w emulsion (11.86 mg tocopherol). $AS03_B$ is an Adjuvant System containing α-Tocopherol and squalene in an o/w emulsion (5.93 mg tocopherol). $AS03_C$ is an Adjuvant System containing α-Tocopherol and squalene in an o/w emulsion (2.97 mg tocopherol). In one embodiment, the immunogenic composition or vaccine comprises AS03.

AS04 is an Adjuvant System containing MPL (50 μg MPL) adsorbed on an aluminum salt (500 μg $Al^{3+}$). In one embodiment, the immunogenic composition or vaccine comprises AS04.

A system involving the use of QS21 and 3D-MPL is disclosed in WO 94/00153. A composition wherein the QS21 is quenched with cholesterol is disclosed in WO 96/33739. An additional adjuvant formulation involving QS21, 3D-MPL and tocopherol in an oil in water emulsion is described in WO 95/17210. In one embodiment the immunogenic composition additionally comprises a saponin, which may be QS21. The formulation may also comprise an oil in water emulsion and tocopherol (WO 95/17210). Unmethylated CpG containing oligonucleotides (WO 96/02555) and other immunomodulatory oligonucleotides (WO 0226757 and WO 03507822) are also preferential inducers of a TH1 response and are suitable for use in the present invention.

Additional adjuvants are those selected from the group of metal salts, oil in water emulsions, Toll like receptor agonists, (in particular Toll like receptor 2 agonist, Toll like receptor 3 agonist, Toll like receptor 4 agonist, Toll like receptor 7 agonist, Toll like receptor 8 agonist and Toll like receptor 9 agonist), saponins or combinations thereof.

The present invention provides a process for preparing an immunogenic composition comprising combining a fusion protein of formula (I) with an adjuvant.

The present invention further provides a vaccine containing an immunogenic composition of the invention and a pharmaceutically acceptable excipient.

Possible excipients include arginine, pluronic acid and/or polysorbate. In a preferred embodiment, polysorbate 80 (for example, TWEEN® 80) is used. In a further embodiment, a final concentration of about 0.03% to about 0.06% is used.

Specifically, a final concentration of about 0.03%, 0.04%, 0.05% or 0.06% polysorbate 80 (w/v) may be used.

The present invention provides a process for preparing an immunogenic composition or vaccine comprising combining a fusion protein of formula (I) with a pharmaceutically acceptable excipient.

The present invention also provides nucleic acids encoding the proteins of the invention. The term "nucleic acid" refers to a polymeric form of nucleotides. Nucleotides can be ribonucleotides, deoxyribonucleotides, or modified forms of either ribonucleotides or deoxyribonucleotides. The term includes single and double forms of DNA. The nucleic acids are preferably substantially free from other nucleic acids.

The present invention provides a process of producing nucleic acids of the invention. Nucleic acids of the invention may be prepared by methods known by those skilled in the art. For example, the nucleic acids of the invention may be synthesized in part or in whole. The nucleic acids may be prepared by digesting longer amino acids or joining shorter amino acids.

The following examples are intended for illustration only and are not intended to limit the scope of the invention in any way.

In the examples, the following terms have the designated meaning:
6×his=six histidines;
xg=centrifugal force (number gravities)
ATP=adenosine triphosphate;
BCA=bicinchoninic acid;
BSA=bovine serum albumin;
° C.=degrees Celsius;
CaCl$_2$=calcium chloride;
CV=column volume;
DNA=deoxyribonucleic acid;
DSC=differential scanning calorimetry;
DTT=dithiothreitol;
dNTP=deoxynucleoside triphosphate;
EDTA=ethylenediaminetetraacetic acid;
FT=flow through;
HCl=hydrogen chloride;
His=his=histidine;
HEPES=4-(2-hydroxyethyl)-1-piperazineethanesulfonic acid;
IMAC=immobilized metal affinity chromatography;
IPTG=isopropyl β-D-1-thiogalactopyranoside;
KCl=potassium chloride;
K$_2$HPO$_4$=dibasic potassium phosphate;
KH$_2$PO$_4$=monobasic potassium phosphate;
LDS=lithium dodecyl sulfate;
L=liter;
MES=2-(N-morpholino)ethanesulfonic acid;
MgCl$_2$=magnesium chloride;
ml=milliliter;
RPM=revolutions per minute;
min=minute;
mM=millimolar;
μL=microliter;
NaCl=sodium chloride;
Na$_2$HPO$_4$=dibasic sodium phosphate;
NaH$_2$PO$_4$=monobasic sodium phosphate;
ng=nanogram;
nm=nanometer;
O/N=overnight;
PBS=phosphate buffered saline;
PCR=polymerase chain reaction;
SB=sample buffer;
sec=second;
w/v=weight/volume.

EXAMPLES

Example 1

Fusion Proteins

Fusion proteins were produced with different signal peptides and amino acid linker sequences. These fusion proteins allowed for secretion of both Protein E and PilA (or fragments thereof) without being restricted to a single bacterial strain. The fusion protein is released into the periplasm after removal of the heterologous signal peptide by a signal peptide peptidase. Fusion protein purified from the bacteria does not contain the heterologous signal peptide. "Purified" proteins are removed from the bacteria and lack the signal peptide.

The following table describes fusion protein constructs made.

TABLE 3

Fusion Protein Constructs containing PilA and Protein E.

| Construct ID | N-terminal | | | | | | C-Terminal |
|---|---|---|---|---|---|---|---|
| LVL312 | FlgI sp | E | PilA fragment (A.A.: 40-149 of SEQ ID NO. 58, SEQ ID NO. 127) | G G | ProtE fragment (A.A.: 18 to 160 of SEQ ID NO. 4, SEQ ID NO. 123) | | GGHHHHHH |
| A.A. | 1 | 19 | 21                    130 | 133 | | 275 | 276    283 |

| Construct ID | | | | | | |
|---|---|---|---|---|---|---|
| LVL291 | pelB sp | ProtE fragment (A.A.: 19 to 160 of SEQ ID NO. 4, SEQ ID NO. 124) | G G | PilA fragment (A.A.: 40-149 of SEQ ID NO. 58, SEQ ID NO. 127) | GGHHHHHH | |
| A.A. | 1    22 | 23                            164 | 167 | 276   277   284 | | |

| Construct ID | | | | | | |
|---|---|---|---|---|---|---|
| LVL268 | pelB sp | D | ProtE fragment (A.A.: 20 to 160 of SEQ ID NO. 4, SEQ ID NO. 125) | G G | PilA fragment (A.A.: 40-149 of SEQ ID NO. 58, SEQ ID NO. 127) | GGHHHHHH |
| A.A. | 1    22 | 24 | 164 | 167 | 276   277   284 | |

TABLE 3-continued

| LVL269 | nadA sp | ATNDDD | ProtE fragment (A.A.: 22 to 160 of SEQ ID NO. 4, SEQ ID NO. 126) | GG | PilA fragment (A.A.: 40-149 of SEQ ID NO. 58, SEQ ID NO. 127) | GGHHHHHH |
|---|---|---|---|---|---|---|
| A.A. | 1 | 23 24-29 30 | | 168 171 | | 280 281 288 |

| LVL270 | MHHHHHH | ProtE fragment (A.A.: 17 to 160 of SEQ ID NO. 4, SEQ ID NO. 122) | GG | PilA fragment (A.A.: 40-149 of SEQ ID NO. 58, SEQ ID NO. 127) |
|---|---|---|---|---|
| A.A. | 1 | 7 8 | 151 154 | 263 |

| LVL315 | pelB sp | MD | ProtE fragment (A.A.: 22 to 160 of SEQ ID NO. 4, SEQ ID NO. 126) | G G | PilA fragment (A.A.: 40-149 of SEQ ID NO. 58, SEQ ID NO. 127) | GGHHHHHHH |
|---|---|---|---|---|---|---|
| | 1 | 22 | 25 | 163 166 | | 275 276 283 |

| LVL317 | pelB sp | ProtE fragment (A.A.: 19 to 160 of SEQ ID NO. 4, SEQ ID NO. 124) | GG | PilA fragment (A.A.: 40-149 of SEQ ID NO. 58, SEQ ID NO. 127) |
|---|---|---|---|---|
| A.A. | 1 | 22 23 | 164 167 | 276 |

| LVL318 | pelB sp | MD | ProtE fragment (A.A.: 22 to 160 of SEQ ID NO. 4, SEQ ID NO. 126) | GG | PilA fragment (A.A.: 40-149 of SEQ ID NO. 58, SEQ ID NO. 127) |
|---|---|---|---|---|---|
| A.A. | 1 | 22 | 25 | 163 166 | 275 |

| LVL702 | pelB sp | ProtE fragment (A.A.: 20 to 160 of SEQ ID NO. 4, SEQ ID NO. 125) | GG | PilA fragment (A.A.: 40-149 of SEQ ID NO. 58, SEQ ID NO. 127) | GGHHHHHH |
|---|---|---|---|---|---|
| A.A. | 1 | 22 23 | 163 166 | | 275 283 |

| LVL736 | pelB sp | ProtE fragment (A.A.: 17 to 160 of SEQ ID NO. 4, SEQ ID NO. 122) | GG | PilA fragment (A.A.: 40-149 of SEQ ID NO. 58, SEQ ID NO. 127) | GGHHHHHH |
|---|---|---|---|---|---|
| A.A. | 1 | 22 23 | 166 169 | | 278 286 |

| LVL737 | pelB sp | ProtE fragment (A.A.: 18 to 160 of SEQ ID NO. 4, SEQ ID NO. 123) | GG | PilA fragment (A.A.: 40-149 of SEQ ID NO. 58, SEQ ID NO. 127) | GGHHHHHH |
|---|---|---|---|---|---|
| A.A. | 1 | 22 23 | 165 168 | | 277 285 |

| LVL738 | pelB sp | ProtE fragment (A.A.: 22 to 160 of SEQ ID NO. 4, SEQ ID NO. 126) | GG | PilA fragment (A.A.: 40-149 of SEQ ID NO. 58, SEQ ID NO. 127) | GGHHHHHH |
|---|---|---|---|---|---|
| A.A. | 1 | 22 23 | 161 164 | | 273 281 |

| LVL739 | pelB sp | ProtE fragment (A.A.: 23 to 160 of SEQ ID NO. 4, SEQ ID NO. 179) | GG | PilA fragment (A.A.: 40-149 of SEQ ID NO. 58, SEQ ID NO. 127) | GGHHHHHH |
|---|---|---|---|---|---|
| A.A. | 1 | 22 23 | 160 163 | | 272 280 |

| LVL740 | pelB sp | ProtE fragment (A.A.: 24 to 160 of SEQ ID NO. 4, SEQ ID NO. 180) | GG | PilA fragment (A.A.: 40-149 of SEQ ID NO. 58, SEQ ID NO. 127) | GGHHHHHH |
|---|---|---|---|---|---|
| A.A. | 1 | 22 23 | 159 162 | | 271 279 |

TABLE 3-continued

| LVL735 | pelB sp | ProtE fragment (A.A.: 22 to 160 of SEQ ID NO. 4, SEQ ID NO. 125) | G G | PilA fragment (A.A.: 40-149 of SEQ ID NO. 58, SEQ ID NO. 127) |
|---|---|---|---|---|
| A.A. | 1 | 22  23 | 163 | 166  275 |

| LVL778 | pelB sp | ProtE fragment (A.A.: 17 to 160 of SEQ ID NO. 4, SEQ ID NO. 122) | G G | PilA fragment (A.A.: 40-149 of SEQ ID NO. 58, SEQ ID NO. 127) |
|---|---|---|---|---|
| A.A. | 1 | 22  23 | 166 | 169  278 |

| LVL779 | pelB sp | ProtE fragment (A.A.: 18 to 160 of SEQ ID NO. 4, SEQ ID NO. 123) | G G | PilA fragment (A.A.: 40-149 of SEQ ID NO. 58, SEQ ID NO. 127) |
|---|---|---|---|---|
| A.A. | 1 | 22  23 | 165 | 168  277 |

| LVL780 | pelB sp | ProtE fragment (A.A.: 22 to 160 of SEQ ID NO. 4, SEQ ID NO. 126) | G G | PilA fragment (A.A.: 40-149 of SEQ ID NO. 58, SEQ ID NO. 127) |
|---|---|---|---|---|
| A.A. | 1 | 22  23 | 161 | 164  273 |

| LVL781 | pelB sp | ProtE fragment (A.A.: 23 to 160 of SEQ ID NO. 4, SEQ ID NO. 179) | G G | PilA fragment (A.A.: 40-149 of SEQ ID NO. 58, SEQ ID NO. 127) |
|---|---|---|---|---|
| A.A. | 1 | 22  23 | 160 | 163  272 |

| LVL782 | pelB sp | ProtE fragment (A.A.: 24 to 160 of SEQ ID NO. 4, SEQ ID NO. 180) | G G | PilA fragment (A.A.: 40-149 of SEQ ID NO. 58, SEQ ID NO. 127) |
|---|---|---|---|---|
| A.A. | 1 | 22  23 | 159 | 162  271 | sp = signal peptide;
A.A. = amino acid

The DNA and amino acid sequences for each of the signal peptides and plasmids listed in Table 3 are set forth below.

Signal Sequences:

pelB signal peptide (DNA)
SEQ ID NO. 129:
atgaaatacctgctgccgaccgctgctgctggtctgctgctcctcgctg cccagccggcgatggcc pelB signal peptide (Amino Acid)
SEQ ID NO. 130:
MKYLLPTAAA GLLLLAAQPA MA FlgI signal peptide (DNA)
SEQ ID NO. 131:
atgattaaatttctctctgcattaattcttctactggtcacgacggcggc tcaggct FlgI signal peptide (Amino Acid)
SEQ ID NO. 132:
MIKFLSALIL LLVTTAAQA NadA signal peptide (DNA)
SEQ ID NO. 133:
atgaaacactttccatccaaagtactgaccacagccatccttgccactt ctgtagcggcgcactggca NadA signal peptide (Amino Acid)
SEQ ID NO. 134:
MKHFPSKVLT TAILATFCSG ALA Fusion Protein Construct Sequences:

The single underlined portion of the amino acid sequences is from PilA from *Haemophilus influenzae* strain 86-028NP. The embolded underlined portion of the amino acid sequences was derived from Protein E from *Haemophilus influenza* strain 772.

LVL312 (DNA) - SEQ ID NO. 135:
atgattaaatttctctctgcattaattcttctactggtcacgacggcggctcaggctgagactaaaaaagcagcggtatctgaattactg caagcgtcagcgccttataaggctgatgtggaattatgtgtatatagcacaaatgaaacaacaaactgtacgggtggaaaaaatg gtattgcagcagatataaccacagcaaaggctatgtaaaatcagtgacaacaagcaacggtgcaataacagtaaaaggggat ggcacattggcaaatatggaatatattttgcaagctacaggtaatgctgcaacaggtgtaacttggacaacaacttgcaaaggaac ggatgcctctttatttccagcaaatttttgcggaagtgtcacacaaggcggcgcgcagattcagaaggctgaacaaaatgatgtgaa gctggcaccgccgactgatgtacgaagcggatatatacgtttggtaaagaatgtgaattattacatcgatagtgaatcgatctgggtg gataaccaagagccacaaattgtacattttgatgcagtggtgaatttagataagggattgtatgtttatcctgagcctaaacgttatgca cgttctgttcgtcagtataagatcttgaattgtgcaaattatcatttaactcaagtacgaactgatttctatgatgaattttgggacagggt ttgcgggcagcacctaaaaagcaaagaaacatacgttaagtttaacacctgatacaacgctttataatgctgctcagattatttgtg cgaactatggtgaagcattttcagttgataaaaaaggcggccaccaccaccaccactaa LVL312 (protein): (flgI sp)((E)(PilA aa 40- 149)(GG)ProtE aa 18- 160)(GGHHHHHH) - SEQ ID NO. 136

MIKFLSALIL LLVTTAAQAE TKKAAVSELL QASAPYKADV ELCVYSTNET

TNCTGGKNGI AADITTAKGY VKSVTTSNGA ITVKGDGTLA NMEYILQATG

NAATGVTWTT TCKGTDASLF PANFCGSVTQ GGAQIQKAEQ NDVKLAPPTD

VRSGYIRLVK NVNYYIDSES IWVDNQEPQI VHFDAVVNLD KGLYVYPEPK

RYARSVRQYK ILNCANYHLT QVRTDFYDEF WGQGLRAAPK KQKKHTLSLT

PDTTLYNAAQ IICANYGEAF SVDKKGGHHH HHH

LVL291 (DNA) - SEQ ID NO. 137:
atgaaatacctgctgccgaccgctgctgctggtctgctgctcctcgctgcccagccggcgatggcccagattcagaaggctgaaca aaatgatgtgaagctggcaccgccgactgatgtacgaagcggatatatacgtttggtaaagaatgtgaattattacatcgatagtga atcgatctggtggataaccaagagccacaaattgtacattttgatgcagtggtgaatttagataagggattgtatgtttatcctgagcc taaacgttatgcacgttctgttcgtcagtataagatcttgaattgtgcaaattatcatttaactcaagtacgaactgatttctatgatgaattt tggggacagggtttgcgggcagcacctaaaaagcaaagaaacatacgttaagtttaacacctgatacaacgctttataatgctgc tcagattatttgtgcgaactatggtgaagcattttcagttgataaaaaaggcggcactaaaaaagcagcggtatctgaattactgcaa gcgtcagcgccttataaggctgatgtggaattatgtgtatatagcacaaatgaaacaacaaactgtacgggtggaaaaaatggtatt gcagcagatataaccacagcaaaaggctatgtaaaatcagtgacaacaagcaacggtgcaataacagtaaaaggggatggc acattggcaaatatggaatatattttgcaagctacaggtaatgctgcaacaggtgtaacttggacaacaacttgcaaaggacgga tgcctctttatttccagcaatttttgcggaagtgtcacacaaggcggccaccaccaccaccactaa LVL291 (Protein)(PelB sp)(ProtE aa 19- 160)(GG)(PilA aa40- 149)(GGHHHHHH) -SEQ ID NO. 138

MKYLLPTAAA GLLLLAAQPA MAQIQKAEQN DVKLAPPTDV RSGYIRLVKN

VNYYIDSESI WVDNQEPQIV HFDAVVNLDK GLYVYPEPKR YARSVRQYKI

LNCANYHLRQ VRTDFYDEFW GQGLRAAPKK QKKHTLSLTP DTTLYNAAQI

ICANYGEAFS VDKKGGTKKA AVSELLQASA PYKADVELCV YSTNETTNCT

GGKNGIAADI TTAKGYVKSV TTSNGAITVK GDGTLANMEY ILQATGNAAT

GVTWTTTCKG TDASLFPANF CGSVTQGGHH HHHH

LVL268 (DNA) - SEQ ID NO. 139:
atgaaatacctgctgccgaccgctgctgctggtctgctgctcctcgctgcccagccggcgatggccgatattcagaaggctgaaca aaatgatgtgaagctggcaccgccgactgatgtacgaagcggatatatacgtttggtaaagaatgtgaattattacatcgatagtga atcgatctggtggataaccaagagccacaaattgtacattttgatgcagtggtgaatttagataagggattgtatgtttatcctgagcc taaacgttatgcacgttctgttcgtcagtataagatcttgaattgtgcaaattatcatttaactcaagtacgaactgatttctatgatgaattt tggggacagggtttgcgggcagcacctaaaaagcaaagaaacatacgttaagtttaacacctgatacaacgctttataatgctgc tcagattatttgtgcgaactatggtgaagcattttcagttgataaaaaaggcggcactaaaaaagcagcggtatctgaattactgcaa gcgtcagcgccttataaggctgatgtggaattatgtgtatatagcacaaatgaaacaacaaactgtacgggtggaaaaaatggtatt gcagcagatataaccacagcaaaaggctatgtaaaatcagtgacaacaagcaacggtgcaataacagtaaaaggggatggc acattggcaaatatggaatatattttgcaagctacaggtaatgctgcaacaggtgtaacttggacaacaacttgcaaaggaacgga tgcctcttttatttccagcaaattttttgcggaagtgtcacacaaggcggccaccaccaccaccaccac LVL268 (protein): (pelB sp)((D)(ProtE aa 20- 160)(GG)(PilA aa40- 149)(GGHHHHHH) - SEQ ID NO. 140:
MKYLLPTAAA GLLLLAAQPA MAD<u>IQKAEQN DVKLAPPTDV RSGYIRLVKN</u>

<u>VNYYIDSESI WVDNQEPQIV HFDAVVNLDK GLYVYPEPKR YARSVRQYKI</u>

<u>LNCANYHLTQ VRTDFYDEFW GQGLRAAPKK QKKHTLSLTP DTTLYNAAQI</u>

<u>ICANYGEAFS VDKKGGTKKA</u> <u>AVSELLQASA PYKADVELCV YSTNETTNCT</u>

<u>GGKNGIAADI TTAKGYVKSV TTSNGAITVK GDGTLANMEY ILQATGNAAT</u>

<u>GVTWTTTCKG TDASLFPANF CGSVTQ</u>GGHH HHHH

LVL269 (DNA) - SEQ ID NO. 141:
atgaaacactttccatccaaagtactgaccacagccatccttgccactttctgtagcggcgcactggcagccacaaacgacgacg ataaggctgaacaaaatgatgtgaagctggcaccgccgactgatgtacgaagcggatatatacgtttggtaaagaatgtgaattatt acatcgatagtgaatcgatctgggtggataaccaagagccacaaattgtacattttgatgcagtggtgaatttagataagggattgtat gtttatcctgagcctaaacgttatgcacgttctgttcgtcagtataagatcttgaattgtgcaaattatcatttaactcaagtacgaactgat ttctatgatgaattttggggacagggtttgcgggcagcacctaaaaagcaaaagaaacatacgttaagtttaacacctgatacaac gctttataatgctgctcagattattgtgcgaactatggtgaagcattttcagttgataaaaaaggcggcactaaaaaagcagcggtat ctgaattactgcaagcgtcagcgccttataaggctgatgtggaattatgtgtatatagcacaaatgaaacaacaaactgtacgggtg gaaaaaatggtattgcagcagatataaccacagcaaaaggctatgtaaaatcagtgacaacaagcaacggtgcaataacagta aaaggggatggcacattggcaaatatggaatatattttgcaagctacaggtaatgctgcaacaggtgtaacttggacaacaacttg caaaggaacggatgcctctttatttccagcaaattttttgcggaagtgtcacacaaggcggccaccaccaccaccaccactaa LVL269 (protein): (nadA sp)(ATNDDD)(ProtE aa 22- 160)(GG)(PilA aa 40-149)(GGHHHHHH) - SEQ ID NO. 142
NKHFPSKVLT TAILATFCSG ALAATNDDDK <u>AEQNDVKLAP PTDVRSGYIR</u>

<u>LVKNVNYYID SESIWVDNQE PQIVHFDAVV NLDKGLYVYP EPKRYARSVR</u>

<u>QYKILNCANY HLTQVRTDFY DEFWGQGLRA APKKQKKHTL SLTPDTTLYN</u>

<u>AAQIICANYG EAFSVDKKGG</u> <u>TKKAAVSELL QASAPYKADV ELCVYSTNET</u>

<u>TNCTGGKNGI AADITTAKGY VKSVTTSNGA ITVKGDGTLA NMEYILQATG</u>

<u>NAATGVTWTT TCKGTDASLF PANFCGSVTQ</u> GGHHHHHH

LVL270 (DNS) - SEQ ID NO. 143:
atgcaccaccaccaccaccacagcgcgcagattcagaaggctgaacaaaatgatgtgaagctggcaccgccgactgatgtacg aagcggatatatacgtttggtaaagaatgtgaattattacatcgatagtgaatcgatctgggtggataaccaagagccacaaattgta cattttgatgcagtggtgaatttagataagggattgtatgtttatcctgagcctaaacgttatgcacgttctgttcgtcagtataagatcttg aattgtgcaaattatcatttaactcaagtacgaactgatttctatgatgaattttggggacagggtttgcgggcagcacctaaaaagca aaagaaacatacgttaagtttaacacctgatacaacgctttataatgctgctcagattattgtgcgaactatggtgaagcattttcagtt gataaaaaaggcggcactaaaaaagcagcggtatctgaattactgcaagcgtcagcgccttataaggctgatgtggaattatgtgt

```
atatagcacaaatgaaacaacaaactgtacgggtggaaaaaatggtattgcagcagatataaccacagcaaaaggctatgtaa aatcagtgacaacaagcaacggtgcaataacagtaaaaggggatggcacattggcaaatatggaatatattttgcaagctacag gtaatgctgcaacaggtgtaacttggacaacaacttgcaaaggaacggatgcctctttatttccagcaaattttttgcggaagtgtcac acaataa
```

LVL270 (protein): (MHHHHHH)(ProtE aa 17-160)(GG)(PilA aa40-149) - SEQ ID NO. 144:

<u>MHHHHHHSAQ IQKAEQNDVK LAPPTDVRSG YIRLVKNVNY YIDSESIWVD</u>

<u>NQEPQIVHFD AVVNLDKGLY VYPEPKRYAR SVRQYKILNC ANYHLTQVRT</u>

<u>DFYDEFWGQG LRAAPKKQKK HTLSLTPDTT LYNAAQIICA NYGEAFSVDK</u>

<u>KGGTKKAAVS ELLQASAPYK ADVELCVYST NETTNCTGGK NGIAADITTA</u>

<u>KGYVKSVTTS NGAITVKGDG TLANMEYILQ ATGNAATGVT WTTTCKGTDA</u>

<u>SLEPANFCGS VTQ</u>

LVL315 (DNA) - SEQ ID NO. 145:
```
atgaaatacctgctgccgaccgctgctgctggtctgctgctcctcgctgcccagccggcgatggccatggataaggctgaacaaaa tgatgtgaagctggcaccgccgactgatgtacgaagcggataatatacgtttggtaaagaatgtgaattattacatcgatagtgaatcg atctgggtggataaccaagagccacaaattgtacattttgatgcagtggtgaatttagataagggattgtatgtttatcctgagcctaaa cgttatgcacgttctgttcgtcagtataagatcttgaattgtgcaaattatcatttaactcaagtacgaactgatttctatgatgaattttggg gacagggtttgcgggcagcacctaaaaagcaaaagaaacatacgttaagtttaacacctgatacaacgctttataatgctgctcag attatttgtgcgaactatggtgaagcattttcagttgataaaaaaggcggcactaaaaaagcagcggtatctgaattactgcaagcgt cagcgccttataaggctgatgtggaattatgtgtatatagcacaaatgaaacaacaaactgtacgggtggaaaaaatggtattgca gcagatataaccacagcaaaaggctatgtaaaatcagtgacaacaagcaacggtgcaataacagtaaaaggggatggcacat tggcaaatatggaatatattttgcaagctacaggtaatgctgcaacaggtgtaacttggacaacaacttgcaaaggaacggatgcc tctttatttccagcaaattttttgcggaagtgtcacacaaggcggccaccaccaccaccaccactaa
```

LVL315 (protein): (pelB sp)(MD)(ProtE aa 22- 160)(GG)(PilA aa40-149)(GGHHHHHH) - SEQ ID NO. 146:

MKYLLPTAAA GLLLLAAQPA MAMDKAEQND VKLAPPTDVR SGYIRLVKNV

<u>NYYIDSESIW VDNQEPQIVH FDAVVNLDKG LYVYPEPKRY ARSVRQYKIL</u>

<u>NCANYHLTQV RTDFYDEFWG QGLRAAPKKQ KKHTLSLTPD TTLYNAAQIL</u>

<u>CANYGEAFSV DKKGGTKKAA VSELLQASAP YKADVELCVY STNETTNCTG</u>

<u>GKNGIAADIT TAKGYVKSVT TSNGAITVKG DGTLANMEYI LQATGNAATG</u>

VTWTTTCKGT DASLFPANFC GSVTQGGHHH HHH

LVL317 (DNA) - SEQ ID NO. 147:
```
atgaaatacctgctgccgaccgctgctgctggtctgctgctcctcgctgcccagccggcgatggcccagattcagaaggctgaaca aaatgatgtgaagctggcaccgccgactgatgtacgaagcggatatatacgtttggtaaagaatgtgaattattacatcgatagtga atcgatctgggtggataaccaagagccacaaattgtacattttgatgcagtggtgaatttagataagggattgtatgtttatcctgagcc taaacgttatgcacgttctgttcgtcagtataagatcttgaattgtgcaaattatcatttaactcaagtacgaactgatttctatgatgaattt tggggacagggtttgcgggcagcacctaaaaagcaaaagaaacatacgttaagtttaacacctgatacaacgctttataatgctgc tcagattatttgtgcgaactatggtgaagcattttcagttgataaaaaaggcggcactaaaaaagcagcggtatctgaattactgcaa gcgtcagcgccttataaggctgatgtggaattatgtgtatatagcacaaatgaaacaacaaactgtacgggtggaaaaaatggtatt
``` gcagcagatataaccacagcaaaaggctatgtaaaatcagtgacaacaagcaacggtgcaataacagtaaaaggggatggc acattggcaaatatggaatatattttgcaagctacaggtaatgctgcaacaggtgtaacttggacaacaacttgcaaaggacgga tgcctctttatttccagcaaattttgcggaagtgtcacacaataa LVL317 (protein): (pelB sp)(ProtE aa 19-160)(GG)(PilA aa40-149) - SEQ ID NO. 148:
MKYLLPTAAA GLLLLAAQPA MAQIQKAEQN DVKLAPPTDV RSGYIRLVKN

VNYYIDSESI WVDNQEPQIV HFDAVVNLDK GLYVYPEPKR YARSVRQYKI

LNCANYHLTQ VRTDFYDEFW GQGLRAAPKK QKKHTLSLTP DTTLYNAAQI

ICANYGEAFS VDKKGGTKKA AVSELLQASA PYKADVELCV YSTNETTNCT

GGKNGIAADI TTAKGYVKSV TTSNGAITVK GDGTLANMEY ILQATGNAAT

GVTWTTTCKG TDASLFPANF CGSVTQ

LVL318 (DNA) - SEQ ID NO. 149:
atgaaatacctgctgccgaccgctgctgctggtctgctgctcctcgctgcccagccggcgatggccatggataaggctgaacaaaa tgatgtgaagctggcaccgccgactgatgtacgaagcggatatatacgtttggtaaagaatgtgaattattacatcgatagtgaatcg atctgggtggataaccaagagccacaaattgtacattttgatgcagtggtgaatttagataagggattgtatgtttatcctgagcctaaa cgttatgcacgttctgttcgtcagtataagatcttgaattgtgcaaattatcatttaactcaagtacgaactgatttctatgatgaattttggg gacagggtttgcgggcagcacctaaaaagcaaaagaaacatacgttaagtttaacacctgatacaacgctttataatgctgctcag attatttgtgcgaactatggtgaagcattttcagttgataaaaaaggcggcactaaaaaagcagcggtatctgaattactgcaagcgt cagcgccttataaggctgatgtggaattatgtgtatatagcacaaatgaaacaacaaactgtacgggtggaaaaaatggtattgca gcagatataaccacagcaaaaggctatgtaaaatcagtgacaacaagcaacggtgcaataacagtaaaaggggatggcacat tggcaaatatggaatatattttgcaagctacaggtaatgctgcaacaggtgtaacttggacaacaacttgcaaaggaacggatgcc tctttatttccagcaaattttgcggaagtgtcacacaataa LVL318 (protein): (pelB sp)(MD)(ProtE aa 22- 160)(GG)(PilA aa40- 149) - SEQ ID NO. 150:
MKYLLPTAAA GLLLLAAQPA MAMDKAEQND VKLAPPTDVR SGYIRLVKNV

NYYIDSESIW VDNQEPQIVH FDAVVNLDKG LYVYPEPKRY ARSVRQYKIL

NCANYHLTQV RTDFYDEFWG QGLRAAPKKQ KKHTLSLTPD TTLYNAAQII

CANYGEAFSV DKKGGTKKAA VSELLQASAP YKADVELCVY STNETTNCTG

GKNGIAADIT TAKGYVKSVT TSNGAITVKG DGTLANMEYI LQATGNAATG

VTWTTTCKGT DASLFPANFC GSVTQ

LVL702 (DNA) - SEQ ID NO. 181:
atgaaatacctgctgccgaccgctgctgctggtctgctgctcctcgctgcccagccggcgatggccattcagaaggctgaacaaaa tgatgtgaagctggcaccgccgactgatgtacgaagcggatatatacgtttggtaaagaatgtgaattattacatcgatagtgaatcg atctgggtggataaccaagagccacaaattgtacattttgatgcagtggtgaatttagataagggattgtatgtttatcctgagcctaaa cgttatgcacgttctgttcgtcagtataagatcttgaattgtgcaaattatcatttaactcaagtacgaactgatttctatgatgaattttggg gacagggtttgcgggcagcacctaaaaagcaaaagaaacatacgttaagtttaacacctgatacaacgctttataatgctgctcag attatttgtgcgaactatggtgaagcattttcagttgataaaaaaggcggcactaaaaaagcagcggtatctgaattactgcaagcgt cagcgccttataaggctgatgtggaattatgtgtatatagcacaaatgaaacaacaaactgtacgggtggaaaaaatggtattgca gcagatataaccacagcaaaaggctatgtaaaatcagtgacaacaagcaacggtgcaataacagtaaaaggggatggcacat tggcaaatatggaatatattttgcaagctacaggtaatgctgcaacaggtgtaacttggacaacaacttgcaaaggacggatgcc tctttatttccagcaaattttgcggaagtgtcacacaaggcggccaccaccaccaccac LVL702 (protein): (pelB sp)(ProtE aa 20- 160)(GG)(PilA aa40- 149)(GGHHHHHH) - SEQ ID
NO. 182:
MKYLLPTAAA GLLLLAAQPA MAIQKAEQND VKLAPPTDVR SGYIRLVKNV

NYYIDSESIW VDNQEPQIVH FDAVVNLDKG LYVYPEPKRY ARSVRQYKIL

NCANYHLTQV RTDFYDEFWG QGLRAAPKKQ KKHTLSLTPD TTLYNAAQII

CANYGEAFSV DKKGGTKKAA VSELLQASAP YKADVELCVY STNETTNCTG

GKNGIAADIT TAKGYVKSVT TSNGAITVKG DGTLANMEYI LQATGNAATG

VTWTTTCKGT DASLFPANFC GSVTQGGHHH HHH

LVL736 (DNA) - SEQ ID NO. 183:
atgaaatacctgctgccgaccgctgctgctggtctgctgctcctcgctgcccagccggcgatggccagcgcccagattcagaaggc tgaacaaaatgatgtgaagctggcaccgccgactgatgtacgaagcggatatatacgtttggtaaagaatgtgaattattacatcga tagtgaatcgatctgggtggataaccaagagccacaaattgtacattttgatgcagtggtgaatttagataagggattgtatgtttatcct gagcctaaacgttatgcacgttctgttcgtcagtataagatcttgaattgtgcaaattatcatttaactcaagtacgaactgatttctatgat gaattttgggacaggggtttgcgggcagcacctaaaaagcaaaagaaacatacgttaagtttaacacctgatacaacgctttataa tgctgctcagattatttgtgcgaactatggtgaagcattttcagttgataaaaaaggcggcactaaaaaagcagcggtatctgaatta ctgcaagcgtcagcgccttataaggctgatgtggaattatgtgtatatagcacaaatgaaacaacaaactgtacgggtggaaaaa atggtattgcagcagatataaccacagcaaaaggctatgtaaaatcagtgacaacaagcaacggtgcaataacagtaaaaggg gatggcacattggcaaatatggaatatattttgcaagctacaggtaatgctgcaacaggtgtaacttggacaacaacttgcaaagg aacggatgcctctttatttccagcaaattttgcggaagtgtcacacaaggcggccaccaccaccaccac LVL736 (protein): (pelB sp)(ProtE aa 17-160)(GG)(PilA aa40-149)(GGHHHHHH) - SEQ ID
NO. 184:
MKYLLPTAAA GLLLLAAQPA MASAQIQKAE QNDVKLAPPT DVRSGYIRLV

KNVNYYIDSE SIWVDNQEPQ IVHFDAVVNL DKGLYVYPEP KRYARSVRQY

KILNCANYHL TQVRTDFYDE FWGQGLRAAP KKQKKHTLSL TPDTTLYNAA

QIICANYGEA FSVDKKGGTK KAAVSELLQA SAPYKADVEL CVYSTNETTN

CTGGKNGIAA DITTAKGYVK SVTTSNGAIT VKGDGTLANM EYILQATGNA

ATGVTWTTTC KGTDASLFPA NFCGSVTQGG HHHHHH

LVL737 (DNA) - SEQ ID NO. 185:
atgaaatacctgctgccgaccgctgctgctggtctgctgctcctcgctgcccagccggcgatggccgcccagattcagaaggctga acaaaatgatgtgaagctggcaccgccgactgatgtacgaagcggatatatacgtttggtaaagaatgtgaattattacatcgatag tgaatcgatctgggtggataaccaagagccacaaattgtacattttgatgcagtggtgaatttagataagggattgtatgtttatcctga gcctaaacgttatgcacgttctgttcgtcagtataagatcttgaattgtgcaaattatcatttaactcaagtacgaactgatttctatgatga attttggggacagggtttgcgggcagcacctaaaaagcaaaagaaacatacgttaagtttaacacctgatacaacgctttataatgc tgctcagattatttgtgcgaactatggtgaagcattttcagttgataaaaaaggcggcactaaaaaagcagcggtatctgaattactg caagcgtcagcgccttataaggctgatgtggaattatgtgtatatagcacaaatgaaacaacaaactgtacgggtggaaaaaatg gtattgcagcagatataaccacagcaaaaggctatgtaaaatcagtgacaacaagcaacggtgcaataacagtaaaagggat ggcacattggcaaatatggaatatattttgcaagctacaggtaatgctgcaacaggtgtaacttggacaacaacttgcaaaggaac ggatgcctctttatttccagcaaattttgcggaagtgtcacacaaggcggccaccaccaccaccac LVL737 (protein): (pelB sp)(ProtE aa 18-160)(GG)(PilA aa40-149)(GGHHHHHH) - SEQ ID NO. 186:
MKYLLPTAAA GLLLLAAQPA MAAQIQKAEQ NDVKLAPPTD VRSGYIRLVK

NVNYYIDSES IWVDNQEPQI VHFDAVVNLD KGLYVYPEPK RYARSVRQYK

ILNCANYHLT QVRTDFYDEF WGQGLRAAPK KQKKHTLSLT PDTTLYNAAQ

IICANYGEAF SVDKKGGTKK AAVSELLQAS APYKADVELC VYSTNETTNC

TGGKNGIAAD ITTAKGYVKS VTTSNGAITV KGDGTLANME YILQATGNAA

TGVTWTTTCK GTDASLFPAN FCGSVTQGGH HHHHH

LVL738 (DNA) - SEQ ID NO. 187:
atgaaatacctgctgccgaccgctgctgctggtctgctgctcctcgctgcccagccggcgatggccaaggctgaacaaaatgatgt gaagctggcaccgccgactgatgtacgaagcggatatatacgtttggtaaagaatgtgaattattacatcgatagtgaatcgatctg ggtggataaccaagagccacaaattgtacattttgatgcagtggtgaatttagataagggattgtatgtttatcctgagcctaaacgtta tgcacgttctgttcgtcagtataagatcttgaattgtgcaaattatcatttaactcaagtacgaactgatttctatgatgaattttggggaca gggtttgcgggcagcacctaaaaagcaaagaaacatacgttaagtttaacacctgatacaacgctttataatgctgctcagattatt tgtgcgaactatggtgaagcattttcagttgataaaaaaggcggcactaaaaaagcagcggtatctgaattactgcaagcgtcagc gccttataaggctgatgtggaattatgtgtatatagcacaaatgaaacaacaaactgtacgggtggaaaaaatggtattgcagcag atataaccacagcaaaaggctatgtaaaatcagtgacaacaagcaacggtgcaataacagtaaaaggggatggcacattggca aatatggaatatattttgcaagctacaggtaatgctgcaacaggtgtaacttggacaacaacttgcaaaggaacggatgcctctttatt tccagcaaattttgcggaagtgtcacacaaggcggccaccaccaccaccac LVL738 (protein): (pelB sp)(ProtE aa 22-160)(GG)(PilA aa40-149)(GGHHHHHH) - SEQ ID NO. 188:
MKYLLPTAAA GLLLLAAQPA MAKAEQNDVK LAPPTDVRSG YIRLVKNVNY

YIDSESIWVD NQEPQIVHFD AVVNLDKGLY VYPEPKRYAR SVRQYKILNC

ANYHLTQVRT DFYDEFWGQG LRAAPKKQKK HRLSLTPDTT LYNAAQIICA

NYGEAFSVDK KGGTKKAAVS ELLQASAPYK ADVELCVYST NETTNCTGGK

NGIAADITTA KGYVKSVTTS NGAITVKGCG TLANMEYILQ ATGNAATGVT

WTTTCKGTDA SLFPANFCGS VTQGGHHHHH H

LVL739 (DNA) - SEQ ID NO. 189:
atgaaatacctgctgccgaccgctgctgctggtctgctgctcctcgctgcccagccggcgatggccgctgaacaaaatgatgtgaa gctggcaccgccgactgatgtacgaagcggatatatacgtttggtaaagaatgtgaattattacatcgatagtgaatcgatctgggtg gataaccaagagccacaaattgtacattttgatgcagtggtgaatttagataagggattgtatgtttatcctgagcctaaacgttatgca cgttctgttcgtcagtataagatcttgaattgtgcaaattatcatttaactcaagtacgaactgatttctatgatgaattttggggacagggt ttgcgggcagcacctaaaaagcaaagaaacatacgttaagtttaacacctgatacaacgctttataatgctgctcagattatttgtg cgaactatggtgaagcattttcagttgataaaaaaggcggcactaaaaaagcagcggtatctgaattactgcaagcgtcagcgcct tataaggctgatgtggaattatgtgtatatagcacaaatgaaacaacaaactgtacgggtggaaaaaatggtattgcagcagatat aaccacagcaaaaggctatgtaaaatcagtgacaacaagcaacggtgcaataacagtaaaaggggatggcacattggcaaat

```
atggaatatattttgcaagctacaggtaatgctgcaacaggtgtaacttggacaacaacttgcaaaggaacggatgcctctttatttcc agcaaattttttgcggaagtgtcacacaaggcggccaccaccaccaccaccac
```

LVL739 (protein): (pelB sp)(ProtE aa 23-160)(GG)(PilA aa40-149)(GGHHHHHH) - SEQ ID NO. 190:

```
MKYLLPTAAA GLLLLAAQPA MAAEQNDVKL APPTDVRSGY IRLVKNVNYY

IDSESIWVDN QEPQIVHFDA VVNLDKGLYV YPEPKRYARS VRQYKILNCA

NYHLTQVRTD FYDEFWGQGL RAAPKKQKKH TLSLTPDTTL YNAAQIICAN

YGEAFSVDKK GGTKKAAVSE LLQASAPYKA DVELCVYSTN ETTNCTGGKN

GIAADITTAK GYVKSVTTSN GAITVKGDGT LANMEYILQA TGNAATGVTW

TTTCKGTDAS LFPANFCGSV TQGGHHHHHH
```

LVL740 (DNA) - SEQ ID NO. 191:
```
atgaaatacctgctgccgaccgctgctgctggtctgctgctcctcgctgcccagccggcgatggccgaacaaaatgatgtgaagct ggcaccgccgactgatgtacgaagcggatatatacgtttggtaaagaatgtgaattattacatcgatagtgaatcgatctgggtggat aaccaagagccacaaattgtacattttgatgcagtggtgaatttagataagggattgtatgtttatcctgagcctaaacgttatgcacgt tctgttcgtcagtataagatcttgaattgtgcaaattatcatttaactcaagtacgaactgatttctatgatgaattttggggacagggtttg cgggcagcacctaaaaagcaaaagaaacatacgttaagtttaacacctgatacaacgctttataatgctgctcagattatttgtgcg aactatggtgaagcattttcagttgataaaaaaggcggcactaaaaaagcagcggtatctgaattactgcaagcgtcagcgccttat aaggctgatgtggaattatgtgtatatagcacaaatgaaacaacaaactgtacgggtggaaaaaatggtattgcagcagatataac cacagcaaaaggctatgtaaaatcagtgacaacaagcaacggtgcaataacagtaaaaggggatggcacattggcaaatatg gaatatattttgcaagctacaggtaatgctgcaacaggtgtaacttggacaacaacttgcaaaggaacggatgcctctttatttccag caaattttttgcggaagtgtcacacaaggcggccaccaccaccaccaccac
```

LVL740 (protein): (pelB sp)(ProtE aa 24-160)(GG)(PilA aa40-149)(GGHHHHHH) - SEQ ID NO. 192:

```
MKYLLPTAAA GLLLLAAQPA MAEQNDVKLA PPTDVRSGYI RLVKNVNYYI

DSESIWVDNQ EPQIVHFDAV VNLDKGLYVY PEPKRYARSV RQYKILNCAN

YHLTQVRTDF YDEFWGQGLR AAPKKQKKHT LSLTPDTTLY NAAQIICANY

GEAFSVDKKG GTKKAAVSEL LQASAPYKAD VELCVYSTNE TTNCTGGKNG

IAADITTAKG YVKSVTTSNG AITVKGDGTL ANMEYILQAT GNAATGVTWT

TTCKGTDASL FPANFCGSVT QGGHHHHHH
```

LVL735 (DNA) - SEQ ID NO. 193:
```
atgaaatacctgctgccgaccgctgctgctggtctgctgctcctcgctgcccagccggcgatggccattcagaaggctgaacaaaa tgatgtgaagctggcaccgccgactgatgtacgaagcggatatatacgtttggtaaagaatgtgaattattacatcgatagtgaatcg atctgggtggataaccaagagccacaaattgtacattttgatgcagtggtgaatttagataagggattgtatgtttatcctgagcctaaa cgttatgcacgttctgttcgtcagtataagatcttgaattgtgcaaattatcatttaactcaagtacgaactgatttctatgatgaatttggg gacagggtttgcgggcagcacctaaaaagcaaaagaaacatacgttaagtttaacacctgatacaacgctttataatgctgctcag attatttgtgcgaactatggtgaagcattttcagttgataaaaaaggcggcactaaaaaagcagcggtatctgaattactgcaagcgt cagcgccttataaggctgatgtggaattatgtgtatatagcacaaatgaaacaacaaactgtacgggtggaaaaaatggtattgca gcagatataaccacagcaaaaggctatgtaaaatcagtgacaacaagcaacggtgcaataacagtaaaaggggatggcacatt
``` ggcaaatatggaatatattttgcaagctacaggtaatgctgcaacaggtgtaacttggacaacaacttgcaaaggaacggatgcct ctttatttccagcaaattttgcggaagtgtcacacaa LVL735 (protein): (pelB sp)(ProtE aa 20-160)(GG)(PilA aa40-149) - SEQ ID NO. 194:
MKYLLPTAAA GLLLLAAQPA <u>MAIQKAEQND VKLAPPTDVR SGYIRLVKNV</u>

<u>NYYIDSESIW VDNQEPQIVH FDAVVNLDKG LYVYPEPKRY ARSVRQYKIL</u>

<u>NCANYHLTQV RTDFYDEFWG QGLRAAPKKQ KKHTLSLTPD TTLYNAAQII</u>

<u>CANYGEAFSV DKKGGTKKAA VSELLQASAP YKADVELCVY STNETTNCTG</u>

<u>GKNGIAADIT TAKGYVKSVT TSNGAITVKG DGTLANMEYI LQATGNAATG</u>

<u>VTWTTTCKGT DASLFPANFC GSVTQ</u>

LVL778 (DNA) - SEQ ID NO. 195:
atgaaatacctgctgccgaccgctgctgctggtctgctgctcctcgctgcccagccggcgatggccagcgcccagattcagaaggc tgaacaaaatgatgtgaagctggcaccgccgactgatgtacgaagcggatatatacgtttggtaaagaatgtgaattattacatcga tagtgaatcgatctgggtggataaccaagagccacaaattgtacattttgatgcagtggtgaatttagataagggattgtatgtttatcct gagcctaaacgttatgcacgttctgttcgtcagtataagatcttgaattgtgcaaattatcatttaactcaagtacgaactgatttctatgat gaattttggggacagggtttgcgggcagcacctaaaaagcaaaagaaacatacgttaagtttaacacctgatacaacgctttataat gctgctcagattatttgtgcgaactatggtgaagcattttcagttgataaaaaaggcggcactaaaaaagcagcggtatctgaattac tgcaagcgtcagcgccttataaggctgatgtggaattatgtgtatatagcacaaatgaaacaacaaactgtacgggtggaaaaaat ggtattgcagcagatataaccacagcaaaaggctatgtaaaatcagtgacaacaagcaacggtgcaataacagtaaaagggg atggcacattggcaaatatggaatatattttgcaagctacaggtaatgctgcaacaggtgtaacttggacaacaacttgcaaagga acggatgcctctttatttccagcaaattttgcggaagtgtcacacaa LVL778 (protein): (pelB sp)(ProtE aa 17-160)(GG)(PilA aa40-149) - SEQ ID NO. 196:
MKYLLPTAAA GLLLLAAQPA MAS<u>AQIQKAE QNDVKLAPPT DVRSGYIRLV</u>

<u>KNVNYYIDSE SIWVDNQEPQ IVHFDAVVNL DKGLYVYPEP KRYARSVRQY</u>

<u>KILNCANYHL TQVRTDFYDE FWGQGLRAAP KKQKKHTLSL TPDTTLYNAA</u>

<u>QIICANYGEA FSVDKKGGTK KAAVSELLQA SAPYKADVEL CVYSTNETTN</u>

<u>CTGGKNGIAA DITTAKGYVK SVTTSNGAIT VKGDGTLANM EYILQATGNA</u>

<u>ATGVTWTTTC KGTDASLFPA NFCGSVTQ</u>

LVL779 (DNA) - SEQ ID NO. 197:
atgaaatacctgctgccgaccgctgctgctggtctgctgctcctcgctgcccagccggcgatggccgcccagattcagaaggctga acaaaatgatgtgaagctggcaccgccgactgatgtacgaagcggatatatacgtttggtaaagaatgtaattattacatcgatag tgaatcgatctgggtggataaccaagagccacaaattgtacattttgatgcagtggtgaatttagataagggattgtatgtttatcctga gcctaaacgttatgcacgttctgttcgtcagtataagatcttgaattgtgcaaattatcatttaactcaagtacgaactgatttctatgatga attttggggacagggtttgcgggcagcacctaaaaagcaaaagaaacatacgttaagtttaacacctgatacaacgctttataatgc tgctcagattatttgtgcgaactatggtgaagcattttcagttgataaaaaaggcggcactaaaaaagcagcggtatctgaattactg caagcgtcagcgccttataaggctgatgtggaattatgtgtatatagcacaaatgaaacaacaaactgtacgggtggaaaaaatg gtattgcagcagatataaccacagcaaaaggctatgtaaaatcagtgacaacaagcaacggtgcaataacagtaaaagggat ggcacattggcaaatatggaatatattttgcaagctacaggtaatgctgcaacaggtgtaacttggacaacaacttgcaaaggaac ggatgcctctttatttccagcaaattttttgcggaagtgtcacacaa LVL779 (protein): (pelB sp)(ProtE aa 18-160)(GG)(PilA aa40-149) - SEQ ID NO. 198:
MKYLLPTAAA GLLLLAAQPA MAAQIQKAEQ NDVKLAPPTD VRSGYIRLVK

NVNYYIDSES IWVDNQEPQI VHFDAVVNLD KGLYVYPEPK RYARSVRQYK

ILNCANYHLT QVRTDFYDEF WGQGLRAAPK KQKKHTLSLT PDTTLYNAAQ

IICANYGEAF SVDKKGGTKK AAVSELLQAS APYKADVELC VYSTNETTNC

TGGKNGIAAD ITTAKGYVKS VTTSNGAITV KGDGTLANME YILQATGNAA

TGVTWTTTCK GTDASLFPAN FCGSVTQ

LVL780 (DNA) - SEQ ID NO. 199:
atgaaatacctgctgccgaccgctgctgctggtctgctgctcctcgctgcccagccggcgatggccaaggctgaacaaaatgatgt gaagctggcaccgccgactgatgtacgaagcggatatatacgtttggtaaagaatgtgaattattacatcgatagtgaatcgatctg ggtggataaccaagagccacaaattgtacattttgatgcagtggtgaatttagataagggattgtatgtttatcctgagcctaaacgtta tgcacgttctgttcgtcagtataagatcttgaattgtgcaaattatcatttaactcaagtacgaactgatttctatgatgaattttggggaca gggtttgcgggcagcacctaaaaagcaaagaaacatacgttaagtttaacacctgatacaacgctttataatgctgctcagattatt tgtgcgaactatggtgaagcattttcagttgataaaaaaggcggcactaaaaaagcagcggtatctgaattactgcaagcgtcagc gccttataaggctgatgtggaattatgtgtatatagcacaaatgaaacaacaaactgtacgggtggaaaaaatggtattgcagcag atataaccacagcaaaaggctatgtaaaatcagtgacaacaagcaacggtgcaataacagtaaaagggatggcacattggca aatatggaatatattttgcaagctacaggtaatgctgcaacaggtgtaacttggacaacaacttgcaaaggaacggatgcctctttatt tccagcaaattttttgcggaagtgtcacacaa LVL780 (protein): (pelB sp)(ProtE aa 22-160)(GG)(PilA aa40-149) - SEQ ID NO. 200:
MKYLLPTAAA GLLLLAAQPA MAKAEQNDVK LAPPTDVRSG YIRLVKNVNY

YIDSESIWVD NQEPQIVHFD AVVNLDKGLY VYPEPKRYAR SVRQYKILNC

ANYHLTQVRT DFYDEFWGQG LRAAPKKQKK HTLSLTPDTT LYNAAQIICA

NYGEAFSVDK KGGTKKAAVS ELLQASAPYK ADVELCVYST NETTNCTGGK

NGIAADITTA KGYVKSVTTS NGAITVKGDG TLANMEYILQ ATGNAATGVT

WTTTCKGTDA SLFPANFCGS VTQ

LVL781 (DNA) - SEQ ID NO. 201:
atgaaatacctgctgccgaccgctgctgctggtctgctgctcctcgctgcccagccggcgatggccgctgaacaaaatgatgtgaa gctggcaccgccgactgatgtacgaagcggatatatacgtttggtaaagaatgtgaattattacatcgatagtgaatcgatctgggtg gataaccaagagccacaaattgtacattttgatgcagtggtgaatttagataagggattgtatgtttatcctgagcctaaacgttatgca cgttctgttcgtcagtataagatcttgaattgtgcaaattatcatttaactcaagtacgaactgatttctatgatgaattttggggacagggt ttgcgggcagcacctaaaaagcaaagaaacatacgttaagtttaacacctgatacaacgctttataatgctgctcagattatttgtg cgaactatggtgaagcattttcagttgataaaaaaggcggcactaaaaaagcagcggtatctgaattactgcaagcgtcagcgcct tataaggctgatgtggaattatgtgtatatagcacaaatgaaacaacaaactgtacgggtggaaaaaatggtattgcagcagatat aaccacagcaaaaggctatgtaaaatcagtgacaacaagcaacggtgcaataacagtaaaaggggatggcacattggcaaat atggatatattttgcaagctacaggtaatgctgcaacaggtgtaacttggacaacaacttgcaaaggaacggatgcctctttatttcc agcaaattttgcggaagtgtcacacaa LVL781 (protein): (pelB sp)(ProtE aa 23-160)(GG)(PilA aa40-149) - SEQ ID NO. 202:
MKYLLPTAAA GLLLLAAQPA MAAEQNDVKL APPTDVRSGY IRLVKNVNYY

IDSESIWVDN QEPQIVHFDA VVNLDKGLYV YPEPKRYARS VRQYKILNCA

NYHLTQVRTD FYDEFWGQGL RAAPKKQKKH TLSLTPDTTL YNAAQIICAN

YGEAFSVDKK GGTKKAAVSE LLQASAPYKA DVELCVYSTN ETTNCTGGKN

GIAADITTAK GYVKSVTTSN GAITVKGDGT LANMEYILQA TGNAATGVTW

TTTCKGTDAS LFPANFCGSV TQ

LVL782 (DNA) - SEQ ID NO. 203:
atgaaatacctgctgccgaccgctgctgctggtctgctgctcctcgctgcccagccggcgatggccgaacaaaatgatgtgaagct ggcaccgccgactgatgtacgaagcggatatatacgtttggtaaagaatgtgaattattacatcgatagtgaatcgatctgggtggat aaccaagagccacaaattgtacattttgatgcagtggtgaatttagataaggggattgtatgtttatcctgagcctaaacgttatgcacgt tctgttcgtcagtataagatcttgaattgtgcaaattatcatttaactcaagtacgaactgatttctatgatgaattttggggacagggtttg cgggcagcacctaaaaagcaaaagaaacatacgttaagtttaacacctgatacaacgctttataatgctgctcagattatttgtgcg aactatggtgaagcattttcagttgataaaaaaggcggcactaaaaaagcagcggtatctgaattactgcaagcgtcagcgccttat aaggctgatgtggaattatgtgtatatagcacaaatgaaacaacaaactgtacgggtggaaaaaatggtattgcagcagatataac cacagcaaaaggctatgtaaaatcagtgacaacaagcaacggtgcaataacagtaaaaggggatggcacattggcaaatatg gaatatattttgcaagctacaggtaatgctgcaacaggtgtaacttggacaacaacttgcaaaggaacggatgcctctttatttccag caaattttgcggaagtgtcacacaa LVL782 (protein): (pelB sp)(ProtE aa 24-160)(GG)(PilA aa40-149) - SEQ ID NO. 204:
MKYLLPTAAA GLLLLAAQPA MAEQNDVKLA PPTDVRSGYI RLVKNVNYYI

DSESIWVDNQ EPQIVHFDAV VNLDKGLYVY PEPKRYARSV RQYKILNCAN

YHLTQVRTDF YDEFWGQGLR AAPKKQKKHT LSLTPDTTLY NAAQIICANY

GEAFSVDKKG GTKKAAVSEL LQASAPYKAD VELCVYSTNE TTNCTGGKNG

IAADITTAKG YVKSVTTSNG AITVKGDGTL ANMEYILQAT GNAATGVTWT

TTCKGTDASL FPANFCGSVT Q

The full length sequence for PE and PilA from which the above sequences were obtained are set forth in SEQ ID NO. 4 (PE) and SEQ ID NO. 58 (PilA), respectively.

Example 2

Vector Construction and Transformation

Primers for amplifying PE from *H. influenzae* strain 772 were designed based on the sequence of *H. influenzae* strain Hi Rd. The 5' primer sequence contains one nucleotide difference compared to the NTHi 772 sequence, introducing an amino acid difference at position 24 when compared with the currently reported NTHi 772 genome sequence. Amino acid #24 in the fusion protein constructs is E (glutamic acid) instead of K (lysine) as found in NTHi 772.

cific components are subsequently exemplified): 36.6 µl of deionized water, 5 µl of buffer #1 10×, 5 µl of dNTPs 2 mM, 2 µl MgCl$_2$ 25 mM, 0.4 µl of primer #1 (50 µM), 0.4 µl of primer #2 (50 µM), 0.5 µl of template (100 ng/µl) and 0.4 µl of KOD HiFi DNA polymerase 2.5 units/µl (NOVAGEN®) was formulated. Polymerase chain reaction involved 25 cycles of 15 seconds of denaturation at 98° C., 2 seconds for annealing at 55° C. and 20 seconds of primer extension at 72° C. The PCR products were purified using QIAQUICK® PCR purification kit (QIAGEN®). This product was used under conditions recommended by the supplier which were: the addition of 5 volumes Buffer PB, provided in the QIAQUICK® PCR purification kit, to 1 volume of the PCR preparation. The PCR preparation with Buffer PB was subsequently mixed by vortex. A QIAQUICK® column was placed into a 2 ml collection tube. To bind DNA in the PCR preparation to the

```
DNA Sequence for PE from H. influenzae strain Rd.
                                                                         SEQ ID NO. 151
atgaaaaaaattattttaacattatcacttgggttacttaccgcttgttctgctcaaatccaaaaggctgaacaaaatgatgtgaagctg gcaccgccgactgatgtacgaagcggatatatacgtttggtaaagaatgtgaattattacatcgatagtgaatcgatctgggtggata accaagagccacaaattgtacattttgatgctgtggtgaatttagataggggattgtatgtttatcctgagcctaaacgttatgcacgttc tgttcgtcagtataagattttgaattgtgcaaattatcatttaactcaaatacgaactgatttctatgatgaattttggggacagggtttgcg ggcagcacctaaaaagcaaaagaaacatacgttaagtttaacacctgatacaacgctttataatgctgctcagattatttgtgcaaat tatggtaaagcattttcagttgataaaaaataa
Protein Sequence for PE from H. influenzae strain Rd.
                                                                         SEQ ID NO. 152
MKKIILTLSL GLLTACSAQI QKAEQNDVKL APPTDVRSGY IRLVKNVNYY

IDSESIWVDN QEPQIVHFDA VVNLDRGLYV YPEPKRYARS VRQYKILNCA

NYHLTQIRTD FYDEFWGQGL RAAPKKQKKH TLSLTPDTTL YNAAQIICAN

YGKAFSVDKK

DNA Sequence for PE from H. influenzae strain 772 (as set forth in: Microbes & Infection,
Corrigendum to "Identification of a novel Haemophilus influenzae protein important for
adhesion to epithelia cells" [Microbes Infect. 10 (2008) 87-97], available online
Jul. 6, 2010, "Article in Press"))
                                                                         SEQ ID NO. 153
atgaaaaaaattattttaacattatcacttgggttacttactgcctgttctgctcaaatccaaaaggctaaacaaaatgatgtgaagctg gcaccgccgactgatgtacgaagcggatatatacgtttggtaaagaatgtgaattattacatcgatagtgaatcgatctgggtggata accaagagccacaaattgtacattttgatgcagtggtgaatttagataagggattgtatgtttatcctgagcctaaacgttatgcacgtt ctgttcgtcagtataagatcttgaattgtgcaaattatcatttaactcaagtacgaactgatttctatgatgaattttggggacagggtttgc gggcagcacctaaaaagcaaaagaaacatacgttaagtttaacacctgatacaacgctttataatgctgctcagattatttgtgcga actatggtaagcattttcagttgataaaaaa
Protein Sequence for PE from H. influenzae strain 772 (as set forth in: Microbes & Infection,
Corrigendum to "Identification of a novel Haemophilus influenzae protein important for
adhesion to epithelia cells" [Microbes Infect. 10 (2008) 87-97], available online
Jul. 6, 2010, "Article in Press"))
                                                                         SEQ ID NO. 154
MKKIILTLSL GLLTACSAQI QKAKQNDVKL APPTDVRSGY IRLVKNVNYY

IDSESIWVDN QEPQIVHFDA VVNLDKGLYV YPEPKRYARS VRQYKILNCA

NYHLTQVRTD FYDEFWGQGL RAAPKKQKKH TLSLTPDTTL YNAAQIICAN

YGEAFSVDKK
```

Vector Construction:

To generate LVL312, LVL291, LVL268, LVL269, LVL270, LVL702, LVL735, LVL778, LVL779, LVL780, LVL781 and LVL782, a polymerase chain reaction (PCR) preparation of the following components was prepared (specolumn, the mixed sample was applied to the QIAQUICK® column and centrifuged for 30-60 seconds at 14 000 RPM. The flow-through was discarded and the QIAQUICK® column was placed back in the same tube. To wash the bound DNA 0.75 ml Buffer PE, provided in the QIAQUICK® PCR purification kit, was added to the QIAQUICK® column, and the column was centrifuged for 30-60 seconds at 14 000 RPM. The flow-through was discarded and the QIAQUICK® column was placed back in the same tube. The QIAQUICK® column was centrifuged once more in the 2 ml collection tube for 1 minute to remove residual wash buffer. Each QIAQUICK® column was placed in a clean 1.5 ml microcentrifuge tube. To elute the DNA, 33 µl water was added to the center of the QIAQUICK® membrane and the column was centrifuged for 1 minute at 14 000 RPM. Restriction enzymes and buffer related were obtained from New England BioLabs. For example, approximately 5 µl of pET26b vector (100 ng/µl), 2 µl of NEBuffer 2 (New England Biolabs, 1× NEBuffer 2: 50 mM NaCl, 10 mM Tris-HCl, 10 mM $MgCl_2$, 1 mM dithiothreitol, pH 7.9 at 25° C.), 1 µl of NdeI (20 000 units/ml), 1 µl of HindIII (20 000 units/ml) and 11 µl of deionized water were mixed and incubated for two hours at 37° C. for DNA digestion. Thereafter, a second step of purification was performed using the QIAQUICK® PCR purification kit (QIAGEN®) with the procedure described above.

Ligation was performed using Quick T4 DNA ligase and Quick Ligation Reaction Buffer from New England BioLabs. For example, around 10 ng of vector and 30 ng of insert in 10 µl of deionized water were mixed with 10 µl of 2× Quick Ligation Reaction Buffer (New England Biolabs, 132 mM Tris-HCl, 20 mM $MgCl_2$, 2 mM dithiothreitol, 2 mM ATP, 15% polyethylene glycol, pH 7.6 at 25° C.) and 1 µl of Quick T4 DNA ligase (New England Biolabs). The enzymatic reaction was incubated for 5 minutes at room temperature before transformation.

To generate LVL315, LVL317, LVL318, LVL736, LVL737, LVL738, LVL739 and LVL740, a PCR preparation of the following components was prepared: 40 µl of deionized water, 5 µl of reaction buffer 10×, 1 µl of dNTPs mix, 1 µl of primer #1 (10 µM), 1 µl of primer #2 (10 µM), 1 µl of template (25 ng/µl) and 1 µl of PfuUltra High-Fidelity DNA polymerase 2.5 units/µl (QuikChange II Site-Directed Mutagenesis Kit, Agilent Technologies, Stratagene Division) was formulated. Polymerase chain reaction involved one cycle of denaturation at 95° C. for 30 sec, 18 cycles of 30 sec of denaturation at 95° C., 1 min for annealing at 55° C. and 5 min 30 sec of primer extension at 68° C. The PCR products were digested using 1 µl of DpnI restriction enzyme at 37° C. for one hour before transformation.

A detailed list of PCR primer sequences used for amplifications is illustrated in Table 4.

To generate pRIT16711, the PE gene fragment coding for amino acids 22 to 160 of SEQ ID NO. 4, which excludes the sequence coding for its corresponding secretion signal, was amplified by PCR from genomic DNA of NTHi strain 772. The amplification primers were designed based on the available strain Hi Rd sequence (at that time, the 772 sequence was not known). The 5' primer sequence contains one mutation compared to the NTHi 772 sequence (sequence as now available), introducing one amino acid difference in PE coding sequence at position 24, glutamic acid (E) instead of lysine (K). After PCR amplification, the insert was cloned in the pET-26(+) expression vector (NOVAGEN®) using BamHI and XhoI restriction sites.

To generate pRIT16671, a DNA fragment coding for a PilA gene fragment (amino acids 40 to 149 of SEQ ID NO. 58, SEQ ID NO. 127), which excludes its leader peptide as well as a portion of the predicted hydrophobic alpha helix, was amplified from genomic DNA of NTHi strain 86-028NP and cloned into the pET15 expression vector. The vector pRIT16790 (containing amino acids 40 to 149 from NTHi strain 86-028NP) was used as a template to generate the vector pRIT16671. The PilA gene fragment was amplified by PCR using the vector pRIT16790 and primers MDES PILA-3 and MDES PILA-4. The PilA fragment was cloned into the pET-26 expression vector using NdeI/XhoI restriction sites. The DNA sequence encoding six histidine (his) amino acids was incorporated into the 5' primer to add six histidines (6×his) at the N-terminal end of the PilA sequence (MDES PILA-3).

To generate LVL312 (FlgI signal peptide-E-PilA fragment-GG-PE fragment-GGHHHHHH), a polymerase chain reaction was performed to amplify the PilA gene (amino acids 40-149/strain 86-028NP) using the pRIT16671 vector as a template and primers CAN534 and CAN537. DNA sequence corresponding to FlgI signal peptide (sp) and glutamic acid (E) amino acid was incorporated into the 5' primer (CAN534). To link the PilA sequence to PE sequence, DNA sequence corresponding to the two glycine (GG) amino acids linker and the N-terminal PE amino acids were incorporated into the 3' primer (CAN537). Another polymerase chain reaction was performed to amplify the PE gene (amino acids 18-160) using pRIT16711 vector as a template and primers CAN536 and CAN538. DNA sequence corresponding to the C-terminal PilA amino acids and GG amino acids were incorporated into the 5' primer to link pilA to PE sequence (CAN536). DNA sequence corresponding to the GG amino acids linker and 6×his amino acids were incorporated into the 3' primer (CAN538). Finally, to generate LVL312, a third polymerase chain reaction was performed to amplify the PilA and PE genes in fusion with the FlgI signal peptide at the N-terminus, a glutamic acid (E) amino acid between FlgI and pilA, a GG linker between PilA and PE sequences and a GG linker between PE and the 6×his amino acids at the C-terminus. To achieve this amplification, the products of the two polymerase chain reactions described above were used as a template with primers CAN534 and CAN538. DNA sequence corresponding to NdeI restriction site was incorporated into the 5' primer and HindIII restriction site was incorporated into the 3' primer. The generated PCR product was then inserted into the pET-26b(+) cloning vector) (NOVAGEN®).

To generate LVL291 (pelB signal peptide-PE fragment-GG-PilA fragment-GG-6×his), a polymerase chain reaction was performed to amplify the PE gene (amino acids 19-160) using the pRIT16711 vector as a template and primers CAN544 and CAN546. DNA sequence corresponding to pelB signal peptide (sp) amino acids was incorporated into the 5' primer (CAN544). To link the PilA sequence to the PE sequence, DNA sequence corresponding to GG amino acids linker and the N-terminal PilA amino acids were incorporated into the 3' primer (CAN546). Another polymerase chain reaction was performed to amplify the PilA gene (amino acids 40-149 of SEQ ID NO. 58, SEQ ID NO. 127) using the pRIT16671 vector as a template with primers CAN545 and CAN535. DNA sequence corresponding to the C-terminal PE amino acids and GG amino acids were incorporated into the 5' primer (CAN545) to link the PilA sequence to the PE sequence. DNA sequence corresponding to linker GG amino acids and 6×his amino acids were incorporated into the 3' primer (CAN535). Finally, to generate LVL291, a third polymerase chain reaction was performed to amplify the PE and PilA genes in fusion with the pelB signal peptide at the N-terminus, a GG linker between the PE and PilA sequences and a GG linker between PilA and 6×his amino acids at the C-terminus. To achieve this amplification, the products of two polymerase chain reactions described above were used as a template with primers CAN544 and CAN535. DNA sequence corresponding to NdeI restriction site was incorporated into the 5' primer and HindIII restriction site was incorporated into the 3' primer. The generated PCR product was then inserted into the pET-26b(+) cloning vector (NOVAGEN®).

To generate LVL268 (pelB signal peptide-D-PE fragment-GG-PilA fragment-GG-6×his), a polymerase chain reaction was performed to amplify the PE gene (amino acids 20-160) using the pRIT16711 vector as a template with primers CAN547 and CAN546. DNA sequence corresponding to the pelB signal peptide (sp) amino acids and aspartic acid (D) amino acid were incorporated into the 5' primer (CAN547). To link the PilA sequence to the PE sequence, DNA sequence corresponding to GG amino acids linker and the N-terminal PilA amino acids were incorporated into the 3' primer (CAN546). Another polymerase chain reaction was performed to amplify the PilA gene (amino acids 40-149/NTHi strain 86-028NP) using the pRIT16671 vector as a template with CAN545 and CAN535. DNA sequence corresponding to the C-terminal PE amino acids and GG amino acids were incorporated into the 5' primer (CAN545) to link the PilA sequence to the PE sequence. DNA sequence corresponding to linker GG amino acids and 6×his amino acids were incorporated into the 3' primer (CAN535). Finally, to generate LVL268, a third polymerase chain reaction was performed to amplify the PE and PilA genes in fusion with the pelB signal peptide at the N-terminus, a D amino acid between pelB signal peptide and PE, a GG linker between PE and pilA sequences and a GG linker between PilA and 6×his amino acids in C-term. To achieve this amplification, the products of the two polymerase chain reactions described above were used as a template with primers CAN547 and CAN535. DNA sequence corresponding to NdeI restriction site was incorporated into the 5' primer and HindIII restriction site was incorporated into the 3' primer. The generated PCR product was then inserted into the pET-26b(+) cloning vector) (NOVAGEN®).

To generate LVL269 (NadA signal peptide-ATNDDD-PE fragment-GG-PilA fragment-GG-6×his), a polymerase chain reaction was performed to amplify the PE gene (amino acids 22-160 of SEQ ID NO. 4) using the pRIT16711 vector as a template with primers CAN548 and CAN546. DNA sequence corresponding to pelB signal peptide (sp) amino acids and ATNDDD amino acids were incorporated into the 5' primer (CAN548). To link the PilA sequence to the PE sequence, DNA sequence corresponding to the GG amino acids linker and the N-terminal PilA amino acids were incorporated into the 3' primer (CAN546). Another polymerase chain reaction was performed to amplify the PilA gene (amino acids 40-149 of SEQ ID NO. 58, SEQ ID NO. 127) using the pRIT16671 vector as a template with primers CAN545 and CAN535. DNA sequence corresponding to the C-terminal PE amino acids and GG amino acids were incorporated into the 5' primer to link the PilA sequence to the PE sequence (CAN545). DNA sequence corresponding to linker GG amino acids and 6×his amino acids were incorporated into the 3' primer (CAN535). Finally, to generate LVL269, a third polymerase chain reaction was performed to amplify the PE and PilA gene in fusion with the NadA signal peptide at the N-terminus, ATNDDD amino acids between the pelB signal peptide and PE, a GG linker between the PE and pilA sequences and a GG linker between PilA and 6×his amino acids at the C-terminus. To achieve this amplification, the products of the two polymerase chain reactions describe above were used as a template with primers CAN548 and CAN535. DNA sequence corresponding to NdeI restriction site was incorporated into the 5' primer and HindIII restriction site was incorporated into the 3' primer. The generated PCR product was then inserted into the pET-26b(+) cloning vector (NOVAGEN®).

To generate LVL270 (M-6×His-PE fragment-GG-PilA fragment), a polymerase chain reaction was performed to amplify the PE gene (amino acids 17-160) using the pRIT16711 vector as a template with primers CAN540 and CAN542. DNA sequence corresponding to 6×his amino acids were incorporated into the 5' primer (CAN540). To link the PilA sequence to the PE sequence, DNA sequence corresponding to the GG amino acids linker and the N-terminal PilA amino acids were incorporated into the 3' primer (CAN542). Another polymerase chain reaction was performed to amplify the PilA gene (amino acids 40-149/NTHi strain 86-028NP) using pRIT16671 vector as a template with primers CAN541 and CAN543. DNA sequence corresponding to the C-terminal PE amino acids and GG amino acids were incorporated into the 5' primer (CAN541) to link the PilA to the PE sequence. Finally, to generate LVL270, a third polymerase chain reaction was performed to amplify the 6-his-PE-GG-PilA gene in fusion. To achieve this amplification, the products of the two polymerase chain reactions describe above were used as a template with primers CAN540 and CAN543. DNA sequence corresponding to NdeI restriction site was incorporated into the 5' primer and HindIII restriction site was incorporated into the 3' primer. The generated PCR product was then inserted into the pET-26b(+) cloning vector (NOVAGEN®).

To generate LVL315 (pelB signal peptide-MD-PE fragment-GG-PilA fragment-GG-6×his), a site-directed mutagenesis was performed to change the N-terminal PE amino acid sequence from QIQ to MD using LVL291 as a template with primers CAN670 and CAN671 and the QuikChange II Site-Directed Mutagenesis Kit (Agilent Technologies, Stratagene Division).

To generate LVL317 (pelB signal peptide-PE fragment-GG-pilA fragment), a site-directed mutagenesis was performed to incorporate a stop codon between the PilA gene and the DNA sequence corresponding to GGHHHHHH amino acid residues (SEQ ID NO: 3) using LVL291 as a template with primers CAN678 and CAN679 and the QuikChange II Site-Directed Mutagenesis Kit (Agilent Technologies, Stratagene Division).

To generate LVL318 (pelB signal peptide-MD-PE-GG-PilA), a site-directed mutagenesis was performed to incorporate a stop codon between the PilA gene and the DNA sequence corresponding to GGHHHHHH amino acid residues (SEQ ID NO: 3) using LVL315 as a template with primers CAN678 and CAN679 and the QuikChange II Site-Directed Mutagenesis Kit (Agilent Technologies, Stratagene Division).

To generate LVL702 (LVL291 ΔQ), a polymerase chain reaction was performed using the LVL291 vector as template and primers CAN1517 and CAN1518. Deletion of three nucleotides corresponding to the amino acid Q at the position 23 on LVL291 sequence was incorporated to the 5' primer. The only difference between LVL702 and LVL291 is the deletion of amino acid Q at the position 23 on LVL291 sequence. NdeI and HindIII restriction sites were incorporated into the 5' and 3' primers respectively. The generated PCR product was then inserted into the pET-26b(+) cloning vector (NOVAGEN®).

To generate LVL735 (LVL317 ΔQ), a polymerase chain reaction was performed using the LVL317 vector as template and primers CAN1517 and CAN1519. Deletion of three nucleotides corresponding to the amino acid Q at the position 23 on LVL317 sequence was incorporated to the 5' primer.

The only difference between LVL735 and LVL317 is the deletion of amino acid Q at the position 23 on LVL317 sequence. NdeI and HindIII restriction sites were incorporated into the 5' and 3' primers respectively. The generated PCR product was then inserted into the pET-26b(+) cloning vector (NOVAGEN®).

To generate LVL736 (LVL291+SA), a site-directed mutagenesis was performed to add amino acids S and A between amino acid 22 and 23 on LVL291 sequence. LVL291 was used as template with primers CAN1531 and CAN1532 and the QuikChange II Site-Directed Mutagenesis Kit (Agilent Technologies, Stratagene Division).

To generate LVL737 (LVL291+A), a site-directed mutagenesis was performed to add amino acid A between amino acid 22 and 23 on LVL291 sequence. LVL291 was used as template with primers CAN1529 and CAN1530 and the QuikChange II Site-Directed Mutagenesis Kit (Agilent Technologies, Stratagene Division).

To generate LVL738 (LVL291 ΔQIQ), a site-directed mutagenesis was performed to delete amino acids Q, I and Q at positions 23 to 25 on LVL291 sequence. LVL291 was used as template with primers CAN1523 and CAN1524 and the QuikChange II Site-Directed Mutagenesis Kit (Agilent Technologies, Stratagene Division).

To generate LVL739 (LVL291 ΔQIQK), a site-directed mutagenesis was performed to delete amino acids Q, I, Q and K at positions 23 to 26 on LVL291 sequence. LVL291 was used as template with primers CAN1525 and CAN1526 and the QuikChange II Site-Directed Mutagenesis Kit (Agilent Technologies, Stratagene Division).

To generate LVL740 (LVL291 ΔQIQKA), a site-directed mutagenesis was performed to delete amino acids Q, I, Q, K and A at positions 23 to 27 on LVL291 sequence. LVL291 was used as template with primers CAN1527 and CAN1528 and the QuikChange II Site-Directed Mutagenesis Kit (Agilent Technologies, Stratagene Division).

To generate LVL778 (LVL736 Δ6×His tag), LVL779 (LVL737 Δ6×His tag), LVL780 (LVL738 Δ6×His tag), LVL781 (LVL739 Δ6×His tag) and LVL782 (LVL740 Δ6×His tag) a polymerase chain reaction was performed using the LVL736, LVL737, LVL738, LVL739 and LVL740 vectors as template, respectively, with primers CAN1669 and CAN543. Deletion of 6×His tag corresponds to the amino acid sequence GGHHHHHH (SEQ ID NO. 3) at the C-terminal sequences. This deletion was incorporated to the 3' primer. NdeI and HindIII restriction sites were incorporated into the 5' and 3' primers respectively. The generated PCR product was then inserted into the pET-26b(+) cloning vector (NOVAGEN®).

TABLE 4

| | PCR primer sequences used for PE, PilA and PE-PilA amplifications |
|---|---|
| Primer ID | DNA Sequence 5'-3' |
| CAN534 | CACACACATATGATTAAATTTCTCTCTGCATTAATTCTTCTACTGGTCACGACGG CGGCTCAGGCTGAGACTAAAAAAGCAGCGGTATCTG (SEQ ID NO. 155) |
| CAN535 | TGTGTGAAGCTTTTAGTGGTGGTGGTGGTGGTGGCCGCCTTGTGTGACACTTCCG CAAAAATTTGC (SEQ ID NO. 156) |
| CAN536 | TTTGCGGAAGTGTCACACAAGGCGGCGCGCAGATTCAGAAGGCTGAACAAAATGA TGT (SEQ ID NO. 157) |
| CAN537 | ACATCATTTTGTTCAGCCTTCTGAATCTGCGCGCCGCCTTGTGTGACACTTCCGC AAA (SEQ ID NO. 158) |
| CAN538 | TGTGTGAAGCTTTTAGTGGTGGTGGTGGTGGTGGCCGCCTTTTTTATCAACTGAA AATG (SEQ ID NO. 159) |
| CAN540 | CACACACATATGCACCACCACCACCACCACAGCGCGCAGATTCAGAAGGCTGAAC AAAATGATGT (SEQ ID NO. 160) |
| CAN541 | CATTTTCAGTTGATAAAAAAGGCGGCACTAAAAAAGCAGCGGTATC (SEQ ID NO. 161) |
| CAN542 | GATACCGCTGCTTTTTTAGTGCCGCCTTTTTTATCAACTGAAAATG (SEQ ID NO. 162) |
| CAN543 | TGTGTGAAGCTTTTATTGTGTGACACTTCCGCAAA (SEQ ID NO. 163) |
| CAN544 | CACACACATATGAAATACCTGCTGCCGACCGCTGCTGCTGGTCTGCTGCTCCTCG CTGCCCAGCCGGCGATGGCCCAGATTCAGAAGGCTGAACAAAATGATGT (SEQ ID NO. 164) |
| CAN545 | GCATTTTCAGTTGATAAAAAAGGCGGCACTAAAAAAGCAGCGGTATCTG (SEQ ID NO. 165) |
| CAN546 | CAGATACCGCTGCTTTTTTAGTGCCGCCTTTTTTATCAACTGAAAATGC (SEQ ID NO. 166) |
| CAN547 | CACACACATATGAAATACCTGCTGCCGACCGCTGCTGCTGGTCTGCTGCTCCTCG CTGCCCAGCCGGCGATGGCCGATATTCAGAAGGCTGAACAAAATGATGT (SEQ ID NO. 167) |
| CAN548 | CACACACATATGAAACACTTTCCATCCAAAGTACTGACCACAGCCATCCTTGCCA CTTTCTGTAGCGGCGCACTGGCAGCCACAAACGACGACGATAAGGCTGAACAAAA TGATG (SEQ ID NO. 168) |

TABLE 4-continued

PCR primer sequences used for PE, PilA and PE-PilA amplifications

| Primer ID | DNA Sequence 5'-3' |
|---|---|
| CAN670 | GCCGGCGATGGCCATGGATAAGGCTGAACAAAATG (SEQ ID NO. 169) |
| CAN671 | CATTTTGTTCAGCCTTATCCATGGCCATCGCCGGC (SEQ ID NO. 170) |
| CAN678 | GGAAGTGTCACACAATAAGGCGGCCACCACCACC (SEQ ID NO. 171) |
| CAN679 | GGTGGTGGTGGCCGCCTTATTGTGTGACACTTCC (SEQ ID NO. 172) |
| CAN1517 | GATATACATATGAAATACCTGCTGCCGACCGCTGCTGCTGGTCTGCTGCTCCTCGCTGCCCAGCCGGCGATGGCCATTCAGAAGGCTGAACAAAA (SEQ ID NO. 205) |
| CAN1518 | GGCCGCAAGCTTTTAGTGGTGGTGGTGGTGGCCGCC (SEQ ID NO. 206) |
| CAN1519 | GGCCGCAAGCTTTTATTGTGTGACACTTCC (SEQ ID NO. 207) |
| CAN1523 | GCTGCCCAGCCGGCGATGGCCAAGGCTGAACAAAATGATGTG (SEQ ID NO. 208) |
| CAN1524 | CACATCATTTTGTTCAGCCTTGGCCATCGCCGGCTGGGCAGC (SEQ ID NO. 209) |
| CAN1525 | GCTGCCCAGCCGGCGATGGCCGCTGAACAAAATGATGTGAAGC (SEQ ID NO. 210) |
| CAN1526 | GCTTCACATCATTTTGTTCAGCGGCCATCGCCGGCTGGGCAGC (SEQ ID NO. 211) |
| CAN1527 | GCTGCCCAGCCGGCGATGGCCGAACAAAATGATGTGAAGCTGG (SEQ ID NO. 212) |
| CAN1528 | CCAGCTTCACATCATTTTGTTCGGCCATCGCCGGCTGGGCAGC (SEQ ID NO. 213) |
| CAN1529 | GCTGCCCAGCCGGCGATGGCCGCCCAGATTCAGAAGGCTGAAC (SEQ ID NO. 214) |
| CAN1530 | GTTCAGCCTTCTGAATCTGGGCGGCCATCGCCGGCTGGGCAGC (SEQ ID NO. 215) |
| CAN1531 | GCTGCCCAGCCGGCGATGGCCAGCGCCCAGATTCAGAAGGCTGAAC (SEQ ID NO. 216) |
| CAN1532 | GTTCAGCCTTCTGAATCTGGGCGCTGGCCATCGCCGGCTGGGCAGC (SEQ ID NO. 217) |
| CAN1669 | CACACACATATGAAATACCTGCTGCCGACC (SEQ ID NO. 218) |
| MDesPILA-3 | GAATTCCATATGCACCATCACCATCACCATACTAAAAAAGCAGCGGTATCTGAA (SEQ ID NO. 173) |
| MDesPILA-4 | GCGCCGCTCGAGTCATTGTGTGACACTTCCGC (SEQ ID NO. 174) |
| MnoNTHi-44 | GCCCAGCCGGCGATGGCCCAGATCCAGAAGGCTGAACAAAATG (SEQ ID NO. 175) |
| MnoNTHi-45 | CATTTTGTTCAGCCTTCTGGATCTGGGCCATCGCCGGCTGGGC (SEQ ID NO. 176) |

Transformation

*Escherichia coli* BLR (DE3) or *E. coli* HMS (DE3) cells were transformed with plasmid DNA according to standard methods with CaCl$_2$-treated cells. (Hanahan D. <<Plasmid transformation by Simanis.>> In Glover, D. M. (Ed), DNA cloning. IRL Press London. (1985): p. 109-135.). Briefly, BLR (DE3) or HMS174(DE3) competent cells were gently thawed on ice. Approximately 4 µl of plasmid (10-100 ng) were mixed using 50-100 µl competent cells. Thereafter, this formulation was incubated on ice for 30 min. To perform the transformation reaction, the formulation was heat pulsed at 42° C. for 45 seconds then incubated on ice for 2 minutes. Approximately 0.5 ml of SOC medium (Super Optimal broth with Catabolite repression) was added to the transformed cells and the cell culture was incubated at 37° C. for one hour before plating on Luria-Bertani (LB) agar with 50 ug/ml kanamycin. Around 100 µl of transformed cell culture was plated and incubated overnight at 37° C.

BLR (DE3): BLR is a recA$^-$ derivative of BL21 (F-ompT hsdSB(rB- mB-) gal dcm (DE3). This *E. coli* strain used for expression of recombinant proteins improves plasmid monomer yields and may help stabilize target plasmids containing repetitive sequences or whose products may cause the loss of the DE3 prophage. (Studier, F. W. (1991) J. Mol. Biol. 219:

37-44). The detailed genotype of *E. coli* BLR (DE3) has been published by NOVAGEN®. (F-ompT hsdSB (rB- mB-) gal dcm Δ(srl-recA)306::Tn10 (TetR) (DE3).

HMS174 (DE3): HMS174 strains provide the recA mutation in a K-12 background. Like BLR, these strains may stabilize certain target genes whose products may cause the loss of the DE3 prophage. The detailed genotype of *E. coli* HMS174 (DE3) has been published by NOVAGEN®. (F-recA1 hsdR(rK12- mK12+) (DE3) (Rif R).

Production Using BLR (DE3) and Characterization of his Tagged Constructs are Described in Example 3 Through Example 6

Example 3

Protein Expression Using Shake Flask

Generally, one confluent agar plate inoculated with *Escherichia coli* BLR (DE3) transformed with recombinant plasmid was stripped, resuspended in culture media and used to inoculate 800 ml of LB broth (Becton, Dickinson and Company) ±1% (weight/volume, w/v) glucose (Laboratoire MAT, catalogue number: GR-0101) and 50 μg/ml kanamycin (Sigma) to obtain O.D.$_{600nm}$ between 0.1 and 0.2. Cultures were incubated at 37° C. with agitation of 250 RPM to reach an O.D.$_{600nm}$ of ~0.8.

One ml of each culture was then collected, centrifuged at 14 000 RPM for 5 minutes and supernatants and pellets were frozen at −20° C. separately.

At an O.D.$_{600nm}$ ~0.8, the BLR (DE3) cultures were cooled down (−20° C., 20 minutes or 4° C., 1 hour, preferably at 4° C. for 1 hour) before inducing the expression of the recombinant protein by addition of 1 mM isopropyl β-D-1-thiogalactopyranoside (IPTG; EMD Chemicals Inc., catalogue number: 5815) and incubation overnight at 16, 22 and 30° C., or 3 hours at 37° C. with agitation of 250 RPM, preferably overnight at 22° C. After the induction period the cultures were centrifuged at 14 000 RPM for 5 minutes or 6 000 RPM for 15 minutes and supernatant (media fraction sample) and pellets (containing soluble and insoluble fractions) were frozen at −20° C. separately.

These conditions are used for periplasmic protein expression.

Example 4

Protein Purification Using Shake Flask, Cell Pastes, His Tagged Constructs

Each bacterial pellet obtained after induction was resuspended in 20 mM 4-(2-hydroxyethyl)-1-piperazineethanesulfonic acid (HEPES) buffer (pH 8.0) containing 500 mM NaCl, 10 mM imidazole and Roche COMPLETE® Protease Inhibitor Cocktail (1 tablet/50 ml of HEPES buffer containing 500 mM NaCl, Roche COMPLETE® ULTRA tablets, Roche Diagnostics Corporation).

Alternatively, 20 to 50 mM bicine buffer may be used instead of HEPES buffer containing NaCl. For example, 20 mM bicine buffer may be used. Bacteria were lysed using a Constant System 1.1 KW 2×30 000 PSI (pounds per square inch). Soluble (supernatant) and insoluble (pellet) components were separated by centrifugation at 20 000 g for 20 min at 4° C.

6-His tagged-proteins were purified under native conditions on immobilized metal affinity chromatography (IMAC) using PROFINIA™ protein purification protocol (Bio-Rad Laboratories, Inc.). The soluble components were loaded on a 5 ml H is Trap column (Bio-Rad Laboratories, Inc.) pre-equilibrated with the same buffer used for bacterial resuspension; the soluble components were added at up to 5 ml/min (producing a "flow through fraction") After loading on the column, the column was washed with 10 column volumes of the same buffer at a rate of 10 ml/min (producing a "wash fraction #1). A second wash using 20 mM bicine buffer or 20 mM HEPES buffer (pH 8.0) containing 500 mM NaCl and 20 mM imidazole was performed, producing a "wash fraction #2). Elution was performed using 2 column volumes of 20 mM HEPES buffer or 50 mM bicine buffer (pH 8.0) containing 500 mM NaCl and 250 mM imidazole at a rate of 10 ml/min, producing an "elution fraction".

To improve the purity of the protein, positive elution fractions from IMAC were pooled and loaded on a size exclusion chromatography (SEC) column (HILOAD™ SUPERDEX™ 200 26/60 from GE Healthcare) preequilibrated in phosphate buffered saline without calcium or magnesium (NaCl 137 mM, KCl 2.7 mM, Na$_2$HPO$_4$ 8.1 mM, KH$_2$PO$_4$ 1.47 mM, pH 7.4). Samples from elution fractions were analyzed by sodium dodecyl sulfate polyacrylamide gel electrophoresis (SDS-PAGE). Samples were concentrated using Centricon 10 000 MW (Millipore).

Protein concentration was determined using spectrometer.

Example 5

SDS-PAGE and Western Blot Analysis of His Tagged Constructs & SDS-PAGE Analysis of Non-His Tagged LVL317 & LVL318 Constructs Soluble and Insoluble Fraction Preparation For example, 1 ml of culture after induction (see, for example, Example 3 above) was centrifuged at 14 000 RPM for 2 min. The pellet was resolubilized using 40 μl of BUG-BUSTER® Protein Extraction Reagent (NOVAGEN®, EMD4 Biosciences, Merck), creating a cell suspension. The cell suspension was incubated on a rotating platform for 10 min at room temperature. The cell suspension was then centrifuged at 14 000 RPM for 2 min to separate the soluble fraction. The resulting pellet (insoluble fraction) was resolubilized using 70 μl of deionized water, 5 μl of dithiothreitol (DTT) 1M and 25 μl of NUPAGE® LDS (Lithium Dodecyl Sulphate) Sample Buffer 4× (INVITROGEN™). The soluble fraction (supernatant from the cell suspension of the resolubilized pellet) was added to 30 μl of deionized water, 5 μl of DTT 1M and 25 μl of LDS Sample Buffer 4×.

Media Fraction Preparation

For example, to prepare the media fraction, 100 μl of the supernatant from the induced whole cell culture following centrifugation (see, for example, Example 3 above) was concentrated by adding 500 μl of RC reagent I (Bio-Rad Laboratories, Inc.); the sample was mixed and incubated for 1 min at room temperature. Then, 500 μl of Reagent II (Bio-Rad Laboratories, Inc.) was added to the sample and mixed. This formulation was centrifuged at 14 000 RPM for 10 min. The pellet was resolubilized using 28 μl of deionized water, 2 μl of DTT 1M and 10 μl of LDS SB 4×.

Purification Fraction Preparation

For example, purified proteins (for example, obtained as described in Example 4) were prepared for SDS-PAGE analysis by adding 70 μl of sample, 5 μl of DTT 1M and 25 μl of LDS Sample Buffer 4×.

SDS-PAGE Analysis and Transfer to Nitrocellulose Membrane

SDS-PAGE analysis and transfer to nitrocellulose membrane were performed according to manufacturer's recommendations (Invitrogen) using NUPAGE® Bis-Tris 4-12% gels. Preparations of samples, buffers and migration conditions were done under conditions recommended by the suppliers.

In one example, the gel was loaded with a 20 ul sample from a master mix comprising 70 μl of a purified protein fraction, 5 μl of DTT 1M and 25 μl of LDS SB 4×.

After samples were run on NUPAGE® Bis-Tris 4-12% gels, the proteins were transferred to nitrocellulose membranes.

Nitrocellulose membranes were blocked for 30 minutes at 37° C., 60 RPM using 3% milk/PBS 1× fresh solution. After the blocking incubation, Primary Antibodies were added (6× His Tag® antibody, Abcam PLC, catalogue number: ab9108) at a dilution of: 1:1000 in 3% milk/PBS 1×fresh solution for 1 hour at 37° C., 60 RPM. After that, membranes were washed three times, for 5 minutes each, at room temperature using 0.02% polsorbate 20 (for example, TWEEN™ 20)/PBS 1×. Secondary Antibodies (alkaline phosphatase (AP) Rabbit anti-IgG (H+L) rabbit, Jackson ImmunoResearch Laboratories, Inc.) were added at dilution 1:14 000 using 3% milk/PBS 1× fresh solution. Membranes were incubated for 1 hour at 37° C., 60 RPM. After that, membranes were washed three times for 5 minutes at room temperature using 0.02% polysorbate 20 (for example, TWEEN™ 20)/PBS 1×before the membrane expositions to 5-bromo-4-chloro-3-indolyl phosphate/nitro blue tetrazolium (for example, BCIP®/NBT from Sigma-Aldrich®, 1 tablet/10 ml water).

See FIG. 1 for SDS-PAGE of induced bacterial extracts for fusion protein constructs LVL291, LVL268 and LVL269. Insoluble fraction (I), Soluble fraction (S) and Culture Media fraction (M) were loaded for LVL291, LVL268 and LVL269 before and after induction (ind).

Figure 2:
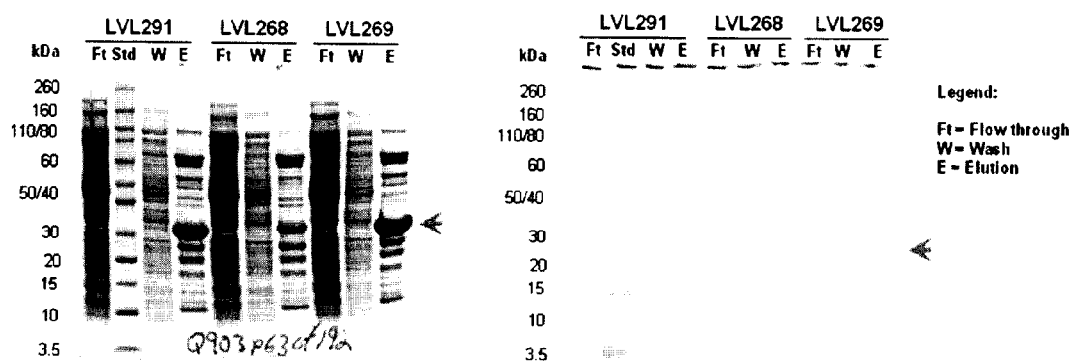
FIG. 2. SDS-PAGE and Western blot related to purification extracts for fusion protein constructs LVL291, LVL268 and LVL269. Flow through fraction (Ft), Wash fraction (W) and Elution fraction (E) were loaded for purification of LVL291, LVL268 and LVL269. Anti-his tag was used to probe extracts.

See FIG. 2 for SDS-PAGE and Western blot related to purification extracts for fusion protein constructs LVL291, LVL268 and LVL269. Flow through fraction (Ft), Wash fraction (W) and Elution fraction (E) were loaded for purification of LVL291, LVL268 and LVL269. Anti-his tag was used to probe extracts.

Figure 3:
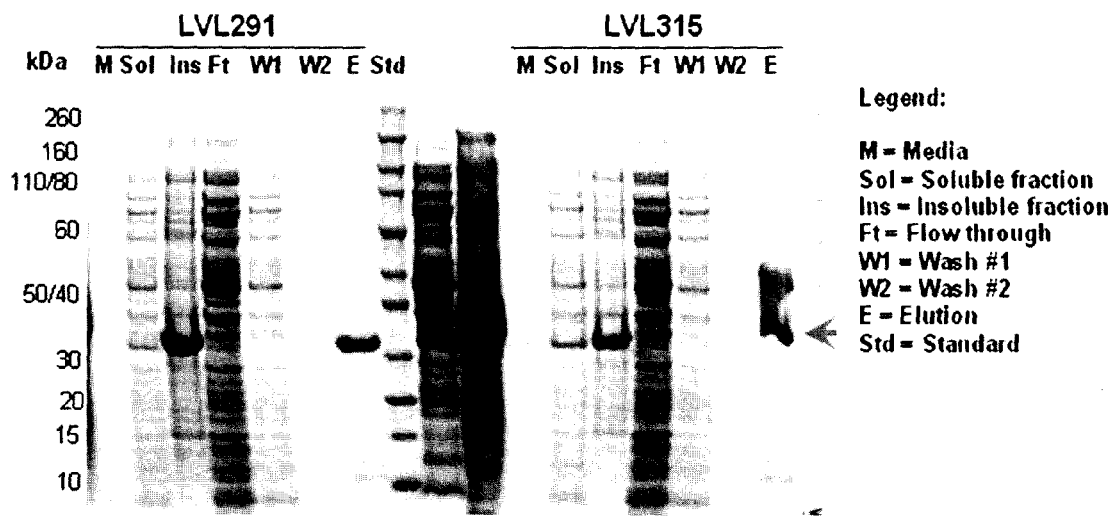
FIG. 3. SDS-PAGE of induced bacterial and purification extracts for fusion protein constructs LVL291 and LVL315. Culture Media fraction (M), Soluble fraction (Sol), Insoluble fraction (Ins), Flow through fraction (Ft), Wash fraction #1 (W1), Wash fraction #2 (W2) and Elution fraction (E) were loaded for LVL291 and LVL315.

See FIG. 3 for SDS-PAGE of induced bacterial and purification extracts for fusion protein constructs LVL291 and LVL315. Culture Media fraction (M), Soluble fraction (Sol), Insoluble fraction (Ins), Flow through fraction (Ft), Wash fraction #1 (W1), Wash fraction #2 (W2) and Elution fraction (E) were loaded for LVL291 and LVL315.

Figure 4:
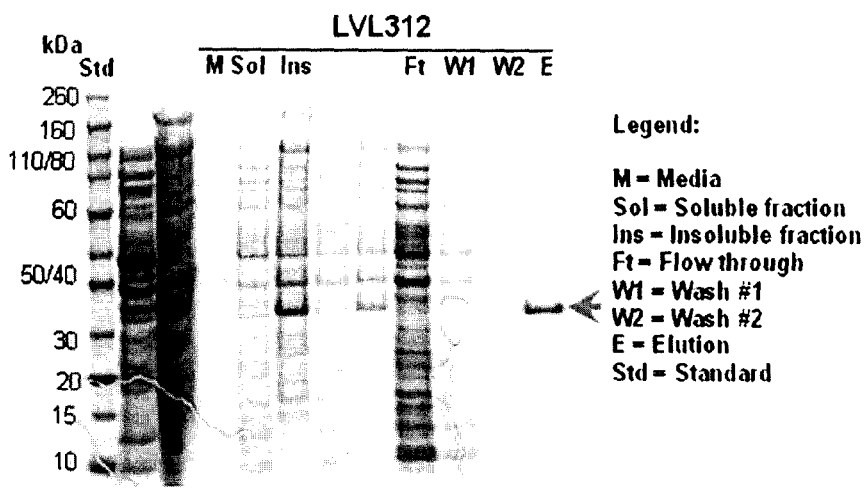
FIG. 4. SDS-PAGE of induced bacterial and purification extracts for fusion protein construct LVL312. Culture Media fraction (M), Soluble fraction (Sol), Insoluble fraction (Ins), Flow Through fraction (Ft), Wash fraction #1 (W1), Wash fraction #2 (W2) and Elution fraction (E) were loaded for LVL312.

See FIG. 4 for SDS-PAGE of induced bacterial and purification extracts for fusion protein construct LVL312. Culture Media fraction (M), Soluble fraction (Sol), Insoluble fraction (Ins), Flow Through fraction (Ft), Wash fraction #1 (W1), Wash fraction #2 (W2) and Elution fraction (E) were loaded for LVL312.

Figure 25:
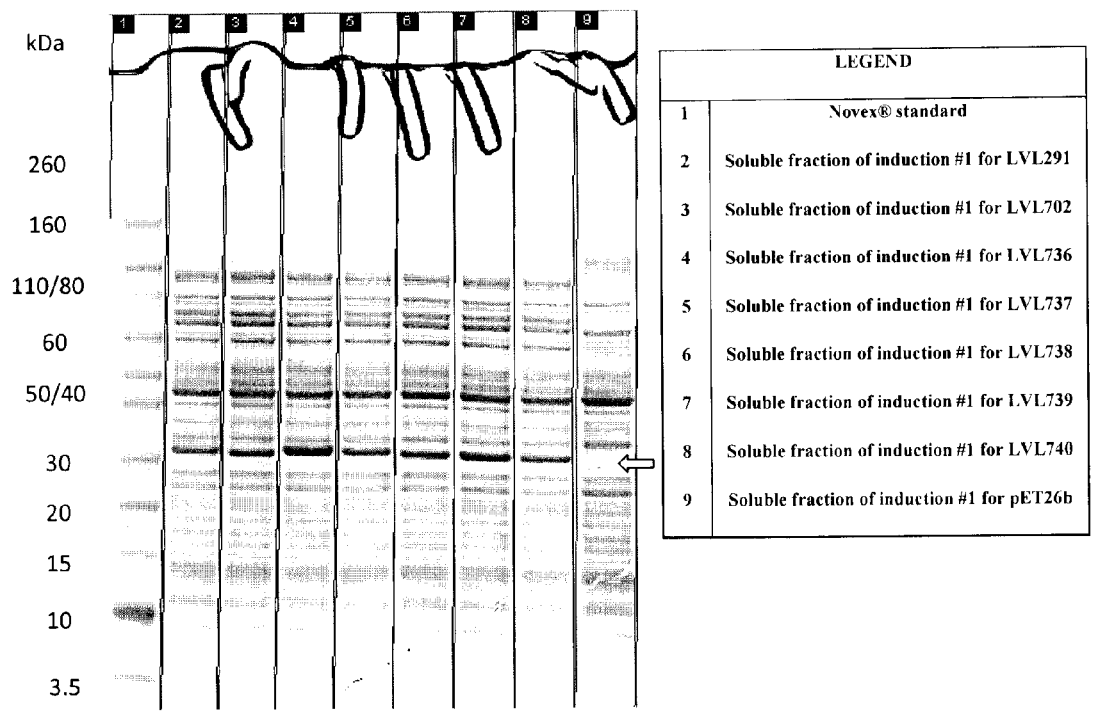
FIG. 25. SDS-PAGE of soluble fractions of induced bacterial extracts for fusion protein constructs LVL291, LVL702, LVL736, LVL737, LVL738, LVL739, LVL740 and pET26b vector (negative control). (a) Experiment 1 (b) Experiment 2 (c) Experiment 3. PE-PilA fusion protein indicated by arrow.
Figure 25:
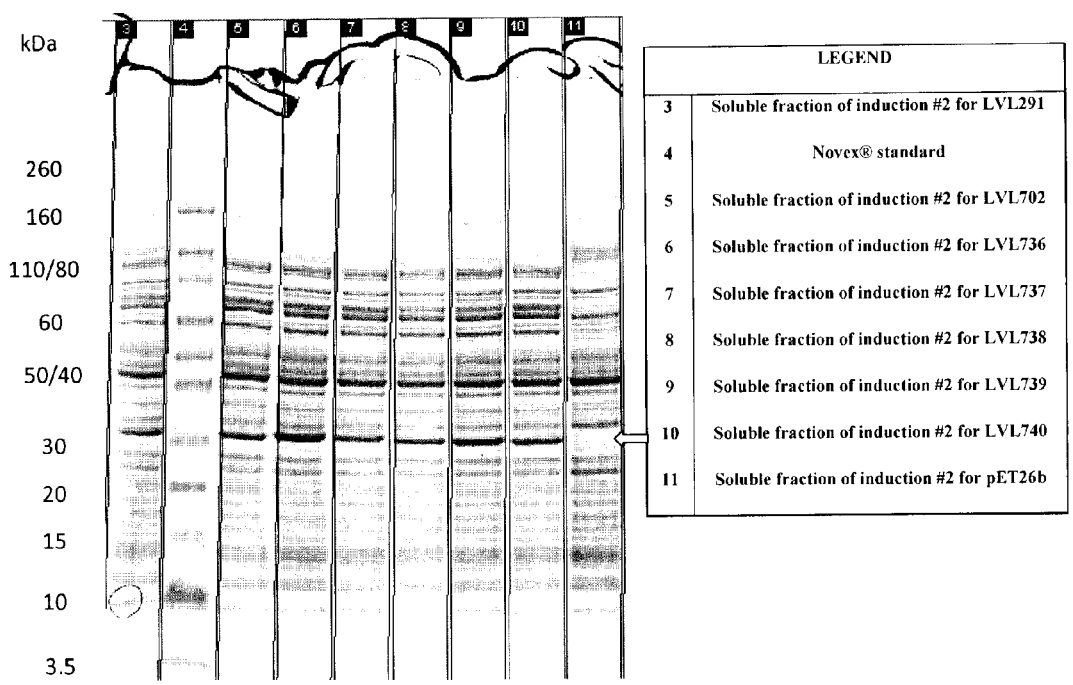
Figure 25:
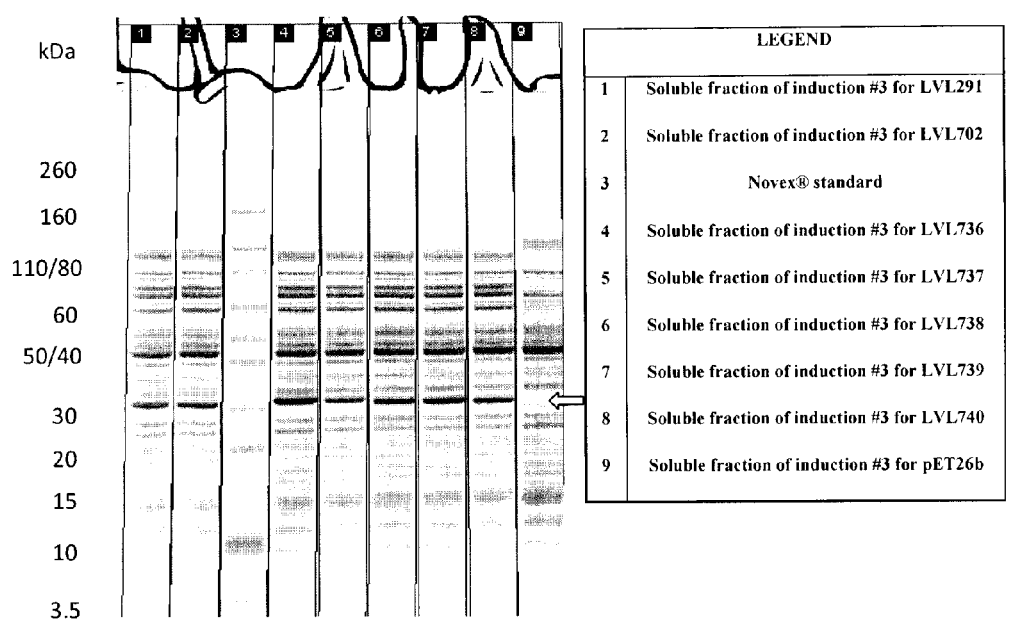

See FIG. 25 for SDS-PAGE of soluble fractions from induced bacterial extracts for fusion protein constructs LVL291, LVL702, LVL736, LVL737, LVL738, LVL739, LVL740 and pET26b vector (negative control). (a) Experiment 1 (b) Experiment 2 (c) Experiment 3. PE-PilA fusion protein indicated by arrow.

Figure 26:
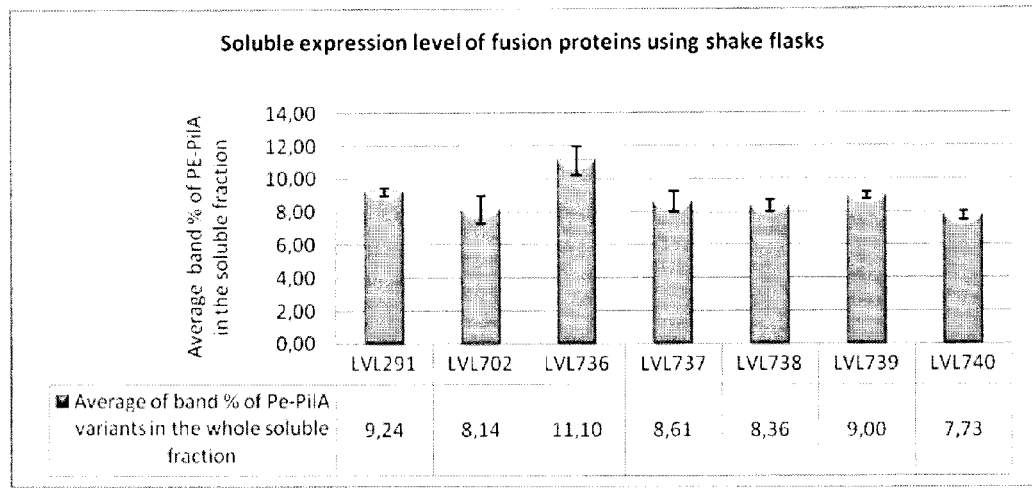
FIG. 26. The average band percentage of fusion protein in the soluble fraction from Experiments 1, 2 and 3.

See FIG. 26 for the average band percentage of fusion protein in the soluble fraction from Experiments 1, 2 and 3.

Figure 5:
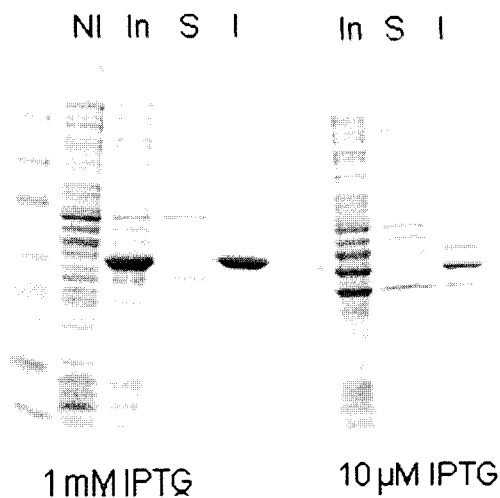
FIG. 5. SDS-PAGE of induced (1 mM and 10 µM IPTG) bacterial extracts for fusion protein construct LVL317. Extracts from before (NI) and after induction (In), Soluble fraction (S), Insoluble fraction (I).
Figure 6:
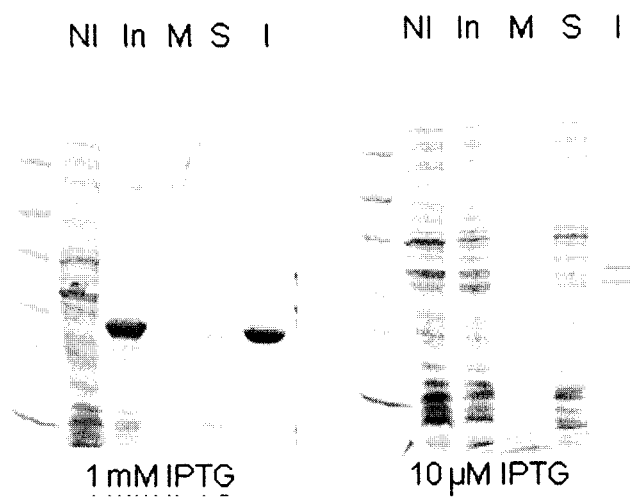
FIG. 6. SDS-PAGE of induced (1 mM and 10 µM IPTG) bacterial extracts for fusion protein construct LVL318. Extracts from before (NI) and after induction (In), Culture Media fraction (M), Soluble fraction (S), Insoluble fraction (I).

LVL317 and LVL318 bacterial extracts used in the SDS-PAGE analysis in FIG. 5 and FIG. 6, respectively, were prepared generally as described above.

FIG. 5. SDS-PAGE of induced (1 mM and 10 μM IPTG) bacterial extracts for fusion protein construct LVL317. Extracts from before (NI) and after induction (In), Soluble fraction (S), Insoluble fraction (I).

FIG. 6. SDS-PAGE of induced (1 mM and 10 μM IPTG) bacterial extracts for fusion protein construct LVL318. Extracts from before (NI) and after induction (In), Culture Media fraction (M), Soluble fraction (S), Insoluble fraction (I).

Proteins separate by SDS-PAGE were transferred to an Immobilon-P membrane. The Coomassie Blue stained protein bands were cut and placed in a sequenator reactor. Sequencing was carried out according to manufacturer's protocol using an Applied Biosystems PROCISE® Protein Sequencer, model 494-cLC.

TABLE 5

Shake flask protein expression profiles and signal peptide cleavage for fusion protein constructs.

| Fusion Protein Construct ID | Description N-term → C-term | Protein Expression profile | Signal peptide cleavage |
|---|---|---|---|
| LVL312 | FlgI sp - E - PilA fragment - GG - PE fragment - GGHHHHHH | In: +++<br>So: +<br>Se: + | Confirmed |
| LVL291 | PelB sp - PE fragment - GG - PilA fragment - GGHHHHHH | In: +++<br>So: ++<br>Se: + | Confirmed |
| LVL268 | PelB sp - D - PE fragment - GG - PilA fragment - GGHHHHHH | In: +++<br>So: ++<br>Se: + | Confirmed |
| LVL269 | NadA sp - ATNDDD - PE fragment - GG - PilA fragment - GGHHHHHH | In: +++<br>So: ++<br>Se: + | Confirmed |
| LVL270 | MHHHHHH - PE fragment - GG - PilA fragment | In: +<br>So: −<br>Se: − | Not tested |

TABLE 5-continued

Shake flask protein expression profiles and signal peptide cleavage for fusion protein constructs.

| Fusion Protein Construct ID | Description N-term → C-term | Protein Expression profile | Signal peptide cleavage |
|---|---|---|---|
| LVL315 | PelB sp - MD - PE fragment - GG - PilA fragment - GGHHHHHH | In: +++<br>So: ++<br>Se: + | Confirmed |
| LVL317 | PelB - PE fragment - GG - PilA fragment | In: +++<br>So: +<br>Se: Nt | Confirmed |
| LVL318 | PelB sp - MD - PE fragment - GG - PilA fragment | In: +++<br>So: +<br>Se: - | |
| LVL702 | PelB sp - PE fragment - GG - PilA fragment - GGHHHHHH | In: +++<br>So: ++<br>Se: Nt | Confirmed |
| LVL736 | PelB sp - PE fragment - GG - PilA fragment - GGHHHHHH | In: +++<br>So: ++<br>Se: Nt | Confirmed |
| LVL737 | PelB sp - PE fragment - GG - PilA fragment - GGHHHHHH | In: +++<br>So: ++<br>Se: Nt | Confirmed |
| LVL738 | PelB sp - PE fragment - GG - PilA fragment - GGHHHHHH | In: +++<br>So: ++<br>Se: Nt | Confirmed |
| LVL739 | PelB sp - PE fragment - GG - PilA fragment - GGHHHHHH | In: +++<br>So: ++<br>Se: Nt | Confirmed |
| LVL740 | PelB sp - PE fragment - GG - PilA fragment - GGHHHHHH | In: +++<br>So: ++<br>Se: Nt | Confirmed |

So = Soluble fraction.
In = Insoluble fraction.
Se = Protein Secreted in the media fraction.
Nt = Not tested.
The following rating were based on a visual inspection (coomassie)
+: low expression;
++: medium expression;
+++: high expression;
-: no expression Example 6

LVL291 Fusion Protein Characterization

Physical Properties of LVL291: Folding of PE and PilA in LVL291 & Melting Point Circular Dichromism:

Analysis of Secondary Structure

Circular dichroism (CD) is used to determine the secondary structure composition of a protein by measuring the difference in the absorption of left-handed polarized light versus right-handed polarized light which is due to structural asymmetry. The shape and the magnitude of the CD spectra in the far-UV region (190-250 nm) are different whether a protein exhibits a beta-sheet, alpha-helix or random coil structure. The relative abundance of each secondary structure type in a given protein sample can be calculated by comparison to reference spectra.

Far UV spectra are measured using an optical path of 0.01 cm from 178 to 250 nm, with a 1 nm resolution and bandwidth on a Jasco J-720 spectropolarimeter. Temperature of the cell is maintained at 23° C. by a Peltier thermostated RTE-111 cell block. A nitrogen flow of 10 L/min is maintained during the measurements.

Figure 7:
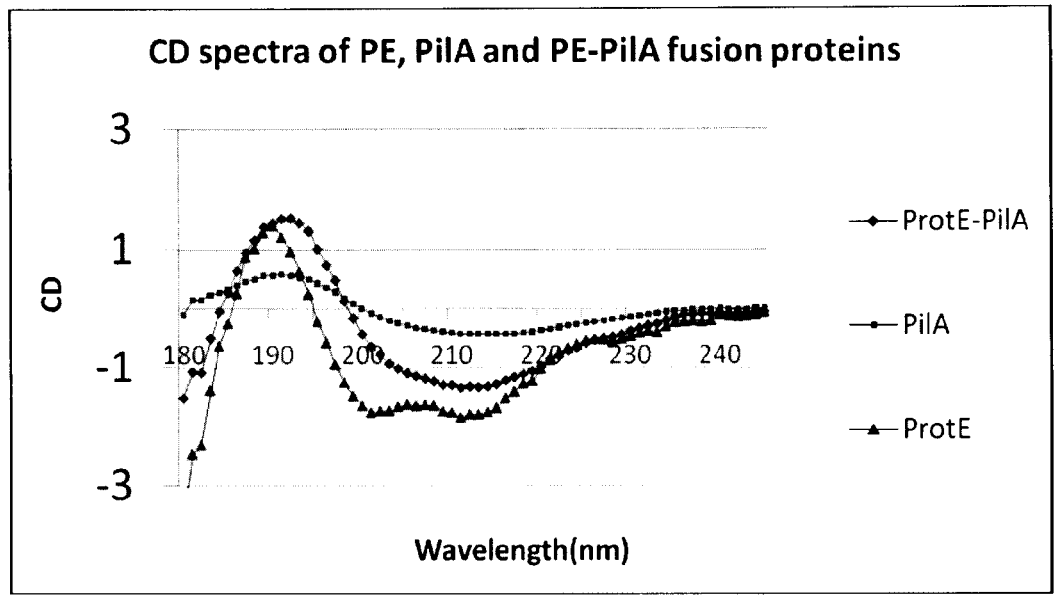
FIG. 7. CD spectra of PE, PilA and PE-PilA fusion proteins.

Results:

The far-UV CD spectra obtained for PE (from construct pRIT16762), PilA (from construct pRIT 16790) and PE-PilA proteins are characteristic of folded proteins containing a mix of alpha and beta structures, but PE is significantly richer in alpha helix than PilA and PE-PilA (FIG. 7, CD spectra of PE, PilA and PE-PilA fusion proteins).

In order to evaluate the integrity of the folding of PE and PilA individual proteins once bound together in a chimeric protein and then verify a possible interaction between both, difference spectra were calculated.

Figure 8:
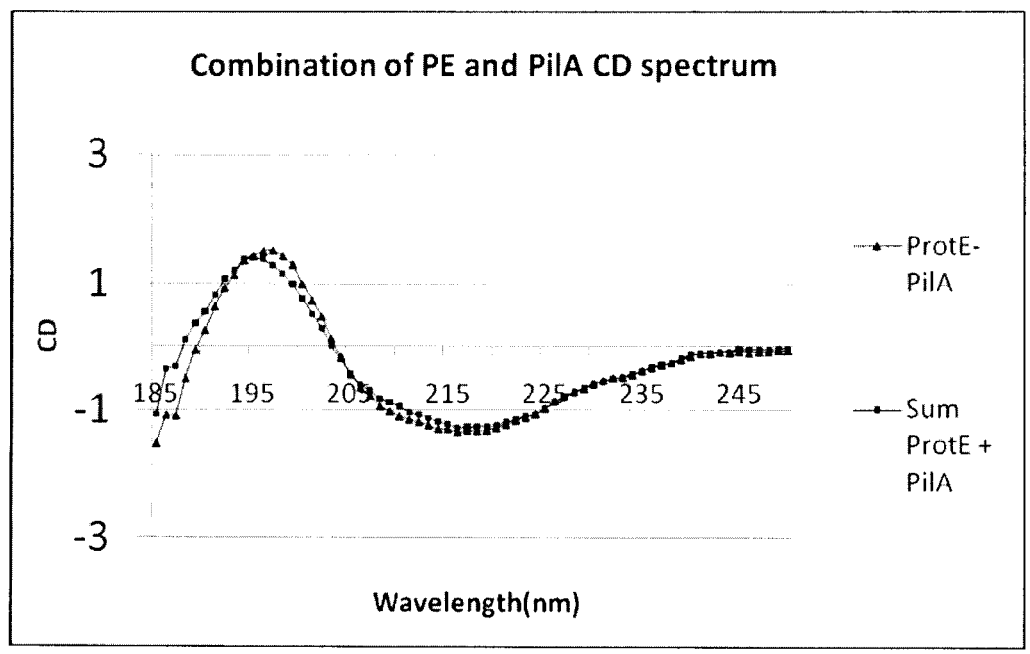
FIG. 8. Combination of PE and PilA CD spectrum.

When the PE and PilA far-UV spectra are combined, the resulting spectrum superposes to the spectrum of PE-PilA chimer (FIG. 8, Combination of PE and PilA CD spectrum). This result suggests that the PE-PilA chimer contains all the secondary structures that are detected in the individual components. It also suggests that the fusion of the proteins has no major impact on the secondary structures of the individual components and consequently that the folding of PE and PilA is not significantly different whether the proteins are separate or in fusion.

Melting Point Evaluation:

In order to evaluate if the expression in fusion has an impact on the thermodynamic properties of the individual proteins, the melting points of PE, PilA and PE-PilA have been evaluated by monitoring the defolding of the alpha helix with temperature by circular dichroism.

The presence of alpha helix is characterized by a minimum in the Circular dichroism signal at 222 nm, so a significant increase in CD signal at 222 nm during temperature increase is an indication of protein denaturation. The determination of the temperature at which the protein undergoes loss in secondary structure allows the determination of the melting point (Tm), which corresponds to the temperature at which half of the proteins have lost their structure.

Melting point can be determined by identification of the inflexion point on the thermal denaturation curve obtained from a temperature versus CD 222 nm plot.

Figure 9:
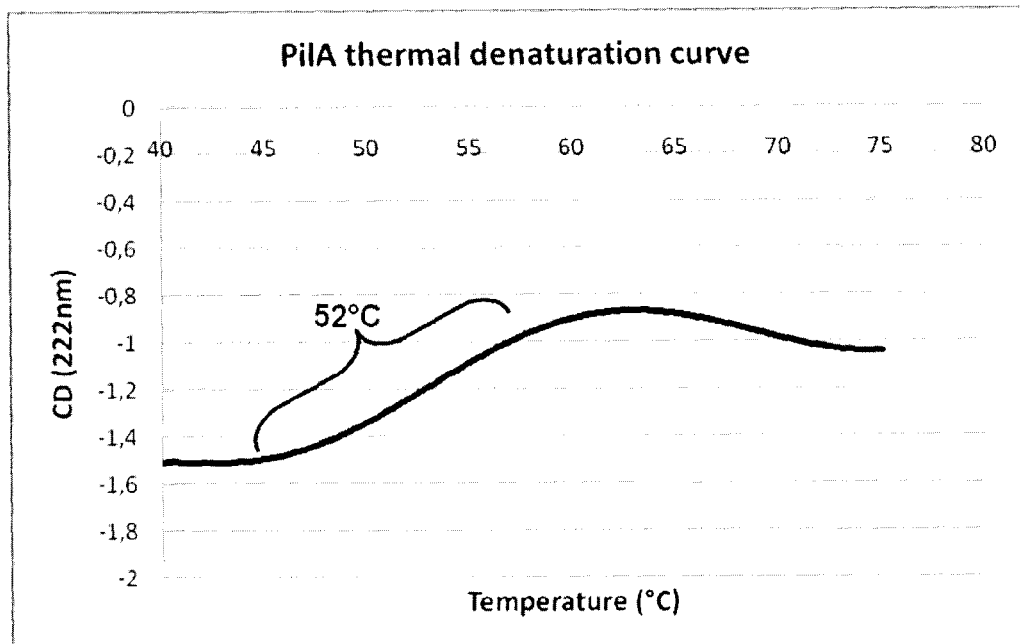
FIG. 9. PilA thermal denaturation curve.
Figure 10:
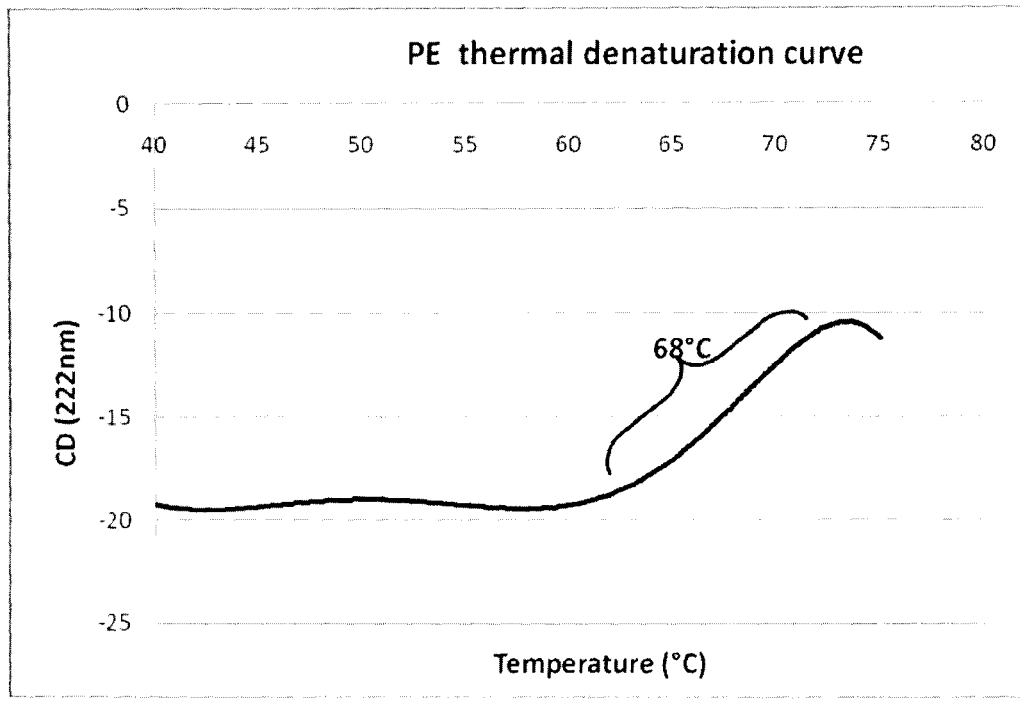
FIG. 10. PE denaturation curve.

Melting point of PilA and PE as determined by far-UV CD are respectively of 52° C. and 68° C. (FIG. 9, PilA thermal denaturation curve; FIG. 10, PE thermal denaturation curve).

Figure 11:
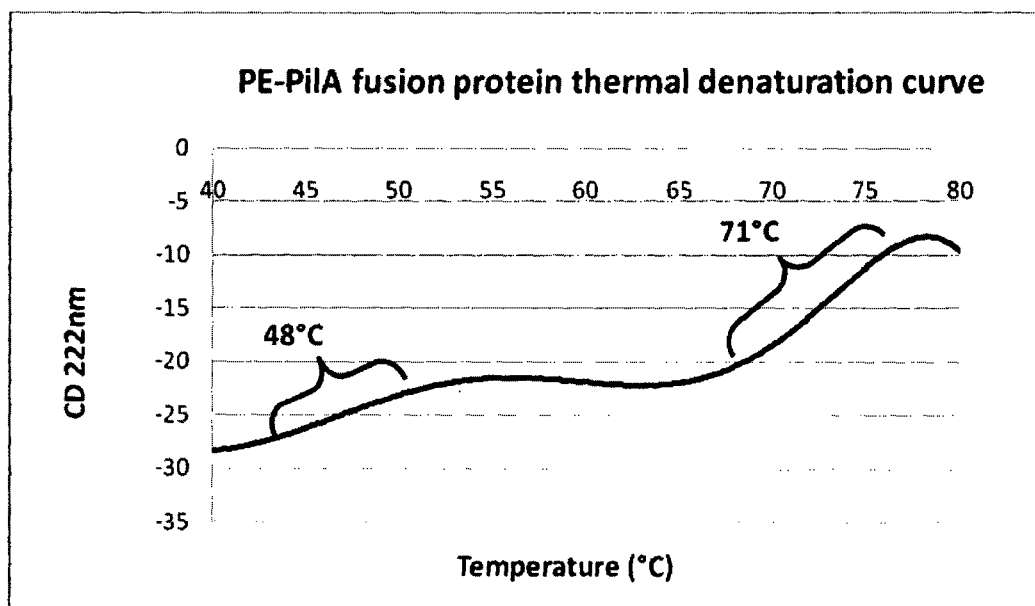
FIG. 11. PE-PilA fusion protein thermal denaturation curve.

The PE-PilA fusion protein exhibits two distinct Tm's at 48° C. and 71° C. (FIG. 11, PE-PilA fusion protein thermal denaturation curve). Those values indicate that the PE and PilA proteins are still independently folded when bound into a chimer and that they defold at a similar temperature whether they are separate or in fusion. The observation that the defolding of the PilA portion at 48° C. doesn't cause precipitation or impact the Tm of the PE portion at 71° C. is a strong indication that the interaction between PE and PilA within the fusion is minimal and that they don't have a major observable impact on each other. The melting points of proteins are sensitive to various external conditions, including buffer composition or presence of interacting molecules; that no major variation is observed upon fusion of PE and PilA is a strong indication of the preservation of most of the structure and of the properties of both PE and PilA when they are bound together.

Example 7

Fermentation Process

Fusion proteins of the invention may be prepared by methods known by those skilled in the art.

Example 8

Protein Purification of PE, PilA, and LVL317

PE Protein Purification from pRIT16762:

To generate the pRIT16762 expression vector, the pRIT16711 vector was digested using BamHI and NcoI restriction enzymes in order to delete 6 amino acid residues between the signal sequence (pelB) and PE. The vector obtained was named pRIT16712. In this vector, there are 3 amino acids between the signal sequence pelB and PE: MDP. In a second step, a site directed mutagenesis was performed to change amino acid sequence from MDP to QIQ using pRIT16712 as template with primers MnoNTHi-44 and MnoNTHi-45 (described in Table 4) and the QuikChange II Site-Directed Mutagenesis Kit (Agilent Technologies, Stratagene Division).

Working seed of *E. coli* BLR(DE3) containing PE QIQ (from the pRIT16762 construct) was thawed from −80° C. and used to prepare 100 ml of pre-culture in LB broth by overnight incubation at 37° C. under agitation at 215 RPM. After overnight incubation, eight flasks containing 800 ml of LB APS were inoculated with 12.5 ml of pre-culture and $OD_{600}$ measured at around 0.06. The cultures were incubated 3 h at 37° C. with shaking. At a $OD_{600}$ of around 0.9, 1 mM IPTG was added to start the induction. During the induction, the cultures were incubated 19 h at 22° C. with shaking. After induction, $OD_{600}$ was at around 2.2. The cell cultures were transferred into 1 L centrifuge bags placed inside 1 L bottles and centrifuged at 4° C. for 30 minutes at 6,000×g and supernatant discarded. 1 ml aliquots of culture pre- and post-induction and supernatant were kept for future analysis.

Lysis of the BLR(DE3) Induced with PE QIQ

The centrifuge bags were removed from the centrifugation bottles, opened and the pellet was expulsed from the bag into a beaker. The eight pellets were pulled together and resuspended in 100 ml of binding buffer (20 mM Hepes, 10 mM imidazole, 500 mM NaCl, pH 8.01). The *E. coli* BLR (DE3) containing the PE QIQ contruct were disrupted with the TS Series Bench Top cell disrupter from Constant Systems Ltd. (1×30 kPsi; 1×15 kPsi). The lysate was centrifuged 30 minutes, 6000 RPM, 4° C. The supernatant was kept and loaded on an IMAC column.

IMAC Purification of PE QIQ

IMAC column (BioRad, Bio-Scale Mini Profinity IMAC cartridge 5 ml) was equilibrated with 5CV of Binding buffer (20 mM HEPES, 10 mM imidazole, 500 mM NaCl, pH 8.01) at 5 ml/min. 100 ml of lysate supernatant was loaded on the IMAC at 2.5 mL/min. Flow-through was collected in 50 ml fractions for future analysis. The column was washed with 3CV of Binding buffer to remove unbound protein. Sample containing unbound proteins was collected in one aliquot of 15 ml in a 50 ml tube. The column was washed with 2CV of Wash buffer (20 mM HEPES, 20 mM imidazole, 500 mM NaCl, pH 8.01) collected in 2 ml fractions in a 96 well plate. The bound protein was then eluted with 6CV of 100% Elution buffer (20 mM HEPES, 250 mM imidazole, 500 mM NaCl, pH 8.01). The eluted protein was collected in 2 ml fractions in 96-well plates. Wash and elution were performed at 5 ml/min.

Size Exclusion Chromatography (SEC) on the IMAC Pool of PE QIQ

SEC column (GE healthcare, HILOAD™ 26/60 SUPERDEX™ 75 prep grade, 60 cm height approx 319 ml volume) was equilibrated with 3CV of SEC buffer (20 mM HEPES, 150 mM NaCl, pH8.49). 11 ml of IMAC eluate was loaded onto the column at a flow rate of 2.5 ml/min. 2 ml fractions were collected from 0.3CV to 0.9CV. Two runs were performed then fractions were analyzed by SDS-PAGE. Fractions from the two runs containing Prot E protein were pooled together ("SEC pool", 48 ml approx total volume). 500 mM of Arginine was added to the SEC pool.

Dosage of the PE QIQ Pooled Samples Generated in the Above SEC Protocol

The SEC pool was dosed with the RCDC (Reducing Agent and Detergent Compatible) method from the Bio-Rad RC DC™ kit following manufacturer's protocol:

For each tested sample and standard, 254 was distributed in microfuge tubes in duplicate. 125 µL of Bio-Rad RC Reagent I was added into each tube; each tube was vortexed and incubate for 1 minute at room temperature. 125 µL of Bio-Rad RC Reagent II is added into each tube; each tube is vortexed and then centrifuged at 14,000×g for 5 minutes. Supernatants are discarded by inverting the tubes on clean, adsorbent tissue paper allowing the liquid to drain completely from the tubes. 25.4 µL of Reagent A (already prepared by mixing 20 µL of Reagent S per 1 ml of Reagent A) is added to each tube; each tube is vortexed and incubated at room temperature for 5 minutes, or until precipitate is completely dissolved. Vortex before proceeding to next step. Add 200 µL of DC reagent B to each tube and vortex immediately. Incubate at room temperature for 15 minutes. Transfer all samples to a 96-well plate and read the absorbance at 750 nm to determine the protein concentration for each unknown protein sample.

The ProtE concentration was 1.069 mg/ml

PilA his-Tagged Protein Purification:

PilA was purified following the general procedure below:

E. coli cells containing a construct encoding PilA or a fragment thereof are suspended in BUGBUSTER® and BENZONASE® nuclease (NOVAGEN®), for example 10 ml BUGBUSTER® and 10 ul BENZONASE® nuclease. The cell lysate is mixed at room temperature on a rotating platform, for example, for 15 minutes. The cell lysate is centrifuged at 4° C., for example at 16,000 g for 20 minutes. The supernatant containing the protein is added to a Ni NTA column containing Ni NTA HIS BIND® resin and mixed at 4° C., for example for 1 hour. The column may consist of 2 ml of Ni NTA HIS BIND® resin (NOVAGEN®) and 10 ml 1× Binding Buffer (from NOVAGEN®'s Ni-NTA Buffer Kit). The column flow through is then collected. The resin is washed two times with 1× wash buffer, for example, containing 300 mM NaCl, 50 mM $NaH_2PO_4$, 25 mM imidazone, pH 8.0). The wash is collected by gravity flow. The protein is eluted from the column with 1× elution buffer, for example, 300 mM NaCl, 50 mM $NaH_2PO_4$, 250 mM imidazone, pH 8.0. The protein may be further purified by dialysis with the Binding Buffer and rerun over a Ni NTA column as described above.

Thrombin Cleavage of PilA.

PilA is then incubated with thrombin (diluted 1/50) at room temperature for 16 h, to remove the histidine tag.

Size Exclusion Chromatography (SEC) on PilA Cleaved with Thrombin.

SEC column (GE healthcare, HILOAD™ 26/60 SUPERDEX™ 75 prep grade, 60 cm height approx 319 ml volume) was equilibrated with 5CV of SEC buffer (20 mM HEPES, 150 mM NaCl, pH8.52). Approximately 10 ml of cleaved PilA was loaded onto the column at a flow rate of 2.5 ml/min. 2 ml fractions collected from 0.3CV to 0.9CV. Two runs were performed then fractions were analyzed by SDS-PAGE. Fractions from the two runs containing cleaved PilA protein were pooled together ("SEC pool", 52 ml approx total volume).

Dosage of PilA, SEC Pool.

The SEC pool was dosed with the RCDC method as described above. The cleaved PilA concentration was at 5.37 mg/ml.

Dialysis of the PilA SEC Pool with PBS 1×pH 7.4 (Dialysis Factor=1600) and Dosage by RCDC The concentration post-dialysis determined by RCDC was at 3.0 mg/ml.

Purification of LVL317

Osmotic Shock

Since LVL317 fusion protein is expressed and processed in bacterial periplasm, the protein was extracted by osmotic shock.

Frozen (−20° C.) harvested E. coli B2448 cell paste containing LVL317 from 4 L of fermentor culture were pooled and resuspended in a hypertonic buffer consisting of 24 mM Tris-HCl, 16% (w/v) sucrose, 9.9% (w/v) glucose, 10 mM EDTA, pH 8.0 up to a final volume of 4 L. The suspension was mixed gently for 30 min at room temperature using a 3-blade propeller installed on RW 16 basic stirrer, at medium speed. The suspension was centrifuged at 15,900 x g for 30 minutes at room temperature. Supernatant (SN1) was kept for gel analysis.

The resulting pellet was resuspended in a hypotonic solution; 38 mM $MgCl_2$, and mixed for 30 min at room temperature. The mixture was centrifuged at 15,900×g for 30 minutes at room temperature and the antigen recovered in the supernatant (SN2).

A clarification of the SN2 was performed by filtration through a 0.45/0.2 μm polyethersulfone Sartorius Sartopore 2 MidiCap filter, at 600 ml/min of flow rate.

The SN2 was diluted 1:3 with 20 mM $NaH_2PO_4$—$Na_2HPO_4$, pH 7.0, the pH adjusted to 7.0 if necessary and another clarification by filtration through a 0.45/0.2 μm polyethersulfone Sartorius Sartopore 2 MidiCap filter, at 600 ml/min was performed.

SP SEPHAROSE™ Fast Flow (SP FF) Chromatography

The diluted/filtered SN2 was loaded and captured on a strong cationic exchanger resin (SP SEPHAROSE™ FF-GE Healthcare) in a 14 cm ID (internal diameter)×20 cm length column (column volume 3100 ml) equilibrated with 2CV of 20 mM $NaH_2PO_4$/$Na_2HPO_4$ buffer pH 7.0. After washing the column with 5CV of 20 mM $NaH_2PO_4$/$Na_2HPO_4$ buffer pH 7.0, the antigen (contained within LVL317) was eluted by increasing the concentration of NaCl up to 100 mM in the same washing buffer.

Figure 12:
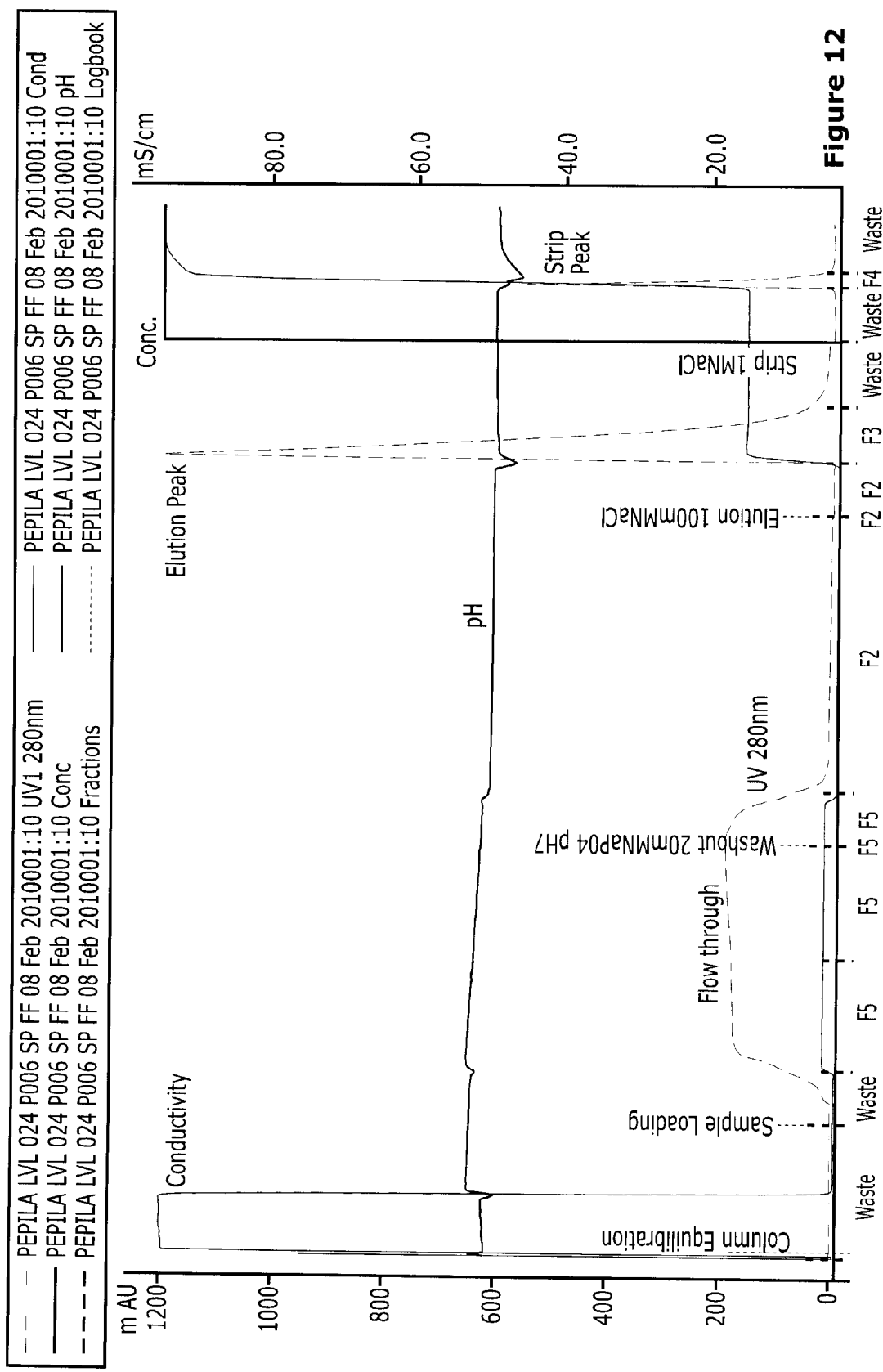
FIG. 12. Typical SP Sepharose™ Fast Flow chromatogram.

See FIG. 12 for a typical SP SEPHAROSE™ Fast Flow chromatogram.

Q SEPHAROSE™ Fast Flow (Q FF) Chromatography

The antigen present in the SP FF Eluate was diluted 1:4 with a 20 mM Tris pH 8.5, pH adjusted to 8.5 if necessary and passed through a strong anionic exchanger resin (Q SEPHAROSE™ FF-GE Healthcare) in a 14 cm ID×11.8 cm length column (column volume 1800 ml) equilibrated with 2CV of 20 mM Tris buffer pH 8.5. The antigen was recovered in the flow-through fraction.

Figure 13:
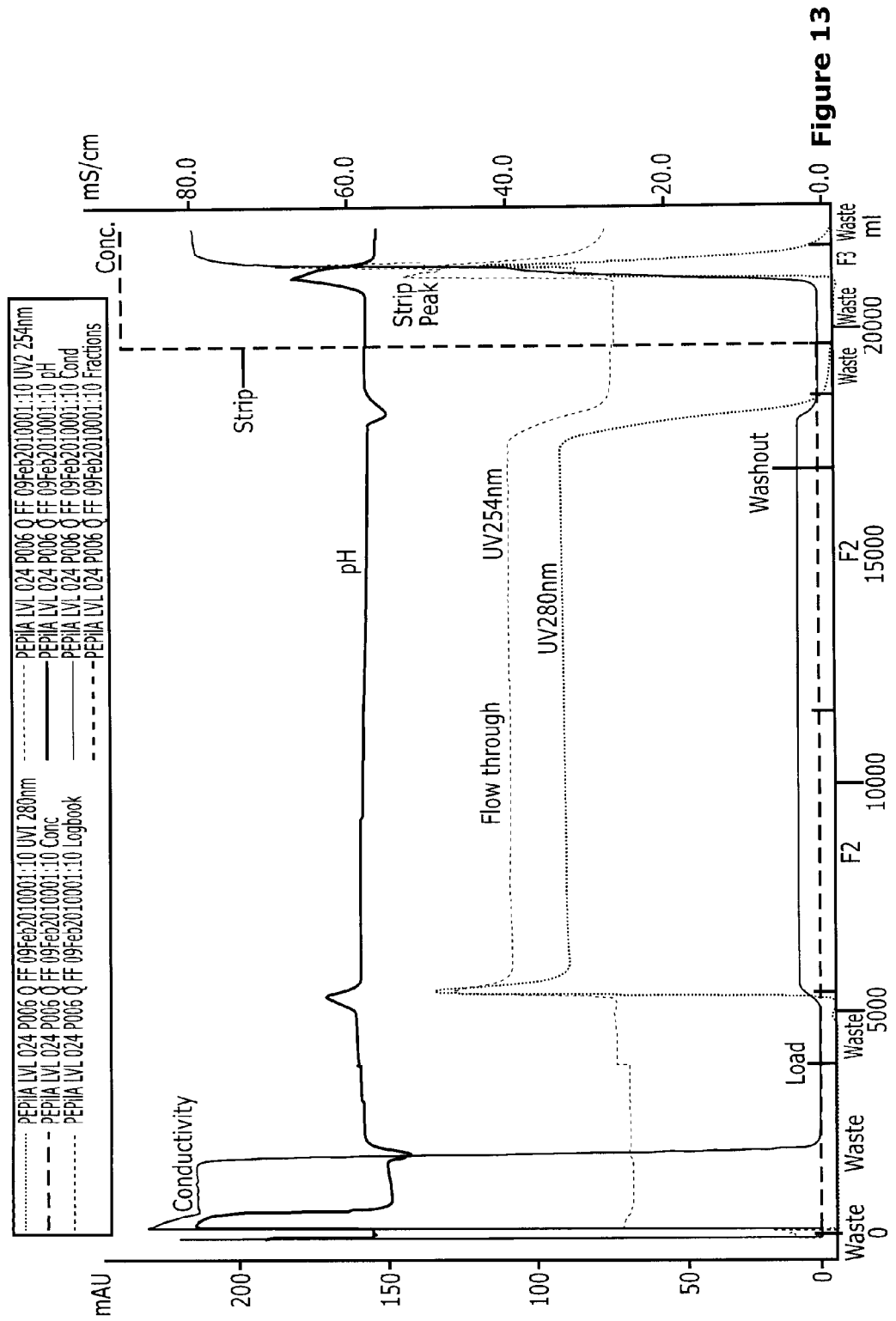
FIG. 13. Typical Q Sepharose™ Fast Flow chromatogram.

See FIG. 13 for a typical Q SEPHAROSE™ Fast Flow chromatogram.

Concentration, Diaflitration, Polysorbate 80 Addition and Sterile Filtration

The Q FF flow-through containing the antigen was concentrated up to 0.7-0.8 mg/ml based on chromatogram UV and diafiltered with 5DV of 10 mM $KH_2PO_4$/$K_2HPO_4$ buffer pH 6.5 using a Pellicon-2™ 10 kDa cutoff membrane (Millipore).

Using a 5% stock solution, polysorbate 80 (for example, TWEEN™ 80) was added to the ultrafiltration retentate and agitated for 30 minutes with magnetic stirrer at 130 rpm at 4° C. The final concentration of polysorbate 80 was 0.04%. Ultrafiltration retentate was sterilized by filtration through a 0.45/0.2 μm Cellulose Acetate membrane (Sartobran 300, Sartorius). The purified bulk was stored at −20° C. or −80° C. Absolute protein concentration was measured by AAA (Amino Acid Analysis) at 0.737 mg/ml.

Example 9

Use of Polysorbate 80

A titration experiment indicated that the addition of polysorbate 80, specifically, TWEEN™ 80 to a final concentration of 0.04% (w/v) to the purified bulk prior to sterile filtration reduced filamentous particle formation and aggregation.

According to DSC analysis, TWEEN™ 80 reduced the degree of structural change (30-45° C.) seen after freeze/thaw cycles after storage at −20° C. and after storage 4 days at 4° C., −20° C. and −80° C. and 37° C.

Example 10

SDS-PAGE and Western Blot Analysis of LVL317

SDS-PAGE and Western Blot Analysis:

NUPAGE®, Bis-Tris 4-12% gel was loaded as described below with 10 μg of sample in NUPAGE® LD sample buffer containing 50 mM DTT heated 5 min at 95° C. (20 μL of sample was loaded for samples having low concentration). Migration: 35 minutes at 200 Volts at room temperature (RT) in NUPAGE®MES Running Buffer. Gel Stained 2 hours in Instant blue (Novexin cat.: ISBO1L) and destained overnight in water.

Lane Contents:

1: MW standard (10 μL)
2: Start (total fraction) (10 μg)
3: SN1 non filtered (10 μg)
4: SN2 not filtered (10 μg)
5: Not extracted (10 μg)
6: Load SP FF (10 μg)
7: Flow through SP FF (6.9 μg)
8: Wash SP FF (20 μL)
9: Elution SP FF (10 μg)
10: Strip SP FF (10 μg)
11: Load Q FF (8.9 μg)
12: Elution Q FF (9.8 μg)
13: Strip Q FF (4.8 μg)
14: TFF retentate before0.04% TWEEN ™ 80 spiked (10 μg)
15: Purified bulk Not filtered 0.04% TWEEN ™ 80 spiked (10 μg)
16: Purified bulk Sterile Filtered 0.04% TWEEN ™ 80 spiked (10 μg)
17: Purified bulk Sterile Filtered 0.04% TWEEN ™ 80 spiked (20 μg + spiked *E. Coli* Cell lysate Rix (1 μg))
18: *E. Coli* Cell lysate Rix (2 μg)
19: *E. Coli* Cell lysate Rix (1 μg)
20: *E. Coli* Cell lysate Rix (0.5 μg)

Figure 14:
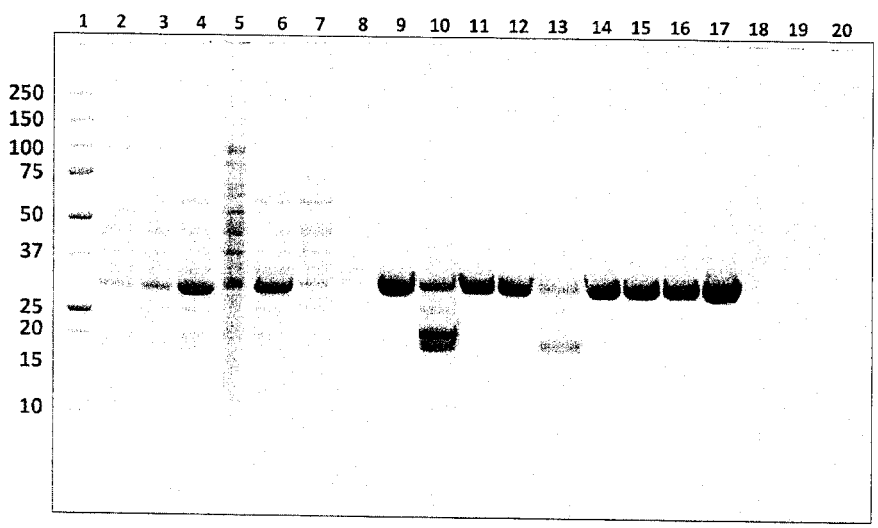
FIG. 14. SDS-PAGE of In-process samples from purification process of PE-PilA fusion protein.

See FIG. 14 for a SDS-PAGE of 1n-process samples from purification process of PE-PilA fusion protein.

For Western Blot, proteins were transferred at 4° C. overnight at 30 Volts in NUPAGE® transfer buffer +20% Methanol, 0.1% SDS on nitrocellulose membrane. Membranes were blocked 1 hour with 50 mM Tris, 150 mM NaCl pH 7.4+5% non-fat dry milk, incubated 2 hours in rabbit polyclonal primary antibody diluted in blocking buffer (anti-Prot-E 1/50 000 and anti-Ecoli (BLR) 1/1 000), washed 3×5 minutes in 50 mM Tris pH 7.4+0.05% Tween 20, incubated 1 hour in secondary antibody (goat anti-rabbit conjugated to alkaline phosphatase diluted 1/5000 in blocking buffer), washed 3×5 minutes in wash buffer and developed in BCIP/NBT substrate (1 tablet per 10 ml). All incubations performed in 25 ml per membrane.

Figure 15:
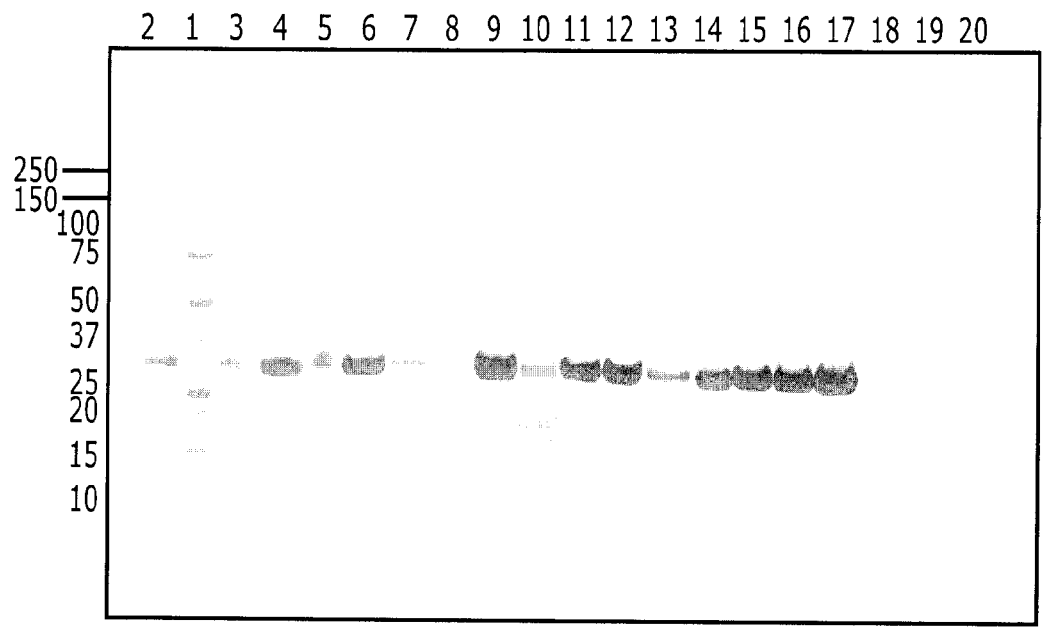
FIG. 15. Western Blot of In-process samples of purification process from PE-PilA fusion protein. Blot using rabbit polyclonal anti-PE.

See FIG. 15 for a Western Blot of 1n-process samples of purification process from PE-PilA fusion protein. Blot using rabbit polyclonal anti-PE.

Lane Contents:

1: MW standard (10 μL)
2: Start (total fraction) (10 μg)
3: SN1 non filtered (10 μg)
4: SN2 not filtered (10 μg)
5: Not extracted (10 μg)
6: Load SP FF (10 μg)
7: Flow through SP FF (6.9 μg)
8: Wash SP FF (20 μL)
9: Elution SP FF (10 μg)
10: Strip SP FF (10 μg)
11: Load Q FF (8.9 μg)
12: Elution Q FF (9.8 μg)
13: Strip Q FF (4.8 μg)
14: TFF retentate before0.04% TWEEN ™ 80 spiked (10 μg)
15: Purified bulk Not filtered 0.04% TWEEN ™ 80 spiked (10 μg)
16: Purified bulk Sterile Filtered 0.04% TWEEN ™ 80 spiked (10 μg)
17: Purified bulk Sterile Filtered 0.04% TWEEN ™ 80 spiked (20 μg + spiked *E. Coli* Cell lysate Rix (1 μg))
18: *E. Coli* Cell lysate Rix (2 μg)
19: *E. Coli* Cell lysate Rix (1 μg)
20: *E. Coli* Cell lysate Rix (0.5 μg)

Figure 16:
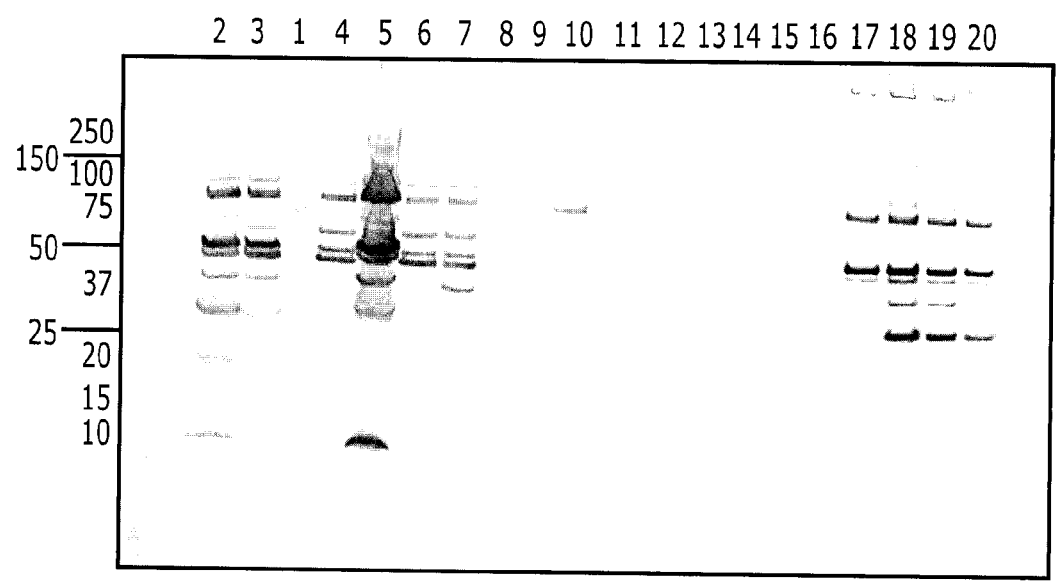
FIG. 16. Western Blot of In-process samples of purification process from PE-PilA fusion protein. Blot using rabbit polyclonal anti-*E. coli*(BLR).

See FIG. 16 for a Western Blot of 1n-process samples of purification process from PE-PilA fusion protein. Blot using rabbit polyclonal anti-*E. coli* (BLR).

Lane Contents:

1: MW standard (10 μL)
2: Start (total fraction) (10 μg)
3: SN1 non filtered (10 μg)
4: SN2 not filtered (10 μg)
5: Not extracted (10 μg)
6: Load SP FF (10 μg)
7: Flow through SP FF (6.9 μg)
8: Wash SP FF (20 μL)
9: Elution SP FF (10 μg)
10: Strip SP FF (10 μg)
11: Load Q FF (8.9 μg)
12: Elution Q FF (9.8 μg)
13: Strip Q FF (4.8 μg)
14: TFF retentate before0.04% TWEEN ™ 80 spiked (10 μg)
15: Purified bulk Not filtered 0.04% TWEEN ™ 80 spiked (10 μg)
16: Purified bulk Sterile Filtered 0.04% TWEEN ™ 80 spiked (10 μg)
17: Purified bulk Sterile Filtered 0.04% TWEEN ™ 80 spiked (20 μg + spiked *E. Coli* Cell lysate Rix (1 μg))
18: *E. Coli* Cell lysate Rix (2 μg)
19: *E. Coli* Cell lysate Rix (1 μg)
20: *E. Coli* Cell lysate Rix (0.5 μg)

SDS-PAGE and Western Blot Figures Comments:

The PE-PilA fusion protein migrates at 30 kDa. The extraction by osmotic shock extracts the fusion protein expressed and processed in bacteria periplasm and reduced contamination from bacteria. Small loss of fusion protein during hypertonic treatment (lane 3). A small proportion is not extracted by hypotonic treatment and remains associatE with cells (lane 5). Small loss in SP FF Flow through (lane 7) and in strip fraction of both columns (lanes 10 and 13). Since the total volume of strip fraction is low the loss of fusion protein is not significant. Degraded bands are visible in strip fractions but not in final product. No significant contamination from *E. coli* host cell proteins in purified bulk (lane 16).

Analysis of LVL735 and LVL778 yielded similar profiles as LVL317.

Example 11

Melting Point Data for PE, PilA and LVL317

Thermal transition of PE-PilA fusion non His-tagged protein (LVL317) was compared with the thermal transition of both PE his-tagged (as described in Example 8) and cleaved PilA (as described in Example 8) proteins, purified as described above.

Before DSC, PE and PilA were dialyzed overnight in 10 mM $K_2HPO_4/KH_2PO_4$ pH 6.5+0.04% Tween 80 (1:250 sample:buffer volume ratio) to have them in the same buffer as the fusion protein. After dialysis, proteins concentration was measured by BCA and adjusted to 300 µg/ml (PE) and 500 µg/ml (PilA).

Analysis done on VP™-DSC from MicroCal, LLC (part of GE Healthcare). The final dialysis buffer was used as reference and subtracted from the scans. DSC scan rate 90° C./hr. In order to evaluate the capacity to measure the thermal transition in the Final Container (FC) after formulation, the fusion protein was diluted to the FC concentration (60 µg/ml). Final container data not shown.

Figure 17:
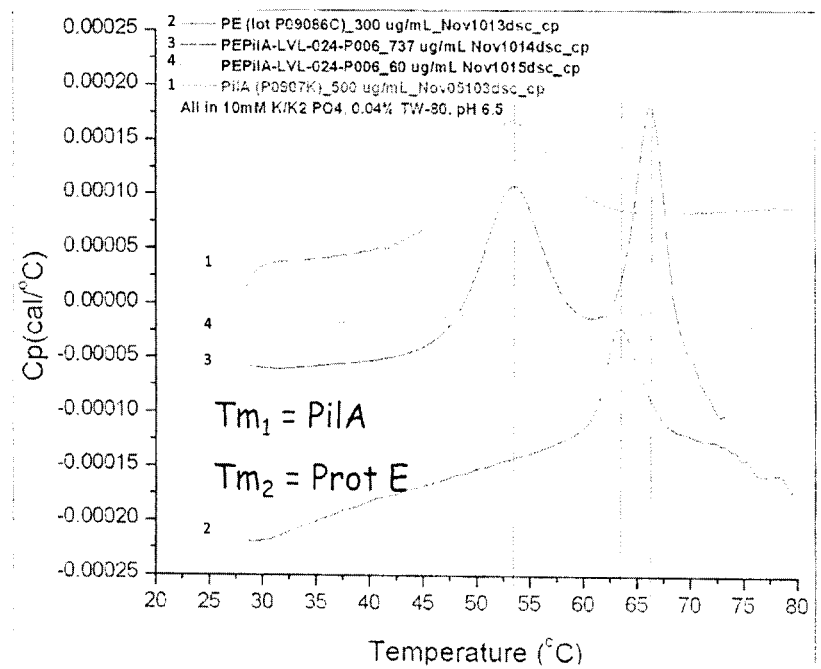
FIG. 17. Thermal transition of PE-PilA fusion protein and PE and PilA proteins. Curves: PilA (1), Protein E (Prot E, PE) (2), PE-PilA Purified Bulk not diluted, 737 µg/ml (3), and PE-PilA Purified Bulk diluted at Final Container concentration 60 µg/ml (4).

Results:

See FIG. 17 for Thermal transition of PE-PilA fusion protein and PE and PilA proteins. Curves: PilA (1), Protein E (Prot E, PE) (2), PE-PilA PB not diluted 737 µg/ml (3), and PE-PilA PB diluted at FC concentration 60 µg/ml (4).

| | |
|---|---|
| 1 - PilA | Tm: 53° C. |
| 2 - Protein E | Tm: 63 |
| 3 - PE-PilA PB (Purified Bulk) not diluted 737 µg/ml | $Tm_1$: 53.7° C. and $Tm_2$: 66.1° C. |
| 4 - PE-PilA PB diluted at FC concentration 60 µg/ml | Tm1: 53.2° C. and Tm2: 67.6° C. |

Two transitions were detected in the purified fusion protein (LVL317) (curves 3 and 4).

The $Tm_1$ (53.7° C.) of the PE-PilA fusion protein is similar to PilA transition (53° C.).

Significant shift of $Tm_2$ in PE-PilA (66.1° C.) as compared to PE transition (63° C.). The fusion of both domains seems to stabilize the PE fragment.

The shift of $Tm_2$ in the diluted fusion protein as compared to undiluted is a concentration artifact arising from the steep decreasing slope typical of aggregation which is concentration dependant.

Antigen folding analysis of LVL735 and LVL778 were similar to that of LVL317.

Example 12

Figure 18:
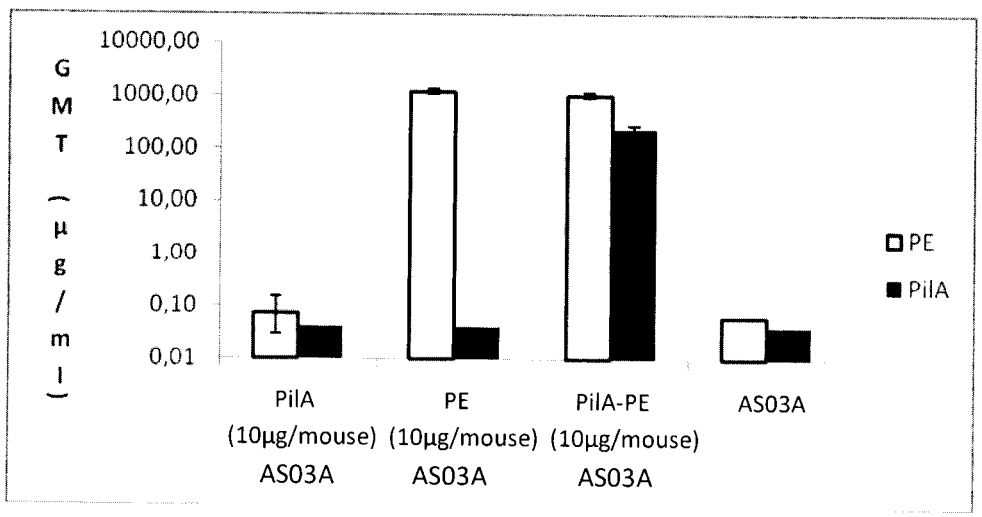
FIG. 18. Antibody responses against LVL291 PE-PilA fusion protein and against monovalent PE and PilA in the Balb/c mouse model.

PE-PilA Fusion Protein Construct LVL291 Anti-PilA Immunogenicity Response in Balb/c Mice The immune response directed against purified LVL291 PE-PilA fusion protein (the LVL291 fusion protein without the heterologous signal peptide) formulated in $AS03_A$ was evaluated in Balb/c mice. Animals (20 mice/group) were immunized by the intramuscular route at days 0, 14 and 28 with 10 µg of PE (from vector pRIT16762), PilA (from vector pRIT16790) or PE-PilA, each formulated in $AS03_A$. The control group was vaccinated with $AS03_A$ alone. Antibody response directed against each antigen was determined in individual sera collected at day 42. No antibody response was obtained with the negative control. As shown in FIG. 18, the antibody response directed against PilA was higher in mice immunized with the PE-PilA fusion compared to antibody response in mice immunized with monovalent PilA. The antibody responses directed against PE were similar in mice immunized with the fusion protein and mice immunized with monovalent PE. GMT=geometric means titer. Data were captured and analyzed with the SOFTMAX® Pro Software (Molecular Devices) running under WINDOWS® (Microsoft); the four parameters logistic log function was used to calculate the standard curve. The four-parameter logistic-log function describes, with a high degree of accuracy, the curve of the reference serum displaying a pronounced sigmoidal shape when plotted on an optical density-versus-concentration (log) scale. Antibody concentrations were calculated at each dilution of mice serum samples by interpolation of the standard curve. The antibody in quality control sera and in unknown serum samples is obtained by averaging the values from all dilutions that fall within the working range (10-80%) of the dilution curve of the reference.

Results are shown in FIG. 18, which graphs the antibody responses against LVL291 PE-PilA fusion protein and against monovalent PE and PilA in the Balb/c mouse model.

Example 13

Murine Nasopharyngeal Colonization Model. Immunization with PE-PilA. Challenge with NTHi Strain 86-028NP and NTHi Strain 3224A Balb/c female mice (20/group) were immunized intranasally at days 0 and 14 with 6 µg of a purified PE-PilA fusion protein (LVL291 for challenge with 86-028NP; LVL317 for challenge with strain 3224A) formulated with LT (heat labile toxin of *Escheria coli*) and on day 28 with 6 µg of a purified PE-PilA fusion protein in phosphate buffered saline (PBS). Control mice (20/group) were vaccinated with LT alone. Mice were subsequently challenged intranasally with $5 \times 10^6$ CFU (colony forming units) of homologous NTHi strain 86-028NP and heterologous NTHi strain 3224A. Homology and heterology are determined by reference to the NTHi strain with which the mice were immunized. Bacterial colonies were counted in nasal cavities removed 1 and 2 days after the challenge. D1=day 1. D2=day 2.

PE-PilA vaccination increased the clearance of NTHi strain 86-028NP and strain 3224A in the nasopharynx at day 1 and day 2 post challenge.

For the experiment performed with NTHi strain 86-028NP: A 2-way fixed ANOVA was performed using the log 10 values of the counts as response, the fixed factors being the group (4 levels) and the day (2 levels). The assumption of variance heterogeneity was rejected and a model with heterogeneous variances was fitted to the data. No significant interaction was detected between the 2 factors. The group fusion PE-PilA (6 μg per mouse) significantly reduced CFU compared with the control group (LT); the geometric mean ratio being equal to 0.06 with a 95% confidence interval of 0.01, 0.25.

For the experiment conducted with NTHi strain 3224A: A 3-way fixed ANOVA was performed using the log 10 values as response, the fixed factors being the group, the day, and the experiment. The Shapiro-Wilk and Levene's test did not reject the assumptions of normality and of homogeneity of variances. No significant interaction between any of the 2 factors or between the 3 factors was detected and only main factors were kept in the analysis. PE-PilA/LT significantly reduced CFU compared with the control group; the geometric mean ratio being equal to 0.11 with a 95% confidence interval of 0.02, 0.61.

Figure 19:
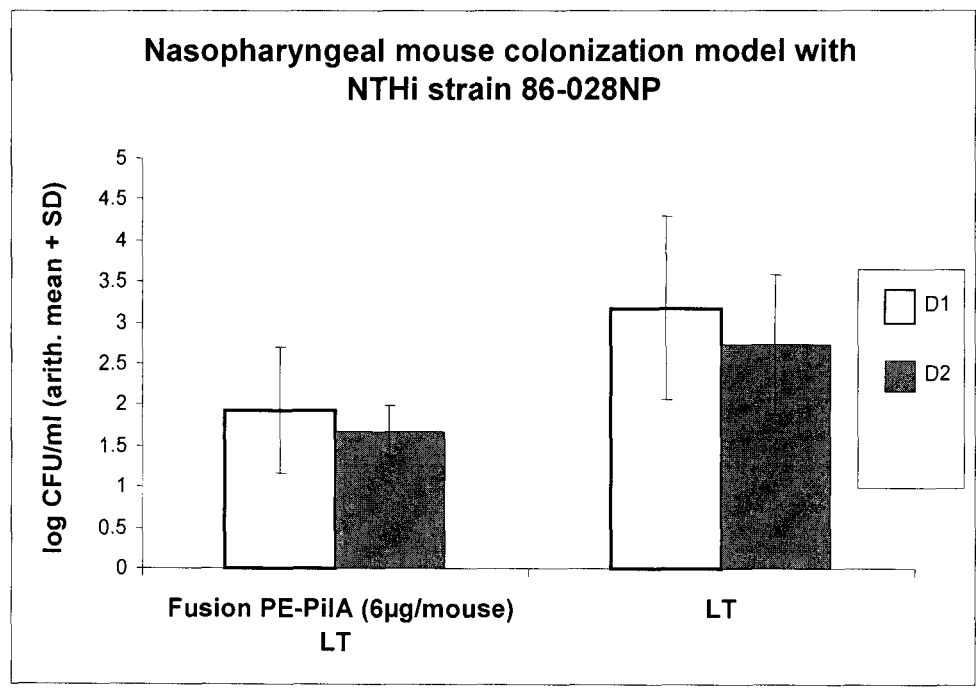
FIG. 19. Effect of PE-PilA fusion protein vaccination on NTHi strain 86-028NP bacterial clearance in mouse nasopharynx.

See FIG. 19 for effect of PE-PilA fusion protein vaccination on NTHi strain 86-028NP bacterial clearance in mouse nasopharynx.

Figure 20:
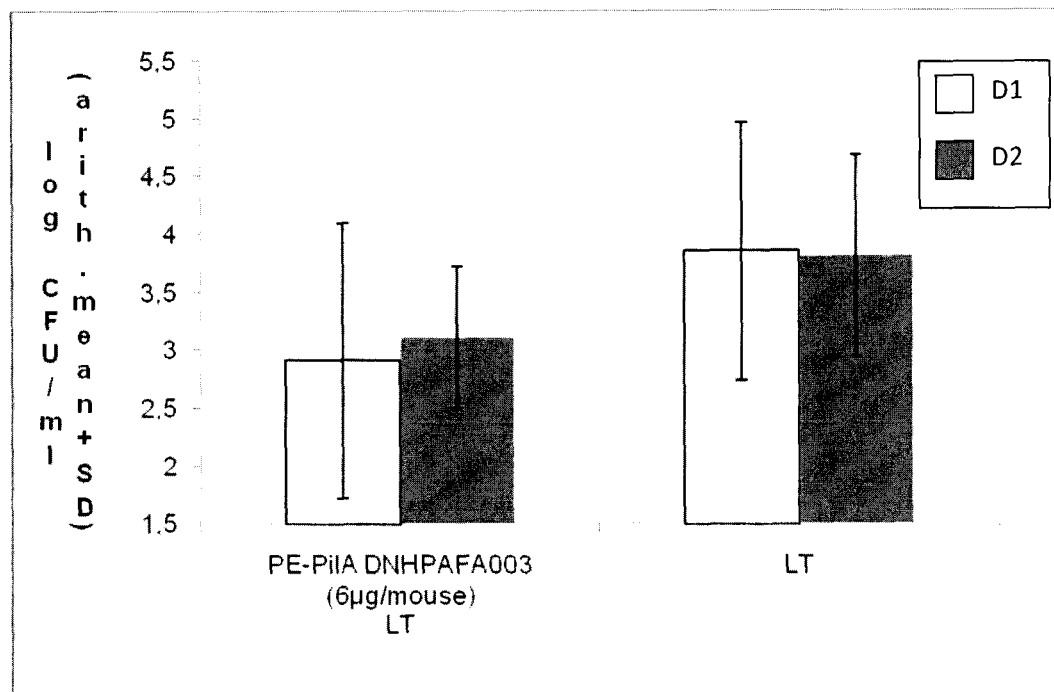
FIG. 20. Effect of PE-PilA fusion protein vaccination on NTHi strain 3224A bacterial clearance in mouse nasopharynx.

See FIG. 20 for effect of PE-PilA fusion protein vaccination on NTHi strain 3224A bacterial clearance in mouse nasopharynx.

Example 14

Murine Nasopharyngeal Colonization Model. Immunization with PilA. Challenge with NTHi strain 3219C Female OF1 mice (20 mice/group) were immunized intranasally at days 0 and 14 with 3 μg PilA (from vector 16790) formulated with LT and at day 28 with 3 μg PilA in PBS. Control mice were vaccinated with LT alone. Mice were subsequently challenged intranasally with $5 \times 10^6$ CFU of NTHi strain 3219C. Bacterial colonies were counted in nasal cavities removed 3 and 4 days after the challenge. D3=day 3. D4=day 4.

Figure 21:
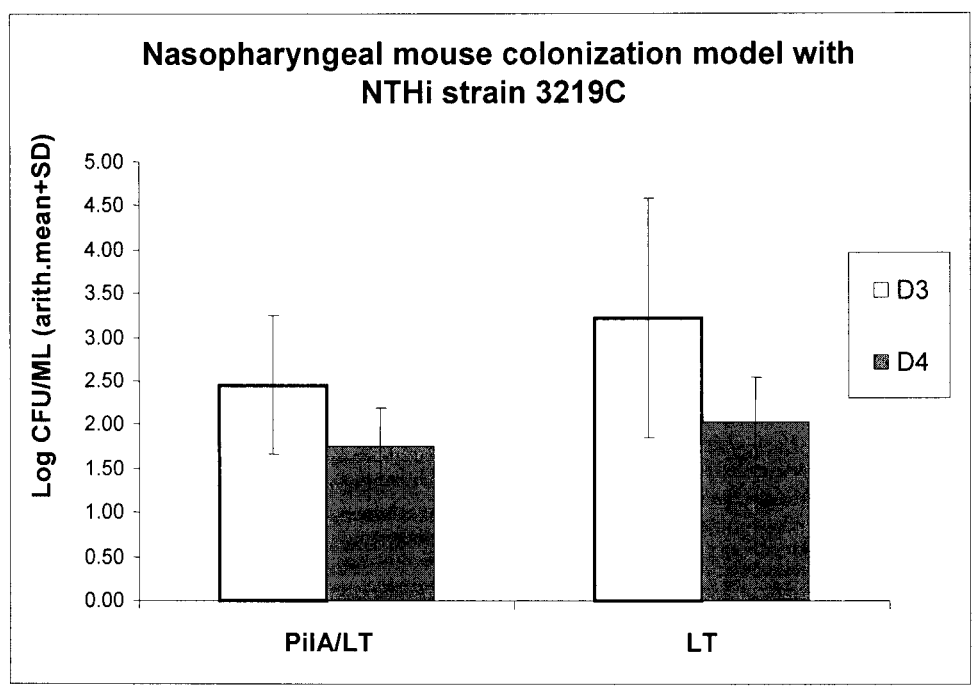
FIG. 21. Effect of PilA vaccination on bacterial clearance in mouse nasopharynx.

See FIG. 21 for effect of PilA vaccination on bacterial clearance in mouse nasopharynx.

Example 15

Murine Nasopharyngeal Colonization Model. Immunization with PE. Challenge with NTHi Strain 3224A Balb/c female mice (20 mice/group) were immunized intranasally at days 0 and 14 with 3 μg PE (from vector pRIT16762) formulated with LT and at day 28 with 3 μg PE in PBS. Control mice were vaccinated with LT alone. Mice were subsequently challenged intranasally with $5 \times 10^6$ CFU of NTHi strain 3224A. Bacterial colonies were counted in nasal cavities removed 3 and 4 days after the challenge. 10 mice were examined on day 3 (D3). 10 mice were examined on day 4 (D4). PE vaccination increased significantly the clearance of NTHi in the naso-pharynx at day 4 post challenge (FIG. 22), using on the Dunn test for statistical analysis.

Figure 22:
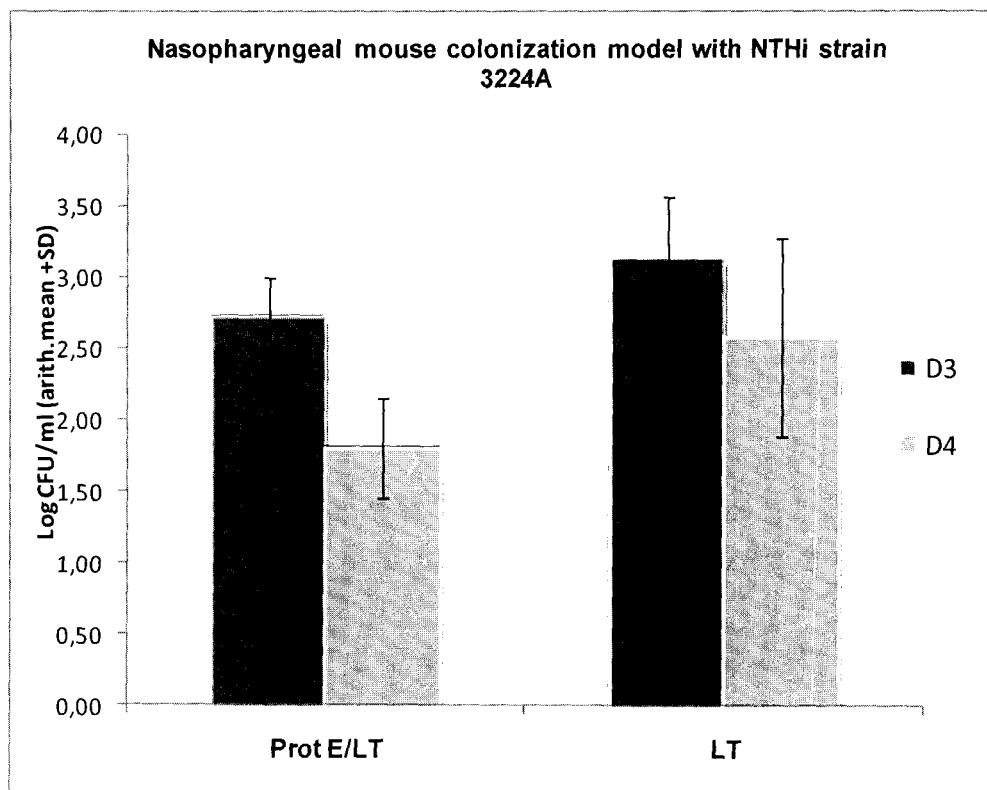
FIG. 22. Effect of PE vaccination on bacterial clearance in mouse nasopharynx.

See FIG. 22 for effect of PE vaccination on bacterial clearance in the nasopharynx of mice.

Example 16

Vibronectin Binding. Inhibition of Vibronectin Binding by LVL317 & LVL735 PE-PilA Fusion Protein The ability of PE in the purified LVL317 PE-PilA fusion protein construct to bind to vitronectin was evaluated. Microtiter plates (POLYSORP™, Nunc, Thermo Fisher Scientific) were coated with PE (from vector pRIT16762) or with purified LVL317 PE-PilA fusion protein (10 μg/ml). Plates were washed four times with NaCl 150 mM-polysorbate 20, 0.05% (for example, TWEEN™ 20) and blocked for one to two hours with PBS-BSA 1%. After four washings, vitronectin (Vitronectin from human plasma, SIGMA-ALDRICH®) was added (10 μg/ml), two fold diluted (12 dilutions), and the plates were incubated for 1 h at room temperature. The plates were then washed 4 times with NaCl 150 mM-polysorbate 20, 0.05% (for example TWEEN™ 20) After washings, the bound vitronectin was detected using peroxydase sheep anti-human vitronectin (US Biological) followed by the addition of ortho-phenylene diamine/$H_2O_2$ substrate. The color developed is directly proportional to the amount of antibody fixed to the vitronectin.

Figure 23:
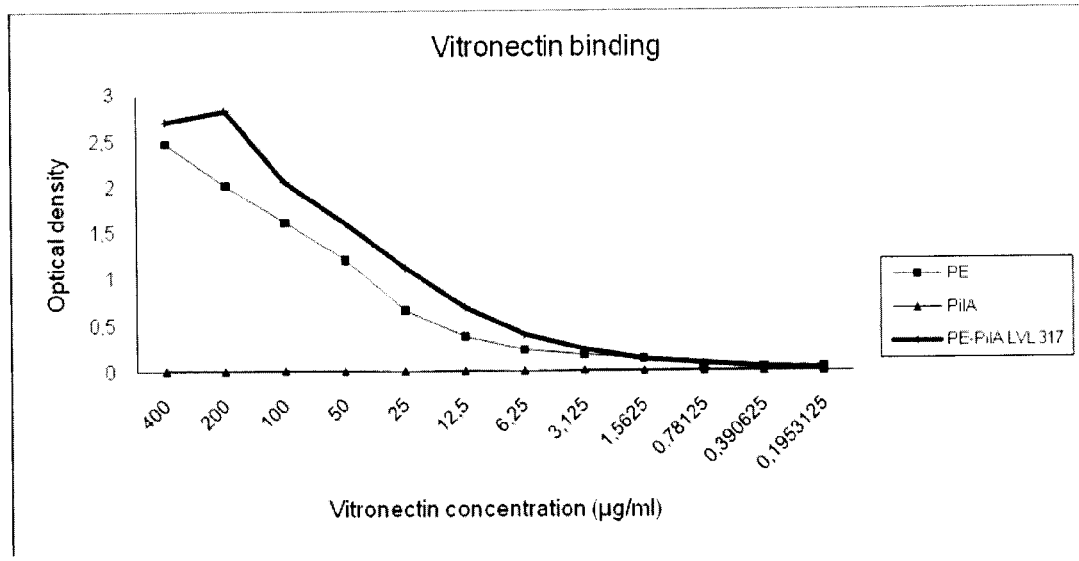
FIG. 23. (a) LVL317 PE-PilA fusion protein binding to vitronectin and (b) LVL317 and LVL735 PE-PilA fusion protein bound to vitronectin.
Figure 23:
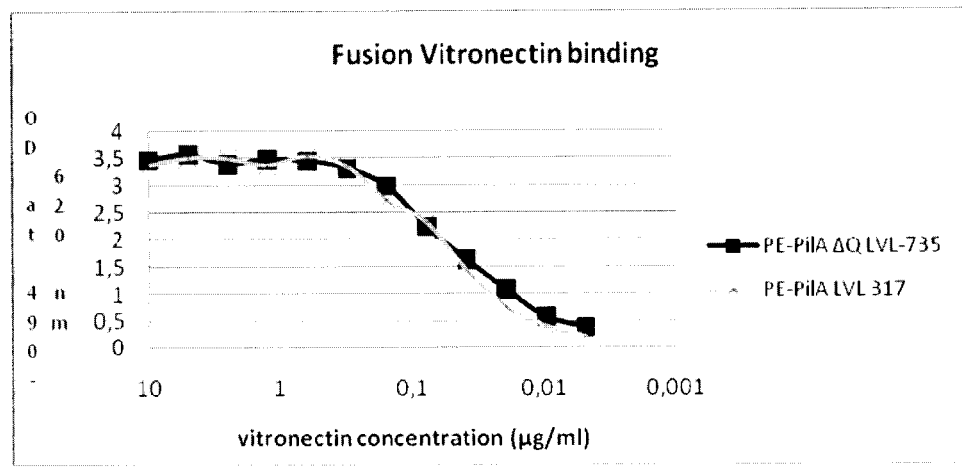

See FIG. 23 for (a) LVL317 PE-PilA fusion protein bound to vitronectin. PilA=PilA from NTHi strain 86-028NP (as described for pRIT16790); PE=Protein E (as described for pRIT16762) and (b) LVL317 and LVL735 PE-PilA fusion protein bound to vitronectin.

Example 17

Vibronectin Binding. Inhibition of Vibronectin Binding by Antibodies Directed Against the LVL291 PE-PilA Fusion Protein Microtiter plates (POLYSORP™, Nunc, Thermo Fisher Scientific) were coated with PE (from vector pRIT16762) or with purified PE-PilA fusion protein (10 μg/ml). Plates were washed four times with NaCl 150 mM-polysorbate 20, 0.05% (for example, TWEEN™ 20) and blocked for two hours with PBS-BSA 1%. After washings, vitronectin (Vitronectin from human plasma, SIGMA-ALDRICH®) was added at 50 μg/ml and purified antibodies anti-PE-PilA (produced and purified in house) were two-fold serially diluted and incubated for 1 h at room temperature. The plates were then washed 4 times with NaCl 150 mM-polysorbate 20, 0.05% (for example, TWEEN™ 20). After four washings, the bound vitronectin was detected using peroxydase sheep anti-Vitronectin (US Biological) followed by the addition of ortho-phenylene diamine/$H_2O_2$ substrate. The color developed is directly proportional to the amount of antibody fixed to the vitronectin. Inhibition of vitronectin binding to PE by polyclonal antibodies directed against PE-PilA was observed.

Figure 24:
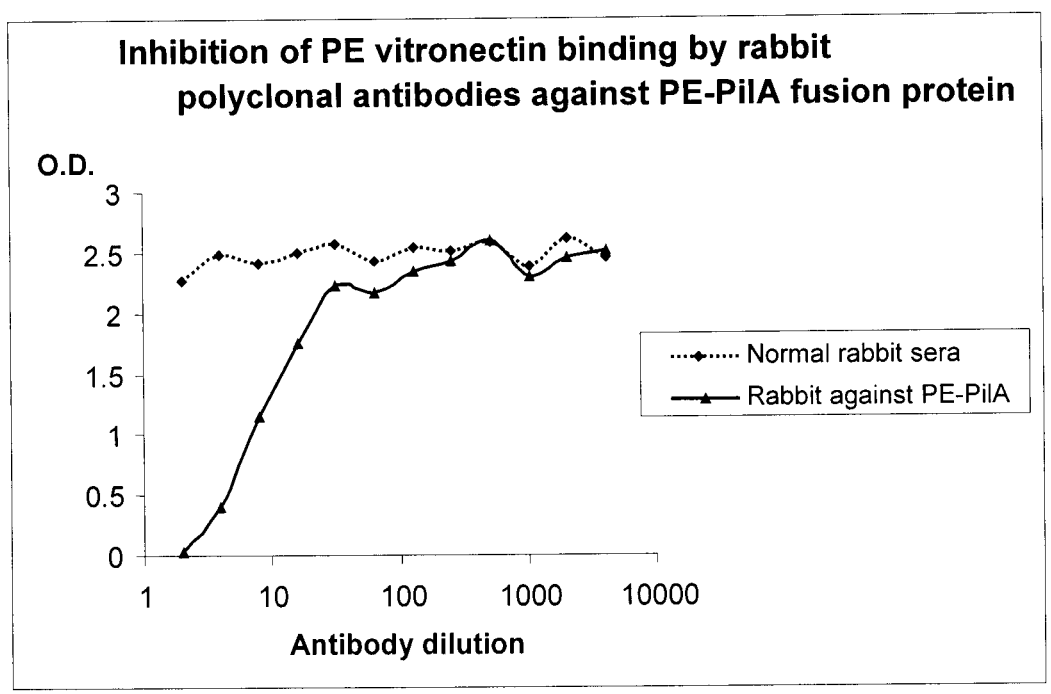
FIG. 24. Inhibition of vitronectin binding by polyclonal antibodies against PE-PilA fusion protein.

See FIG. 24 for inhibition of vitronectin binding by polyclonal antibodies against PE-PilA fusion protein.

Example 18

Antigenicity of LVL291 PE-PilA Fusion Protein. ELISA

Purified LVL291 PE-PilA fusion protein was validated in an antigenicity test with monovalent proteins as control. The fusion protein was tested in a sandwich ELISA developed with polyclonal antibodies (rabbit and guinea pig) generated against the PE gene fragment coding for amino acids 22 to 160 of SEQ ID NO: 4 (as described for pRIT16711) or against PilA from NTHi strain 86-028NP (from vector pRIT16790).

PilA or PE was added at 100 ng/ml and serially two fold diluted. After 30 minutes incubation and after washing, the bound antigen was detected by a rabbit polyclonal serum obtained after immunisation with PE or PilA. The bound antibodies were detected using a peroxydase anti-rabbit Ig (Jackson ImmunoResearch Laboratories, Inc.) followed by the addition of ortho-phenylene-diamine/$H_2O_2$ substrate. The color developed is directly proportional to the amount of antigen present. Absorbance readings were measured using a spectrophotometer for microtiter plates. The antigenicity of the samples was determined by comparison to the curve of the full length PE or full length PilA reference antigen and is expressed in ug/ml. The reference represented 100% of antigenicity.

As observed in the Table 6: Antigenicity was observed with the purified LVL291 PE-PilA fusion protein compared to the monovalent PE and PilA antigens.

TABLE 6

Relative antigenicity obtained with purified LVL291 PE-PilA fusion protein in the antigenicity test.

|  | PE relative antigenicity (%) |
|---|---|
| Protein E as Reference | 100 |
| PE-PilA | 130-148 |
| PilA as Reference | 100 |
| PE-PilA | 120-152 |

Example 19

Immunogenicity of LVL735 PE-PilA Fusion Protein

Female Balb/c mice (n=34) were immunized by the intramuscular route at days 0, 14 and 28 with 50 µl of vaccine formulation containing 1, 0.2 or 0.04 µg of PE-PilA fusion protein LVL317 or LVL735 formulated within $AS01_E$ or $AlPO_4$ (aluminium phosphate). The antibody responses to PE and PilA were determined in individual sera collected at day 42 and the IgG level against PE and PilA was measured and expressed in µg/ml.

Figure 27:
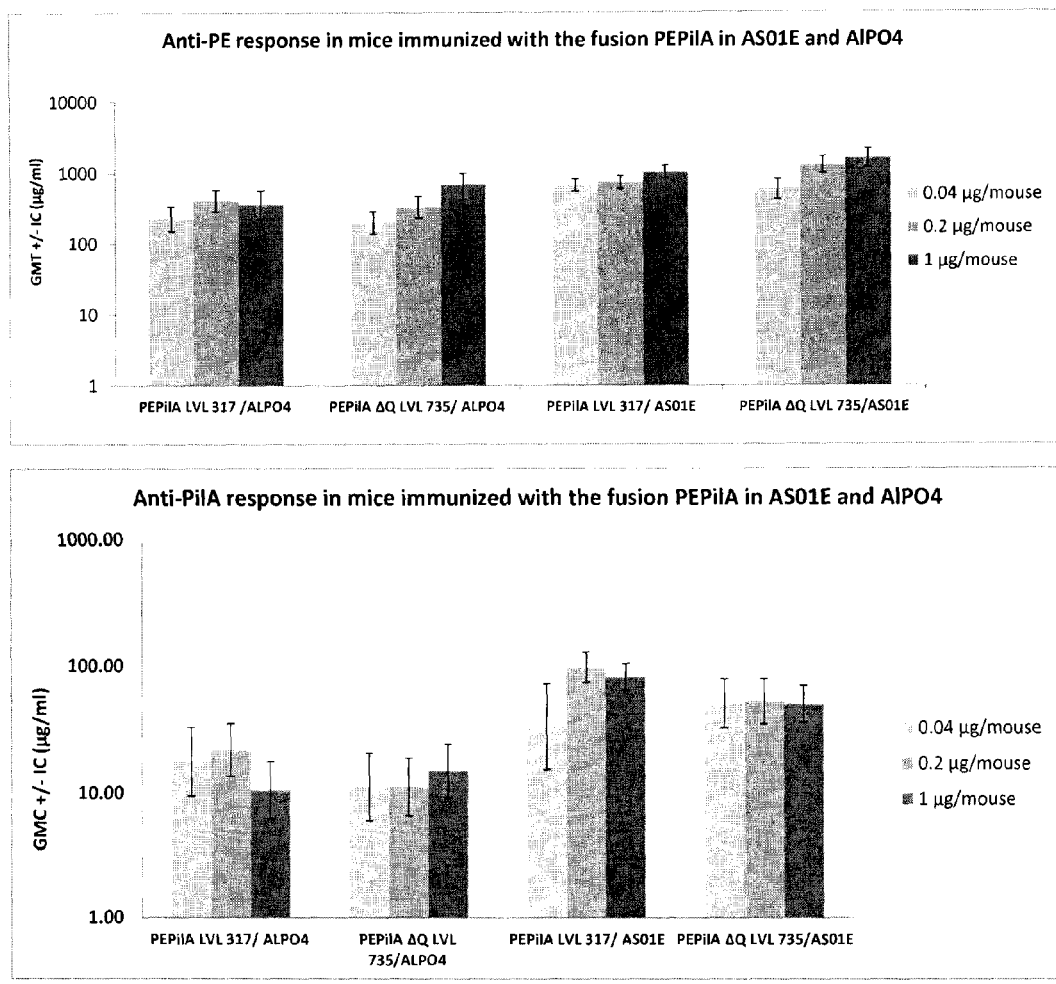
FIG. 27. PE and PilA antibody response to LVL317 and LVL735.

See FIG. 27 for PE and PilA antibody response to LVL317 and LVL735. GMC=geometric mean concentration. GMT=geometric means titer. IC=confidence intervals.

Example 20

Protective Efficacy of the LVL735 and LVL317 Fusion Proteins in a Mouse Model of Non-Typeable *Haemophilus influenzae* Nasopharyngeal Colonization Female Balb/c mice were intranasally immunized at days 0 and 14 with 10 µl of vaccine formulation containing 5.8 µg of LVL735 or LVL317 admixed with 0.5 µg of *E. coli* labile toxin (LT). A booster dose of 5.8 µg of non-adjuvanted LVL735 or LVL317 was administered at day 28. Control mice were vaccinated with LT alone at days 0 and 14, and PBS at day 28. Animals were intranasally challenged with $5\times10^6$ cfu of NTHi 3224A strain at day 42. Bacterial colonies were counted in nasal cavities removed 1 and 2 days after the challenge (n=10/time-point). Nasal cavities are homogenized in medium and a bacterial quantification is performed. Results are well expressed in CFU/ml.

Figure 28:
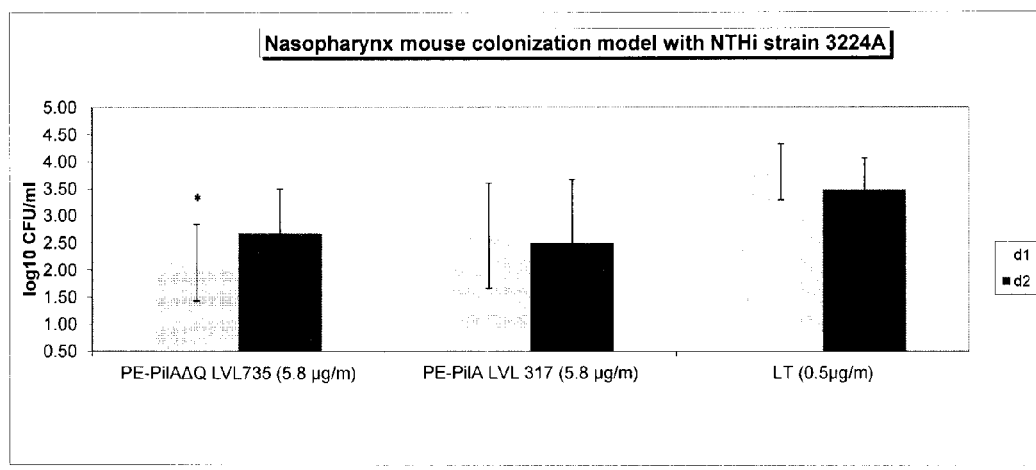
FIG. 28. Effect of LVL735 and LVL317 vaccination on bacterial clearance in a mouse model of non-typeable *Haemophilus influenzae* nasopharyngeal colonization.

See FIG. 28 for the effect of LVL735 and LVL317 vaccination on bacterial clearance in a mouse model of non-typeable *Haemophilus influenzae* nasopharyngeal colonization.

The invention claimed is:

1. A fusion protein selected from the group consisting of SEQ ID NO. 148, SEQ ID NO. 150, SEQ ID NO. 194, SEQ ID NO. 196, SEQ ID NO. 198, SEQ ID NO. 200, SEQ ID NO. 202 and SEQ ID NO. 204.

2. A fusion protein of claim 1 wherein the signal peptide has been removed.

3. The fusion protein of SEQ ID NO. 148 wherein the signal peptide has been removed, SEQ ID NO. 177 (QIQKAEQN DVKLAPPTDV RSGYIRLVKN VNYYIDSESI WVDNQEPQIV HFDAVVNLDK GLYVYPEPKR YARSVRQYKI LNCANYHLTQ VRTDFYDEFW GQGLRAAPKK QKKHTLSLTP DTTLYNAAQI ICANYGEAFS VDKKGGTKKA AVSELLQASA PYKADVELCV YSTNETTNCT GGKNGIAADI TTAKGYVKSV TTSNGAITVK GDGTLANMEY ILQATGNAAT GVTWTTTCKG TDASLFPANF CGSVTQ).

4. The fusion protein of SEQ ID NO. 194 wherein the signal peptide has been removed, SEQ ID NO. 219 (IQKAEQND VKLAPPTDVR SGYIRLVKNV NYYIDSESIW VDNQEPQIVH FDAVVNLDKG LYVYPEPKRY ARSVRQYKIL NCANYHLTQV RTDFYDEFWG QGLRAAPKKQ KKHTLSLTPD TTLYNAAQII CANYGEAFSV DKKGGTKKAA VSELLQASAP YKADVELCVY STNETTNCTG GKNGIAADIT TAKGYVKSVT TSNGAITVKG DGTLANMEYI LQATGNAATG VTWTTTCKGT DASLFPANFC GSVTQ).

5. An immunogenic composition comprising the fusion protein of SEQ ID NO. 177 (QIQKAEQN DVKLAPPTDV RSGYIRLVKN VNYYIDSESI WVDNQEPQIV HFDAVVNLDK GLYVYPEPKR YARSVRQYKI LNCANYHLTQ VRTDFYDEFW GQGLRAAPKK QKKHTLSLTP DTTLYNAAQI ICANYGEAFS VDKKGGTKKA AVSELLQASA PYKADVELCV YSTNETTNCT GGKNGIAADI TTAKGYVKSV TTSNGAITVK GDGTLANMEY ILQATGNAAT GVTWTTTCKG TDASLFPANF CGSVTQ).

6. An immunogenic composition comprising the fusion protein of SEQ ID NO.219 (IQKAEQND VKLAPPTDVR SGYIRLVKNV NYYIDSESIW VDNQEPQIVH FDAVVNLDKG LYVYPEPKRY ARSVRQYKIL NCANYHLTQV RTDFYDEFWG QGLRAAPKKQ KKHTLSLTPD TTLYNAAQII CANYGEAFSV DKKGGTKKAA VSELLQASAP YKADVELCVY STNETTNCTG GKNGIAADIT TAKGYVKSVT TSNGAITVKG DGTLANMEYI LQATGNAATG VTWTTTCKGT DASLFPANFC GSVTQ).

* * * * *

SEQUENCE LISTING

```
<160> NUMBER OF SEQ ID NOS: 219

<210> SEQ ID NO 1
<211> LENGTH: 25
<212> TYPE: PRT
<213> ORGANISM: Haemophilus influenzae

<400> SEQUENCE: 1

Pro Lys Arg Tyr Ala Arg Ser Val Arg Gln Tyr Lys Ile Leu Asn Cys
1               5                   10                  15

Ala Asn Tyr His Leu Thr Gln Val Arg
            20                  25

<210> SEQ ID NO 2
<211> LENGTH: 7
<212> TYPE: PRT
<213> ORGANISM: Artificial Sequence
<220> FEATURE:
<223> OTHER INFORMATION: synthetic construct

<400> SEQUENCE: 2

Met His His His His His His
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic construct

<400> SEQUENCE: 3

Gly Gly His His His His His His
```

<210> SEQ ID NO 4
<211> LENGTH: 160
<212> TYPE: PRT
<213> ORGANISM: Haemophilus influenzae

<400> SEQUENCE: 4

```
Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160
```

<210> SEQ ID NO 5
<211> LENGTH: 160
<212> TYPE: PRT
<213> ORGANISM: Haemophilus influenzae

<400> SEQUENCE: 5

```
Met Lys Lys Ile Ile Leu Thr Leu Ser Leu Gly Leu Leu Thr Ala Cys
 1               5                  10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160
```

```
<210> SEQ ID NO 6
<211> LENGTH: 160
<212> TYPE: PRT
<213> ORGANISM: Haemophilus influenzae

<400> SEQUENCE: 6

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Arg Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 7
<211> LENGTH: 160
<212> TYPE: PRT
<213> ORGANISM: Haemophilus influenzae

<400> SEQUENCE: 7

Met Lys Lys Ile Ile Leu Thr Leu Ser Leu Gly Leu Leu Thr Ala Cys
 1               5                  10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160

<210> SEQ ID NO 8
<211> LENGTH: 160
<212> TYPE: PRT
```

<213> ORGANISM: Haemophilus influenzae

<400> SEQUENCE: 8

```
Met Lys Lys Ile Ile Leu Thr Leu Ser Leu Gly Leu Leu Thr Ala Cys
 1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160
```

<210> SEQ ID NO 9
<211> LENGTH: 160
<212> TYPE: PRT
<213> ORGANISM: Haemophilus influenzae

<400> SEQUENCE: 9

```
Met Lys Lys Ile Ile Leu Thr Leu Ser Leu Gly Leu Leu Thr Ala Cys
 1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160
```

<210> SEQ ID NO 10
<211> LENGTH: 160
<212> TYPE: PRT
<213> ORGANISM: Haemophilus influenzae

<400> SEQUENCE: 10

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Met Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 11
<211> LENGTH: 160
<212> TYPE: PRT
<213> ORGANISM: Haemophilus influenzae

<400> SEQUENCE: 11

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Glu Ala Phe Ser Val Asp Lys Lys
145                 150                 155                 160

<210> SEQ ID NO 12
<211> LENGTH: 159
<212> TYPE: PRT
<213> ORGANISM: Haemophilus influenzae

<400> SEQUENCE: 12

Met Lys Lys Ile Ile Leu Thr Leu Ser Leu Gly Leu Leu Thr Ala Cys
1               5                   10                  15

```
Ser Ala Gln Ile Gln Lys Ala Glu Gln Asn Asp Met Lys Leu Ala Pro
         20                  25                  30

Pro Thr Asp Val Arg Ser Gly Tyr Ile Arg Leu Val Lys Asn Val Asn
             35                  40                  45

Tyr Tyr Ile Asp Ser Glu Ser Ile Val Asp Asn Gln Glu Pro Gln Ile
 50                  55                  60

Val His Phe Asp Ala Val Val Asn Leu Asp Lys Gly Leu Tyr Val Tyr
 65                  70                  75                  80

Pro Glu Pro Lys Arg Tyr Ala Arg Ser Val Arg Gln Tyr Lys Ile Leu
                 85                  90                  95

Asn Cys Ala Asn Tyr His Leu Thr Gln Val Arg Thr Asp Phe Tyr Asp
                100                 105                 110

Glu Phe Trp Gly Gln Gly Leu Arg Ala Ala Pro Lys Lys Gln Lys Lys
                115                 120                 125

His Thr Leu Ser Leu Thr Pro Asp Thr Thr Leu Tyr Asn Ala Ala Gln
             130                 135                 140

Ile Ile Cys Ala Asn Tyr Gly Lys Ala Phe Ser Val Asp Lys Lys
145                 150                 155

<210> SEQ ID NO 13
<211> LENGTH: 160
<212> TYPE: PRT
<213> ORGANISM: Haemophilus influenzae

<400> SEQUENCE: 13

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
         20                  25                  30

Pro Thr Asp Val Arg Ser Gly Tyr Ile Arg Leu Val Lys Asn Val Asn
             35                  40                  45

Tyr Tyr Ile Asp Ser Glu Ser Ile Trp Val Asp Asn Gln Glu Pro Gln
 50                  55                  60

Ile Val His Phe Asp Thr Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
             130                 135                 140

Gln Ile Ile Cys Ala Asn Tyr Gly Lys Ala Phe Ser Val Asp Lys Lys
145                 150                 155                 160

<210> SEQ ID NO 14
<211> LENGTH: 160
<212> TYPE: PRT
<213> ORGANISM: Haemophilus influenzae

<400> SEQUENCE: 14

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
         20                  25                  30
```

```
Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Lys Ala Phe Ser Val Asp Lys Lys
145                 150                 155                 160
```

<210> SEQ ID NO 15
<211> LENGTH: 194
<212> TYPE: PRT
<213> ORGANISM: Haemophilus influenzae

<400> SEQUENCE: 15

```
Met Lys Lys Ile Ile Leu Thr Leu Ser Leu Gly Leu Leu Thr Ala Cys
  1               5                  10                  15

Ser Ala Gln Thr Gln Lys Ala Glu Gln Asn Asp Val Lys Leu Thr Pro
                 20                  25                  30

Pro Thr Asp Val Gln Ser Gly Tyr Val Arg Leu Val Lys Asn Val Asn
                 35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Ile Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Lys Ala Phe Ser Val Asp Lys Asn
145                 150                 155                 160

Lys Lys Ile Cys Thr Leu Ile Ser Leu Asn Phe Ile Gln Leu Leu Gly
                165                 170                 175

Cys Arg Glu Tyr Ser Ile Phe Leu Gln Leu Leu Leu Phe Tyr Cys Trp
                180                 185                 190

His Phe
```

<210> SEQ ID NO 16
<211> LENGTH: 195
<212> TYPE: PRT
<213> ORGANISM: Haemophilus influenzae

<400> SEQUENCE: 16

```
Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
            85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Lys Ala Phe Ser Val Asp Lys Lys
145                 150                 155                 160

Ile Lys Lys Ile Cys Thr Leu Ile Ser Leu Asn Phe Ile Gln Leu Leu
            165                 170                 175

Gly Cys Arg Glu Tyr Ser Ile Phe Leu Gln Leu Leu Phe Tyr Cys
            180                 185                 190

Trp His Phe
        195

<210> SEQ ID NO 17
<211> LENGTH: 160
<212> TYPE: PRT
<213> ORGANISM: Haemophilus influenzae

<400> SEQUENCE: 17

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Met Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
            85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Lys Ala Phe Ser Val Asp Lys Lys
145                 150                 155                 160

<210> SEQ ID NO 18
```

```
<211> LENGTH: 160
<212> TYPE: PRT
<213> ORGANISM: Haemophilus influenzae

<400> SEQUENCE: 18

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 19
<211> LENGTH: 160
<212> TYPE: PRT
<213> ORGANISM: Haemophilus influenzae

<400> SEQUENCE: 19

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Glu Ala Phe Ser Val Asp Lys Lys
145                 150                 155                 160

<210> SEQ ID NO 20
<211> LENGTH: 160
<212> TYPE: PRT
<213> ORGANISM: Haemophilus influenzae
```

<400> SEQUENCE: 20

| Met | Lys | Lys | Ile | Ile | Leu | Thr | Leu | Ser | Leu | Gly | Leu | Leu | Thr | Ala | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Ala | Gln | Thr | Gln | Lys | Val | Glu | Gln | Asn | Asp | Val | Lys | Leu | Thr | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Pro | Thr | Asp | Val | Arg | Ser | Gly | Phe | Val | Arg | Leu | Val | Lys | Asn | Val | Asn |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Tyr | Tyr | Ile | Asp | Ser | Glu | Ser | Ile | Trp | Val | Asp | Asn | Gln | Glu | Pro | Gln |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ile | Val | His | Phe | Asp | Ala | Val | Val | Asn | Leu | Asp | Lys | Gly | Leu | Tyr | Val |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Tyr | Pro | Glu | Pro | Lys | Arg | Tyr | Ala | Arg | Ser | Val | Arg | Gln | Tyr | Lys | Ile |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Leu | Asn | Cys | Ala | Asn | Tyr | His | Leu | Thr | Gln | Val | Arg | Thr | Asp | Phe | Tyr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Asp | Glu | Phe | Trp | Gly | Gln | Gly | Leu | Arg | Ala | Ala | Pro | Lys | Lys | Gln | Lys |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Lys | His | Thr | Leu | Ser | Leu | Thr | Pro | Asp | Thr | Thr | Leu | Tyr | Asn | Ala | Ala |
|-----|-----|-----|-----|-----|-----|-----|-----|-----|-----|-----|-----|-----|-----|-----|-----|
|     |     | 130 |     |     |     |     | 135 |     |     |     |     | 140 |     |     |     |

| Gln | Ile | Ile | Cys | Ala | Asn | Tyr | Gly | Lys | Ala | Phe | Leu | Val | Asp | Lys | Lys |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

<210> SEQ ID NO 21
<211> LENGTH: 160
<212> TYPE: PRT
<213> ORGANISM: Haemophilus influenzae

<400> SEQUENCE: 21

| Met | Lys | Lys | Ile | Ile | Leu | Thr | Leu | Ser | Leu | Gly | Leu | Leu | Thr | Ala | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Ala | Gln | Ile | Gln | Lys | Ala | Lys | Gln | Asn | Asp | Val | Lys | Leu | Ala | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Pro | Thr | Asp | Val | Arg | Ser | Gly | Tyr | Ile | Arg | Leu | Val | Lys | Asn | Val | Asn |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Tyr | Tyr | Ile | Asp | Ser | Glu | Ser | Ile | Trp | Val | Asp | Asn | Gln | Glu | Pro | Gln |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ile | Val | His | Phe | Asp | Ala | Val | Asn | Leu | Asp | Lys | Gly | Leu | Tyr | Val |     |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Tyr | Pro | Glu | Pro | Lys | Arg | Tyr | Ala | Arg | Ser | Val | Arg | Gln | Tyr | Lys | Ile |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Leu | Asn | Cys | Ala | Asn | Tyr | His | Leu | Thr | Gln | Val | Arg | Thr | Asp | Phe | Tyr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Asp | Glu | Phe | Trp | Gly | Gln | Gly | Leu | Arg | Ala | Ala | Pro | Lys | Lys | Gln | Lys |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Lys | His | Thr | Leu | Ser | Leu | Thr | Pro | Asp | Thr | Thr | Leu | Tyr | Asn | Ala | Ala |
|-----|-----|-----|-----|-----|-----|-----|-----|-----|-----|-----|-----|-----|-----|-----|-----|
|     |     | 130 |     |     |     |     | 135 |     |     |     |     | 140 |     |     |     |

| Gln | Ile | Ile | Cys | Ala | Asn | Tyr | Gly | Glu | Ala | Phe | Ser | Val | Asp | Lys | Lys |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

<210> SEQ ID NO 22
<211> LENGTH: 160
<212> TYPE: PRT
<213> ORGANISM: Haemophilus influenzae

<400> SEQUENCE: 22

```
Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 23
<211> LENGTH: 160
<212> TYPE: PRT
<213> ORGANISM: Haemophilus influenzae

<400> SEQUENCE: 23

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Glu Ala Phe Ser Val Asp Lys Lys
145                 150                 155                 160

<210> SEQ ID NO 24
<211> LENGTH: 160
<212> TYPE: PRT
<213> ORGANISM: Haemophilus influenzae

<400> SEQUENCE: 24

Met Lys Lys Ile Ile Leu Thr Leu Ser Leu Gly Leu Leu Thr Ala Cys
1               5                   10                  15
```

Ser Ala Gln Thr Gln Lys Val Glu Gln Asn Asp Val Lys Leu Thr Pro
            20                  25                  30

Pro Thr Asp Val Arg Ser Gly Tyr Val Arg Leu Val Lys Asn Val Asn
            35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Lys Ala Phe Ser Val Asp Lys Lys
145                 150                 155                 160

<210> SEQ ID NO 25
<211> LENGTH: 160
<212> TYPE: PRT
<213> ORGANISM: Haemophilus influenzae

<400> SEQUENCE: 25

Met Lys Lys Ile Ile Leu Thr Leu Ser Leu Gly Leu Leu Thr Ala Cys
  1               5                  10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Glu Ala Phe Ser Val Asp Lys Lys
145                 150                 155                 160

<210> SEQ ID NO 26
<211> LENGTH: 160
<212> TYPE: PRT
<213> ORGANISM: Haemophilus influenzae

<400> SEQUENCE: 26

Met Lys Lys Ile Ile Leu Thr Leu Ser Leu Gly Leu Leu Thr Ala Cys
  1               5                  10                  15

Ser Ala Gln Thr Gln Lys Val Glu Gln Asn Asp Val Lys Leu Thr Ala
            20                  25                  30

```
Pro Thr Asp Val Arg Ser Gly Tyr Val Arg Leu Val Lys Asn Ala Asn
        35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 27
<211> LENGTH: 160
<212> TYPE: PRT
<213> ORGANISM: Haemophilus influenzae

<400> SEQUENCE: 27

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
                 20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Ile Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 28
<211> LENGTH: 160
<212> TYPE: PRT
<213> ORGANISM: Haemophilus influenzae

<400> SEQUENCE: 28

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
                 20                  25                  30

Pro Thr Asp Val Arg Ser Gly Tyr Ile Arg Leu Val Lys Asn Val Asn
        35                  40                  45
```

```
Tyr Tyr Ile Asp Ser Glu Ser Ile Trp Val Asp Asn Gln Glu Pro Gln
        50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Lys Ala Phe Ser Val Asp Lys Lys
145                 150                 155                 160

<210> SEQ ID NO 29
<211> LENGTH: 160
<212> TYPE: PRT
<213> ORGANISM: Haemophilus influenzae

<400> SEQUENCE: 29

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
                 20                  25                  30

Pro Thr Asp Val Arg Ser Gly Tyr Ile Arg Leu Val Lys Asn Val Asn
                 35                  40                  45

Tyr Tyr Ile Asp Ser Glu Ser Ile Trp Val Asp Asn Gln Glu Pro Gln
        50                  55                  60

Ile Val His Phe Asp Thr Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Lys Ala Phe Ser Val Asp Lys Lys
145                 150                 155                 160

<210> SEQ ID NO 30
<211> LENGTH: 160
<212> TYPE: PRT
<213> ORGANISM: Haemophilus influenzae

<400> SEQUENCE: 30

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
                 20                  25                  30

Pro Thr Asp Val Arg Ser Gly Tyr Ile Arg Leu Val Lys Asn Val Asn
                 35                  40                  45

Tyr Tyr Ile Asp Ser Glu Ser Ile Trp Val Asp Asn Gln Glu Pro Gln
        50                  55                  60
```

```
Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 31
<211> LENGTH: 160
<212> TYPE: PRT
<213> ORGANISM: Haemophilus influenzae

<400> SEQUENCE: 31

Met Lys Lys Ile Ile Leu Thr Leu Ser Leu Gly Leu Leu Thr Ala Cys
  1               5                  10                  15

Ser Ala Gln Ile Gln Lys Ala Lys Gln Asn Asp Val Lys Leu Ala Pro
             20                  25                  30

Pro Thr Asp Val Arg Ser Gly Tyr Ile Arg Leu Val Lys Asn Val Asn
         35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160

<210> SEQ ID NO 32
<211> LENGTH: 160
<212> TYPE: PRT
<213> ORGANISM: Haemophilus influenzae

<400> SEQUENCE: 32

Met Lys Lys Ile Ile Leu Thr Leu Ser Leu Gly Leu Leu Thr Ala Cys
  1               5                  10                  15

Ser Ala Gln Ile Gln Lys Ala Glu Gln Asn Asp Val Lys Leu Ala Pro
             20                  25                  30

Pro Thr Asp Val Arg Ser Gly Tyr Ile Arg Leu Val Lys Asn Val Asn
         35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80
```

```
Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 33
<211> LENGTH: 160
<212> TYPE: PRT
<213> ORGANISM: Haemophilus influenzae

<400> SEQUENCE: 33

Met Lys Lys Ile Ile Leu Thr Leu Ser Leu Gly Leu Leu Thr Ala Cys
1               5                   10                  15

Ser Ala Gln Thr Gln Lys Val Glu Gln Asn Asp Val Lys Leu Thr Pro
            20                  25                  30

Pro Thr Asp Val Arg Ser Gly Tyr Val Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 34
<211> LENGTH: 160
<212> TYPE: PRT
<213> ORGANISM: Haemophilus influenzae

<400> SEQUENCE: 34

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95
```

```
Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160
```

<210> SEQ ID NO 35
<211> LENGTH: 160
<212> TYPE: PRT
<213> ORGANISM: Haemophilus influenzae

<400> SEQUENCE: 35

```
Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Glu Ala Phe Ser Val Asp Lys Lys
145                 150                 155                 160
```

<210> SEQ ID NO 36
<211> LENGTH: 160
<212> TYPE: PRT
<213> ORGANISM: Haemophilus influenzae

<400> SEQUENCE: 36

```
Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110
```

```
Asp Glu Phe Trp Gly Gln Gly Leu Arg Ala Ala Pro Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160
```

<210> SEQ ID NO 37
<211> LENGTH: 160
<212> TYPE: PRT
<213> ORGANISM: Haemophilus influenzae

<400> SEQUENCE: 37

```
Met Lys Lys Ile Ile Leu Thr Leu Ser Leu Gly Leu Leu Thr Ala Cys
1               5                   10                  15

Ser Ala Gln Thr Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160
```

<210> SEQ ID NO 38
<211> LENGTH: 160
<212> TYPE: PRT
<213> ORGANISM: Haemophilus influenzae

<400> SEQUENCE: 38

```
Met Lys Lys Ile Ile Leu Thr Leu Ser Leu Gly Leu Leu Thr Ala Cys
1               5                   10                  15

Ser Ala Gln Thr Gln Lys Val Glu Gln Asn Asp Val Lys Leu Thr Ala
            20                  25                  30

Pro Ala Asp Val Arg Ser Gly Tyr Val Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125
```

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 39
<211> LENGTH: 159
<212> TYPE: PRT
<213> ORGANISM: Haemophilus influenzae

<400> SEQUENCE: 39

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Tyr Lys Ile Leu
                85                  90                  95

Asn Cys Ala Asn Tyr His Leu Thr Gln Val Arg Thr Asp Phe Tyr Asp
            100                 105                 110

Glu Phe Trp Gly Gln Gly Leu Arg Ala Ala Pro Lys Lys Gln Lys Lys
        115                 120                 125

His Thr Leu Ser Leu Thr Pro Asp Thr Thr Leu Tyr Asn Ala Ala Gln
    130                 135                 140

Ile Ile Cys Ala Asn Tyr Gly Glu Ala Phe Ser Val Asp Lys Lys
145                 150                 155

<210> SEQ ID NO 40
<211> LENGTH: 159
<212> TYPE: PRT
<213> ORGANISM: Haemophilus influenzae

<400> SEQUENCE: 40

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Tyr Lys Ile Leu
                85                  90                  95

Asn Cys Ala Asn Tyr His Leu Thr Gln Val Arg Thr Asp Phe Tyr Asp
            100                 105                 110

Glu Phe Trp Gly Gln Gly Leu Arg Ala Ala Pro Lys Lys Gln Lys Lys
        115                 120                 125

His Thr Leu Ser Leu Thr Pro Asp Thr Thr Leu Tyr Asn Ala Ala Gln
    130                 135                 140

Ile Ile Cys Ala Asn Tyr Gly Glu Ala Phe Ser Val Asp Lys Lys
145                 150                 155

<210> SEQ ID NO 41
<211> LENGTH: 160
<212> TYPE: PRT
<213> ORGANISM: Haemophilus influenzae

<400> SEQUENCE: 41

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 42
<211> LENGTH: 160
<212> TYPE: PRT
<213> ORGANISM: Haemophilus influenzae

<400> SEQUENCE: 42

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 43
<211> LENGTH: 160
<212> TYPE: PRT
<213> ORGANISM: Haemophilus influenzae

<400> SEQUENCE: 43

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Lys Ala Phe Ser Val Asp Lys Lys
145                 150                 155                 160

<210> SEQ ID NO 44
<211> LENGTH: 160
<212> TYPE: PRT
<213> ORGANISM: Haemophilus influenzae

<400> SEQUENCE: 44

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Lys Ala Phe Ser Val Asp Lys Lys
145                 150                 155                 160

<210> SEQ ID NO 45
<211> LENGTH: 160

<212> TYPE: PRT
<213> ORGANISM: Haemophilus influenzae

<400> SEQUENCE: 45

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Thr Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Ser Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 46
<211> LENGTH: 160
<212> TYPE: PRT
<213> ORGANISM: Haemophilus influenzae

<400> SEQUENCE: 46

Met Lys Lys Ile Ile Leu Thr Leu Ser Leu Gly Leu Leu Thr Ala Cys
1               5                   10                  15

Ser Ala Gln Thr Gln Lys Val Glu Gln Asn Asp Val Lys Leu Thr Pro
            20                  25                  30

Pro Thr Asp Val Arg Ser Gly Tyr Val Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Val Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 47
<211> LENGTH: 160
<212> TYPE: PRT
<213> ORGANISM: Haemophilus influenzae

```
<400> SEQUENCE: 47

Met Lys Lys Ile Ile Leu Thr Leu Ser Leu Gly Leu Leu Thr Ala Cys
1               5                   10                  15

Ser Ala Gln Thr Gln Lys Val Glu Gln Asn Asp Val Lys Leu Thr Pro
            20                  25                  30

Pro Thr Asp Val Arg Ser Gly Tyr Val Arg Leu Val Lys Asn Val Asn
                35                  40                  45

Tyr Tyr Ile Asp Ser Glu Ser Ile Trp Val Asp Asn Gln Glu Pro Gln
        50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Val Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 48
<211> LENGTH: 160
<212> TYPE: PRT
<213> ORGANISM: Haemophilus influenzae

<400> SEQUENCE: 48

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
                35                  40                  45

Tyr Tyr Ile Asp Ser Glu Ser Ile Trp Val Asp Asn Gln Glu Pro Gln
        50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Glu Ala Phe Ser Val Asp Lys Lys
145                 150                 155                 160

<210> SEQ ID NO 49
<211> LENGTH: 160
<212> TYPE: PRT
<213> ORGANISM: Haemophilus influenzae

<400> SEQUENCE: 49

Met Lys Lys Ile Ile Leu Thr Leu Ser Leu Gly Leu Leu Thr Ala Cys
```

```
                1               5                   10                  15
Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
        50                  55                  60

Ile Val His Phe Asp Thr Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 50
<211> LENGTH: 160
<212> TYPE: PRT
<213> ORGANISM: Haemophilus influenzae

<400> SEQUENCE: 50

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
        50                  55                  60

Ile Val His Phe Asp Thr Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys Ala Asn Tyr Gly Lys Ala Phe Ser Val Asp Lys Lys
145                 150                 155                 160

<210> SEQ ID NO 51
<211> LENGTH: 160
<212> TYPE: PRT
<213> ORGANISM: Haemophilus influenzae

<400> SEQUENCE: 51

Met Lys Lys Ile Ile Leu Thr Leu Ser Leu Gly Leu Leu Thr Ala Cys
1               5                   10                  15

Ser Ala Gln Thr Gln Lys Ala Glu Gln Asn Asp Val Lys Leu Thr Pro
```

```
                    20                  25                  30
Pro Thr Asp Val Arg Ser Gly Tyr Ile Arg Leu Val Lys Asn Val Asn
                35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
               100                 105                 110

Asp Glu Phe Trp Gly Gln Gly Leu Arg Ala Ala Pro Lys Lys Gln Lys
               115                 120                 125

Lys His Thr Leu Ser Leu Thr Pro Asp Thr Thr Leu Tyr Asn Ala Ala
               130                 135                 140

Gln Ile Ile Cys Ala Asn Tyr Gly Lys Ala Phe Ser Val Asp Lys Lys
145                 150                 155                 160

<210> SEQ ID NO 52
<211> LENGTH: 160
<212> TYPE: PRT
<213> ORGANISM: Haemophilus influenzae

<400> SEQUENCE: 52

Met Lys Lys Ile Ile Leu Thr Leu Ser Leu Gly Leu Leu Thr Ala Cys
 1               5                  10                  15

Ser Ala Gln Ile Gln Lys Ala Lys Gln Asn Asp Val Lys Leu Ala Pro
                20                  25                  30

Pro Thr Asp Val Arg Ser Gly Tyr Ile Arg Leu Val Lys Asn Val Asn
                35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
               100                 105                 110

Asp Glu Phe Trp Gly Gln Gly Leu Arg Ala Ala Pro Lys Lys Gln Lys
               115                 120                 125

Lys His Thr Leu Ser Leu Thr Pro Asp Thr Thr Leu Tyr Asn Ala Ala
               130                 135                 140

Gln Ile Ile Cys Ala Asn Tyr Gly Lys Ala Phe Ser Val Asp Lys Lys
145                 150                 155                 160

<210> SEQ ID NO 53
<211> LENGTH: 160
<212> TYPE: PRT
<213> ORGANISM: Haemophilus influenzae

<400> SEQUENCE: 53

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
```

```
                 35                  40                  45

Tyr Tyr Ile Asp Ser Glu Ser Ile Trp Val Asp Asn Gln Glu Pro Gln
 50                  55                  60

Ile Val His Phe Asp Thr Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Lys Ala Phe Ser Val Asp Lys Lys
145                 150                 155                 160

<210> SEQ ID NO 54
<211> LENGTH: 160
<212> TYPE: PRT
<213> ORGANISM: Haemophilus influenzae

<400> SEQUENCE: 54

Met Lys Lys Ile Ile Leu Thr Leu Ser Leu Gly Leu Leu Thr Ala Cys
  1               5                  10                  15

Ser Ala Gln Thr Gln Lys Ala Glu Gln Asn Asp Val Lys Leu Ala Pro
                 20                  25                  30

Pro Thr Asp Val Arg Ser Gly Tyr Ile Arg Leu Val Lys Asn Val Asn
                 35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Ile Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Lys Ala Phe Ser Val Asp Lys Lys
145                 150                 155                 160

<210> SEQ ID NO 55
<211> LENGTH: 160
<212> TYPE: PRT
<213> ORGANISM: Haemophilus influenzae

<400> SEQUENCE: 55

Met Lys Lys Ile Ile Leu Thr Leu Ser Leu Gly Leu Leu Thr Ala Cys
  1               5                  10                  15

Ser Ala Gln Ile Gln Lys Ala Lys Gln Asn Asp Val Lys Leu Ala Pro
                 20                  25                  30

Pro Thr Asp Val Arg Ser Gly Tyr Ile Arg Leu Val Lys Asn Val Asn
                 35                  40                  45

Tyr Tyr Ile Asp Ser Glu Ser Ile Trp Val Asp Asn Gln Glu Pro Gln
```

```
            50                  55                  60
Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Glu Ala Phe Ser Val Asp Lys Lys
145                 150                 155                 160
```

<210> SEQ ID NO 56
<211> LENGTH: 160
<212> TYPE: PRT
<213> ORGANISM: Haemophilus influenzae

<400> SEQUENCE: 56

```
Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
                 20                  25                  30

Pro Thr Asp Val Arg Ser Gly Tyr Ile Arg Leu Val Lys Asn Val Asn
                 35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln Ile Ile Cys Ala Asn Tyr Gly Lys Ala Phe Ser Val Asp Lys Lys
145                 150                 155                 160
```

<210> SEQ ID NO 57
<211> LENGTH: 159
<212> TYPE: PRT
<213> ORGANISM: Haemophilus influenzae

<400> SEQUENCE: 57

```
Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Met Lys Leu Ala Pro
                 20                  25                  30

Pro Thr Asp Val Arg Ser Gly Tyr Ile Arg Leu Val Lys Asn Val Asn
                 35                  40                  45

Tyr Tyr Ile Asp Ser Glu Ser Ile Val Asp Asn Gln Glu Pro Gln Ile
 50                  55                  60

Val His Phe Asp Ala Val Val Asn Leu Asp Lys Gly Leu Tyr Val Tyr
```

```
                65                  70                  75                  80
Pro Glu Pro Lys Arg Tyr Ala Arg Ser Val Arg Gln Tyr Lys Ile Leu
                    85                  90                  95

Asn Cys Ala Asn Tyr His Leu Thr Gln Val Arg Thr Asp Phe Tyr Asp
                100                 105                 110

Glu Phe Trp Gly Gln Gly Leu Arg Ala Ala Pro Lys Lys Gln Lys Lys
            115                 120                 125

His Thr Leu Ser Leu Thr Pro Asp Thr Thr Leu Tyr Asn Ala Ala Gln
        130                 135                 140

Ile Ile Cys Ala Asn Tyr Gly Lys Ala Phe Ser Val Asp Lys Lys
145                 150                 155

<210> SEQ ID NO 58
<211> LENGTH: 149
<212> TYPE: PRT
<213> ORGANISM: Haemophilus influenzae

<400> SEQUENCE: 58

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 59
<211> LENGTH: 149
<212> TYPE: PRT
<213> ORGANISM: Haemophilus influenzae

<400> SEQUENCE: 59

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Lys Cys Thr Gly Gly Lys Asn Gly Ile Ala
65                  70                  75                  80

Ala Asp Ile Thr Thr Ala Lys Gly Tyr Val Lys Ser Val Thr Thr Ser
```

```
                 85                  90                  95

Asn Gly Ala Ile Thr Val Ala Gly Asn Gly Thr Leu Asp Gly Met Ser
                100                 105                 110

Tyr Thr Leu Thr Ala Glu Gly Asp Ser Ala Lys Gly Val Thr Trp Lys
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 60
<211> LENGTH: 149
<212> TYPE: PRT
<213> ORGANISM: Haemophilus influenzae

<400> SEQUENCE: 60

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
                100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 61
<211> LENGTH: 149
<212> TYPE: PRT
<213> ORGANISM: Haemophilus influenzae

<400> SEQUENCE: 61

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Lys Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Gly Lys Pro Ser Ser Cys Ser Gly Gly Ser Asn Gly Ile Ala
65                  70                  75                  80

Ala Asp Ile Thr Thr Ala Lys Gly Tyr Val Ala Ser Val Ile Thr Gln
                85                  90                  95

Ser Gly Gly Ile Thr Val Lys Gly Asp Gly Thr Leu Ala Asn Met Glu
```

```
                    100                 105                 110
Tyr Ile Leu Gln Ala Ala Gly Asn Ala Ala Ala Gly Val Thr Trp Thr
                115                 120                 125

Thr Thr Cys Lys Gly Thr Asp Ala Ser Leu Phe Pro Ala Asn Phe Cys
            130                 135                 140

Gly Ser Val Thr Gln
145

<210> SEQ ID NO 62
<211> LENGTH: 149
<212> TYPE: PRT
<213> ORGANISM: Haemophilus influenzae

<400> SEQUENCE: 62

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
                100                 105                 110

Tyr Ile Leu Gln Ala Thr Gly Asn Ala Ala Thr Gly Val Thr Trp Thr
                115                 120                 125

Thr Thr Cys Lys Gly Thr Asp Ala Ser Leu Phe Pro Ala Asn Phe Cys
            130                 135                 140

Gly Ser Val Thr Gln
145

<210> SEQ ID NO 63
<211> LENGTH: 149
<212> TYPE: PRT
<213> ORGANISM: Haemophilus influenzae

<400> SEQUENCE: 63

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ser Asp Val Glu Leu Cys Val Tyr
        50                  55                  60

Ser Thr Gly Lys Pro Ser Thr Cys Ser Gly Gly Ser Asn Gly Ile Ala
65                  70                  75                  80

Ala Asp Ile Thr Thr Val Lys Gly Tyr Val Lys Ser Val Thr Thr Ser
                85                  90                  95

Asn Gly Ala Ile Thr Val Ala Gly Asn Gly Thr Leu Asp Gly Met Ser
                100                 105                 110

Tyr Thr Leu Thr Ala Glu Gly Asp Ser Ala Lys Gly Val Thr Trp Thr
```

```
            115                 120                 125
Thr Thr Cys Lys Gly Thr Asp Ala Ser Leu Phe Pro Ala Asn Phe Cys
        130                 135                 140

Gly Ser Val Thr Gln
145

<210> SEQ ID NO 64
<211> LENGTH: 149
<212> TYPE: PRT
<213> ORGANISM: Haemophilus influenzae

<400> SEQUENCE: 64

Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 65
<211> LENGTH: 149
<212> TYPE: PRT
<213> ORGANISM: Haemophilus influenzae

<400> SEQUENCE: 65

Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
```

Gly Ser Val Thr Gln
145

<210> SEQ ID NO 66
<211> LENGTH: 149
<212> TYPE: PRT
<213> ORGANISM: Haemophilus influenzae

<400> SEQUENCE: 66

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Val Ser Glu Leu
            35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 67
<211> LENGTH: 149
<212> TYPE: PRT
<213> ORGANISM: Haemophilus influenzae

<400> SEQUENCE: 67

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Lys Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
    50                  55                  60

Ser Thr Asn Glu Ile Thr Asn Cys Met Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Ala Gly Val Thr Trp Thr
            115                 120                 125

Thr Thr Cys Lys Gly Thr Asp Ala Ser Leu Phe Pro Ala Asn Phe Cys
130                 135                 140

Gly Ser Ile Thr Gln

-continued

145

<210> SEQ ID NO 68
<211> LENGTH: 149
<212> TYPE: PRT
<213> ORGANISM: Haemophilus influenzae

<400> SEQUENCE: 68

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ser Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
    130                 135                 140

Arg Ser Val Thr Lys
145

<210> SEQ ID NO 69
<211> LENGTH: 149
<212> TYPE: PRT
<213> ORGANISM: Haemophilus influenzae

<400> SEQUENCE: 69

Met Lys Leu Thr Thr Leu Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Ser Cys Thr Gly Gly Lys Asn Gly Ile Ala
65                  70                  75                  80

Ala Asp Ile Lys Thr Ala Lys Gly Tyr Val Ala Ser Val Ile Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Ala Ala Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Lys
145

```
<210> SEQ ID NO 70
<211> LENGTH: 149
<212> TYPE: PRT
<213> ORGANISM: Haemophilus influenzae

<400> SEQUENCE: 70

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Ser Cys Ser Gly Gly Ser Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 71
<211> LENGTH: 149
<212> TYPE: PRT
<213> ORGANISM: Haemophilus influenzae

<400> SEQUENCE: 71

Met Lys Leu Thr Thr Leu Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Ser Cys Thr Gly Gly Lys Asn Gly Ile Ala
65                  70                  75                  80

Ala Asp Ile Lys Thr Ala Lys Gly Tyr Val Ala Ser Val Ile Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Ala Ala Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Lys
145

<210> SEQ ID NO 72
<211> LENGTH: 149
<212> TYPE: PRT
```

<213> ORGANISM: Haemophilus influenzae

<400> SEQUENCE: 72

Met Lys Leu Thr Thr Leu Gln Thr Leu Lys Lys Gly Phe Thr Leu Ile
1               5                   10                  15

Glu Leu Met Ile Val Ile Ala Ile Ala Ile Leu Ala Thr Ile Ala
                20                  25                  30

Ile Pro Ser Tyr Gln Asn Tyr Thr Lys Lys Ala Ala Val Ser Glu Leu
                35                  40                  45

Leu Gln Ala Ser Ala Pro Tyr Lys Ala Asp Val Glu Leu Cys Val Tyr
        50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 73
<211> LENGTH: 149
<212> TYPE: PRT
<213> ORGANISM: Haemophilus influenzae

<400> SEQUENCE: 73

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
                20                  25                  30

Ile Pro Ser Tyr Gln Asn Tyr Thr Lys Lys Ala Ser Val Ser Glu Leu
                35                  40                  45

Leu Gln Ala Ser Ala Pro Tyr Lys Ser Asp Val Glu Leu Cys Val Tyr
        50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
            115                 120                 125

Thr Thr Cys Lys Gly Thr Asp Ala Ser Leu Phe Pro Ala Asn Phe Cys
130                 135                 140

Arg Ser Val Thr Lys
145

<210> SEQ ID NO 74
<211> LENGTH: 149
<212> TYPE: PRT
<213> ORGANISM: Haemophilus influenzae

<400> SEQUENCE: 74

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 75
<211> LENGTH: 149
<212> TYPE: PRT
<213> ORGANISM: Haemophilus influenzae

<400> SEQUENCE: 75

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Glu Ala Ser Leu Phe Pro Ala Asn Phe Cys
    130                 135                 140

Gly Ser Val Thr Gln
145

<210> SEQ ID NO 76
<211> LENGTH: 149
<212> TYPE: PRT
<213> ORGANISM: Haemophilus influenzae

<400> SEQUENCE: 76

Met Lys Leu Thr Thr Gln Gln Thr Leu Lys Lys Gly Phe Thr Leu Ile
1               5                   10                  15

```
Glu Leu Met Ile Val Ile Ala Ile Ala Ile Leu Ala Thr Ile Ala
             20                  25                  30

Ile Pro Ser Tyr Gln Asn Tyr Thr Lys Lys Ala Ser Val Ser Glu Leu
         35                  40                  45

Leu Gln Ala Ser Ala Pro Tyr Lys Ala Asp Val Glu Leu Cys Val Tyr
     50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Ala Ser Val Lys Thr Gln
                 85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
            115                 120                 125

Thr Thr Cys Lys Gly Thr Asp Ala Ser Leu Phe Pro Ala Asn Phe Cys
    130                 135                 140

Arg Ser Val Thr Lys
145

<210> SEQ ID NO 77
<211> LENGTH: 149
<212> TYPE: PRT
<213> ORGANISM: Haemophilus influenzae

<400> SEQUENCE: 77

Met Lys Leu Thr Thr Leu Gln Thr Leu Lys Lys Gly Phe Thr Leu Ile
 1               5                  10                  15

Glu Leu Met Ile Val Ile Ala Ile Ala Ile Leu Ala Thr Ile Ala
             20                  25                  30

Ile Pro Ser Tyr Gln Asn Tyr Thr Lys Lys Ala Ala Val Ser Glu Leu
         35                  40                  45

Leu Gln Ala Ser Ala Pro Tyr Lys Ala Asp Val Glu Leu Cys Val Tyr
     50                  55                  60

Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Ala Ser Val Lys Thr Gln
                 85                  90                  95

Ser Gly Gly Ile Thr Val Lys Gly Asn Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 78
<211> LENGTH: 149
<212> TYPE: PRT
<213> ORGANISM: Haemophilus influenzae

<400> SEQUENCE: 78

Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
             20                  25                  30
```

```
Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
 50                  55                  60

Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
                115                 120                 125

Thr Thr Cys Lys Gly Thr Asp Ala Ser Leu Phe Pro Ala Asn Phe Cys
            130                 135                 140

Arg Ser Val Thr Lys
145

<210> SEQ ID NO 79
<211> LENGTH: 149
<212> TYPE: PRT
<213> ORGANISM: Haemophilus influenzae

<400> SEQUENCE: 79

Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
 50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
                115                 120                 125

Thr Thr Cys Lys Gly Thr Glu Ala Ser Leu Phe Pro Ala Asn Phe Cys
            130                 135                 140

Gly Ser Val Thr Gln
145

<210> SEQ ID NO 80
<211> LENGTH: 149
<212> TYPE: PRT
<213> ORGANISM: Haemophilus influenzae

<400> SEQUENCE: 80

Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45
```

```
Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Ala Ser Val Lys Thr Gln
                 85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Glu Ala Ser Leu Phe Pro Ala Asn Phe Cys
        130                 135                 140

Gly Ser Val Thr Gln
145

<210> SEQ ID NO 81
<211> LENGTH: 149
<212> TYPE: PRT
<213> ORGANISM: Haemophilus influenzae

<400> SEQUENCE: 81

Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
             20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ser Asp Val Glu Leu Cys Val Tyr
    50                  55                  60

Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Ala Gly Asn Gly Thr Leu Asp Gly Met Ser
            100                 105                 110

Tyr Thr Leu Thr Ala Glu Gly Asp Ser Ala Lys Gly Val Thr Trp Lys
            115                 120                 125

Thr Thr Cys Lys Gly Thr Asp Ala Ser Leu Phe Pro Ala Asn Phe Cys
        130                 135                 140

Gly Ser Val Thr Lys
145

<210> SEQ ID NO 82
<211> LENGTH: 149
<212> TYPE: PRT
<213> ORGANISM: Haemophilus influenzae

<400> SEQUENCE: 82

Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
             20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
    50                  55                  60
```

```
Ser Thr Asn Glu Ala Thr Lys Cys Thr Gly Gly Lys Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
        115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 83
<211> LENGTH: 149
<212> TYPE: PRT
<213> ORGANISM: Haemophilus influenzae

<400> SEQUENCE: 83

Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
                 20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
     50                  55                  60

Ser Thr Asn Glu Ala Thr Lys Cys Thr Gly Gly Lys Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
        115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 84
<211> LENGTH: 149
<212> TYPE: PRT
<213> ORGANISM: Haemophilus influenzae

<400> SEQUENCE: 84

Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
                 20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
     50                  55                  60

Ser Thr Asn Glu Thr Thr Asn Cys Thr Gly Gly Lys Asn Gly Ile Ala
 65                  70                  75                  80
```

```
Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 85
<211> LENGTH: 149
<212> TYPE: PRT
<213> ORGANISM: Haemophilus influenzae

<400> SEQUENCE: 85

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Ile Ser Glu Leu
        35                  40                  45

Leu Gln Ala Ser Ala Pro Tyr Lys Ser Asp Val Glu Leu Cys Val Tyr
    50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
    130                 135                 140

Arg Ser Val Thr Lys
145

<210> SEQ ID NO 86
<211> LENGTH: 149
<212> TYPE: PRT
<213> ORGANISM: Haemophilus influenzae

<400> SEQUENCE: 86

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95
```

```
Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Glu Ala Ser Leu Phe Pro Ala Asn Phe Cys
            130                 135                 140

Gly Ser Val Thr Gln
145

<210> SEQ ID NO 87
<211> LENGTH: 149
<212> TYPE: PRT
<213> ORGANISM: Haemophilus influenzae

<400> SEQUENCE: 87

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
            85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
            130                 135                 140

Gly Ser Val Thr Gln
145

<210> SEQ ID NO 88
<211> LENGTH: 149
<212> TYPE: PRT
<213> ORGANISM: Haemophilus influenzae

<400> SEQUENCE: 88

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ser Asp Val Glu Leu Cys Val Tyr
        50                  55                  60

Ser Thr Gly Lys Pro Ser Thr Cys Ser Gly Gly Ser Asn Gly Ile Ala
65                  70                  75                  80

Ala Asp Ile Thr Thr Val Lys Gly Tyr Val Lys Ser Val Thr Thr Ser
            85                  90                  95

Asn Gly Ala Ile Thr Val Ala Gly Asn Gly Thr Leu Asp Gly Met Ser
            100                 105                 110
```

```
Tyr Thr Leu Thr Ala Glu Gly Asp Ser Ala Lys Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 89
<211> LENGTH: 149
<212> TYPE: PRT
<213> ORGANISM: Haemophilus influenzae

<400> SEQUENCE: 89

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 90
<211> LENGTH: 149
<212> TYPE: PRT
<213> ORGANISM: Haemophilus influenzae

<400> SEQUENCE: 90

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Thr Gly Asn Ala Ala Thr Gly Val Thr Trp Thr
        115                 120                 125
```

```
Thr Thr Cys Lys Gly Thr Asp Ala Ser Leu Phe Pro Ala Asn Phe Cys
        130                 135                 140

Gly Ser Val Thr Gln
145

<210> SEQ ID NO 91
<211> LENGTH: 149
<212> TYPE: PRT
<213> ORGANISM: Haemophilus influenzae

<400> SEQUENCE: 91

Met Lys Leu Thr Thr Gln Gln Thr Leu Lys Lys Gly Phe Thr Leu Ile
  1               5                  10                  15

Glu Leu Met Ile Val Ile Ala Ile Ile Ala Ile Leu Ala Thr Ile Ala
                 20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
         50                  55                  60

Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Ala Gly Asn Gly Thr Leu Asp Arg Met Ser
            100                 105                 110

Tyr Thr Leu Thr Ala Glu Gly Asp Ser Ala Lys Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 92
<211> LENGTH: 149
<212> TYPE: PRT
<213> ORGANISM: Haemophilus influenzae

<400> SEQUENCE: 92

Met Lys Leu Thr Thr Gln Gln Thr Leu Lys Lys Gly Phe Thr Leu Ile
  1               5                  10                  15

Glu Leu Met Ile Val Ile Ala Ile Ile Ala Ile Leu Ala Thr Ile Ala
                 20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
         50                  55                  60

Ser Thr Gly Lys Pro Ser Ser Cys Ser Gly Gly Ser Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140
```

Gly Ser Val Thr Gln
145

<210> SEQ ID NO 93
<211> LENGTH: 149
<212> TYPE: PRT
<213> ORGANISM: Haemophilus influenzae

<400> SEQUENCE: 93

Met Lys Leu Thr Thr Gln Thr Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ser Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Ile Thr Gln
                85                  90                  95

Ser Gly Gly Ile Thr Val Lys Gly Asn Gly Thr Leu Thr Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Ile Thr Gln
145

<210> SEQ ID NO 94
<211> LENGTH: 149
<212> TYPE: PRT
<213> ORGANISM: Haemophilus influenzae

<400> SEQUENCE: 94

Met Lys Leu Thr Thr Leu Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Gly Lys Pro Ser Thr Cys Ser Gly Gly Asn Asn Gly Ile Ala
65                  70                  75                  80

Ala Asp Ile Lys Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 95
<211> LENGTH: 149
<212> TYPE: PRT
<213> ORGANISM: Haemophilus influenzae

<400> SEQUENCE: 95

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Ser Cys Ser Gly Gly Ser Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
        115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 96
<211> LENGTH: 149
<212> TYPE: PRT
<213> ORGANISM: Haemophilus influenzae

<400> SEQUENCE: 96

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Ala Thr Lys Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
        115                 120                 125

Thr Thr Cys Lys Gly Thr Asp Thr Ser Leu Phe Pro Ala Asn Phe Cys
130                 135                 140

Gly Ser Val Thr Gln
145

<210> SEQ ID NO 97

<211> LENGTH: 149
<212> TYPE: PRT
<213> ORGANISM: Haemophilus influenzae

<400> SEQUENCE: 97

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 98
<211> LENGTH: 149
<212> TYPE: PRT
<213> ORGANISM: Haemophilus influenzae

<400> SEQUENCE: 98

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 99
<211> LENGTH: 149
<212> TYPE: PRT
<213> ORGANISM: Haemophilus influenzae

<400> SEQUENCE: 99

| Met | Lys | Leu | Thr | Thr | Gln | Gln | Thr | Leu | Lys | Lys | Gly | Phe | Thr | Leu | Ile |
| 1 | | | | 5 | | | | | 10 | | | | | 15 | |

| Glu | Leu | Met | Ile | Val | Ile | Ala | Ile | Ala | Ile | Leu | Ala | Thr | Ile | Ala |
| | | | 20 | | | | | 25 | | | | | 30 | |

| Ile | Pro | Ser | Tyr | Gln | Asn | Tyr | Thr | Lys | Lys | Ala | Ala | Val | Ser | Glu | Leu |
| | | 35 | | | | | 40 | | | | | 45 | | | |

| Leu | Gln | Ala | Ser | Ala | Pro | Tyr | Lys | Ala | Asp | Val | Glu | Leu | Cys | Val | Tyr |
| | 50 | | | | | 55 | | | | | 60 | | | | |

| Ser | Thr | Gly | Lys | Pro | Ser | Thr | Cys | Ser | Gly | Gly | Ser | Asn | Gly | Ile | Ala |
| 65 | | | | | 70 | | | | | 75 | | | | | 80 |

| Ala | Asp | Ile | Thr | Thr | Ala | Lys | Gly | Tyr | Val | Ala | Ser | Val | Lys | Thr | Gln |
| | | | | 85 | | | | | 90 | | | | | 95 | |

| Ser | Gly | Gly | Ile | Thr | Val | Lys | Gly | Asn | Gly | Thr | Leu | Ala | Asn | Met | Glu |
| | | | | 100 | | | | | 105 | | | | | 110 | |

| Tyr | Ile | Leu | Gln | Ala | Lys | Gly | Asn | Ala | Thr | Ala | Gly | Val | Thr | Trp | Thr |
| | | | | 115 | | | | | 120 | | | | | 125 | |

| Thr | Thr | Cys | Lys | Gly | Thr | Asp | Ala | Ser | Leu | Phe | Pro | Ala | Asn | Phe | Cys |
| | | | 130 | | | | | 135 | | | | | 140 | | |

Arg Ser Val Thr Lys
145

<210> SEQ ID NO 100
<211> LENGTH: 149
<212> TYPE: PRT
<213> ORGANISM: Haemophilus influenzae

<400> SEQUENCE: 100

| Met | Lys | Leu | Thr | Thr | Gln | Gln | Thr | Leu | Lys | Lys | Gly | Phe | Thr | Leu | Ile |
| 1 | | | | 5 | | | | | 10 | | | | | 15 | |

| Glu | Leu | Met | Ile | Val | Ile | Ala | Ile | Ala | Ile | Leu | Ala | Thr | Ile | Ala |
| | | | 20 | | | | | 25 | | | | | 30 | |

| Ile | Pro | Ser | Tyr | Gln | Asn | Tyr | Thr | Lys | Lys | Ala | Ala | Val | Ser | Glu | Leu |
| | | 35 | | | | | 40 | | | | | 45 | | | |

| Leu | Gln | Ala | Ser | Ala | Pro | Tyr | Lys | Ala | Asp | Val | Glu | Leu | Cys | Val | Tyr |
| | 50 | | | | | 55 | | | | | 60 | | | | |

| Ser | Thr | Gly | Lys | Pro | Ser | Thr | Cys | Ser | Gly | Gly | Ser | Asn | Gly | Ile | Ala |
| 65 | | | | | 70 | | | | | 75 | | | | | 80 |

| Ala | Asp | Ile | Thr | Thr | Ala | Lys | Gly | Tyr | Val | Ala | Ser | Val | Lys | Thr | Gln |
| | | | | 85 | | | | | 90 | | | | | 95 | |

| Ser | Gly | Gly | Ile | Thr | Val | Lys | Gly | Asn | Gly | Thr | Leu | Ala | Asn | Met | Glu |
| | | | | 100 | | | | | 105 | | | | | 110 | |

| Tyr | Ile | Leu | Gln | Ala | Lys | Gly | Asn | Ala | Thr | Ala | Gly | Val | Thr | Trp | Thr |
| | | | | 115 | | | | | 120 | | | | | 125 | |

| Thr | Thr | Cys | Lys | Gly | Thr | Asp | Ala | Ser | Leu | Phe | Pro | Ala | Asn | Phe | Cys |
| | | | 130 | | | | | 135 | | | | | 140 | | |

Arg Ser Val Thr Lys
145

<210> SEQ ID NO 101
<211> LENGTH: 149
<212> TYPE: PRT
<213> ORGANISM: Haemophilus influenzae

<400> SEQUENCE: 101

-continued

```
Met Lys Leu Thr Thr Gln Gln Thr Leu Lys Lys Gly Phe Thr Leu Ile
 1               5                  10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
 50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
               100                 105                 110

Tyr Ile Leu Gln Ala Thr Gly Asn Ala Ala Thr Gly Val Thr Trp Thr
               115                 120                 125

Thr Thr Cys Lys Gly Thr Asp Ala Ser Leu Phe Pro Ala Asn Phe Cys
           130                 135                 140

Gly Ser Val Thr Gln
145
```

<210> SEQ ID NO 102
<211> LENGTH: 149
<212> TYPE: PRT
<213> ORGANISM: Haemophilus influenzae

<400> SEQUENCE: 102

```
Met Lys Leu Thr Thr Gln Gln Thr Leu Lys Lys Gly Phe Thr Leu Ile
 1               5                  10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
 50                  55                  60

Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
               100                 105                 110

Tyr Ile Leu Gln Ala Lys Gly Asn Ala Thr Ala Gly Val Thr Trp Thr
               115                 120                 125

Thr Thr Cys Lys Gly Thr Asp Ala Ser Leu Phe Pro Ala Asn Phe Cys
           130                 135                 140

Arg Ser Val Thr Lys
145
```

<210> SEQ ID NO 103
<211> LENGTH: 149
<212> TYPE: PRT
<213> ORGANISM: Haemophilus influenzae

<400> SEQUENCE: 103

```
Met Lys Leu Thr Thr Gln Gln Thr Leu Lys Lys Gly Phe Thr Leu Ile
 1               5                  10                  15
```

```
Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Ala Thr Lys Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145
```

<210> SEQ ID NO 104
<211> LENGTH: 149
<212> TYPE: PRT
<213> ORGANISM: Haemophilus influenzae

<400> SEQUENCE: 104

```
Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145
```

<210> SEQ ID NO 105
<211> LENGTH: 149
<212> TYPE: PRT
<213> ORGANISM: Haemophilus influenzae

<400> SEQUENCE: 105

```
Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30
```

```
Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
 50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
             85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
    130                 135                 140

Gly Ser Val Thr Gln
145
```

<210> SEQ ID NO 106
<211> LENGTH: 149
<212> TYPE: PRT
<213> ORGANISM: Haemophilus influenzae
<220> FEATURE:
<221> NAME/KEY: VARIANT
<222> LOCATION: (1)...(149)
<223> OTHER INFORMATION: Xaa = glutamine or leucine

<400> SEQUENCE: 106

```
Met Lys Leu Thr Thr Gln Gln Thr Leu Lys Lys Gly Phe Thr Leu Ile
  1               5                  10                  15

Glu Leu Met Ile Val Ile Ala Ile Ile Ala Ile Leu Ala Thr Ile Ala
             20                  25                  30

Ile Pro Ser Tyr Gln Asn Tyr Thr Lys Lys Ala Ala Val Ser Glu Leu
         35                  40                  45

Leu Gln Ala Ser Ala Pro Tyr Lys Ala Asp Val Glu Leu Cys Val Tyr
 50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
             85                  90                  95

Asn Gly Ala Ile Thr Val Lys Gly Asp Gly Thr Leu Ala Asn Met Glu
            100                 105                 110

Tyr Ile Leu Xaa Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
    130                 135                 140

Gly Ser Val Thr Gln
145
```

<210> SEQ ID NO 107
<211> LENGTH: 149
<212> TYPE: PRT
<213> ORGANISM: Haemophilus influenzae

<400> SEQUENCE: 107

```
Met Lys Leu Thr Thr Gln Gln Thr Leu Lys Lys Gly Phe Thr Leu Ile
  1               5                  10                  15

Glu Leu Met Ile Val Ile Ala Ile Ile Ala Ile Leu Ala Thr Ile Ala
             20                  25                  30
```

-continued

Ile Pro Ser Tyr Gln Asn Tyr Thr Lys Lys Ala Ala Val Ser Glu Leu
              35                  40                  45

Leu Gln Ala Ser Ala Pro Tyr Lys Ala Asp Val Glu Leu Cys Val Tyr
 50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Lys Gly Asp Gly Thr Leu Ala Asn Met Glu
             100                 105                 110

Tyr Ile Leu Gln Ala Thr Gly Asn Ala Ala Thr Gly Val Thr Trp Thr
             115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 108
<211> LENGTH: 149
<212> TYPE: PRT
<213> ORGANISM: Haemophilus influenzae

<400> SEQUENCE: 108

Met Lys Leu Thr Thr Gln Gln Thr Leu Lys Lys Gly Phe Thr Leu Ile
  1               5                  10                  15

Glu Leu Met Ile Val Ile Ala Ile Ile Ala Ile Leu Ala Thr Ile Ala
             20                  25                  30

Ile Pro Ser Tyr Gln Asn Tyr Thr Lys Lys Ala Ala Val Ser Glu Leu
              35                  40                  45

Leu Gln Ala Ser Ala Pro Tyr Lys Ala Asp Val Glu Leu Cys Val Tyr
 50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Lys Gly Asp Gly Thr Leu Ala Asn Met Glu
             100                 105                 110

Tyr Ile Leu Gln Ala Thr Gly Asn Ala Ala Thr Gly Val Thr Trp Thr
             115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 109
<211> LENGTH: 149
<212> TYPE: PRT
<213> ORGANISM: Haemophilus influenzae

<400> SEQUENCE: 109

Met Lys Leu Thr Thr Leu Gln Leu Lys Lys Gly Phe Thr Leu Ile
  1               5                  10                  15

Glu Leu Met Ile Val Ile Ala Ile Ile Ala Ile Leu Ala Thr Ile Ala
             20                  25                  30

Ile Pro Ser Tyr Gln Asn Tyr Thr Lys Lys Ala Ala Val Ser Glu Leu
              35                  40                  45

```
Leu Gln Ala Ser Ala Pro Tyr Lys Ala Asp Val Glu Leu Cys Val Tyr
         50                  55                  60

Ser Thr Gly Lys Pro Ser Thr Cys Ser Gly Gly Asn Asn Gly Ile Ala
 65                  70                  75                  80

Ala Asp Ile Lys Thr Ala Lys Gly Tyr Val Ala Ser Val Lys Thr Gln
                 85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145
```

<210> SEQ ID NO 110
<211> LENGTH: 149
<212> TYPE: PRT
<213> ORGANISM: Haemophilus influenzae

<400> SEQUENCE: 110

```
Met Lys Leu Thr Thr Leu Gln Thr Leu Lys Lys Gly Phe Thr Leu Ile
  1               5                  10                  15

Glu Leu Met Ile Val Ile Ala Ile Ala Ile Leu Ala Thr Ile Ala
                 20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
         50                  55                  60

Ser Thr Gly Lys Pro Ser Thr Cys Ser Gly Gly Asn Asn Gly Ile Ala
 65                  70                  75                  80

Ala Asp Ile Lys Thr Ala Lys Gly Tyr Val Ala Ser Val Lys Thr Gln
                 85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145
```

<210> SEQ ID NO 111
<211> LENGTH: 149
<212> TYPE: PRT
<213> ORGANISM: Haemophilus influenzae

<400> SEQUENCE: 111

```
Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
                 20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
         50                  55                  60
```

```
Ser Thr Asn Glu Thr Thr Ser Cys Thr Gly Gly Lys Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Ala Gly Asn Gly Thr Leu Asp Gly Met Ser
            100                 105                 110

Tyr Thr Leu Thr Ala Glu Gly Asp Ser Ala Lys Gly Val Thr Trp Lys
        115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 112
<211> LENGTH: 149
<212> TYPE: PRT
<213> ORGANISM: Haemophilus influenzae

<400> SEQUENCE: 112

Met Lys Leu Thr Thr Gln Gln Thr Leu Lys Lys Gly Phe Thr Leu Ile
  1               5                  10                  15

Glu Leu Met Ile Val Ile Ala Ile Ala Ile Leu Ala Thr Ile Ala
             20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
 50                  55                  60

Ser Thr Asn Glu Thr Thr Ser Cys Thr Gly Gly Lys Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Ala Gly Asn Gly Thr Leu Asp Gly Met Ser
            100                 105                 110

Tyr Thr Leu Thr Ala Glu Gly Asp Ser Ala Lys Gly Val Thr Trp Lys
        115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 113
<211> LENGTH: 149
<212> TYPE: PRT
<213> ORGANISM: Haemophilus influenzae

<400> SEQUENCE: 113

Met Lys Leu Thr Thr Leu Gln Thr Leu Lys Lys Gly Phe Thr Leu Ile
  1               5                  10                  15

Glu Leu Met Ile Val Ile Ala Ile Ile Ala Ile Leu Ala Thr Ile Ala
             20                  25                  30

Ile Pro Ser Tyr Gln Asn Tyr Thr Lys Lys Ala Ala Val Ser Glu Leu
             35                  40                  45

Leu Gln Ala Ser Ala Pro Tyr Lys Ala Asp Val Glu Leu Cys Val Tyr
 50                  55                  60

Ser Thr Gly Lys Pro Ser Thr Cys Ser Gly Gly Asn Asn Gly Ile Ala
 65                  70                  75                  80
```

```
Ala Asp Ile Lys Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 114
<211> LENGTH: 149
<212> TYPE: PRT
<213> ORGANISM: Haemophilus influenzae

<400> SEQUENCE: 114

Met Lys Leu Thr Thr Leu Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Thr Cys Ser Gly Gly Asn Asn Gly Ile Ala
65                  70                  75                  80

Ala Asp Ile Lys Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 115
<211> LENGTH: 149
<212> TYPE: PRT
<213> ORGANISM: Haemophilus influenzae

<400> SEQUENCE: 115

Met Lys Leu Thr Thr Leu Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Thr Cys Ser Gly Gly Asn Asn Gly Ile Ala
65                  70                  75                  80

Ala Asp Ile Lys Thr Ala Lys Gly Tyr Val Ala Ser Val Lys Thr Gln
                85                  90                  95
```

```
Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
        130                 135                 140

Gly Ser Val Thr Gln
145

<210> SEQ ID NO 116
<211> LENGTH: 149
<212> TYPE: PRT
<213> ORGANISM: Haemophilus influenzae

<400> SEQUENCE: 116

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
            115                 120                 125

Thr Thr Cys Lys Gly Thr Glu Ala Ser Leu Phe Pro Ala Asn Phe Cys
        130                 135                 140

Gly Ser Val Thr Gln
145

<210> SEQ ID NO 117
<211> LENGTH: 149
<212> TYPE: PRT
<213> ORGANISM: Haemophilus influenzae

<400> SEQUENCE: 117

Met Lys Leu Thr Thr Leu Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Gly Lys Pro Ser Thr Cys Ser Gly Gly Asn Asn Gly Ile Ala
65                  70                  75                  80

Ala Asp Ile Lys Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110
```

```
Tyr Ile Leu Gln Ala Thr Gly Asn Ala Ala Thr Gly Val Thr Trp Thr
            115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 118
<211> LENGTH: 149
<212> TYPE: PRT
<213> ORGANISM: Haemophilus influenzae

<400> SEQUENCE: 118

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
            115                 120                 125

Thr Thr Cys Lys Gly Thr Asp Ala Ser Leu Phe Pro Ala Asn Phe Cys
130                 135                 140

Arg Ser Val Thr Lys
145

<210> SEQ ID NO 119
<211> LENGTH: 149
<212> TYPE: PRT
<213> ORGANISM: Haemophilus influenzae

<400> SEQUENCE: 119

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
50                  55                  60

Ser Thr Asn Glu Ala Thr Lys Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Ser Gly Asn Ala Ala Thr Gly Val Thr Trp Thr
            115                 120                 125
```

```
Thr Thr Cys Lys Gly Thr Asp Ala Ser Leu Phe Pro Ala Asn Phe Cys
    130                 135                 140

Gly Ser Val Thr Gln
145

<210> SEQ ID NO 120
<211> LENGTH: 149
<212> TYPE: PRT
<213> ORGANISM: Haemophilus influenzae

<400> SEQUENCE: 120

Met Lys Leu Thr Thr Leu Gln Thr Leu Lys Lys Gly Phe Thr Leu Ile
  1               5                  10                  15

Glu Leu Met Ile Val Ile Ala Ile Ile Ala Ile Leu Ala Thr Ile Ala
                 20                  25                  30

Ile Pro Ser Tyr Gln Asn Tyr Thr Lys Lys Ala Ala Val Ser Glu Leu
                 35                  40                  45

Leu Gln Ala Ser Ala Pro Tyr Lys Ala Asp Val Glu Leu Cys Val Tyr
         50                  55                  60

Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Ala Ser Val Lys Thr Gln
                 85                  90                  95

Ser Gly Gly Ile Thr Val Lys Gly Asn Gly Thr Leu Ala Asn Met Glu
                100                 105                 110

Tyr Ile Leu Gln Ala Thr Gly Asn Ala Ala Thr Gly Val Thr Trp Thr
                115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 121
<211> LENGTH: 149
<212> TYPE: PRT
<213> ORGANISM: Haemophilus influenzae

<400> SEQUENCE: 121

Met Lys Leu Thr Thr Gln Gln Thr Leu Lys Lys Gly Phe Thr Leu Ile
  1               5                  10                  15

Glu Leu Met Ile Val Ile Ala Ile Ile Ala Ile Leu Ala Thr Ile Ala
                 20                  25                  30

Ile Pro Ser Tyr Gln Asn Tyr Thr Lys Lys Ala Ser Val Ser Glu Leu
                 35                  40                  45

Leu Gln Ala Ser Ala Pro Tyr Lys Ser Asp Val Glu Leu Cys Val Tyr
         50                  55                  60

Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Ala Ser Val Lys Thr Gln
                 85                  90                  95

Ser Gly Gly Ile Thr Val Lys Gly Asn Gly Thr Leu Ala Asn Met Glu
                100                 105                 110

Tyr Ile Leu Gln Ala Lys Gly Asn Ala Thr Ala Gly Val Thr Trp Thr
                115                 120                 125

Thr Thr Cys Lys Gly Thr Asp Ala Ser Leu Phe Pro Ala Asn Phe Cys
    130                 135                 140
```

Arg Ser Val Thr Lys
145

<210> SEQ ID NO 122
<211> LENGTH: 144
<212> TYPE: PRT
<213> ORGANISM: Haemophilus influenzae

<400> SEQUENCE: 122

Ser Ala Gln Ile Gln Lys Ala Glu Gln Asn Asp Val Lys Leu Ala Pro
1               5                   10                  15

Pro Thr Asp Val Arg Ser Gly Tyr Ile Arg Leu Val Lys Asn Val Asn
            20                  25                  30

Tyr Tyr Ile Asp Ser Glu Ser Ile Trp Val Asp Asn Gln Glu Pro Gln
        35                  40                  45

Ile Val His Phe Asp Ala Val Val Asn Leu Asp Lys Gly Leu Tyr Val
    50                  55                  60

Tyr Pro Glu Pro Lys Arg Tyr Ala Arg Ser Val Arg Gln Tyr Lys Ile
65                  70                  75                  80

Leu Asn Cys Ala Asn Tyr His Leu Thr Gln Val Arg Thr Asp Phe Tyr
                85                  90                  95

Asp Glu Phe Trp Gly Gln Gly Leu Arg Ala Ala Pro Lys Lys Gln Lys
            100                 105                 110

Lys His Thr Leu Ser Leu Thr Pro Asp Thr Thr Leu Tyr Asn Ala Ala
        115                 120                 125

Gln Ile Ile Cys Ala Asn Tyr Gly Glu Ala Phe Ser Val Asp Lys Lys
    130                 135                 140

<210> SEQ ID NO 123
<211> LENGTH: 143
<212> TYPE: PRT
<213> ORGANISM: Haemophilus influenzae

<400> SEQUENCE: 123

Ala Gln Ile Gln Lys Ala Glu Gln Asn Asp Val Lys Leu Ala Pro Pro
1               5                   10                  15

Thr Asp Val Arg Ser Gly Tyr Ile Arg Leu Val Lys Asn Val Asn Tyr
            20                  25                  30

Tyr Ile Asp Ser Glu Ser Ile Trp Val Asp Asn Gln Glu Pro Gln Ile
        35                  40                  45

Val His Phe Asp Ala Val Val Asn Leu Asp Lys Gly Leu Tyr Val Tyr
    50                  55                  60

Pro Glu Pro Lys Arg Tyr Ala Arg Ser Val Arg Gln Tyr Lys Ile Leu
65                  70                  75                  80

Asn Cys Ala Asn Tyr His Leu Thr Gln Val Arg Thr Asp Phe Tyr Asp
                85                  90                  95

Glu Phe Trp Gly Gln Gly Leu Arg Ala Ala Pro Lys Lys Gln Lys Lys
            100                 105                 110

His Thr Leu Ser Leu Thr Pro Asp Thr Thr Leu Tyr Asn Ala Ala Gln
        115                 120                 125

Ile Ile Cys Ala Asn Tyr Gly Glu Ala Phe Ser Val Asp Lys Lys
    130                 135                 140

<210> SEQ ID NO 124
<211> LENGTH: 142
<212> TYPE: PRT
<213> ORGANISM: Haemophilus influenzae

<400> SEQUENCE: 124

Gln Ile Gln Lys Ala Glu Gln Asn Asp Val Lys Leu Ala Pro Pro Thr
1               5                   10                  15

Asp Val Arg Ser Gly Tyr Ile Arg Leu Val Lys Asn Val Asn Tyr Tyr
            20                  25                  30

Ile Asp Ser Glu Ser Ile Trp Val Asp Asn Gln Glu Pro Gln Ile Val
        35                  40                  45

His Phe Asp Ala Val Val Asn Leu Asp Lys Gly Leu Tyr Val Tyr Pro
    50                  55                  60

Glu Pro Lys Arg Tyr Ala Arg Ser Val Arg Gln Tyr Lys Ile Leu Asn
65                  70                  75                  80

Cys Ala Asn Tyr His Leu Thr Gln Val Arg Thr Asp Phe Tyr Asp Glu
                85                  90                  95

Phe Trp Gly Gln Gly Leu Arg Ala Ala Pro Lys Lys Gln Lys Lys His
            100                 105                 110

Thr Leu Ser Leu Thr Pro Asp Thr Thr Leu Tyr Asn Ala Ala Gln Ile
        115                 120                 125

Ile Cys Ala Asn Tyr Gly Glu Ala Phe Ser Val Asp Lys Lys
130                 135                 140

<210> SEQ ID NO 125
<211> LENGTH: 141
<212> TYPE: PRT
<213> ORGANISM: Haemophilus influenzae

<400> SEQUENCE: 125

Ile Gln Lys Ala Glu Gln Asn Asp Val Lys Leu Ala Pro Pro Thr Asp
1               5                   10                  15

Val Arg Ser Gly Tyr Ile Arg Leu Val Lys Asn Val Asn Tyr Tyr Ile
            20                  25                  30

Asp Ser Glu Ser Ile Trp Val Asp Asn Gln Glu Pro Gln Ile Val His
        35                  40                  45

Phe Asp Ala Val Val Asn Leu Asp Lys Gly Leu Tyr Val Tyr Pro Glu
    50                  55                  60

Pro Lys Arg Tyr Ala Arg Ser Val Arg Gln Tyr Lys Ile Leu Asn Cys
65                  70                  75                  80

Ala Asn Tyr His Leu Thr Gln Val Arg Thr Asp Phe Tyr Asp Glu Phe
                85                  90                  95

Trp Gly Gln Gly Leu Arg Ala Ala Pro Lys Lys Gln Lys Lys His Thr
            100                 105                 110

Leu Ser Leu Thr Pro Asp Thr Thr Leu Tyr Asn Ala Ala Gln Ile Ile
        115                 120                 125

Cys Ala Asn Tyr Gly Glu Ala Phe Ser Val Asp Lys Lys
130                 135                 140

<210> SEQ ID NO 126
<211> LENGTH: 139
<212> TYPE: PRT
<213> ORGANISM: Haemophilus influenzae

<400> SEQUENCE: 126

Lys Ala Glu Gln Asn Asp Val Lys Leu Ala Pro Pro Thr Asp Val Arg
1               5                   10                  15

Ser Gly Tyr Ile Arg Leu Val Lys Asn Val Asn Tyr Tyr Ile Asp Ser
            20                  25                  30

Glu Ser Ile Trp Val Asp Asn Gln Glu Pro Gln Ile Val His Phe Asp
         35                  40                  45

Ala Val Val Asn Leu Asp Lys Gly Leu Tyr Val Tyr Pro Glu Pro Lys
 50                  55                  60

Arg Tyr Ala Arg Ser Val Arg Gln Tyr Lys Ile Leu Asn Cys Ala Asn
 65                  70                  75                  80

Tyr His Leu Thr Gln Val Arg Thr Asp Phe Tyr Asp Glu Phe Trp Gly
                 85                  90                  95

Gln Gly Leu Arg Ala Ala Pro Lys Lys Gln Lys Lys His Thr Leu Ser
                100                 105                 110

Leu Thr Pro Asp Thr Thr Leu Tyr Asn Ala Ala Gln Ile Ile Cys Ala
            115                 120                 125

Asn Tyr Gly Glu Ala Phe Ser Val Asp Lys Lys
        130                 135

<210> SEQ ID NO 127
<211> LENGTH: 110
<212> TYPE: PRT
<213> ORGANISM: Haemophilus influenzae

<400> SEQUENCE: 127

Thr Lys Lys Ala Ala Val Ser Glu Leu Leu Gln Ala Ser Ala Pro Tyr
 1               5                  10                  15

Lys Ala Asp Val Glu Leu Cys Val Tyr Ser Thr Asn Gly Thr Thr Asn
                 20                  25                  30

Cys Thr Gly Gly Lys Asn Gly Ile Ala Ala Asp Ile Thr Thr Ala Lys
             35                  40                  45

Gly Tyr Val Lys Ser Val Thr Thr Ser Asn Gly Ala Ile Thr Val Lys
         50                  55                  60

Gly Asp Gly Thr Leu Ala Asn Met Glu Tyr Ile Leu Gln Ala Thr Gly
 65                  70                  75                  80

Asn Ala Ala Thr Gly Val Thr Trp Thr Thr Thr Cys Lys Gly Thr Asp
                 85                  90                  95

Ala Ser Leu Phe Pro Ala Asn Phe Cys Gly Ser Val Thr Gln
            100                 105                 110

<210> SEQ ID NO 128
<211> LENGTH: 25
<212> TYPE: PRT
<213> ORGANISM: Haemophilus influenzae

<400> SEQUENCE: 128

Pro Lys Arg Tyr Ala Arg Ser Val Arg Gln Tyr Lys Ile Leu Asn Cys
 1               5                  10                  15

Ala Asn Tyr His Leu Thr Gln Val Arg
                 20                  25

<210> SEQ ID NO 129
<211> LENGTH: 66
<212> TYPE: DNA
<213> ORGANISM: Artificial Sequence
<220> FEATURE:
<223> OTHER INFORMATION: pelB signal peptide

<400> SEQUENCE: 129
atgaaatacc tgctgccgac cgctgctgct ggtctgctgc tcctcgctgc ccagccggcg    60
atggcc                                                              66

```
<210> SEQ ID NO 130
<211> LENGTH: 22
<212> TYPE: PRT
<213> ORGANISM: Artificial Sequence
<220> FEATURE:
<223> OTHER INFORMATION: pelB signal peptide

<400> SEQUENCE: 130

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 131
<211> LENGTH: 57
<212> TYPE: DNA
<213> ORGANISM: Artificial Sequence
<220> FEATURE:
<223> OTHER INFORMATION: FlgI signal peptide

<400> SEQUENCE: 131
atgattaaat tctctctgc attaattctt ctactggtca cgacggcggc tcaggct         57

<210> SEQ ID NO 132
<211> LENGTH: 19
<212> TYPE: PRT
<213> ORGANISM: Artificial Sequence
<220> FEATURE:
<223> OTHER INFORMATION: FlgI signal peptide

<400> SEQUENCE: 132

Met Ile Lys Phe Leu Ser Ala Leu Ile Leu Leu Val Thr Thr Ala
1               5                   10                  15

Ala Gln Ala

<210> SEQ ID NO 133
<211> LENGTH: 69
<212> TYPE: DNA
<213> ORGANISM: Artificial Sequence
<220> FEATURE:
<223> OTHER INFORMATION: NadA signal peptide

<400> SEQUENCE: 133
atgaaacact tccatccaa agtactgacc acagccatcc ttgccacttt ctgtagcggc      60
gcactggca                                                            69

<210> SEQ ID NO 134
<211> LENGTH: 23
<212> TYPE: PRT
<213> ORGANISM: Artificial Sequence
<220> FEATURE:
<223> OTHER INFORMATION: NadA signal peptide

<400> SEQUENCE: 134

Met Lys His Phe Pro Ser Lys Val Leu Thr Thr Ala Ile Leu Ala Thr
1               5                   10                  15

Phe Cys Ser Gly Ala Leu Ala
            20

<210> SEQ ID NO 135
<211> LENGTH: 852
<212> TYPE: DNA
<213> ORGANISM: Artificial Sequence
<220> FEATURE:
<223> OTHER INFORMATION: LVL312
```

<400> SEQUENCE: 135

```
atgattaaat ttctctctgc attaattctt ctactggtca cgacggcggc tcaggctgag      60
actaaaaaag cagcggtatc tgaattactg caagcgtcag cgccttataa ggctgatgtg     120
gaattatgtg tatatagcac aaatgaaaca acaaactgta cgggtggaaa aaatggtatt     180
gcagcagata taaccacagc aaaaggctat gtaaaatcag tgacaacaag caacggtgca     240
ataacagtaa aaggggatgg cacattggca aatatggaat atattttgca agctacaggt     300
aatgctgcaa caggtgtaac ttggacaaca acttgcaaag gaacggatgc ctctttattt     360
ccagcaaatt tttgcggaag tgtcacacaa ggcggcgcgc agattcagaa ggctgaacaa     420
aatgatgtga agctggcacc gccgactgat gtacgaagcg gatatatacg tttggtaaag     480
aatgtgaatt attacatcga tagtgaatcg atctgggtgg ataaccaaga gccacaaatt     540
gtacattttg atgcagtggt gaatttagat aagggattgt atgtttatcc tgagcctaaa     600
cgttatgcac gttctgttcg tcagtataag atcttgaatt gtgcaaatta tcatttaact     660
caagtacgaa ctgatttcta tgatgaattt tggggacagg gtttgcgggc agcacctaaa     720
aagcaaaaga acatacgtt aagtttaaca cctgatacaa cgctttataa tgctgctcag     780
attatttgtg cgaactatgg tgaagcattt tcagttgata aaaaaggcgg ccaccaccac     840
caccaccact aa                                                         852
```

<210> SEQ ID NO 136
<211> LENGTH: 283
<212> TYPE: PRT
<213> ORGANISM: Artificial Sequence
<220> FEATURE:
<223> OTHER INFORMATION: LVL312

<400> SEQUENCE: 136

```
Met Ile Lys Phe Leu Ser Ala Leu Ile Leu Leu Val Thr Thr Ala
 1               5                  10                  15

Ala Gln Ala Glu Thr Lys Lys Ala Ala Val Ser Glu Leu Leu Gln Ala
            20                  25                  30

Ser Ala Pro Tyr Lys Ala Asp Val Glu Leu Cys Val Tyr Ser Thr Asn
        35                  40                  45

Glu Thr Thr Asn Cys Thr Gly Gly Lys Asn Gly Ile Ala Ala Asp Ile
    50                  55                  60

Thr Thr Ala Lys Gly Tyr Val Lys Ser Val Thr Thr Ser Asn Gly Ala
65                  70                  75                  80

Ile Thr Val Lys Gly Asp Gly Thr Leu Ala Asn Met Glu Tyr Ile Leu
                85                  90                  95

Gln Ala Thr Gly Asn Ala Ala Thr Gly Val Thr Trp Thr Thr Thr Cys
            100                 105                 110

Lys Gly Thr Asp Ala Ser Leu Phe Pro Ala Asn Phe Cys Gly Ser Val
        115                 120                 125

Thr Gln Gly Gly Ala Gln Ile Gln Lys Ala Glu Gln Asn Asp Val Lys
    130                 135                 140

Leu Ala Pro Pro Thr Asp Val Arg Ser Gly Tyr Ile Arg Leu Val Lys
145                 150                 155                 160

Asn Val Asn Tyr Tyr Ile Asp Ser Glu Ser Ile Trp Val Asp Asn Gln
                165                 170                 175

Glu Pro Gln Ile Val His Phe Asp Ala Val Val Asn Leu Asp Lys Gly
            180                 185                 190
```

Leu Tyr Val Tyr Pro Glu Pro Lys Arg Tyr Ala Arg Ser Val Arg Gln
            195                 200                 205

Tyr Lys Ile Leu Asn Cys Ala Asn Tyr His Leu Thr Gln Val Arg Thr
        210                 215                 220

Asp Phe Tyr Asp Glu Phe Trp Gly Gln Gly Leu Arg Ala Ala Pro Lys
225                 230                 235                 240

Lys Gln Lys Lys His Thr Leu Ser Leu Thr Pro Asp Thr Thr Leu Tyr
                245                 250                 255

Asn Ala Ala Gln Ile Ile Cys Ala Asn Tyr Gly Glu Ala Phe Ser Val
            260                 265                 270

Asp Lys Lys Gly Gly His His His His His His
            275                 280

<210> SEQ ID NO 137
<211> LENGTH: 855
<212> TYPE: DNA
<213> ORGANISM: Artificial Sequence
<220> FEATURE:
<223> OTHER INFORMATION: LVL291

<400> SEQUENCE: 137
atgaaatacc tgctgccgac cgctgctgct ggtctgctgc tcctcgctgc ccagccggcg     60
atggcccaga ttcagaaggc tgaacaaaat gatgtgaagc tggcaccgcc gactgatgta    120
cgaagcggat atatacgttt ggtaaagaat gtgaattatt acatcgatag tgaatcgatc    180
tgggtggata ccaagagcc acaaattgta catttgatg cagtggtgaa tttagataag    240
ggattgtatg tttatcctga gcctaaacgt tatgcacgtt ctgttcgtca gtataagatc    300
ttgaattgtg caaattatca tttaactcaa gtacgaactg atttctatga tgaattttgg    360
ggacaggggt tgcgggcagc acctaaaaag caaagaaac atacgttaag tttaacacct    420
gatacaacgc tttataatgc tgctcagatt atttgtgcga actatggtga agcattttca    480
gttgataaaa aaggcggcac taaaaaagca gcggtatctg aattactgca agcgtcagcg    540
ccttataagg ctgatgtgga attatgtgta tatagcacaa atgaaacaac aaactgtacg    600
ggtggaaaaa atggtattgc agcagatata accacagcaa aaggctatgt aaaatcagtg    660
acaacaagca acggtgcaat aacagtaaaa ggggatggca cattggcaaa tatgaatat    720 attttgcaag ctacaggtaa tgctgcaaca ggtgtaactt ggacaacaac ttgcaaagga    780
acggatgcct ctttatttcc agcaaatttt tgcggaagtg tcacacaagg cggccaccac    840
caccaccacc actaa                                                     855

<210> SEQ ID NO 138
<211> LENGTH: 284
<212> TYPE: PRT
<213> ORGANISM: Artificial Sequence
<220> FEATURE:
<223> OTHER INFORMATION: LVL291

<400> SEQUENCE: 138

Met Lys Tyr Leu Leu Pro Thr Ala Ala Ala Gly Leu Leu Leu Leu Ala
 1               5                  10                  15

Ala Gln Pro Ala Met Ala Gln Ile Gln Lys Ala Glu Gln Asn Asp Val
            20                  25                  30

Lys Leu Ala Pro Pro Thr Asp Val Arg Ser Gly Tyr Ile Arg Leu Val
        35                  40                  45

Lys Asn Val Asn Tyr Tyr Ile Asp Ser Glu Ser Ile Trp Val Asp Asn
    50                  55                  60

Gln Glu Pro Gln Ile Val His Phe Asp Ala Val Val Asn Leu Asp Lys
65                  70                  75                  80

Gly Leu Tyr Val Tyr Pro Glu Pro Lys Arg Tyr Ala Arg Ser Val Arg
            85                  90                  95

Gln Tyr Lys Ile Leu Asn Cys Ala Asn Tyr His Leu Thr Gln Val Arg
        100                 105                 110

Thr Asp Phe Tyr Asp Glu Phe Trp Gly Gln Gly Leu Arg Ala Ala Pro
    115                 120                 125

Lys Lys Gln Lys Lys His Thr Leu Ser Leu Thr Pro Asp Thr Thr Leu
130                 135                 140

Tyr Asn Ala Ala Gln Ile Ile Cys Ala Asn Tyr Gly Glu Ala Phe Ser
145                 150                 155                 160

Val Asp Lys Lys Gly Gly Thr Lys Lys Ala Ala Val Ser Glu Leu Leu
            165                 170                 175

Gln Ala Ser Ala Pro Tyr Lys Ala Asp Val Glu Leu Cys Val Tyr Ser
        180                 185                 190

Thr Asn Glu Thr Thr Asn Cys Thr Gly Gly Lys Asn Gly Ile Ala Ala
    195                 200                 205

Asp Ile Thr Thr Ala Lys Gly Tyr Val Lys Ser Val Thr Thr Ser Asn
210                 215                 220

Gly Ala Ile Thr Val Lys Gly Asp Gly Thr Leu Ala Asn Met Glu Tyr
225                 230                 235                 240

Ile Leu Gln Ala Thr Gly Asn Ala Ala Thr Gly Val Thr Trp Thr Thr
            245                 250                 255

Thr Cys Lys Gly Thr Asp Ala Ser Leu Phe Pro Ala Asn Phe Cys Gly
        260                 265                 270

Ser Val Thr Gln Gly Gly His His His His His
        275                 280

<210> SEQ ID NO 139
<211> LENGTH: 852
<212> TYPE: DNA
<213> ORGANISM: Artificial Sequence
<220> FEATURE:
<223> OTHER INFORMATION: LVL268

<400> SEQUENCE: 139
atgaaatacc tgctgccgac cgctgctgct ggtctgctgc tcctcgctgc ccagccggcg    60
atggccgata ttcagaaggc tgaacaaaat gatgtgaagc tggcaccgcc gactgatgta    120
cgaagcggat atatacgttt ggtaaagaat gtgaattatt acatcgatag tgaatcgatc    180
tgggtggata ccaagagcc acaaattgta cattttgatg cagtggtgaa tttagataag    240
ggattgtatg tttatcctga gcctaaacgt tatgcacgtt ctgttcgtca gtataagatc    300
ttgaattgtg caaattatca tttaactcaa gtacgaactg atttctatga tgaattttgg    360
ggacagggtt tgcgggcagc acctaaaaag caaagaaac atacgttaag tttaacacct    420
gatacaacgc tttataatgc tgctcagatt atttgtgcga actatggtga agcattttca    480
gttgataaaa aaggcggcac taaaaaagca gcggtatctg aattactgca agcgtcagcg    540
ccttataagc tgatgtgga attatgtgta tatagcacaa atgaaacaac aaactgtacg    600
ggtggaaaaa atggtattgc agcagatata accacagcaa aaggctatgt aaaatcagtg    660
acaacaagca acggtgcaat aacagtaaaa gggatggca cattggcaaa tatggaatat    720
attttgcaag ctacaggtaa tgctgcaaca ggtgtaactt ggacaacaac ttgcaaagga    780

```
acggatgcct ctttatttcc agcaaatttt tgcggaagtg tcacacaagg cggccaccac    840
caccaccacc ac                                                         852
```

<210> SEQ ID NO 140
<211> LENGTH: 284
<212> TYPE: PRT
<213> ORGANISM: Artificial Sequence
<220> FEATURE:
<223> OTHER INFORMATION: LVL268

<400> SEQUENCE: 140

```
Met Lys Tyr Leu Leu Pro Thr Ala Ala Ala Gly Leu Leu Leu Leu Ala
 1               5                  10                  15

Ala Gln Pro Ala Met Ala Asp Ile Gln Lys Ala Glu Gln Asn Asp Val
            20                  25                  30

Lys Leu Ala Pro Pro Thr Asp Val Arg Ser Gly Tyr Ile Arg Leu Val
        35                  40                  45

Lys Asn Val Asn Tyr Tyr Ile Asp Ser Glu Ser Ile Trp Val Asp Asn
    50                  55                  60

Gln Glu Pro Gln Ile Val His Phe Asp Ala Val Val Asn Leu Asp Lys
65                  70                  75                  80

Gly Leu Tyr Val Tyr Pro Glu Pro Lys Arg Tyr Ala Arg Ser Val Arg
                85                  90                  95

Gln Tyr Lys Ile Leu Asn Cys Ala Asn Tyr His Leu Thr Gln Val Arg
            100                 105                 110

Thr Asp Phe Tyr Asp Glu Phe Trp Gly Gln Gly Leu Arg Ala Ala Pro
        115                 120                 125

Lys Lys Gln Lys Lys His Thr Leu Ser Leu Thr Pro Asp Thr Thr Leu
130                 135                 140

Tyr Asn Ala Ala Gln Ile Ile Cys Ala Asn Tyr Gly Glu Ala Phe Ser
145                 150                 155                 160

Val Asp Lys Lys Gly Gly Thr Lys Lys Ala Ala Val Ser Glu Leu Leu
                165                 170                 175

Gln Ala Ser Ala Pro Tyr Lys Ala Asp Val Glu Leu Cys Val Tyr Ser
            180                 185                 190

Thr Asn Glu Thr Thr Asn Cys Thr Gly Gly Lys Asn Gly Ile Ala Ala
        195                 200                 205

Asp Ile Thr Thr Ala Lys Gly Tyr Val Lys Ser Val Thr Thr Ser Asn
    210                 215                 220

Gly Ala Ile Thr Val Lys Gly Asp Gly Thr Leu Ala Asn Met Glu Tyr
225                 230                 235                 240

Ile Leu Gln Ala Thr Gly Asn Ala Ala Thr Gly Val Thr Trp Thr Thr
                245                 250                 255

Thr Cys Lys Gly Thr Asp Ala Ser Leu Phe Pro Ala Asn Phe Cys Gly
            260                 265                 270

Ser Val Thr Gln Gly Gly His His His His His
        275                 280
```

<210> SEQ ID NO 141
<211> LENGTH: 867
<212> TYPE: DNA
<213> ORGANISM: Artificial Sequence
<220> FEATURE:
<223> OTHER INFORMATION: LVL269

<400> SEQUENCE: 141

```
atgaaacact ttccatccaa agtactgacc acagccatcc ttgccacttt ctgtagcggc    60
```

-continued

```
gcactggcag ccacaaacga cgacgataag gctgaacaaa atgatgtgaa gctggcaccg      120
ccgactgatg tacgaagcgg atatatacgt ttggtaaaga atgtgaatta ttacatcgat      180
agtgaatcga tctgggtgga taaccaagag ccacaaattg tacattttga tgcagtggtg      240
aatttagata agggattgta tgtttatcct gagcctaaac gttatgcacg ttctgttcgt      300
cagtataaga tcttgaattg tgcaaattat catttaactc aagtacgaac tgatttctat      360
gatgaatttt ggggacaggg tttgcgggca gcacctaaaa agcaaaagaa acatacgtta      420
agtttaacac ctgatacaac gctttataat gctgctcaga ttatttgtgc gaactatggt      480
gaagcatttt cagttgataa aaaaggcggc actaaaaaag cagcggtatc tgaattactg      540
caagcgtcag cgccttataa ggctgatgtg gaattatgtg tatatagcac aaatgaaaca      600
acaaactgta cgggtggaaa aaatggtatt gcagcagata taaccacagc aaaaggctat      660
gtaaaatcag tgacaacaag caacggtgca ataacagtaa aagggatgg cacattggca       720 aatatggaat atattttgca agctacaggt aatgctgcaa caggtgtaac ttggacaaca      780
acttgcaaag gaacggatgc ctctttattt ccagcaaatt tttgcggaag tgtcacacaa      840
ggcggccacc accaccacca ccactaa                                          867
```

<210> SEQ ID NO 142
<211> LENGTH: 288
<212> TYPE: PRT
<213> ORGANISM: Artificial Sequence
<220> FEATURE:
<223> OTHER INFORMATION: LVL269

<400> SEQUENCE: 142

```
Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Lys Ala Glu
            20                  25                  30

Gln Asn Asp Val Lys Leu Ala Pro Pro Thr Asp Val Arg Ser Gly Tyr
        35                  40                  45

Ile Arg Leu Val Lys Asn Val Asn Tyr Tyr Ile Asp Ser Glu Ser Ile
    50                  55                  60

Trp Val Asp Asn Gln Glu Pro Gln Ile Val His Phe Asp Ala Val Val
65                  70                  75                  80

Asn Leu Asp Lys Gly Leu Tyr Val Tyr Pro Glu Pro Lys Arg Tyr Ala
                85                  90                  95

Arg Ser Val Arg Gln Tyr Lys Ile Leu Asn Cys Ala Asn Tyr His Leu
            100                 105                 110

Thr Gln Val Arg Thr Asp Phe Tyr Asp Glu Phe Trp Gly Gln Gly Leu
        115                 120                 125

Arg Ala Ala Pro Lys Lys Gln Lys Lys His Thr Leu Ser Leu Thr Pro
    130                 135                 140

Asp Thr Thr Leu Tyr Asn Ala Ala Gln Ile Ile Cys Ala Asn Tyr Gly
145                 150                 155                 160

Glu Ala Phe Ser Val Asp Lys Lys Gly Gly Thr Lys Lys Ala Ala Val
                165                 170                 175

Ser Glu Leu Leu Gln Ala Ser Ala Pro Tyr Lys Ala Asp Val Glu Leu
            180                 185                 190

Cys Val Tyr Ser Thr Asn Glu Thr Thr Asn Cys Thr Gly Gly Lys Asn
        195                 200                 205

Gly Ile Ala Ala Asp Ile Thr Thr Ala Lys Gly Tyr Val Lys Ser Val
```

Thr Thr Ser Asn Gly Ala Ile Thr Val Lys Gly Asp Gly Thr Leu Ala
225                 230                 235                 240

Asn Met Glu Tyr Ile Leu Gln Ala Thr Gly Asn Ala Ala Thr Gly Val
            245                 250                 255

Thr Trp Thr Thr Thr Cys Lys Gly Thr Asp Ala Ser Leu Phe Pro Ala
        260                 265                 270

Asn Phe Cys Gly Ser Val Thr Gln Gly Gly His His His His His His
            275                 280                 285

<210> SEQ ID NO 143
<211> LENGTH: 792
<212> TYPE: DNA
<213> ORGANISM: Artificial Sequence
<220> FEATURE:
<223> OTHER INFORMATION: LVL270

<400> SEQUENCE: 143
atgcaccacc accaccacca cagcgcgcag attcagaagg ctgaacaaaa tgatgtgaag    60
ctggcaccgc cgactgatgt acgaagcgga tatatacgtt tggtaaagaa tgtgaattat   120
tacatcgata gtgaatcgat ctgggtggat aaccaagagc cacaaattgt acattttgat   180
gcagtggtga atttagataa gggattgtat gtttatcctg agcctaaacg ttatgcacgt   240
tctgttcgtc agtataagat cttgaattgt gcaaattatc atttaactca gtacgaactg   300
gatttctatg atgaattttg gggacagggt ttgcgggcag cacctaaaaa gcaaaagaaa   360
catacgttaa gtttaacacc tgatacaacg ctttataatg ctgctcagat tatttgtgcg   420
aactatggtg aagcattttc agttgataaa aaaggcggca ctaaaaaagc agcggtatct   480
gaattactgc aagcgtcagc gcctataag gctgatgtgg aattatgtgt atatagcaca   540
aatgaaacaa caaactgtac gggtggaaaa atggtattg cagcagatat aaccacagca   600
aaaggctatg taaaatcagt gacaacaagc aacggtgcaa taacagtaaa aggggatggc   660
acattggcaa atatggaata tattttgcaa gctacaggta atgctgcaac aggtgtaact   720
tggacaacaa cttgcaaagg aacggatgcc tctttatttc cagcaaattt ttgcggaagt   780
gtcacacaat aa                                                       792

<210> SEQ ID NO 144
<211> LENGTH: 263
<212> TYPE: PRT
<213> ORGANISM: Artificial Sequence
<220> FEATURE:
<223> OTHER INFORMATION: LVL270

<400> SEQUENCE: 144

Met His His His His His His Ser Ala Gln Ile Gln Lys Ala Glu Gln
  1               5                  10                  15

Asn Asp Val Lys Leu Ala Pro Pro Thr Asp Val Arg Ser Gly Tyr Ile
             20                  25                  30

Arg Leu Val Lys Asn Val Asn Tyr Tyr Ile Asp Ser Glu Ser Ile Trp
         35                  40                  45

Val Asp Asn Gln Glu Pro Gln Ile Val His Phe Asp Ala Val Val Asn
     50                  55                  60

Leu Asp Lys Gly Leu Tyr Val Tyr Pro Glu Pro Lys Arg Tyr Ala Arg
 65                  70                  75                  80

Ser Val Arg Gln Tyr Lys Ile Leu Asn Cys Ala Asn Tyr His Leu Thr
                 85                  90                  95

Gln Val Arg Thr Asp Phe Tyr Asp Glu Phe Trp Gly Gln Gly Leu Arg
            100                 105                 110

Ala Ala Pro Lys Lys Gln Lys Lys His Thr Leu Ser Leu Thr Pro Asp
        115                 120                 125

Thr Thr Leu Tyr Asn Ala Ala Gln Ile Ile Cys Ala Asn Tyr Gly Glu
130                 135                 140

Ala Phe Ser Val Asp Lys Lys Gly Gly Thr Lys Lys Ala Ala Val Ser
145                 150                 155                 160

Glu Leu Leu Gln Ala Ser Ala Pro Tyr Lys Ala Asp Val Glu Leu Cys
                165                 170                 175

Val Tyr Ser Thr Asn Glu Thr Asn Cys Thr Gly Gly Lys Asn Gly
                180                 185                 190

Ile Ala Ala Asp Ile Thr Thr Ala Lys Gly Tyr Val Lys Ser Val Thr
            195                 200                 205

Thr Ser Asn Gly Ala Ile Thr Val Lys Gly Asp Gly Thr Leu Ala Asn
    210                 215                 220

Met Glu Tyr Ile Leu Gln Ala Thr Gly Asn Ala Ala Thr Gly Val Thr
225                 230                 235                 240

Trp Thr Thr Thr Cys Lys Gly Thr Asp Ala Ser Leu Phe Pro Ala Asn
                245                 250                 255

Phe Cys Gly Ser Val Thr Gln
            260

```
<210> SEQ ID NO 145
<211> LENGTH: 852
<212> TYPE: DNA
<213> ORGANISM: Artificial Sequence
<220> FEATURE:
<223> OTHER INFORMATION: LVL315

<400> SEQUENCE: 145
atgaaatacc tgctgccgac cgctgctgct ggtctgctgc tcctcgctgc ccagccggcg      60
atggccatgg ataaggctga acaaaatgat gtgaagctgg caccgccgac tgatgtacga     120
agcggatata tacgtttggt aaagaatgtg aattattaca tcgatagtga atcgatctgg     180
gtggataacc aagagccaca aattgtacat tttgatgcag tggtgaattt agataaggga     240
ttgtatgttt atcctgagcc taaacgttat gcacgttctg ttcgtcagta taagatcttg     300
aattgtgcaa attatcattt aactcaagta cgaactgatt tctatgatga attttgggga     360
cagggtttgc gggcagcacc taaaaagcaa aagaaacata cgttaagttt aacacctgat     420
acaacgcttt ataatgctgc tcagattatt tgtgcgaact atggtgaagc attttcagtt     480
gataaaaaag gcggcactaa aaaagcagcg gtatctgaat tactgcaagc gtcagcgcct     540
tataaggctg atgtggaatt atgtgtatat agcacaaatg aaacaacaaa ctgtacgggt     600
ggaaaaaatg gtattgcagc agatataacc acagcaaaag gctatgtaaa atcagtgaca     660
acaagcaacg gtgcaataac agtaaaaggg gatggcacat tggcaaatat ggaatatatt     720
ttgcaagcta caggtaatgc tgcaacaggt gtaacttgga caacaacttg caaggaacg      780
gatgcctctt tatttccagc aaattttgc ggaagtgtca cacaaggcgg ccaccaccac     840
caccaccact aa                                                         852
```

```
<210> SEQ ID NO 146
<211> LENGTH: 283
<212> TYPE: PRT
<213> ORGANISM: Artificial Sequence
```

<220> FEATURE:
<223> OTHER INFORMATION: LVL315

<400> SEQUENCE: 146

Met Lys Tyr Leu Leu Pro Thr Ala Ala Ala Gly Leu Leu Leu Ala
1               5                   10                  15

Ala Gln Pro Ala Met Ala Met Asp Lys Ala Glu Gln Asn Asp Val Lys
            20                  25                  30

Leu Ala Pro Pro Thr Asp Val Arg Ser Gly Tyr Ile Arg Leu Val Lys
            35                  40                  45

Asn Val Asn Tyr Tyr Ile Asp Ser Glu Ser Ile Trp Val Asp Asn Gln
50                      55                  60

Glu Pro Gln Ile Val His Phe Asp Ala Val Val Asn Leu Asp Lys Gly
65                  70                  75                  80

Leu Tyr Val Tyr Pro Glu Pro Lys Arg Tyr Ala Arg Ser Val Arg Gln
                85                  90                  95

Tyr Lys Ile Leu Asn Cys Ala Asn Tyr His Leu Thr Gln Val Arg Thr
            100                 105                 110

Asp Phe Tyr Asp Glu Phe Trp Gly Gln Gly Leu Arg Ala Ala Pro Lys
        115                 120                 125

Lys Gln Lys Lys His Thr Leu Ser Leu Thr Pro Asp Thr Thr Leu Tyr
    130                 135                 140

Asn Ala Ala Gln Ile Ile Cys Ala Asn Tyr Gly Glu Ala Phe Ser Val
145                 150                 155                 160

Asp Lys Lys Gly Gly Thr Lys Lys Ala Ala Val Ser Glu Leu Leu Gln
                165                 170                 175

Ala Ser Ala Pro Tyr Lys Ala Asp Val Glu Leu Cys Val Tyr Ser Thr
            180                 185                 190

Asn Glu Thr Thr Asn Cys Thr Gly Gly Lys Asn Gly Ile Ala Ala Asp
        195                 200                 205

Ile Thr Thr Ala Lys Gly Tyr Val Lys Ser Val Thr Thr Ser Asn Gly
    210                 215                 220

Ala Ile Thr Val Lys Gly Asp Gly Thr Leu Ala Asn Met Glu Tyr Ile
225                 230                 235                 240

Leu Gln Ala Thr Gly Asn Ala Ala Thr Gly Val Thr Trp Thr Thr Thr
                245                 250                 255

Cys Lys Gly Thr Asp Ala Ser Leu Phe Pro Ala Asn Phe Cys Gly Ser
            260                 265                 270

Val Thr Gln Gly Gly His His His His His
            275                 280

<210> SEQ ID NO 147
<211> LENGTH: 831
<212> TYPE: DNA
<213> ORGANISM: Artificial Sequence
<220> FEATURE:
<223> OTHER INFORMATION: LVL317

<400> SEQUENCE: 147
atgaaatacc tgctgccgac cgctgctgct ggtctgctgc tcctcgctgc ccagccggcg        60
atggcccaga ttcagaaggc tgaacaaaat gatgtgaagc tggcaccgcc gactgatgta       120
cgaagcggat atatacgttt ggtaaagaat gtgaattatt acatcgatag tgaatcgatc       180
tgggtggata ccaagagcc acaaattgta cattttgatg cagtggtgaa tttagataag        240
ggattgtatg tttatcctga gcctaaacgt tatgcacgtt ctgttcgtca gtataagatc       300

```
ttgaattgtg caaattatca tttaactcaa gtacgaactg atttctatga tgaattttgg      360
ggacagggtt tgcgggcagc acctaaaaag caaagaaac atacgttaag tttaacacct       420
gatacaacgc tttataatgc tgctcagatt atttgtgcga actatggtga agcattttca     480
gttgataaaa aaggcggcac taaaaaagca gcggtatctg aattactgca agcgtcagcg     540
ccttataagg ctgatgtgga attatgtgta tatagcacaa atgaaacaac aaactgtacg     600
ggtgaaaaaa atggtattgc agcagatata accacagcaa aaggctatgt aaaatcagtg     660
acaacaagca acggtgcaat aacagtaaaa ggggatggca cattggcaaa tatggaatat     720
attttgcaag ctacaggtaa tgctgcaaca ggtgtaactt ggacaacaac ttgcaaagga     780
acggatgcct ctttatttcc agcaaatttt tgcggaagtg tcacacaata a              831
```

<210> SEQ ID NO 148
<211> LENGTH: 276
<212> TYPE: PRT
<213> ORGANISM: Artificial Sequence
<220> FEATURE:
<223> OTHER INFORMATION: LVL317

<400> SEQUENCE: 148

```
Met Lys Tyr Leu Leu Pro Thr Ala Ala Ala Gly Leu Leu Leu Leu Ala
 1               5                  10                  15
Ala Gln Pro Ala Met Ala Gln Ile Gln Lys Ala Glu Gln Asn Asp Val
            20                  25                  30
Lys Leu Ala Pro Pro Thr Asp Val Arg Ser Gly Tyr Ile Arg Leu Val
        35                  40                  45
Lys Asn Val Asn Tyr Tyr Ile Asp Ser Glu Ser Ile Trp Val Asp Asn
    50                  55                  60
Gln Glu Pro Gln Ile Val His Phe Asp Ala Val Val Asn Leu Asp Lys
65                  70                  75                  80
Gly Leu Tyr Val Tyr Pro Glu Pro Lys Arg Tyr Ala Arg Ser Val Arg
                85                  90                  95
Gln Tyr Lys Ile Leu Asn Cys Ala Asn Tyr His Leu Thr Gln Val Arg
            100                 105                 110
Thr Asp Phe Tyr Asp Glu Phe Trp Gly Gln Gly Leu Arg Ala Ala Pro
        115                 120                 125
Lys Lys Gln Lys Lys His Thr Leu Ser Leu Thr Pro Asp Thr Thr Leu
    130                 135                 140
Tyr Asn Ala Ala Gln Ile Ile Cys Ala Asn Tyr Gly Glu Ala Phe Ser
145                 150                 155                 160
Val Asp Lys Lys Gly Thr Lys Lys Ala Val Ser Glu Leu Leu
                165                 170                 175
Gln Ala Ser Ala Pro Tyr Lys Ala Asp Val Glu Leu Cys Val Tyr Ser
            180                 185                 190
Thr Asn Glu Thr Thr Asn Cys Thr Gly Gly Lys Asn Gly Ile Ala Ala
        195                 200                 205
Asp Ile Thr Thr Ala Lys Gly Tyr Val Lys Ser Val Thr Thr Ser Asn
    210                 215                 220
Gly Ala Ile Thr Val Lys Gly Asp Gly Thr Leu Ala Asn Met Glu Tyr
225                 230                 235                 240
Ile Leu Gln Ala Thr Gly Asn Ala Ala Thr Gly Val Thr Trp Thr Thr
                245                 250                 255
Thr Cys Lys Gly Thr Asp Ala Ser Leu Phe Pro Ala Asn Phe Cys Gly
            260                 265                 270
```

Ser Val Thr Gln
        275

<210> SEQ ID NO 149
<211> LENGTH: 828
<212> TYPE: DNA
<213> ORGANISM: Artificial Sequence
<220> FEATURE:
<223> OTHER INFORMATION: LVL318

<400> SEQUENCE: 149

```
atgaaatacc tgctgccgac cgctgctgct ggtctgctgc tcctcgctgc ccagccggcg      60
atggccatgg ataaggctga acaaaatgat gtgaagctgg caccgccgac tgatgtacga     120
agcggatata tacgtttggt aaagaatgtg aattattaca tcgatagtga atcgatctgg     180
gtggataacc aagagccaca aattgtacat tttgatgcag tggtgaattt agataaggga     240
ttgtatgttt atcctgagcc taaacgttat gcacgttctg ttcgtcagta taagatcttg     300
aattgtgcaa attatcattt aactcaagta cgaactgatt tctatgatga attttgggga     360
cagggtttgc gggcagcacc taaaaagcaa agaaacata cgttaagttt aacacctgat     420
acaacgcttt ataatgctgc tcagattatt tgtgcgaact atggtgaagc attttcagtt     480
gataaaaaag gcggcactaa aaaagcagcg gtatctgaat tactgcaagc gtcagcgcct     540
tataaggctg atgtggaatt atgtgtatat agcacaaatg aaacaacaaa ctgtacgggt     600
ggaaaaaatg gtattgcagc agatataacc acagcaaaag gctatgtaaa atcagtgaca     660
acaagcaacg gtgcaataac agtaaaaggg gatggcacat ggcaaatat ggaatatatt     720
ttgcaagcta caggtaatgc tgcaacaggt gtaacttgga caacaacttg caaaggaacg     780
gatgcctctt tatttccagc aaattttgc ggaagtgtca cacaataa               828
```

<210> SEQ ID NO 150
<211> LENGTH: 275
<212> TYPE: PRT
<213> ORGANISM: Artificial Sequence
<220> FEATURE:
<223> OTHER INFORMATION: LVL318

<400> SEQUENCE: 150

Met Lys Tyr Leu Leu Pro Thr Ala Ala Ala Gly Leu Leu Leu Leu Ala
1               5                   10                  15

Ala Gln Pro Ala Met Ala Met Asp Lys Ala Glu Gln Asn Asp Val Lys
            20                  25                  30

Leu Ala Pro Pro Thr Asp Val Arg Ser Gly Tyr Ile Arg Leu Val Lys
        35                  40                  45

Asn Val Asn Tyr Tyr Ile Asp Ser Glu Ser Ile Trp Val Asp Asn Gln
    50                  55                  60

Glu Pro Gln Ile Val His Phe Asp Ala Val Val Asn Leu Asp Lys Gly
65                  70                  75                  80

Leu Tyr Val Tyr Pro Glu Pro Lys Arg Tyr Ala Arg Ser Val Arg Gln
                85                  90                  95

Tyr Lys Ile Leu Asn Cys Ala Asn Tyr His Leu Thr Gln Val Arg Thr
            100                 105                 110

Asp Phe Tyr Asp Glu Phe Trp Gly Gln Gly Leu Arg Ala Ala Pro Lys
        115                 120                 125

Lys Gln Lys Lys His Thr Leu Ser Leu Thr Pro Asp Thr Thr Leu Tyr
    130                 135                 140

Asn Ala Ala Gln Ile Ile Cys Ala Asn Tyr Gly Glu Ala Phe Ser Val

```
          145                 150                 155                 160
Asp Lys Lys Gly Gly Thr Lys Ala Ala Val Ser Glu Leu Leu Gln
                    165                 170                 175

Ala Ser Ala Pro Tyr Lys Ala Asp Val Glu Leu Cys Val Tyr Ser Thr
                180                 185                 190

Asn Glu Thr Thr Asn Cys Thr Gly Lys Asn Gly Ile Ala Ala Asp
                195                 200                 205

Ile Thr Thr Ala Lys Gly Tyr Val Lys Ser Val Thr Thr Ser Asn Gly
210                 215                 220

Ala Ile Thr Val Lys Gly Asp Gly Thr Leu Ala Asn Met Glu Tyr Ile
225                 230                 235                 240

Leu Gln Ala Thr Gly Asn Ala Ala Thr Gly Val Thr Trp Thr Thr Thr
                    245                 250                 255

Cys Lys Gly Thr Asp Ala Ser Leu Phe Pro Ala Asn Phe Cys Gly Ser
                260                 265                 270

Val Thr Gln
        275

<210> SEQ ID NO 151
<211> LENGTH: 483
<212> TYPE: DNA
<213> ORGANISM: Haemophilus influenzae

<400> SEQUENCE: 151
atgaaaaaaa ttattttaac attatcactt gggttactta ccgcttgttc tgctcaaatc      60
caaaaggctg aacaaaatga tgtgaagctg caccgccga ctgatgtacg aagcggatat     120
atacgtttgg taagaatgt gaattattac atcgatagtg aatcgatctg gtggataac      180 caagagccac aaattgtaca ttttgatgct gtggtgaatt tagataggg attgtatgtt     240 tatcctgagc ctaaacgtta tgcacgttct gttcgtcagt ataagatttt gaattgtgca     300
aattatcatt taactcaaat acgaactgat ttctatgatg aattttgggg acagggtttg     360
cgggcagcac ctaaaaagca aagaaacat acgttaagtt taacacctga tacaacgctt     420
tataatgctg ctcagattat ttgtgcaaat tatggtaaag cattttcagt tgataaaaaa     480
taa                                                                    483

<210> SEQ ID NO 152
<211> LENGTH: 160
<212> TYPE: PRT
<213> ORGANISM: Haemophilus influenzae

<400> SEQUENCE: 152

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asn Gln Glu Pro Gln
        50                  55                  60

Ile Val His Phe Asp Ala Val Val Asn Leu Asp Arg Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
```

```
            100                 105                 110
Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 153
<211> LENGTH: 480
<212> TYPE: DNA
<213> ORGANISM: Haemophilus influenzae

<400> SEQUENCE: 153
atgaaaaaaa ttattttaac attatcactt gggttactta ctgcctgttc tgctcaaatc      60
caaaaggcta acaaaatga tgtgaagctg gcaccgccga ctgatgtacg aagcggatat     120
atacgtttgg taagaatgt gaattattac atcgatagtg aatcgatctg ggtggataac     180
caagagccac aaattgtaca ttttgatgca gtggtgaatt tagataaggg attgtatgtt     240
tatcctgagc ctaaacgtta tgcacgttct gttcgtcagt ataagatctt gaattgtgca     300
aattatcatt taactcaagt acgaactgat ttctatgatg aattttgggg acagggtttg     360
cgggcagcac ctaaaaagca aagaaacat acgttaagtt taacacctga tacaacgctt      420
tataatgctg ctcagattat ttgtgcgaac tatggtgaag cattttcagt tgataaaaaa     480

<210> SEQ ID NO 154
<211> LENGTH: 160
<212> TYPE: PRT
<213> ORGANISM: Haemophilus influenzae

<400> SEQUENCE: 154

Met Lys Lys Ile Ile Leu Thr Leu Ser Leu Gly Leu Leu Thr Ala Cys
  1               5                  10                  15

Ser Ala Gln Ile Gln Lys Ala Lys Gln Asn Asp Val Lys Leu Ala Pro
             20                  25                  30

Pro Thr Asp Val Arg Ser Gly Tyr Ile Arg Leu Val Lys Asn Val Asn
         35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160

<210> SEQ ID NO 155
<211> LENGTH: 91
<212> TYPE: DNA
<213> ORGANISM: Artificial Sequence
<220> FEATURE:
```

<223> OTHER INFORMATION: primer

<400> SEQUENCE: 155
cacacacata tgattaaatt tctctctgca ttaattcttc tactggtcac gacggcggct    60
caggctgaga ctaaaaaagc agcggtatct g    91

<210> SEQ ID NO 156
<211> LENGTH: 66
<212> TYPE: DNA
<213> ORGANISM: Artificial Sequence
<220> FEATURE:
<223> OTHER INFORMATION: primer

<400> SEQUENCE: 156
tgtgtgaagc ttttagtggt ggtggtggtg gtggccgcct tgtgtgacac ttccgcaaaa    60
atttgc    66

<210> SEQ ID NO 157
<211> LENGTH: 58
<212> TYPE: DNA
<213> ORGANISM: Artificial Sequence
<220> FEATURE:
<223> OTHER INFORMATION: primer

<400> SEQUENCE: 157
tttgcggaag tgtcacacaa ggcggcgcgc agattcagaa ggctgaacaa aatgatgt    58

<210> SEQ ID NO 158
<211> LENGTH: 58
<212> TYPE: DNA
<213> ORGANISM: Artificial Sequence
<220> FEATURE:
<223> OTHER INFORMATION: primer

<400> SEQUENCE: 158
acatcatttt gttcagcctt ctgaatctgc gcgccgcctt gtgtgacact tccgcaaa    58

<210> SEQ ID NO 159
<211> LENGTH: 59
<212> TYPE: DNA
<213> ORGANISM: Artificial Sequence
<220> FEATURE:
<223> OTHER INFORMATION: primer

<400> SEQUENCE: 159
tgtgtgaagc ttttagtggt ggtggtggtg gtggccgcct tttttatcaa ctgaaaatg    59

<210> SEQ ID NO 160
<211> LENGTH: 65
<212> TYPE: DNA
<213> ORGANISM: Artificial Sequence
<220> FEATURE:
<223> OTHER INFORMATION: primer

<400> SEQUENCE: 160
cacacacata tgcaccacca ccaccaccac agcgcgcaga ttcagaaggc tgaacaaaat    60
gatgt    65

<210> SEQ ID NO 161
<211> LENGTH: 46
<212> TYPE: DNA
<213> ORGANISM: Artificial Sequence
<220> FEATURE:
<223> OTHER INFORMATION: primer

<400> SEQUENCE: 161
cattttcagt tgataaaaaa ggcggcacta aaaaagcagc ggtatc                46

<210> SEQ ID NO 162
<211> LENGTH: 46
<212> TYPE: DNA
<213> ORGANISM: Artificial Sequence
<220> FEATURE:
<223> OTHER INFORMATION: primer

<400> SEQUENCE: 162
gataccgctg ctttttagt gccgcctttt ttatcaactg aaaatg                 46

<210> SEQ ID NO 163
<211> LENGTH: 35
<212> TYPE: DNA
<213> ORGANISM: Artificial Sequence
<220> FEATURE:
<223> OTHER INFORMATION: primer

<400> SEQUENCE: 163
tgtgtgaagc ttttattgtg tgacacttcc gcaaa                            35

<210> SEQ ID NO 164
<211> LENGTH: 104
<212> TYPE: DNA
<213> ORGANISM: Artificial Sequence
<220> FEATURE:
<223> OTHER INFORMATION: primer

<400> SEQUENCE: 164
cacacacata tgaaatacct gctgccgacc gctgctgctg gtctgctgct cctcgctgcc     60
cagccggcga tggcccagat tcagaaggct gaacaaaatg atgt                    104

<210> SEQ ID NO 165
<211> LENGTH: 49
<212> TYPE: DNA
<213> ORGANISM: Artificial Sequence
<220> FEATURE:
<223> OTHER INFORMATION: primer

<400> SEQUENCE: 165
gcattttcag ttgataaaaa aggcggcact aaaaaagcag cggtatctg              49

<210> SEQ ID NO 166
<211> LENGTH: 49
<212> TYPE: DNA
<213> ORGANISM: Artificial Sequence
<220> FEATURE:
<223> OTHER INFORMATION: primer

<400> SEQUENCE: 166
cagataccgc tgcttttttta gtgccgcctt ttttatcaac tgaaaatgc             49

<210> SEQ ID NO 167
<211> LENGTH: 104
<212> TYPE: DNA
<213> ORGANISM: Artificial Sequence
<220> FEATURE:
<223> OTHER INFORMATION: primer

<400> SEQUENCE: 167
cacacacata tgaaatacct gctgccgacc gctgctgctg gtctgctgct cctcgctgcc     60
cagccggcga tggccgatat tcagaaggct gaacaaaatg atgt                104

<210> SEQ ID NO 168
<211> LENGTH: 115
<212> TYPE: DNA
<213> ORGANISM: Artificial Sequence
<220> FEATURE:
<223> OTHER INFORMATION: primer

<400> SEQUENCE: 168
cacacacata tgaaacactt tccatccaaa gtactgacca cagccatcct tgccactttc      60
tgtagcggcg cactggcagc cacaaacgac gacgataagg ctgaacaaaa tgatg          115

<210> SEQ ID NO 169
<211> LENGTH: 35
<212> TYPE: DNA
<213> ORGANISM: Artificial Sequence
<220> FEATURE:
<223> OTHER INFORMATION: primer

<400> SEQUENCE: 169
gccggcgatg gccatggata aggctgaaca aaatg                                35

<210> SEQ ID NO 170
<211> LENGTH: 35
<212> TYPE: DNA
<213> ORGANISM: Artificial Sequence
<220> FEATURE:
<223> OTHER INFORMATION: primer

<400> SEQUENCE: 170
cattttgttc agccttatcc atggccatcg ccggc                                35

<210> SEQ ID NO 171
<211> LENGTH: 34
<212> TYPE: DNA
<213> ORGANISM: Artificial Sequence
<220> FEATURE:
<223> OTHER INFORMATION: primer

<400> SEQUENCE: 171
ggaagtgtca cacataagg cggccaccac cacc                                  34

<210> SEQ ID NO 172
<211> LENGTH: 34
<212> TYPE: DNA
<213> ORGANISM: Artificial Sequence
<220> FEATURE:
<223> OTHER INFORMATION: primer

<400> SEQUENCE: 172
ggtggtggtg gccgccttat tgtgtgacac ttcc                                 34

<210> SEQ ID NO 173
<211> LENGTH: 54
<212> TYPE: DNA
<213> ORGANISM: Artificial Sequence
<220> FEATURE:
<223> OTHER INFORMATION: primer

<400> SEQUENCE: 173
gaattccata tgcaccatca ccatcaccat actaaaaaag cagcggtatc tgaa            54

<210> SEQ ID NO 174
<211> LENGTH: 32

<212> TYPE: DNA
<213> ORGANISM: Artificial Sequence
<220> FEATURE:
<223> OTHER INFORMATION: primer

<400> SEQUENCE: 174
gcgccgctcg agtcattgtg tgacacttcc gc            32

<210> SEQ ID NO 175
<211> LENGTH: 43
<212> TYPE: DNA
<213> ORGANISM: Artificial Sequence
<220> FEATURE:
<223> OTHER INFORMATION: primer

<400> SEQUENCE: 175
gcccagccgg cgatggccca gatccagaag gctgaacaaa atg            43

<210> SEQ ID NO 176
<211> LENGTH: 43
<212> TYPE: DNA
<213> ORGANISM: Artificial Sequence
<220> FEATURE:
<223> OTHER INFORMATION: primer

<400> SEQUENCE: 176
cattttgttc agccttctgg atctgggcca tcgccggctg ggc            43

<210> SEQ ID NO 177
<211> LENGTH: 254
<212> TYPE: PRT
<213> ORGANISM: Artificial Sequence
<220> FEATURE:
<223> OTHER INFORMATION: Fusion protein

<400> SEQUENCE: 177

Gln Ile Gln Lys Ala Glu Gln Asn Asp Val Lys Leu Ala Pro Pro Thr
1               5                   10                  15

Asp Val Arg Ser Gly Tyr Ile Arg Leu Val Lys Asn Val Asn Tyr Tyr
            20                  25                  30

Ile Asp Ser Glu Ser Ile Trp Val Asp Asn Gln Glu Pro Gln Ile Val
        35                  40                  45

His Phe Asp Ala Val Val Asn Leu Asp Lys Gly Leu Tyr Val Tyr Pro
    50                  55                  60

Glu Pro Lys Arg Tyr Ala Arg Ser Val Arg Gln Tyr Lys Ile Leu Asn
65                  70                  75                  80

Cys Ala Asn Tyr His Leu Thr Gln Val Arg Thr Asp Phe Tyr Asp Glu
                85                  90                  95

Phe Trp Gly Gln Gly Leu Arg Ala Ala Pro Lys Lys Gln Lys Lys His
            100                 105                 110

Thr Leu Ser Leu Thr Pro Asp Thr Thr Leu Tyr Asn Ala Ala Gln Ile
        115                 120                 125

Ile Cys Ala Asn Tyr Gly Glu Ala Phe Ser Val Asp Lys Lys Gly Gly
    130                 135                 140

Thr Lys Lys Ala Ala Val Ser Glu Leu Leu Gln Ala Ser Ala Pro Tyr
145                 150                 155                 160

Lys Ala Asp Val Glu Leu Cys Val Tyr Ser Thr Asn Glu Thr Thr Asn
                165                 170                 175

Cys Thr Gly Gly Lys Asn Gly Ile Ala Ala Asp Ile Thr Thr Ala Lys
            180                 185                 190

Gly Tyr Val Lys Ser Val Thr Thr Ser Asn Gly Ala Ile Thr Val Lys
            195                 200                 205

Gly Asp Gly Thr Leu Ala Asn Met Glu Tyr Ile Leu Gln Ala Thr Gly
        210                 215                 220

Asn Ala Ala Thr Gly Val Thr Trp Thr Thr Thr Cys Lys Gly Thr Asp
225                 230                 235                 240

Ala Ser Leu Phe Pro Ala Asn Phe Cys Gly Ser Val Thr Gln
            245                 250

<210> SEQ ID NO 178
<211> LENGTH: 6
<212> TYPE: PRT
<213> ORGANISM: Artificial Sequence
<220> FEATURE:
<223> OTHER INFORMATION: Synthetic construct

<400> SEQUENCE: 178

Ala Thr Asn Asp Asp Asp
1               5

<210> SEQ ID NO 179
<211> LENGTH: 138
<212> TYPE: PRT
<213> ORGANISM: Haemophilus influenzae

<400> SEQUENCE: 179

Ala Glu Gln Asn Asp Val Lys Leu Ala Pro Pro Thr Asp Val Arg Ser
1               5                   10                  15

Gly Tyr Ile Arg Leu Val Lys Asn Val Asn Tyr Tyr Ile Asp Ser Glu
            20                  25                  30

Ser Ile Trp Val Asp Asn Gln Glu Pro Gln Ile Val His Phe Asp Ala
        35                  40                  45

Val Val Asn Leu Asp Lys Gly Leu Tyr Val Tyr Pro Glu Pro Lys Arg
    50                  55                  60

Tyr Ala Arg Ser Val Arg Gln Tyr Lys Ile Leu Asn Cys Ala Asn Tyr
65                  70                  75                  80

His Leu Thr Gln Val Arg Thr Asp Phe Tyr Asp Glu Phe Trp Gly Gln
                85                  90                  95

Gly Leu Arg Ala Ala Pro Lys Lys Gln Lys Lys His Thr Leu Ser Leu
            100                 105                 110

Thr Pro Asp Thr Thr Leu Tyr Asn Ala Ala Gln Ile Ile Cys Ala Asn
        115                 120                 125

Tyr Gly Glu Ala Phe Ser Val Asp Lys Lys
    130                 135

<210> SEQ ID NO 180
<211> LENGTH: 137
<212> TYPE: PRT
<213> ORGANISM: Haemophilus influenzae

<400> SEQUENCE: 180

Glu Gln Asn Asp Val Lys Leu Ala Pro Pro Thr Asp Val Arg Ser Gly
1               5                   10                  15

Tyr Ile Arg Leu Val Lys Asn Val Asn Tyr Tyr Ile Asp Ser Glu Ser
            20                  25                  30

Ile Trp Val Asp Asn Gln Glu Pro Gln Ile Val His Phe Asp Ala Val
        35                  40                  45

Val Asn Leu Asp Lys Gly Leu Tyr Val Tyr Pro Glu Pro Lys Arg Tyr
    50                  55                  60

Ala Arg Ser Val Arg Gln Tyr Lys Ile Leu Asn Cys Ala Asn Tyr His
65                  70                  75                  80

Leu Thr Gln Val Arg Thr Asp Phe Tyr Asp Glu Phe Trp Gly Gln Gly
                85                  90                  95

Leu Arg Ala Ala Pro Lys Lys Gln Lys Lys His Thr Leu Ser Leu Thr
            100                 105                 110

Pro Asp Thr Thr Leu Tyr Asn Ala Ala Gln Ile Ile Cys Ala Asn Tyr
        115                 120                 125

Gly Glu Ala Phe Ser Val Asp Lys Lys
    130                 135

<210> SEQ ID NO 181
<211> LENGTH: 849
<212> TYPE: DNA
<213> ORGANISM: Artificial Sequence
<220> FEATURE:
<223> OTHER INFORMATION: LVL702

<400> SEQUENCE: 181
atgaaatacc tgctgccgac cgctgctgct ggtctgctgc tcctcgctgc ccagccggcg      60
atggccattc agaaggctga acaaaatgat gtgaagctgg caccgccgac tgatgtacga     120
agcggatata tacgtttggt aaagaatgtg aattattaca tcgatagtga atcgatctgg     180
gtggataacc aagagccaca aattgtacat tttgatgcag tggtgaattt agataaggga     240
ttgtatgttt atcctgagcc taaacgttat gcacgttctg ttcgtcagta taagatcttg     300
aattgtgcaa attatcattt aactcaagta cgaactgatt tctatgatga attttgggga     360
cagggtttgc gggcagcacc taaaaagcaa agaaacata cgttaagttt aacacctgat      420
acaacgcttt ataatgctgc tcagattatt tgtgcgaact atggtgaagc attttcagtt     480
gataaaaaag gcggcactaa aaaagcagcg tatctgaat tactgcaagc gtcagcgcct      540
tataaggctg atgtggaatt atgtgtatat agcacaaatg aaacaacaaa ctgtacgggt     600
ggaaaaaatg gtattgcagc agatataacc acagcaaaag gctatgtaaa atcagtgaca     660
acaagcaacg gtgcaataac agtaaaaggg gatggcacat tggcaaatat ggaatatatt     720
ttgcaagcta caggtaatgc tgcaacaggt gtaacttgga caacaacttg caaaggaacg     780
gatgcctctt tatttccagc aaattttttgc ggaagtgtca cacaaggcgg ccaccaccac     840
caccaccac                                                             849

<210> SEQ ID NO 182
<211> LENGTH: 283
<212> TYPE: PRT
<213> ORGANISM: Artificial Sequence
<220> FEATURE:
<223> OTHER INFORMATION: LVL702

<400> SEQUENCE: 182

Met Lys Tyr Leu Leu Pro Thr Ala Ala Ala Gly Leu Leu Leu Leu Ala
1               5                   10                  15

Ala Gln Pro Ala Met Ala Ile Gln Lys Ala Glu Gln Asn Asp Val Lys
            20                  25                  30

Leu Ala Pro Pro Thr Asp Val Arg Ser Gly Tyr Ile Arg Leu Val Lys
        35                  40                  45

Asn Val Asn Tyr Tyr Ile Asp Ser Glu Ser Ile Trp Val Asp Asn Gln
    50                  55                  60

Glu Pro Gln Ile Val His Phe Asp Ala Val Val Asn Leu Asp Lys Gly

```
            65                  70                  75                  80
Leu Tyr Val Tyr Pro Glu Pro Lys Arg Tyr Ala Arg Ser Val Arg Gln
                    85                  90                  95

Tyr Lys Ile Leu Asn Cys Ala Asn Tyr His Leu Thr Gln Val Arg Thr
            100                 105                 110

Asp Phe Tyr Asp Glu Phe Trp Gly Gln Gly Leu Arg Ala Ala Pro Lys
        115                 120                 125

Lys Gln Lys Lys His Thr Leu Ser Leu Thr Pro Asp Thr Thr Leu Tyr
    130                 135                 140

Asn Ala Ala Gln Ile Ile Cys Ala Asn Tyr Gly Glu Ala Phe Ser Val
145                 150                 155                 160

Asp Lys Lys Gly Gly Thr Lys Ala Ala Val Ser Glu Leu Leu Gln
                165                 170                 175

Ala Ser Ala Pro Tyr Lys Ala Asp Val Glu Leu Cys Val Tyr Ser Thr
                180                 185                 190

Asn Glu Thr Thr Asn Cys Thr Gly Gly Lys Asn Gly Ile Ala Ala Asp
                195                 200                 205

Ile Thr Thr Ala Lys Gly Tyr Val Lys Ser Val Thr Thr Ser Asn Gly
        210                 215                 220

Ala Ile Thr Val Lys Gly Asp Gly Thr Leu Ala Asn Met Glu Tyr Ile
225                 230                 235                 240

Leu Gln Ala Thr Gly Asn Ala Ala Thr Gly Val Thr Trp Thr Thr Thr
                245                 250                 255

Cys Lys Gly Thr Asp Ala Ser Leu Phe Pro Ala Asn Phe Cys Gly Ser
                260                 265                 270

Val Thr Gln Gly Gly His His His His His His
                275                 280

<210> SEQ ID NO 183
<211> LENGTH: 858
<212> TYPE: DNA
<213> ORGANISM: Artificial Sequence
<220> FEATURE:
<223> OTHER INFORMATION: LVL736

<400> SEQUENCE: 183
atgaaatacc tgctgccgac cgctgctgct ggtctgctgc tcctcgctgc ccagccggcg      60
atggccagcg cccagattca gaaggctgaa caaaatgatg tgaagctggc accgccgact     120
gatgtacgaa gcggatatat acgtttggta agaatgtgaa attattacat cgatagtgaa     180
tcgatctggg tggataacca agagccacaa attgtacatt ttgatgcagt ggtgaattta     240
gataagggat tgtatgttta tcctgagcct aaacgttatg cacgttctgt tcgtcagtat     300
aagatcttga attgtgcaaa ttatcattta actcaagtac gaactgattt ctatgatgaa     360
ttttggggac agggtttgcg ggcagcacct aaaaagcaaa agaaacatac gttaagttta     420
acacctgata caacgcttta taatgctgct cagattattt gtgcgaacta tggtgaagca     480
ttttcagttg ataaaaaagg cggcactaaa aaagcagcgg tatctgaatt actgcaagcg     540
tcagcgcctt ataaggctga tgtggaatta tgtgtatata gcacaaatga acaacaaac     600 tgtacgggtg gaaaaaatgg tattgcagca gatataacca cagcaaaagg ctatgtaaaa     660
tcagtgacaa caagcaacgg tgcaataaca gtaaagggg atggcacatt ggcaaatatg     720
gaatatattt tgcaagctac aggtaatgct gcaacaggtg taacttggac aacaacttgc     780
aaaggaacgg atgcctcttt atttccagca aattttttgcg gaagtgtcac acaaggcggc     840
```
caccaccacc accaccac                                                        858

<210> SEQ ID NO 184
<211> LENGTH: 286
<212> TYPE: PRT
<213> ORGANISM: Artificial Sequence
<220> FEATURE:
<223> OTHER INFORMATION: LVL736

<400> SEQUENCE: 184

Met Lys Tyr Leu Leu Pro Thr Ala Ala Ala Gly Leu Leu Leu Leu Ala
 1               5                  10                  15

Ala Gln Pro Ala Met Ala Ser Ala Gln Ile Gln Lys Ala Glu Gln Asn
            20                  25                  30

Asp Val Lys Leu Ala Pro Pro Thr Asp Val Arg Ser Gly Tyr Ile Arg
        35                  40                  45

Leu Val Lys Asn Val Asn Tyr Tyr Ile Asp Ser Glu Ser Ile Trp Val
    50                  55                  60

Asp Asn Gln Glu Pro Gln Ile Val His Phe Asp Ala Val Val Asn Leu
65                  70                  75                  80

Asp Lys Gly Leu Tyr Val Tyr Pro Glu Pro Lys Arg Tyr Ala Arg Ser
                85                  90                  95

Val Arg Gln Tyr Lys Ile Leu Asn Cys Ala Asn Tyr His Leu Thr Gln
            100                 105                 110

Val Arg Thr Asp Phe Tyr Asp Glu Phe Trp Gly Gln Gly Leu Arg Ala
        115                 120                 125

Ala Pro Lys Lys Gln Lys Lys His Thr Leu Ser Leu Thr Pro Asp Thr
    130                 135                 140

Thr Leu Tyr Asn Ala Ala Gln Ile Ile Cys Ala Asn Tyr Gly Glu Ala
145                 150                 155                 160

Phe Ser Val Asp Lys Lys Gly Gly Thr Lys Lys Ala Ala Val Ser Glu
                165                 170                 175

Leu Leu Gln Ala Ser Ala Pro Tyr Lys Ala Asp Val Glu Leu Cys Val
            180                 185                 190

Tyr Ser Thr Asn Glu Thr Thr Asn Cys Thr Gly Gly Lys Asn Gly Ile
        195                 200                 205

Ala Ala Asp Ile Thr Thr Ala Lys Gly Tyr Val Lys Ser Val Thr Thr
    210                 215                 220

Ser Asn Gly Ala Ile Thr Val Lys Gly Asp Gly Thr Leu Ala Asn Met
225                 230                 235                 240

Glu Tyr Ile Leu Gln Ala Thr Gly Asn Ala Ala Thr Gly Val Thr Trp
                245                 250                 255

Thr Thr Thr Cys Lys Gly Thr Asp Ala Ser Leu Phe Pro Ala Asn Phe
            260                 265                 270

Cys Gly Ser Val Thr Gln Gly Gly His His His His His His
        275                 280                 285

<210> SEQ ID NO 185
<211> LENGTH: 855
<212> TYPE: DNA
<213> ORGANISM: Artificial Sequence
<220> FEATURE:
<223> OTHER INFORMATION: LVL737

<400> SEQUENCE: 185
atgaaatacc tgctgccgac cgctgctgct ggtctgctgc tcctcgctgc ccagccggcg      60
atggccgccc agattcagaa ggctgaacaa aatgatgtga agctggcacc gccgactgat     120

-continued

```
gtacgaagcg gatatatacg tttggtaaag aatgtgaatt attacatcga tagtgaatcg    180
atctgggtgg ataaccaaga gccacaaatt gtacattttg atgcagtggt gaatttagat    240
aagggattgt atgtttatcc tgagcctaaa cgttatgcac gttctgttcg tcagtataag    300
atcttgaatt gtgcaaatta tcatttaact caagtacgaa ctgatttcta tgatgaattt    360
tggggacagg gtttgcgggc agcacctaaa aagcaaaaga acatacgtt aagtttaaca     420 cctgatacaa cgctttataa tgctgctcag attatttgtg cgaactatgg tgaagcattt    480
tcagttgata aaaaaggcgg cactaaaaaa gcagcggtat ctgaattact gcaagcgtca    540 gcgcccttata aggctgatgt ggaattatgt gtatatagca caaatgaaac aacaaactgt    600
acgggtggaa aaaatggtat tgcagcagat ataaccacag caaaaggcta tgtaaaatca    660
gtgacaacaa gcaacggtgc aataacagta aaagggatg gcacattggc aaatatggaa     720
tatattttgc aagctacagg taatgctgca acaggtgtaa cttggacaac aacttgcaaa    780
ggaacggatg cctctttatt tccagcaaat ttttgcggaa gtgtcacaca aggcggccac    840
caccaccacc accac                                                     855
```

```
<210> SEQ ID NO 186
<211> LENGTH: 285
<212> TYPE: PRT
<213> ORGANISM: Artificial Sequence
<220> FEATURE:
<223> OTHER INFORMATION: LVL737

<400> SEQUENCE: 186
```

```
Met Lys Tyr Leu Leu Pro Thr Ala Ala Ala Gly Leu Leu Leu Leu Ala
 1               5                  10                  15

Ala Gln Pro Ala Met Ala Ala Gln Ile Gln Lys Ala Glu Gln Asn Asp
            20                  25                  30

Val Lys Leu Ala Pro Pro Thr Asp Val Arg Ser Gly Tyr Ile Arg Leu
        35                  40                  45

Val Lys Asn Val Asn Tyr Tyr Ile Asp Ser Glu Ser Ile Trp Val Asp
    50                  55                  60

Asn Gln Glu Pro Gln Ile Val His Phe Asp Ala Val Asn Leu Asp
 65                  70                  75                  80

Lys Gly Leu Tyr Val Tyr Pro Glu Pro Lys Arg Tyr Ala Arg Ser Val
                85                  90                  95

Arg Gln Tyr Lys Ile Leu Asn Cys Ala Asn Tyr His Leu Thr Gln Val
            100                 105                 110

Arg Thr Asp Phe Tyr Asp Glu Phe Trp Gly Gln Gly Leu Arg Ala Ala
        115                 120                 125

Pro Lys Lys Gln Lys Lys His Thr Leu Ser Leu Thr Pro Asp Thr Thr
    130                 135                 140

Leu Tyr Asn Ala Ala Gln Ile Ile Cys Ala Asn Tyr Gly Glu Ala Phe
145                 150                 155                 160

Ser Val Asp Lys Lys Gly Gly Thr Lys Lys Ala Ala Val Ser Glu Leu
                165                 170                 175

Leu Gln Ala Ser Ala Pro Tyr Lys Ala Asp Val Glu Leu Cys Val Tyr
            180                 185                 190

Ser Thr Asn Glu Thr Thr Asn Cys Thr Gly Gly Lys Asn Gly Ile Ala
        195                 200                 205

Ala Asp Ile Thr Thr Ala Lys Gly Tyr Val Lys Ser Val Thr Thr Ser
    210                 215                 220
```

```
Asn Gly Ala Ile Thr Val Lys Gly Asp Gly Thr Leu Ala Asn Met Glu
225                 230                 235                 240

Tyr Ile Leu Gln Ala Thr Gly Asn Ala Ala Thr Gly Val Thr Trp Thr
                245                 250                 255

Thr Thr Cys Lys Gly Thr Asp Ala Ser Leu Phe Pro Ala Asn Phe Cys
            260                 265                 270

Gly Ser Val Thr Gln Gly Gly His His His His His
            275                 280                 285
```

<210> SEQ ID NO 187
<211> LENGTH: 843
<212> TYPE: DNA
<213> ORGANISM: Artificial Sequence
<220> FEATURE:
<223> OTHER INFORMATION: LVL738

<400> SEQUENCE: 187

```
atgaaatacc tgctgccgac cgctgctgct ggtctgctgc tcctcgctgc ccagccggcg      60
atggccaagg ctgaacaaaa tgatgtgaag ctggcaccgc cgactgatgt acgaagcgga     120
tatatacgtt tggtaaagaa tgtgaattat tacatcgata gtgaatcgat ctgggtggat     180
aaccaagagc cacaaattgt acattttgat gcagtggtga atttagataa gggattgtat     240
gtttatcctg agcctaaacg ttatgcacgt tctgttcgtc agtataagat cttgaattgt     300
gcaaattatc atttaactca agtacgaact gatttctatg atgaatttg gggacagggt      360
ttgcgggcag cacctaaaaa gcaaagaaa catacgttaa gtttaacacc tgatacaacg      420
ctttataatg ctgctcagat tatttgtgcg aactatggtg aagcatttc agttgataaa     480
aaaggcggca ctaaaaaagc agcggtatct gaattactgc aagcgtcagc gccttataag     540
gctgatgtgg aattatgtgt atatagcaca atgaaacaa caaactgtac gggtggaaaa     600
aatggtattg cagcagatat aaccacagca aaaggctatg taaaatcagt gacaacaagc     660
aacggtgcaa taacagtaaa aggggatggc acattggcaa atatggaata tattttgcaa     720
gctacaggta atgctgcaac aggtgtaact tggacaacaa cttgcaaagg aacggatgcc     780
tcttatttc agcaaatttt ttgcggaagt gtcacacaag cggccacca ccaccaccac      840
cac                                                                   843
```

<210> SEQ ID NO 188
<211> LENGTH: 281
<212> TYPE: PRT
<213> ORGANISM: Artificial Sequence
<220> FEATURE:
<223> OTHER INFORMATION: LVL738

<400> SEQUENCE: 188

```
Met Lys Tyr Leu Leu Pro Thr Ala Ala Ala Gly Leu Leu Leu Leu Ala
 1               5                  10                  15

Ala Gln Pro Ala Met Ala Lys Ala Glu Gln Asn Asp Val Lys Leu Ala
                20                  25                  30

Pro Pro Thr Asp Val Arg Ser Gly Tyr Ile Arg Leu Val Lys Asn Val
            35                  40                  45

Asn Tyr Tyr Ile Asp Ser Glu Ser Ile Trp Val Asp Asn Gln Glu Pro
50                  55                  60

Gln Ile Val His Phe Asp Ala Val Val Asn Leu Asp Lys Gly Leu Tyr
65                  70                  75                  80

Val Tyr Pro Glu Pro Lys Arg Tyr Ala Arg Ser Val Arg Gln Tyr Lys
                85                  90                  95
```

Ile Leu Asn Cys Ala Asn Tyr His Leu Thr Gln Val Arg Thr Asp Phe
            100                 105                 110

Tyr Asp Glu Phe Trp Gly Gln Gly Leu Arg Ala Ala Pro Lys Lys Gln
        115                 120                 125

Lys Lys His Thr Leu Ser Leu Thr Pro Asp Thr Thr Leu Tyr Asn Ala
130                 135                 140

Ala Gln Ile Ile Cys Ala Asn Tyr Gly Glu Ala Phe Ser Val Asp Lys
145                 150                 155                 160

Lys Gly Gly Thr Lys Lys Ala Ala Val Ser Glu Leu Leu Gln Ala Ser
                165                 170                 175

Ala Pro Tyr Lys Ala Asp Val Glu Leu Cys Val Tyr Ser Thr Asn Glu
            180                 185                 190

Thr Thr Asn Cys Thr Gly Gly Lys Asn Gly Ile Ala Ala Asp Ile Thr
        195                 200                 205

Thr Ala Lys Gly Tyr Val Lys Ser Val Thr Thr Ser Asn Gly Ala Ile
210                 215                 220

Thr Val Lys Gly Asp Gly Thr Leu Ala Asn Met Glu Tyr Ile Leu Gln
225                 230                 235                 240

Ala Thr Gly Asn Ala Ala Thr Gly Val Thr Trp Thr Thr Thr Cys Lys
                245                 250                 255

Gly Thr Asp Ala Ser Leu Phe Pro Ala Asn Phe Cys Gly Ser Val Thr
            260                 265                 270

Gln Gly Gly His His His His His His
        275                 280

<210> SEQ ID NO 189
<211> LENGTH: 840
<212> TYPE: DNA
<213> ORGANISM: Artificial Sequence
<220> FEATURE:
<223> OTHER INFORMATION: LVL739

<400> SEQUENCE: 189

```
atgaaatacc tgctgccgac cgctgctgct ggtctgctgc tcctcgctgc ccagccggcg      60
atggccgctg aacaaaatga tgtgaagctg gcaccgccga ctgatgtacg aagcggatat     120
atacgtttgg taagaatgt gaattattac atcgatagtg aatcgatctg ggtggataac     180
caagagccac aaattgtaca ttttgatgca gtggtgaatt tagataaggg attgtatgtt     240
tatcctgagc ctaaacgtta tgcacgttct gttcgtcagt ataagatctt gaattgtgca     300
aattatcatt taactcaagt acgaactgat ttctatgatg aattttgggg acagggtttg     360
cgggcagcac ctaaaaagca aagaaacat acgttaagtt taacacctga taacgcctt     420
tataatgctg ctcagattat ttgtgcgaac tatggtgaag catttcagt tgataaaaaa     480
ggcggcacta aaaagcagc ggtatctgaa ttactgcaag cgtcagcgcc ttataaggct     540
gatgtggaat atgtgtata tagcacaaat gaaacaacaa actgtacggg tggaaaaaat     600
ggtattgcag cagatataac cacagcaaaa ggctatgtaa aatcagtgac aacaagcaac     660
ggtgcaataa cagtaaaagg ggatggcaca ttggcaaata tggaatatat tttgcaagct     720
acaggtaatg ctgcaacagg tgtaacttgg acaacaactt gcaaaggaac ggatgcctct     780
ttatttccag caaattttg cggaagtgtc acacaaggcg gccaccacca ccaccaccac     840
```

<210> SEQ ID NO 190
<211> LENGTH: 280
<212> TYPE: PRT

-continued

<213> ORGANISM: Artificial Sequence
<220> FEATURE:
<223> OTHER INFORMATION: LVL739

<400> SEQUENCE: 190

Met Lys Tyr Leu Leu Pro Thr Ala Ala Ala Gly Leu Leu Leu Leu Ala
1               5                   10                  15

Ala Gln Pro Ala Met Ala Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Glu Ala Phe Ser Val Asp Lys Lys
145                 150                 155                 160

Gly Gly Thr Lys Lys Ala Ala Val Ser Glu Leu Leu Gln Ala Ser Ala
                165                 170                 175

Pro Tyr Lys Ala Asp Val Glu Leu Cys Val Tyr Ser Thr Asn Glu Thr
            180                 185                 190

Thr Asn Cys Thr Gly Gly Lys Asn Gly Ile Ala Ala Asp Ile Thr Thr
        195                 200                 205

Ala Lys Gly Tyr Val Lys Ser Val Thr Thr Ser Asn Gly Ala Ile Thr
210                 215                 220

Val Lys Gly Asp Gly Thr Leu Ala Asn Met Glu Tyr Ile Leu Gln Ala
225                 230                 235                 240

Thr Gly Asn Ala Ala Thr Gly Val Thr Trp Thr Thr Cys Lys Gly
                245                 250                 255

Thr Asp Ala Ser Leu Phe Pro Ala Asn Phe Cys Gly Ser Val Thr Gln
            260                 265                 270

Gly Gly His His His His His His
        275                 280

<210> SEQ ID NO 191
<211> LENGTH: 837
<212> TYPE: DNA
<213> ORGANISM: Artificial Sequence
<220> FEATURE:
<223> OTHER INFORMATION: LVL740

<400> SEQUENCE: 191
atgaaatacc tgctgccgac cgctgctgct ggtctgctgc tcctcgctgc ccagccggcg     60
atggccgaac aaaatgatgt gaagctggca ccgccgactg atgtacgaag cggatatata    120
cgtttggtaa agaatgtgaa ttattacatc gatagtgaat cgatctgggt ggataaccaa    180
gagccacaaa ttgtacattt tgatgcagtg gtgaatttag ataagggatt gtatgtttat    240
cctgagccta acgttatgc acgttctgtt cgtcagtata agatcttgaa ttgtgcaaat    300

```
tatcatttaa ctcaagtacg aactgatttc tatgatgaat tttggggaca gggtttgcgg    360
gcagcaccta aaaagcaaaa gaaacatacg ttaagtttaa cacctgatac aacgctttat    420
aatgctgctc agattatttg tgcgaactat ggtgaagcat tttcagttga taaaaaggc    480 ggcactaaaa aagcagcggt atctgaatta ctgcaagcgt cagcgcctta taaggctgat    540
gtggaattat gtgtatatag cacaaatgaa caacaaact gtacgggtgg aaaaaatggt    600
attgcagcag atataaccac agcaaaaggc tatgtaaaat cagtgacaac aagcaacggt    660
gcaataacag taaaagggga tggcacattg gcaaatatgg aatatatttt gcaagctaca    720
ggtaatgctg caacaggtgt aacttggaca acaacttgca aaggaacgga tgcctcttta    780
tttccagcaa attttgcggg aagtgtcaca caaggcggcc accaccacca ccaccac      837
```

<210> SEQ ID NO 192
<211> LENGTH: 279
<212> TYPE: PRT
<213> ORGANISM: Artificial Sequence
<220> FEATURE:
<223> OTHER INFORMATION: LVL740

<400> SEQUENCE: 192

```
Met Lys Tyr Leu Leu Pro Thr Ala Ala Ala Gly Leu Leu Leu Leu Ala
 1               5                  10                  15

Ala Gln Pro Ala Met Ala Glu Gln Asn Asp Val Lys Leu Ala Pro Pro
            20                  25                  30

Thr Asp Val Arg Ser Gly Tyr Ile Arg Leu Val Lys Asn Val Asn Tyr
        35                  40                  45

Tyr Ile Asp Ser Glu Ser Ile Trp Val Asp Asn Gln Glu Pro Gln Ile
    50                  55                  60

Val His Phe Asp Ala Val Val Asn Leu Asp Lys Gly Leu Tyr Val Tyr
65                  70                  75                  80

Pro Glu Pro Lys Arg Tyr Ala Arg Ser Val Arg Gln Tyr Lys Ile Leu
                85                  90                  95

Asn Cys Ala Asn Tyr His Leu Thr Gln Val Arg Thr Asp Phe Tyr Asp
            100                 105                 110

Glu Phe Trp Gly Gln Gly Leu Arg Ala Ala Pro Lys Lys Gln Lys Lys
        115                 120                 125

His Thr Leu Ser Leu Thr Pro Asp Thr Thr Leu Tyr Asn Ala Ala Gln
    130                 135                 140

Ile Ile Cys Ala Asn Tyr Gly Glu Ala Phe Ser Val Asp Lys Lys Gly
145                 150                 155                 160

Gly Thr Lys Lys Ala Ala Val Ser Glu Leu Leu Gln Ala Ser Ala Pro
                165                 170                 175

Tyr Lys Ala Asp Val Glu Leu Cys Val Tyr Ser Thr Asn Glu Thr Thr
            180                 185                 190

Asn Cys Thr Gly Gly Lys Asn Gly Ile Ala Ala Asp Ile Thr Thr Ala
        195                 200                 205

Lys Gly Tyr Val Lys Ser Val Thr Thr Ser Asn Gly Ala Ile Thr Val
    210                 215                 220

Lys Gly Asp Gly Thr Leu Ala Asn Met Glu Tyr Ile Leu Gln Ala Thr
225                 230                 235                 240

Gly Asn Ala Ala Thr Gly Val Thr Trp Thr Thr Thr Cys Lys Gly Thr
                245                 250                 255

Asp Ala Ser Leu Phe Pro Ala Asn Phe Cys Gly Ser Val Thr Gln Gly
            260                 265                 270
```

Gly His His His His His His
        275

<210> SEQ ID NO 193
<211> LENGTH: 825
<212> TYPE: DNA
<213> ORGANISM: Artificial Sequence
<220> FEATURE:
<223> OTHER INFORMATION: LVL735

<400> SEQUENCE: 193

| | | | | | |
|---|---|---|---|---|---|
| atgaaatacc | tgctgccgac | cgctgctgct | ggtctgctgc | tcctcgctgc | ccagccggcg | 60 |
| atggccattc | agaaggctga | acaaaatgat | gtgaagctgg | caccgccgac | tgatgtacga | 120 |
| agcggatata | tacgtttggt | aaagaatgtg | aattattaca | tcgatagtga | atcgatctgg | 180 |
| gtggataacc | aagagccaca | aattgtacat | tttgatgcag | tggtgaattt | agataaggga | 240 |
| ttgtatgttt | atcctgagcc | taaacgttat | gcacgttctg | ttcgtcagta | taagatcttg | 300 |
| aattgtgcaa | attatcattt | aactcaagta | cgaactgatt | tctatgatga | attttgggga | 360 |
| cagggtttgc | gggcagcacc | taaaaagcaa | aagaaacata | cgttaagttt | aacacctgat | 420 |
| acaacgcttt | ataatgctgc | tcagattatt | tgtgcgaact | atggtgaagc | attttcagtt | 480 |
| gataaaaaag | gcggcactaa | aaaagcagcg | gtatctgaat | tactgcaagc | gtcagcgcct | 540 |
| tataaggctg | atgtggaatt | atgtgtatat | agcacaaata | aaacaacaaa | ctgtacgggt | 600 |
| ggaaaaaatg | gtattgcagc | agatataacc | acagcaaaag | gctatgtaaa | atcagtgaca | 660 |
| acaagcaacg | gtgcaataac | agtaaaaggg | gatggcacat | tggcaaatat | ggaatatatt | 720 |
| ttgcaagcta | caggtaatgc | tgcaacaggt | gtaacttgga | caacaacttg | caaggaacg | 780 |
| gatgcctctt | tatttccagc | aaattttgc | ggaagtgtca | cacaa | | 825 |

<210> SEQ ID NO 194
<211> LENGTH: 275
<212> TYPE: PRT
<213> ORGANISM: Artificial Sequence
<220> FEATURE:
<223> OTHER INFORMATION: LVL735

<400> SEQUENCE: 194

Met Lys Tyr Leu Leu Pro Thr Ala Ala Ala Gly Leu Leu Leu Leu Ala
  1               5                  10                  15

Ala Gln Pro Ala Met Ala Ile Gln Lys Ala Glu Gln Asn Asp Val Lys
         20                  25                  30

Leu Ala Pro Pro Thr Asp Val Arg Ser Gly Tyr Ile Arg Leu Val Lys
     35                  40                  45

Asn Val Asn Tyr Tyr Ile Asp Ser Glu Ser Ile Trp Val Asp Asn Gln
 50                  55                  60

Glu Pro Gln Ile Val His Phe Asp Ala Val Val Asn Leu Asp Lys Gly
 65                  70                  75                  80

Leu Tyr Val Tyr Pro Glu Pro Lys Arg Tyr Ala Arg Ser Val Arg Gln
                 85                  90                  95

Tyr Lys Ile Leu Asn Cys Ala Asn Tyr His Leu Thr Gln Val Arg Thr
            100                 105                 110

Asp Phe Tyr Asp Glu Phe Trp Gly Gln Gly Leu Arg Ala Ala Pro Lys
        115                 120                 125

Lys Gln Lys Lys His Thr Leu Ser Leu Thr Pro Asp Thr Thr Leu Tyr
    130                 135                 140

Asn Ala Ala Gln Ile Ile Cys Ala Asn Tyr Gly Glu Ala Phe Ser Val
145                 150                 155                 160

Asp Lys Lys Gly Gly Thr Lys Lys Ala Ala Val Ser Glu Leu Leu Gln
                165                 170                 175

Ala Ser Ala Pro Tyr Lys Ala Asp Val Glu Leu Cys Val Tyr Ser Thr
                180                 185                 190

Asn Glu Thr Thr Asn Cys Thr Gly Gly Lys Asn Gly Ile Ala Ala Asp
            195                 200                 205

Ile Thr Thr Ala Lys Gly Tyr Val Lys Ser Val Thr Ser Asn Gly
210                 215                 220

Ala Ile Thr Val Lys Gly Asp Gly Thr Leu Ala Asn Met Glu Tyr Ile
225                 230                 235                 240

Leu Gln Ala Thr Gly Asn Ala Ala Thr Gly Val Thr Trp Thr Thr
                245                 250                 255

Cys Lys Gly Thr Asp Ala Ser Leu Phe Pro Ala Asn Phe Cys Gly Ser
                260                 265                 270

Val Thr Gln
        275

<210> SEQ ID NO 195
<211> LENGTH: 834
<212> TYPE: DNA
<213> ORGANISM: Artificial Sequence
<220> FEATURE:
<223> OTHER INFORMATION: LVL778

<400> SEQUENCE: 195

| | | |
|---|---|---|
| atgaaatacc tgctgccgac cgctgctgct ggtctgctgc tcctcgctgc ccagccggcg | 60 |
| atggccagcg cccagattca gaaggctgaa caaaatgatg tgaagctggc accgccgact | 120 |
| gatgtacgaa gcggatatat acgtttggta agaatgtgaa attattacat cgatagtgaa | 180 |
| tcgatctggg tggataacca agagccacaa attgtacatt ttgatgcagt ggtgaattta | 240 |
| gataagggat tgtatgttta tcctgagcct aaacgttatg cacgttctgt tcgtcagtat | 300 |
| aagatcttga attgtgcaaa ttatcattta actcaagtac gaactgattt ctatgatgaa | 360 |
| ttttggggac agggtttgcg ggcagcacct aaaaagcaaa agaaacatac gttaagttta | 420 |
| acacctgata caacgcttta taatgctgct cagattattt gtgcgaacta tggtgaagca | 480 |
| ttttcagttg ataaaaaagg cggcactaaa aaagcagcgg tatctgaatt actgcaagcg | 540 |
| tcagcgcctt ataaggctga tgtggaatta tgtgtatata gcacaaatga acaacaaac | 600 |
| tgtacgggtg gaaaaaatgg tattgcagca gatataacca cagcaaaagg ctatgtaaaa | 660 |
| tcagtgacaa caagcaacgg tgcaataaca gtaaaagggg atggcacatt ggcaaatatg | 720 |
| gaatatattt gcaagctac aggtaatgct gcaacaggtg taacttggac aacaacttgc | 780 |
| aaaggaacgg atgcctcttt atttccagca aattttgcg aagtgtcac acaa | 834 |

<210> SEQ ID NO 196
<211> LENGTH: 278
<212> TYPE: PRT
<213> ORGANISM: Artificial Sequence
<220> FEATURE:
<223> OTHER INFORMATION: LVL778

<400> SEQUENCE: 196

Met Lys Tyr Leu Leu Pro Thr Ala Ala Ala Gly Leu Leu Leu Leu Ala
1               5                   10                  15

Ala Gln Pro Ala Met Ala Ser Ala Gln Ile Gln Lys Ala Glu Gln Asn

```
                    20                  25                  30
Asp Val Lys Leu Ala Pro Pro Thr Asp Val Arg Ser Gly Tyr Ile Arg
            35                  40                  45
Leu Val Lys Asn Val Asn Tyr Tyr Ile Asp Ser Glu Ser Ile Trp Val
         50                  55                  60
Asp Asn Gln Glu Pro Gln Ile Val His Phe Asp Ala Val Val Asn Leu
 65                  70                  75                  80
Asp Lys Gly Leu Tyr Val Tyr Pro Glu Pro Lys Arg Tyr Ala Arg Ser
                 85                  90                  95
Val Arg Gln Tyr Lys Ile Leu Asn Cys Ala Asn Tyr His Leu Thr Gln
            100                 105                 110
Val Arg Thr Asp Phe Tyr Asp Glu Phe Trp Gly Gln Gly Leu Arg Ala
            115                 120                 125
Ala Pro Lys Lys Gln Lys Lys His Thr Leu Ser Leu Thr Pro Asp Thr
         130                 135                 140
Thr Leu Tyr Asn Ala Ala Gln Ile Ile Cys Ala Asn Tyr Gly Glu Ala
145                 150                 155                 160
Phe Ser Val Asp Lys Lys Gly Gly Thr Lys Lys Ala Ala Val Ser Glu
                165                 170                 175
Leu Leu Gln Ala Ser Ala Pro Tyr Lys Ala Asp Val Glu Leu Cys Val
            180                 185                 190
Tyr Ser Thr Asn Glu Thr Thr Asn Cys Thr Gly Gly Lys Asn Gly Ile
            195                 200                 205
Ala Ala Asp Ile Thr Thr Ala Lys Gly Tyr Val Lys Ser Val Thr Thr
         210                 215                 220
Ser Asn Gly Ala Ile Thr Val Lys Gly Asp Gly Thr Leu Ala Asn Met
225                 230                 235                 240
Glu Tyr Ile Leu Gln Ala Thr Gly Asn Ala Ala Thr Gly Val Thr Trp
                245                 250                 255
Thr Thr Thr Cys Lys Gly Thr Asp Ala Ser Leu Phe Pro Ala Asn Phe
            260                 265                 270
Cys Gly Ser Val Thr Gln
         275

<210> SEQ ID NO 197
<211> LENGTH: 831
<212> TYPE: DNA
<213> ORGANISM: Artificial Sequence
<220> FEATURE:
<223> OTHER INFORMATION: LVL779

<400> SEQUENCE: 197
atgaaatacc tgctgccgac cgctgctgct ggtctgctgc tcctcgctgc ccagccggcg    60
atggccgccc agattcagaa ggctgaacaa atgatgtga agctggcacc gccgactgat   120
gtacgaagcg gatatatacg tttggtaaag aatgtgaatt attacatcga tagtgaatcg   180
atctgggtgg ataaccaaga gccacaaatt gtacattttg atgcagtggt gaatttagat   240
aagggattgt atgtttatcc tgagcctaaa cgttatgcac gttctgttcg tcagtataag   300
atcttgaatt gtgcaaatta tcatttaact caagtacgaa ctgatttcta tgatgaattt   360
tggggacagg gtttgcgggc agcacctaaa agcaaaaga acatacgtt aagtttaaca   420 cctgatacaa cgctttataa tgctgctcag attatttgtg cgaactatgg tgaagcattt   480
tcagttgata aaaaggcgg cactaaaaaa gcagcggtat ctgaattact gcaagcgtca   540
gcgccttata aggctgatgt ggaattatgt gtatatagca caaatgaaac aacaaactgt   600
```

```
acgggtggaa aaaatggtat tgcagcagat ataaccacag caaaaggcta tgtaaaatca    660
gtgacaacaa gcaacggtgc aataacagta aaggggatg gcacattggc aaatatggaa     720
tatattttgc aagctacagg taatgctgca acaggtgtaa cttggacaac aacttgcaaa    780
ggaacggatg cctctttatt tccagcaaat ttttgcggaa gtgtcacaca a              831
```

<210> SEQ ID NO 198
<211> LENGTH: 277
<212> TYPE: PRT
<213> ORGANISM: Artificial Sequence
<220> FEATURE:
<223> OTHER INFORMATION: LVL779

<400> SEQUENCE: 198

```
Met Lys Tyr Leu Leu Pro Thr Ala Ala Gly Leu Leu Leu Ala
  1               5                  10                  15

Ala Gln Pro Ala Met Ala Ala Gln Ile Gln Lys Ala Glu Gln Asn Asp
         20                  25                  30

Val Lys Leu Ala Pro Pro Thr Asp Val Arg Ser Gly Tyr Ile Arg Leu
     35                  40                  45

Val Lys Asn Val Asn Tyr Tyr Ile Asp Ser Glu Ser Ile Trp Val Asp
 50                  55                  60

Asn Gln Glu Pro Gln Ile Val His Phe Asp Ala Val Asn Leu Asp
65                  70                  75                  80

Lys Gly Leu Tyr Val Tyr Pro Glu Pro Lys Arg Tyr Ala Arg Ser Val
                 85                  90                  95

Arg Gln Tyr Lys Ile Leu Asn Cys Ala Asn Tyr His Leu Thr Gln Val
             100                 105                 110

Arg Thr Asp Phe Tyr Asp Glu Phe Trp Gly Gln Gly Leu Arg Ala Ala
         115                 120                 125

Pro Lys Lys Gln Lys Lys His Thr Leu Ser Leu Thr Pro Asp Thr Thr
    130                 135                 140

Leu Tyr Asn Ala Ala Gln Ile Ile Cys Ala Asn Tyr Gly Glu Ala Phe
145                 150                 155                 160

Ser Val Asp Lys Lys Gly Gly Thr Lys Ala Ala Val Ser Glu Leu
                165                 170                 175

Leu Gln Ala Ser Ala Pro Tyr Lys Ala Asp Val Glu Leu Cys Val Tyr
            180                 185                 190

Ser Thr Asn Glu Thr Thr Asn Cys Thr Gly Gly Lys Asn Gly Ile Ala
        195                 200                 205

Ala Asp Ile Thr Thr Ala Lys Gly Tyr Val Lys Ser Val Thr Thr Ser
    210                 215                 220

Asn Gly Ala Ile Thr Val Lys Gly Asp Gly Thr Leu Ala Asn Met Glu
225                 230                 235                 240

Tyr Ile Leu Gln Ala Thr Gly Asn Ala Ala Thr Gly Val Thr Trp Thr
                245                 250                 255

Thr Thr Cys Lys Gly Thr Asp Ala Ser Leu Phe Pro Ala Asn Phe Cys
            260                 265                 270

Gly Ser Val Thr Gln
        275
```

<210> SEQ ID NO 199
<211> LENGTH: 819
<212> TYPE: DNA
<213> ORGANISM: Artificial Sequence
<220> FEATURE:

<223> OTHER INFORMATION: LVL780

<400> SEQUENCE: 199

```
atgaaatacc tgctgccgac cgctgctgct ggtctgctgc tcctcgctgc ccagccggcg    60
atggccaagg ctgaacaaaa tgatgtgaag ctggcaccgc cgactgatgt acgaagcgga   120
tatatacgtt tggtaaagaa tgtgaattat tacatcgata gtgaatcgat ctgggtggat   180
aaccaagagc cacaaattgt acattttgat gcagtggtga atttagataa gggattgtat   240
gtttatcctg agcctaaacg ttatgcacgt tctgttcgtc agtataagat cttgaattgt   300
gcaaattatc atttaactca gtacgaact gatttctatg atgaattttg gggacagggt   360
ttgcgggcag cacctaaaaa gcaaagaaa catacgttaa gtttaacacc tgatacaacg   420
ctttataatg ctgctcagat tatttgtgcg aactatggtg aagcattttc agttgataaa   480
aaaggcggca ctaaaaaagc agcggtatct gaattactgc aagcgtcagc gccttataag   540
gctgatgtgg aattatgtgt atatagcaca atgaaacaa caaactgtac gggtggaaaa   600
aatggtattg cagcagatat aaccacagca aaaggctatg taaaatcagt gacaacaagc   660
aacggtgcaa taacagtaaa aggggatggc acattggcaa atatggaata tatttttgcaa   720
gctacaggta atgctgcaac aggtgtaact tggacaacaa cttgcaaagg aacggatgcc   780
tctttatttc agcaaatttt ttgcggaagt gtcacacaa                          819
```

<210> SEQ ID NO 200
<211> LENGTH: 273
<212> TYPE: PRT
<213> ORGANISM: Artificial Sequence
<220> FEATURE:
<223> OTHER INFORMATION: LVL780

<400> SEQUENCE: 200

```
Met Lys Tyr Leu Leu Pro Thr Ala Ala Gly Leu Leu Leu Leu Ala
 1               5                  10                  15

Ala Gln Pro Ala Met Ala Lys Ala Glu Gln Asn Asp Val Lys Leu Ala
            20                  25                  30

Pro Pro Thr Asp Val Arg Ser Gly Tyr Ile Arg Leu Val Lys Asn Val
        35                  40                  45

Asn Tyr Tyr Ile Asp Ser Glu Ser Ile Trp Val Asp Asn Gln Glu Pro
    50                  55                  60

Gln Ile Val His Phe Asp Ala Val Val Asn Leu Asp Lys Gly Leu Tyr
65                  70                  75                  80

Val Tyr Pro Glu Pro Lys Arg Tyr Ala Arg Ser Val Arg Gln Tyr Lys
                85                  90                  95

Ile Leu Asn Cys Ala Asn Tyr His Leu Thr Gln Val Arg Thr Asp Phe
            100                 105                 110

Tyr Asp Glu Phe Trp Gly Gln Gly Leu Arg Ala Ala Pro Lys Lys Gln
        115                 120                 125

Lys Lys His Thr Leu Ser Leu Thr Pro Asp Thr Thr Leu Tyr Asn Ala
    130                 135                 140

Ala Gln Ile Ile Cys Ala Asn Tyr Gly Glu Ala Phe Ser Val Asp Lys
145                 150                 155                 160

Lys Gly Gly Thr Lys Lys Ala Ala Val Ser Glu Leu Leu Gln Ala Ser
                165                 170                 175

Ala Pro Tyr Lys Ala Asp Val Glu Leu Cys Val Tyr Ser Thr Asn Glu
            180                 185                 190

Thr Thr Asn Cys Thr Gly Gly Lys Asn Gly Ile Ala Ala Asp Ile Thr
```

```
                    195                 200                 205
Thr Ala Lys Gly Tyr Val Lys Ser Val Thr Thr Ser Asn Gly Ala Ile
            210                 215                 220

Thr Val Lys Gly Asp Gly Thr Leu Ala Asn Met Glu Tyr Ile Leu Gln
225                 230                 235                 240

Ala Thr Gly Asn Ala Ala Thr Gly Val Thr Trp Thr Thr Cys Lys
                245                 250                 255

Gly Thr Asp Ala Ser Leu Phe Pro Ala Asn Phe Cys Gly Ser Val Thr
                260                 265                 270

Gln

<210> SEQ ID NO 201
<211> LENGTH: 816
<212> TYPE: DNA
<213> ORGANISM: Artificial Sequence
<220> FEATURE:
<223> OTHER INFORMATION: LVL781

<400> SEQUENCE: 201
atgaaatacc tgctgccgac cgctgctgct ggtctgctgc tcctcgctgc ccagccggcg      60
atggccgctg aacaaaatga tgtgaagctg gcaccgccga ctgatgtacg aagcggatat     120
atacgtttgg taaagaatgt gaattattac atcgatagtg aatcgatctg ggtggataac     180
caagagccac aaattgtaca ttttgatgca gtggtgaatt tagataaggg attgtatgtt     240
tatcctgagc ctaaacgtta tgcacgttct gttcgtcagt ataagatctt gaattgtgca     300
aattatcatt taactcaagt acgaactgat ttctatgatg aattttgggg acagggtttg     360
cgggcagcac ctaaaaagca aagaaacat acgttaagtt taacacctga tacaacgctt      420
tataatgctc tcagattat ttgtgcgaac atggtgaag cattttcagt tgataaaaaa       480
ggcggcacta aaaagcagc ggtatctgaa ttactgcaag cgtcagcgcc ttataaggct      540
gatgtggaat tatgtgtata tagcacaaat gaaacaacaa actgtacggg tggaaaaaat     600
ggtattgcag cagatataac cacagcaaaa ggctatgtaa aatcagtgac aacaagcaac     660
ggtgcaataa cagtaaaagg ggatggcaca ttggcaaata tggaatatat tttgcaagct     720
acaggtaatg ctgcaacagg tgtaacttgg acaacaactt gcaaggaac ggatgcctct      780 ttatttccag caaattttg cggaagtgtc acacaa                                816

<210> SEQ ID NO 202
<211> LENGTH: 272
<212> TYPE: PRT
<213> ORGANISM: Artificial Sequence
<220> FEATURE:
<223> OTHER INFORMATION: LVL781

<400> SEQUENCE: 202

Met Lys Tyr Leu Leu Pro Thr Ala Ala Ala Gly Leu Leu Leu Leu Ala
1               5                   10                  15

Ala Gln Pro Ala Met Ala Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80
```

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Glu Ala Phe Ser Val Asp Lys Lys
145                 150                 155                 160

Gly Gly Thr Lys Lys Ala Ala Val Ser Glu Leu Leu Gln Ala Ser Ala
                165                 170                 175

Pro Tyr Lys Ala Asp Val Glu Leu Cys Val Tyr Ser Thr Asn Glu Thr
            180                 185                 190

Thr Asn Cys Thr Gly Gly Lys Asn Gly Ile Ala Ala Asp Ile Thr Thr
        195                 200                 205

Ala Lys Gly Tyr Val Lys Ser Val Thr Thr Ser Asn Gly Ala Ile Thr
    210                 215                 220

Val Lys Gly Asp Gly Thr Leu Ala Asn Met Glu Tyr Ile Leu Gln Ala
225                 230                 235                 240

Thr Gly Asn Ala Ala Thr Gly Val Thr Trp Thr Thr Cys Lys Gly
                245                 250                 255

Thr Asp Ala Ser Leu Phe Pro Ala Asn Phe Cys Gly Ser Val Thr Gln
            260                 265                 270

<210> SEQ ID NO 203
<211> LENGTH: 813
<212> TYPE: DNA
<213> ORGANISM: Artificial Sequence
<220> FEATURE:
<223> OTHER INFORMATION: LVL782

<400> SEQUENCE: 203

```
atgaaatacc tgctgccgac cgctgctgct ggtctgctgc tcctcgctgc ccagccggcg    60
atggccgaac aaaatgatgt gaagctggca ccgccgactg atgtacgaag cggatatata   120
cgtttggtaa agaatgtgaa ttattacatc gatagtgaat cgatctgggt ggataaccaa   180
gagccacaaa ttgtacattt tgatgcagtg gtgaatttag ataagggatt gtatgtttat   240
cctgagccta acgttatgc acgttctgtt cgtcagtata agatcttgaa ttgtgcaaat   300
tatcatttaa ctcaagtacg aactgatttc tatgatgaat tttggggaca gggtttgcgg   360
gcagcaccta aaaagcaaaa gaaacatacg ttaagtttaa cacctgatac aacgctttat   420
aatgctgctc agattatttg tgcgaactat ggtgaagcat tttcagttga taaaaaaggc   480
ggcactaaaa aagcagcggt atctgaatta ctgcaagcgt cagcgcctta taaggctgat   540
gtggaattat gtgtatatag cacaaatgaa acaacaaact gtacgggtgg aaaaaatggt   600
attgcagcag atataaccac agcaaaaggc tatgtaaaat cagtgacaac aagcaacggt   660
gcaataacag taaaagggga tggcacattg gcaaatatgg aatatatttt gcaagctaca   720
ggtaatgctg caacaggtgt aacttggaca caaacttgca aggaacgga tgcctcttta   780 tttccagcaa attttttgcgg aagtgtcaca caa                             813
```

<210> SEQ ID NO 204
<211> LENGTH: 271
<212> TYPE: PRT
<213> ORGANISM: Artificial Sequence

<220> FEATURE:
<223> OTHER INFORMATION: LVL782

<400> SEQUENCE: 204

Met Lys Tyr Leu Leu Pro Thr Ala Ala Ala Gly Leu Leu Leu Leu Ala
1               5                   10                  15

Ala Gln Pro Ala Met Ala Glu Gln Asn Asp Val Lys Leu Ala Pro Pro
            20                  25                  30

Thr Asp Val Arg Ser Gly Tyr Ile Arg Leu Val Lys Asn Val Asn Tyr
        35                  40                  45

Tyr Ile Asp Ser Glu Ser Ile Trp Val Asp Asn Gln Glu Pro Gln Ile
50                  55                  60

Val His Phe Asp Ala Val Val Asn Leu Asp Lys Gly Leu Tyr Val Tyr
65                  70                  75                  80

Pro Glu Pro Lys Arg Tyr Ala Arg Ser Val Arg Gln Tyr Lys Ile Leu
                85                  90                  95

Asn Cys Ala Asn Tyr His Leu Thr Gln Val Arg Thr Asp Phe Tyr Asp
            100                 105                 110

Glu Phe Trp Gly Gln Gly Leu Arg Ala Ala Pro Lys Lys Gln Lys Lys
        115                 120                 125

His Thr Leu Ser Leu Thr Pro Asp Thr Thr Leu Tyr Asn Ala Ala Gln
130                 135                 140

Ile Ile Cys Ala Asn Tyr Gly Glu Ala Phe Ser Val Asp Lys Lys Gly
145                 150                 155                 160

Gly Thr Lys Lys Ala Ala Val Ser Glu Leu Leu Gln Ala Ser Ala Pro
                165                 170                 175

Tyr Lys Ala Asp Val Glu Leu Cys Val Tyr Ser Thr Asn Glu Thr Thr
            180                 185                 190

Asn Cys Thr Gly Gly Lys Asn Gly Ile Ala Ala Asp Ile Thr Thr Ala
        195                 200                 205

Lys Gly Tyr Val Lys Ser Val Thr Thr Ser Asn Gly Ala Ile Thr Val
210                 215                 220

Lys Gly Asp Gly Thr Leu Ala Asn Met Glu Tyr Ile Leu Gln Ala Thr
225                 230                 235                 240

Gly Asn Ala Ala Thr Gly Val Thr Trp Thr Thr Cys Lys Gly Thr
                245                 250                 255

Asp Ala Ser Leu Phe Pro Ala Asn Phe Cys Gly Ser Val Thr Gln
            260                 265                 270

<210> SEQ ID NO 205
<211> LENGTH: 95
<212> TYPE: DNA
<213> ORGANISM: Artificial Sequence
<220> FEATURE:
<223> OTHER INFORMATION: primer

<400> SEQUENCE: 205
gatatacata tgaaatacct gctgccgacc gctgctgctg gtctgctgct cctcgctgcc    60
cagccggcga tggccattca gaaggctgaa caaaa                              95

<210> SEQ ID NO 206
<211> LENGTH: 39
<212> TYPE: DNA
<213> ORGANISM: Artificial Sequence
<220> FEATURE:
<223> OTHER INFORMATION: primer

<400> SEQUENCE: 206

-continued ggccgcaagc ttttagtggt ggtggtggtg gtggccgcc           39

<210> SEQ ID NO 207
<211> LENGTH: 30
<212> TYPE: DNA
<213> ORGANISM: Artificial Sequence
<220> FEATURE:
<223> OTHER INFORMATION: primer

<400> SEQUENCE: 207
ggccgcaagc ttttattgtg tgacacttcc                     30

<210> SEQ ID NO 208
<211> LENGTH: 42
<212> TYPE: DNA
<213> ORGANISM: Artificial Sequence
<220> FEATURE:
<223> OTHER INFORMATION: primer

<400> SEQUENCE: 208
gctgcccagc cggcgatggc caaggctgaa caaaatgatg tg       42

<210> SEQ ID NO 209
<211> LENGTH: 42
<212> TYPE: DNA
<213> ORGANISM: Artificial Sequence
<220> FEATURE:
<223> OTHER INFORMATION: primer

<400> SEQUENCE: 209
cacatcattt tgttcagcct tggccatcgc cggctgggca gc       42

<210> SEQ ID NO 210
<211> LENGTH: 43
<212> TYPE: DNA
<213> ORGANISM: Artificial Sequence
<220> FEATURE:
<223> OTHER INFORMATION: primer

<400> SEQUENCE: 210
gctgcccagc cggcgatggc cgctgaacaa aatgatgtga agc      43

<210> SEQ ID NO 211
<211> LENGTH: 43
<212> TYPE: DNA
<213> ORGANISM: Artificial Sequence
<220> FEATURE:
<223> OTHER INFORMATION: primer

<400> SEQUENCE: 211
gcttcacatc attttgttca gcggccatcg ccggctgggc agc      43

<210> SEQ ID NO 212
<211> LENGTH: 43
<212> TYPE: DNA
<213> ORGANISM: Artificial Sequence
<220> FEATURE:
<223> OTHER INFORMATION: primer

<400> SEQUENCE: 212
gctgcccagc cggcgatggc cgaacaaaat gatgtgaagc tgg      43

<210> SEQ ID NO 213
<211> LENGTH: 43
<212> TYPE: DNA

```
<213> ORGANISM: Artificial Sequence
<220> FEATURE:
<223> OTHER INFORMATION: primer

<400> SEQUENCE: 213
ccagcttcac atcatttgt tcggccatcg ccggctgggc agc         43

<210> SEQ ID NO 214
<211> LENGTH: 43
<212> TYPE: DNA
<213> ORGANISM: Artificial Sequence
<220> FEATURE:
<223> OTHER INFORMATION: primer

<400> SEQUENCE: 214
gctgcccagc cggcgatggc cgcccagatt cagaaggctg aac         43

<210> SEQ ID NO 215
<211> LENGTH: 43
<212> TYPE: DNA
<213> ORGANISM: Artificial Sequence
<220> FEATURE:
<223> OTHER INFORMATION: primer

<400> SEQUENCE: 215
gttcagcctt ctgaatctgg gcggccatcg ccggctgggc agc         43

<210> SEQ ID NO 216
<211> LENGTH: 46
<212> TYPE: DNA
<213> ORGANISM: Artificial Sequence
<220> FEATURE:
<223> OTHER INFORMATION: primer

<400> SEQUENCE: 216
gctgcccagc cggcgatggc cagcgcccag attcagaagg ctgaac         46

<210> SEQ ID NO 217
<211> LENGTH: 46
<212> TYPE: DNA
<213> ORGANISM: Artificial Sequence
<220> FEATURE:
<223> OTHER INFORMATION: primer

<400> SEQUENCE: 217
gttcagcctt ctgaatctgg gcgctggcca tcgccggctg ggcagc         46

<210> SEQ ID NO 218
<211> LENGTH: 30
<212> TYPE: DNA
<213> ORGANISM: Artificial Sequence
<220> FEATURE:
<223> OTHER INFORMATION: primer

<400> SEQUENCE: 218
cacacacata tgaaatacct gctgccgacc         30

<210> SEQ ID NO 219
<211> LENGTH: 253
<212> TYPE: PRT
<213> ORGANISM: Artificial Sequence
<220> FEATURE:
<223> OTHER INFORMATION: FUSION PROTEIN

<400> SEQUENCE: 219

Ile Gln Lys Ala Glu Gln Asn Asp Val Lys Leu Ala Pro Pro Thr Asp
```

```
                 1               5                  10                 15
         Val Arg Ser Gly Tyr Ile Arg Leu Val Lys Asn Val Asn Tyr Tyr Ile
                         20                 25                 30

Asp Ser Glu Ser Ile Trp Val Asp Asn Gln Glu Pro Gln Ile Val His
                     35                 40                 45

Phe Asp Ala Val Val Asn Leu Asp Lys Gly Leu Tyr Val Tyr Pro Glu
                 50                 55                 60

Pro Lys Arg Tyr Ala Arg Ser Val Arg Gln Tyr Lys Ile Leu Asn Cys
         65                  70                 75                 80

Ala Asn Tyr His Leu Thr Gln Val Arg Thr Asp Phe Tyr Asp Glu Phe
                         85                 90                 95

Trp Gly Gln Gly Leu Arg Ala Ala Pro Lys Lys Gln Lys Lys His Thr
                         100                105                110

Leu Ser Leu Thr Pro Asp Thr Thr Leu Tyr Asn Ala Ala Gln Ile Ile
                     115                120                125

Cys Ala Asn Tyr Gly Glu Ala Phe Ser Val Asp Lys Lys Gly Gly Thr
                     130                135                140

Lys Lys Ala Ala Val Ser Glu Leu Leu Gln Ala Ser Ala Pro Tyr Lys
         145                 150                155                160

Ala Asp Val Glu Leu Cys Val Tyr Ser Thr Asn Glu Thr Thr Asn Cys
                         165                170                175

Thr Gly Gly Lys Asn Gly Ile Ala Ala Asp Ile Thr Thr Ala Lys Gly
                     180                185                190

Tyr Val Lys Ser Val Thr Thr Ser Asn Gly Ala Ile Thr Val Lys Gly
                     195                200                205

Asp Gly Thr Leu Ala Asn Met Glu Tyr Ile Leu Gln Ala Thr Gly Asn
                     210                215                220

Ala Ala Thr Gly Val Thr Trp Thr Thr Thr Cys Lys Gly Thr Asp Ala
         225                 230                235                240

Ser Leu Phe Pro Ala Asn Phe Cys Gly Ser Val Thr Gln
                         245                250
```